(12) United States Patent
Bolea et al.

(10) Patent No.: US 8,399,493 B2
(45) Date of Patent: Mar. 19, 2013

(54) PYRIDINONE DERIVATIVES AND THEIR USE AS POSITIVE ALLOSTERIC MODULATORS OF MGLUR2-RECEPTORS

(75) Inventors: Christelle Martine Bolea, Geneva (CH); Vanthea Nhem, Geneva (CH); Terry Patrick Finn, Geneva (CH); Emmanuel Christian Le Poul, Geneva (CH); Jean-Philippe Francois Christian Rocher, Geneva (CH); Robert Johannes Lutjens, Geneva (CH)

(73) Assignees: Janssen Pharmaceuticals, Inc., Titusville, NJ (US); Addex Pharmaceuticals S.A., Geneva (CH)

( * ) Notice: Subject to any disclaimer, the term of this patent is extended or adjusted under 35 U.S.C. 154(b) by 1318 days.

(21) Appl. No.: 11/575,433

(22) PCT Filed: Sep. 16, 2005

(86) PCT No.: PCT/EP2005/054636
§ 371 (c)(1),
(2), (4) Date: Mar. 16, 2007

(87) PCT Pub. No.: WO2006/030032
PCT Pub. Date: Mar. 23, 2006

(65) Prior Publication Data
US 2007/0213323 A1    Sep. 13, 2007

(30) Foreign Application Priority Data
Sep. 17, 2004 (GB) .................................. 0420722.1

(51) Int. Cl.
*A61K 31/4412* (2006.01)
*A61K 31/4427* (2006.01)

(52) U.S. Cl. ........ 514/345; 514/335; 514/340; 514/341; 514/342; 514/343

(58) Field of Classification Search .................. None
See application file for complete search history.

(56) References Cited

U.S. PATENT DOCUMENTS

| | | | |
|---|---|---|---|
| 4,066,651 A | 1/1978 | Brittain et al. | |
| 4,358,453 A | 11/1982 | Bristol et al. | |
| 4,550,166 A | 10/1985 | Moran et al. | |
| 5,032,602 A | 7/1991 | Fey et al. | |
| 5,236,917 A | 8/1993 | Dunlap et al. | |
| 5,356,911 A | 10/1994 | Muller-Gliemann et al. | |
| 5,371,074 A | 12/1994 | Dunlap et al. | |
| 5,374,513 A | 12/1994 | Ohzeki et al. | |
| 5,498,774 A | 3/1996 | Mitsudera et al. | |
| 5,596,012 A | 1/1997 | Dunlap et al. | |
| 5,650,422 A | 7/1997 | Dunlap et al. | |
| 5,874,432 A | 2/1999 | Dunlap et al. | |
| 5,948,911 A | 9/1999 | Pamukcu et al. | |
| 6,110,920 A | 8/2000 | Rochus et al. | |
| 6,133,271 A | 10/2000 | Pamukcu et al. | |
| 6,607,563 B2 | 8/2003 | Ohashi et al. | |
| 7,456,289 B2 | 11/2008 | Hsieh et al. | |
| 7,572,807 B2 | 8/2009 | Li et al. | |
| 7,579,360 B2 | 8/2009 | Li et al. | |
| 2003/0171380 A1 | 9/2003 | Arvantis et al. | |
| 2005/0113283 A1 | 5/2005 | Solow-cordero et al. | |
| 2007/0066582 A1 | 3/2007 | Herold et al. | |
| 2007/0275984 A1 | 11/2007 | Imogai et al. | |
| 2009/0031422 A1 | 1/2009 | Aaron et al. | |
| 2009/0124609 A1 | 5/2009 | Albrecht et al. | |
| 2009/0124612 A1 | 5/2009 | Albrecht et al. | |
| 2009/0203668 A1 | 8/2009 | Li et al. | |
| 2009/0318436 A1 | 12/2009 | Albrecht et al. | |
| 2010/0063092 A1 | 3/2010 | Cid-Nunez | |
| 2010/0087487 A1 | 4/2010 | Cid-Nunez | |
| 2010/0099715 A1 | 4/2010 | Cid-Nunez et al. | |
| 2010/0166655 A1 | 7/2010 | Imogai et al. | |
| 2010/0240688 A1 | 9/2010 | Cid-Nunez | |
| 2010/0240706 A1 | 9/2010 | Cid-Nunez | |
| 2010/0286206 A1 | 11/2010 | Cid-Nunez | |
| 2011/0275624 A1 | 11/2011 | Cid-Nunez et al. | |
| 2011/0306642 A1 | 12/2011 | Cid-Nunez et al. | |

FOREIGN PATENT DOCUMENTS

| | | |
|---|---|---|
| CA | 1019323 | 10/1977 |
| CA | 2390948 | 12/2000 |
| CN | 1842532 | 10/2006 |
| CN | 102002040 | 4/2011 |
| EP | 0430385 | 6/1991 |
| EP | 447118 | 9/1991 |
| EP | 0452002 | 10/1991 |

(Continued)

OTHER PUBLICATIONS

DiMichele et al., Psychopathology, (Mar.-Apr. 2004), 37(2), pp. 98-104 (Abstract).*
Rosowsky et al, "2,4-Diaminothieno [2.3-d]dipyrimidines as Antifolates and Antimalarials 3. Synthesis of 5,6-Disubstituted Derivatives and Related Tetracyclic Analogs", Journal of Medicinal Chemistry, vol. 16, No. 3, 1973, pp. 191-194.
Benneyworth et al., "A Selective Positive Allosteric Modulator of Metabotropic Glutamate Receptor Subtype 2 Blocks a Hallucinogenic Drug Model of Psychosis," Mol. Pharmacol., 2007, 72, 477-484.
International Search Report dated Sep. 7, 2007, for international application No. PCT/EP2007/052442.

(Continued)

*Primary Examiner* — Phyllis G. Spivack
(74) *Attorney, Agent, or Firm* — Gardner Groff Greenwald & Villanueva, PC

(57) ABSTRACT

The present invention relates to methods for treating or controlling schizophrenia in a mammal using compounds having the Formula (I), wherein $M_1$ and $M_2$ are defined in the application.

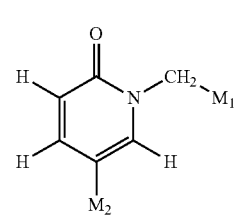

(I)

9 Claims, 4 Drawing Sheets

FOREIGN PATENT DOCUMENTS

| | | |
|---|---|---|
| EP | A10482939 | 4/1992 |
| EP | A1006112 | 6/2000 |
| EP | 1764099 | 3/2007 |
| GB | 1502312 | 3/1978 |
| JP | H02503317 | 10/1990 |
| JP | A2000072751 | 3/2000 |
| JP | 2002308882 | 10/2002 |
| JP | 2008509714 | 4/2008 |
| RU | 1796625 | 2/1993 |
| RU | C12143433 | 12/1999 |
| WO | 9504733 | 2/1995 |
| WO | 9511233 | 4/1995 |
| WO | 9710238 | 3/1997 |
| WO | 9721701 | 6/1997 |
| WO | 9811075 | 3/1998 |
| WO | 9817668 | 4/1998 |
| WO | 9824780 | 6/1998 |
| WO | 9832762 | 7/1998 |
| WO | 9962908 | 12/1999 |
| WO | 0003990 | 1/2000 |
| WO | 0034244 | 6/2000 |
| WO | 0129025 | 4/2001 |
| WO | 0132632 | 5/2001 |
| WO | 0156990 | 8/2001 |
| WO | 0168097 | 9/2001 |
| WO | 0170731 | 9/2001 |
| WO | 0183481 | 11/2001 |
| WO | 0196308 | 12/2001 |
| WO | 0210807 | 2/2002 |
| WO | 0212236 | 2/2002 |
| WO | 0222598 | 3/2002 |
| WO | 0228837 | 4/2002 |
| WO | 02074025 | 9/2002 |
| WO | 02090333 | 11/2002 |
| WO | 02096318 | 12/2002 |
| WO | 02096363 | 12/2002 |
| WO | 03029209 | 4/2003 |
| WO | 03044021 | 5/2003 |
| WO | 03/059884 | 7/2003 |
| WO | 03062392 | 7/2003 |
| WO | 03065994 | 8/2003 |
| WO | 03068230 | 8/2003 |
| WO | 03068750 | 8/2003 |
| WO | 2004017950 | 3/2004 |
| WO | 2004018386 | 3/2004 |
| WO | 2004021984 | 3/2004 |
| WO | 2004031189 | 4/2004 |
| WO | 2004072025 | 8/2004 |
| WO | 2004078175 | 9/2004 |
| WO | 2004092123 | 10/2004 |
| WO | 2004092135 | 10/2004 |
| WO | 2005/002585 | 1/2005 |
| WO | 2005021552 | 3/2005 |
| WO | 2005028445 | 3/2005 |
| WO | 2005040337 | 5/2005 |
| WO | 2005080356 | 9/2005 |
| WO | 2005097052 | 10/2005 |
| WO | 2006012622 | 2/2006 |
| WO | 2006014918 | 2/2006 |
| WO | 2006015158 | 2/2006 |
| WO | 2006015737 | 2/2006 |
| WO | 2006018727 | 2/2006 |
| WO | 2006020879 | 2/2006 |
| WO | 2006/030031 | 3/2006 |
| WO | 2006030032 | 3/2006 |
| WO | 2006074041 | 7/2006 |
| WO | 2007031558 | 3/2007 |
| WO | 2007039439 | 4/2007 |
| WO | 2007059257 | 5/2007 |
| WO | 2007103760 | 9/2007 |
| WO | 2007113276 | 10/2007 |
| WO | 2007122258 | 11/2007 |
| WO | 2007135527 | 11/2007 |
| WO | 2007135529 | 11/2007 |
| WO | 2008006540 | 1/2008 |
| WO | 2008008539 | 1/2008 |
| WO | 2008012622 | 1/2008 |
| WO | 2008045393 | 4/2008 |
| WO | 2008051197 | 5/2008 |
| WO | 2008057855 | 5/2008 |
| WO | 2008076225 | 6/2008 |
| WO | 2008078091 | 7/2008 |
| WO | 2008078100 | 7/2008 |
| WO | 2008107125 | 9/2008 |
| WO | 2008107479 | 9/2008 |
| WO | 2008107480 | 9/2008 |
| WO | 2008107481 | 9/2008 |
| WO | 2008124085 | 10/2008 |
| WO | 2009033702 | 3/2009 |
| WO | 2009033703 | 3/2009 |
| WO | 2009033704 | 3/2009 |
| WO | 2009045753 | 4/2009 |
| WO | 2009062676 | 5/2009 |
| WO | 2009091374 | 7/2009 |
| WO | 2009124609 | 10/2009 |
| WO | 2010022076 | 2/2010 |
| WO | 2010022081 | 2/2010 |
| WO | 2010043396 | 4/2010 |
| WO | 2010060589 | 6/2010 |
| WO | 2010063054 | 6/2010 |
| WO | 2010089303 | 8/2010 |
| WO | 2010117926 | 10/2010 |
| WO | 2010025890 | 11/2010 |
| WO | 2010123424 | 11/2010 |
| WO | 2010130422 | 11/2010 |
| WO | 2010130423 | 11/2010 |

OTHER PUBLICATIONS

Chemical Abstracts, Azimov et al. abstract No. 78798, vol. 105 No. 10, 1986.
Anxiolytic and Side-Effect Profile of LY354740: A Potent, Highly Selective, Orally Active Agonist for Group II Metabotropic Glutamate Receptors, Helton et al., J. of Pharmacology and Experimental Therapeutics, p. 651-660, vol. 284, No. 2, 1997.
Eisa et al., "Synthesis of some novel tetrazole derivatives as potential antimicrobial agents," Pakistan J. of Scientific and Industrial Res, vol. 33, 1990, pp. 417-420.
Ruggero Galici, Carrie K. Jones, Kamondanai Hemstapat, Yi Nong, Nicholas G. Echemendia, Lilly C. Williams, Tomas de Paulis, and P. Jeffrey Conn, "Biphenyl-indanone A, a Positive Allosteric Modulator of the Metabotropic Glutamate Receptor Subtype 2, Has Antipsychotic- and Anxiolytic-Like Effects in Mice," JPET 318:173-185 2006. If.
The Synthesis of Perloline, 6-(3,4-Dimethoxyphenyl)-5-hydroxy-5,6-dihydrobenzo[c][2,7]napththyridin-4(3H)-one, Prager et al., Aust. J. Chem., 1983, 36, 1441-53.
A 'Biogenetic Like' Synthesis of Perloline, 6-(3,4-Dimethoxyphenyl)-5-hydroxy-5,6-dihydrobenzo[c][2,7]naphthyridin-4(3H)-one, Duong, et al., Aust. J. Chem., 1983, 36, 1431-40.
Ring Transformation of Uracils to 3-Pyridones. Hydrolysis of 6-(2-Dimethylaminovinyl) Uracils, Senda et al., Heterocycles, vol. 9, No. 6, 1978 (6 pages).
Synthese von 3-Cyan-6-methyl-4-pyridyl-und 3-cyan-4-methyl-6-pyridyl-pyrid-2(1H)-onen und -thionen, Hanfeld, et al., Pharmazie 43 (1988), H.11, 762-764.
Studies with Polyfunctionally Substituted Heteroaromatics: New Routes for the Synthesis of Polyfunctionally Substituted Pyridines and 1,2,4-Triazolo[1,5-a]pyridines, Al-Omran, et al., Heteratom. Chemistry, vol. 6, No. 6, 1995, 545-551.
Diels-Alder Reactions of the Heterodiene System in 2(1H)-Pyrazinones, Tutonda, et al., Tetrahedron Letters, vol. 27, No. 22, pp. 2509-2512, 1986.
Cycloadditions of Cyanoketenes to Cinnamylideneamines and Benzylideneamines. Synthetic Scope, Stereochemistry, and Mechanism, Moore, et al., J. Org. Chem, 1985, 50, 4231-4238.
Reactions of Some 4-Methylene-4H-pyran Derivatives with Primary and Secondary Amines, VanAllan, et al., Journal of Heterocyclic Chemistry, vol. 7, Jun. 1970, 495-507.
A One-Step Preparation of Functionalized 3-Cyano-2-Pyridones, Jain, et al., Tetrahedron Letters, vol. 36, No. 19, pp. 3307-3310, 1995.
A new Synthetic Approach to the C-D Ring Portion of Streptonigrin Analogues, Kilama, et al., Journal of Heterocyclic Chemistry, vol. 27, Jul.-Aug. 1990, 1437-1440.

A Convenient Method for the Preparation of 2-Pyridone Derivatives, Kambe et al., 1977, vol. 12, pp. 841-842.
Torp-Ziegler Cyclization in the Synthesis of 3-Amino-4-Cyanopyrrole Derivatives, Ryndina, et al., Chemistry of Heterocyclic Compounds, vol. 36, No. 12, 2000, pp. 1409-1420.
Derivatives of 2-Pyridone, Wenner, et al., Journal of Organic Chemistry, 1946, vol. 11, pp. 751-759.
Alkylations at the Methyl or alpha-Methylene Group of 6- or 4-Alkyl-3-cyano-2(1)-pyridones through Dianions, Boatman, et al., Journal of Organic Chemistry, 1965, vol. 30 Pt 11, pp. 3593-3597.
Chemical Abstract, Yalyaheva et al., Heterocycles, p. 687, vol. 107, 1987.
Chemical Abstracts, Ershov et al., 1985, vol. 103, Pt 21, pp. 678.
Therapeutic potential of non-competitive, subtype-selective metabotropic glutamate receptor ligands, V. Mutel, Expert Opin. Ther. Patents (2002), 12 (12) pp. 1845-1852.
Regulation of Neurotransmitter Release by Metabotropic Glutamate Receptors, Cartmell et al., J. Neurochem., p. 889-907, vol. 75, No. 3, 2000.
The selective group mGlu2/3 receptor agonist LY379268 suppresses REM sleep and fast EEG in the rat, Feinberg et al., Pharmacology, Biochemistry and Behavior 73 (2002) 467-474.
A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, Galici et al., J of Pharmacology and Experimental Therapeutics, p. 1181-1187, vol. 315, No. 3.
Activation of Group II Metabotropic Glutamate Receptors Inhibits Synaptic Excitation of the Subsantia Nigra Pars Reticulata, Bradley et al., J. of Neuroscience, May 1, 2000, 20(9):3085-3094.
Anxiolytic effects of a novel group II metabotropic glutamate receptor agonist (LY354740) in the fear-potentiated startle paradigm in humans, Grillon, et al., Psychopharmacology (2003) 168:446-454.
Excited by Glutamate, Science, p. 1866-1868, vol. 300, Jun. 20, 2003.
Benzazoles as allosteric potentiators of metabotropic glutamate receptor 2 (mGluR2): Efficacy in an animal model for schizophrenia, Govek et al., Bioorg. Med. Chem Lett. 15 (2005) 4068-4072.
Metabotropic glutamate 2 receptor potentiators: receptor modulation, frequency-dependent synaptic activity, and efficacy in preclinical anxiety and psychosis model(s), Johnson et al., Psychopharmacology (2005) 179: 271-283.
Discovery of Allosteric Potentiators for the Metabotropic Glutamate 2 Receptor: Synthesis and Subtype Selectivity of N-(4-(2-Methoxyphenoxy)phenyl)-N-(2,2,2-trifluoroethylsulfonyl)pyrid-3-ylmethyl-amine, Johnson et al., J. Med. Chem. 2003, 46, 3189-3192.
Effects of metabotropic glutamate2/3 receptor agonist (LY544344/LY354740) on panic anxiety induced by cholecystokinin tetrapeptide in health humans: preliminary results, Kellner et al., Psychopharmacology (2005) 179: 310-315.
Allosteric modulators of metabotropic glutamate receptors: lessons learnt from mGlu1, mGlu2 and mGlu5 potentiators and antagonists, Johnson et al., Biochemical Society Transactions (2004) vol. 32, part 5, 881-887.
Selective, Non-Amino Acid Allosteric mGlu2 Receptor Potentiators Inhibit Dural Plasma Protein Extravasation; A Potential Role In The Treatment Of Migraine, Johnson et al., Abstracts/Neuropharmacology 43 (2002) 291.
Khimia Geterotsiklicheskikh Soedinenii, 1985, vol. 5, PT 1985, 646-649.
Glutamate receptors: brain function and signal transduction, Nakanishi, et al., Brain Research Reviews 26 (1998) 230-235.
Activation of Metabotropic Glutamate Receptor-1 Accelerates NMDA Receptor Trafficking, Lan et al., Abstracts/ Neuropharmacology 43 (2002) 294.
Glutamate metabotropic receptors as targets for drug therapy in epilepsy, Moldrich et al., European Journal of Pharmacology 476 (2003) 3-16.
Metabotropic glutamate receptor 2 modulates excitatory synaptic transmission in the rat globus pallidus, Poisik, et al., Neuropharmacology 49 (2005) 57-69.

Pharmacological Characterization and Identification of Amino Acids Involved in the Positive Modulation of Metabotropic Glutamate Receptor Subtype 2, Schaffhauser et al., Mol. Pharmacol 64:798-810, 2003, vol. 64, No. 4.
The metabotropic glutamate receptor 5 antagonist MPEP and the mGluR2 agonist LY379268 modify disease progression in a transgenic mouse model of Huntington's disease, Schiefer, et al., Brain Research 1019 (2004) 246-254.
Phenyl-tetrazolyl Acetophenones: Discovery of Positive Allosteric Potentiators for the Metabotropic Glutamate 2 Receptor, Pinkerton, et al., J. Med. Chem 2004, 47, 4595-4599.
Pharmacological agents acting at subtypes of metabotropic glutamate receptors, Schoepp, Neuropharmacology 38 (1999) 1431-1476.
Group II mGluR receptor agonists are effective in persistent and neuropathic pain models in rats, Simmons, et al., Pharmacology, Biochemistry and Behavior 73 (2002) 419-427.
Preclinical Pharmacology of mGlu2/3 Receptor Agonists: Novel Agents for Schizophrenia?, Schoepp et al., CNS & Neurological Disorders, 2002, 1, 215-225.
Khimia Geterotsiklicheskikh Soedinenii, 1986, vol. 1986, PT 8, 1118-1123.
International Search Report for International Application No. PCT/EP2007/052442 dated Sep. 7, 2007.
Distribution of a metabotropic glutamate receptor, mGluR2, in the central nervous system of the rat and mouse: an immunohistochemical study with a monoclonal antibody, Ohishi, Neuroscience Research 30 (1998) 65-82.
Nell et al., "Preparation of 4-amino-3,5-dicyano-2-thiopyridines as cardiovascular agents", CA149:32326 (2008).
Acta Chimica Slovencia, 2005, vol. 52, No. 4, pp. 391-397.
Bohme et al., "Darstellng und Umsetzungen von 3-Arylamino-2-halogencrotononitilen", Chem. Ber., 1976, 109, 2908-2913.
Braish et al., "Construction of the (1x,5x,6x)-6-Amino-3-azabicyclo[3.1.0]hexane Ring System," Synlett, 1996, 1100-1102.
Brighty et al., "Synthesis of (1x,5x,6x)-6-Amino-3-azabicyclo[3.1.0]hexane, a Novel Achiral Diamine," Synlett, 1996, 1097-1099.
Clark et al., "Synthesis of Thieno[2,3-d]pyrimidines from 4,6-Dichloropyrimidine-5-carbaldehydes", Journal Heterocyclic Chem, 1993, vol. 30, 1065-1072.
Erlenmeyer et al., "Uber einige Derivate des 2-Aminothiazols", Helvetica Chim Acta, 1949, 35-38.
Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.
Ghammamy et al., "Cetyltrimethylammonium Bromochromate: A New and Efficient Oxidant for Organic Substrates", Synthetic Communications, 2007, 37, 599-605.
Hamaguchi et al., "Effects of Hetero Atom Substituents in the decomposition of Pyrazolines: Abnormal Behavior of Methoxy Group Compared with Arylthio of Arylseleno Group.", Heterocycles, 1986, vol. 24, 2111-2115.
Haper, "Agonist-Stimulated [35S]GTPyS Binding," Current Protocols in Pharmacology, 1998, Unit 2.6, 1-10.
Harriman et al. "Synthesis of 4-Substituted 4-Arylpiperidines", Tetrahedron Letters, 2000, 41, 8853-8856.
Helton et al. "Anxiolytic and Side-Effect Profile fo LY354740: A Potent, Highly Selective, Orally Active Agonist for Group II Metobotropic Glutamate Receptors", Journal of Phamacology and Experimental Therapeutics, 1998, 284, 2, 651-660.
Hughes, "Progress In The Mitsunobu Reaction. A Review," Organic Preparations and Procedures International, 1996, 127-164.
Hughes, "The Mitsunobu Reaction", Organinc Reactions, 1992, vol. 42, 335-656.
International Search Report dated Feb. 7, 2008 for application No. PCT/EP08/52767.
International Search Report dated Oct. 26, 2009 for international application No. PCT/EP2009/006326.
International Search Report dated Oct. 6, 2008 for application No. PCT/EP08/52766.
International Search Report dated Oct. 6, 2008 for application No. PCT/EP08/52768.

Kiselyov et al., "A one pot synthesis of polysubstituted inidazo[1,2-a]pyridines", Tetrahedron Letters, 2006, 47, 2941-2944.

Kitano et al., "Synthesis and antifouling activity of 3-isocyanotheonellin and its analogues", Jour Chem Soc Perkin Trans, 2002, 2251-2255, The Royal Society of Chemistry.

Klemm et al. "Chemistry of Thienopyridines. VIII. Substitution Products Derived from Thieno[2,3-b] pyridine 7-Oxide (1)", Journal of Heterocyclic Chemistry, 1970, 7(1), 81-89.

Larock, "Comprehensive Organic Transformations", VCH Publishers, 1989, 595-596.

Lee et al., "Benzylic Bromination of Alkylbenzenes with Sodium Bromate-Bromotrimethylsilane", Bull. Korean Chem. Soc, 1995, vol. 16, pp. 371-374.

McElvain et al. "Piperidine Derivatives. XXX. 1,4-Dialkyl-4-arylpiperidines", J. Am. Chem. Soc, 1958, 80, 3915-3923.

Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.

Mutel et al., "Characterization of (2S,2'R,3'R)-2-(2',3'-[3H]-Dicarboxycyclopropyl)glycine Binding in Rat Brain," J Neurochemistry, 71(6), 1998, 2558-2564.

Nakamura et al., "An Efficient Synthesis of Platelet-Activating Factor (PAF) J'IJI-Qalkyl-2-~-(3-Isoxazolyl)-SN_GLYCERO-3-Phosphocholine, a New PAF Agonist. Utilization of the 3-Isoxazolyloxy Group as a Protected Hydroxyl." Tetrahedron Letters, 1990, vol. 31, 699-702.

Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.

Pin et al., "New perspectives for the development of selective metabotropic glutamate receptor ligands," European J of Pharmacology, 1999, 375, 277-294.

Potts et al. "1,2,4-Triazoles. XII. Derivatives of the s-Triazolo[4,3-a]pyridine Ring System", Journal of Organic Chemistry, 1966, 251-260.

Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.

Rani et al. "Thiazoline Analogues of Epiderstatin, New Inhibitiors of Cell Cycle of TsFT-210 Cells", Journal of Antibiotics, 1995, 48(10), 1179-1181.

Renslo et al., "Synthesis of Aza-, Oxa-, and Thiabicyclo[3.1.0]hexane Heterocycles from a Common Synthetic Intermediate," Organic Letters, 2005, vol. 7, No. 13, 2627-2630, American Chemical Society, USA.

Roma et al., "1,8-Naphthyridines VII. New substituted 5-amino[l,2,4]triazolo[4,3-a] [1,8]naphthyridine-6-carboxamides and their isosteric analogues, exhibiting notable anti-inflammatory and/or analgesic activities, but no acute gastrolesivity",Eouropean Journal of Medical Chemistry. 2008, 43, 1665-1680.

Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998/.

Shiba et al. "Synthesis and binding affinities of methylvesamicol analogs for the acetylcholine transporter and sigma receptor", Bioorganic and Medicinal Chemistry, 2006, 14, 2620-2626.

SIPO Office Action Jun. 30, 2010.

Stewart et al. "Discovery of Inhibitors of Cell Adhesion Molecule Expression in Human Endothelial Cell. 1. Selective Inhibition of ICAM-1 and E-Selectin Expression", J Med Chem, 2001, 44, 998-1002.

Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505

Vilsmaier et al., "Diastereoselective Syntheses of N-Protected Derivatives of la,5a,6fi-6-Amino-3-azabicyclo [3.101] hexane; A Route to Trovafloxacin 6fl-Diastereomer," Synthesis, 1998, 739-744.

Wang et al. "A simple and effcient automatable one step synthesis of triazolopyridines form carboxylic acids", Tetrahedron Letters, 2007, 48, 2237-2240.

Watanbe et al. "Pd/P(t-Bu)3-Catalyzed Synthesis of Aromatic Amines", Journal of TOSOH Research, 1999, vol. 43, 38-50.

Malames et al. "N-Substituted Spirosuccinimide, Spiropyridazine, Spiroazetidine, and Acetic Acid Aidose Reductase Inhibitiors Derived From Isoquinoline-1,3-dinoes. 2", J Med Chem., 1994, 37(13), 2059-2070.

Cook et al. "Diethylaminoalkyl Ester Hydrochlorides of N-Alkyl-4-carbostyrilcarboxylic Acids", J Am. Chem. Soc., 1952, 74, 543-554.

Nakano et al. "1-Alkyl-3-phenylpyridinium 1-Alkyl-2(1H)-pyridone 3-Phenyl 5-Phenyl", Annual Report of Tohoku College of Pharmacy, 1998, 45, 145-148.

Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508.

Vippagunta et al., "Crystalline Solids", Adv. Drug Deliv. Rev., 2001, 48, 3-26.

Chrostopoulos., "Allosteric Binding Sites on Cell-Sturcture Receptors: Novel Targets for Drug Discovery", Nature Rev., Mar. 2002, 1, 198-210.

Wikipedia, "Allosteric Regulation", 2010, 1-4.

Azume et al., "Synthesis and reactions of 4-choloro-1, 2-dihydro-6-methyl-2-oxo-3-pyridinecarbonitrile", CA139:197340 (2003).

* cited by examiner

PYRIDINONE DERIVATIVES AND THEIR USE AS POSITIVE ALLOSTERIC MODULATORS OF MGLUR2-RECEPTORS

IN THE CROSS-REFERENCE TO RELATED APPLICATIONS

This application claims priority to Great Britain Application No. 0420722.1, filed Sep. 17, 2004, which is hereby incorporated herein by reference in its entirety for all purposes.

SUMMARY OF THE INVENTION

The present invention relates to novel compounds, in particular novel pyridinone-derivatives that are positive allosteric modulators of metabotropic receptors-subtype 2 ("mGluR2") which are useful for the treatment or prevention of neurological and psychiatric disorders associated with glutamate dysfunction and diseases in which the mGluR2 subtype of metabotropic receptors is involved. The invention is also directed to the pharmaceutical compositions, the processes to prepare such compounds and compositions and the use of such compounds for the prevention and treatment of such diseases in which mGluR2 is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), the NMDA, AMPA and kainate receptors which are responsible for fast excitatory transmission (Nakanishi et al., (1998) Brain Res Brain Res Rev., 26:230-235).

In addition, glutamate activates metabotropic glutamate receptors (mGluRs) which have a more modulatory role that contributes to the fine-tuning of synaptic efficacy.

The mGluRs are seven-transmembrane G protein-coupled receptors (GPCRs) belonging to family 3 of GPCRs along with the calcium-sensing, GABAb, and pheromone receptors.

Glutamate activates the mGluRs through binding to the large extracellular amino-terminal domain of the receptor, herein called the orthosteric binding site. This binding induces a conformational change in the receptor which results in the activation of the G-protein and intracellular signalling pathways.

The mGluR family is composed of eight members. They are classified into three groups (group I comprising mGluR1 and mGluR5; group II comprising mGluR2 and mGluR3; group III comprising mGluR4, mGluR6, mGluR7, and mGluR8) according to sequence homology, pharmacological profile, and nature of intracellular signalling cascades activated (Schoepp et al. (1999) Neuropharmacology, 38:1431-76).

Among mGluR members, the mGluR2 subtype is negatively coupled to adenylate cyclase via activation of Gαi-protein, and its activation leads to inhibition of glutamate release in the synapse (Cartmell & Schoepp (2000) J Neurochem 75:889-907). In the CNS, mGluR2 receptors are abundant mainly throughout cortex, thalamic regions, accessory olfactory bulb, hippocampus, amygdala, caudate-putamen and nucleus accumbens (Ohishi et al. (1998) Neurosci Res 30:65-82).

Activating mGluR2 was shown in clinical trials to be efficacious to treat anxiety disorders (Levine et al. (2002) Neuropharmacology 43: 294; Holden (2003) Science 300:1866-68; Grillon et al. (2003) Psychopharmacology 168:446-54; Kellner et al. (2005) Psychopharmacology 179: 310-15). In addition, activating mGluR2 in various animal models was shown to be efficacious, thus representing a potential novel therapeutic approach for the treatment of schizophrenia (reviewed in Schoepp & Marek (2002) Curr Drug Targets. 1:215-25), epilepsy (reviewed in Moldrich et al. (2003) Eur J Pharmacol. 476:3-16), migraine (Johnson et al. (2002) Neuropharmacology 43:291), addiction/drug dependence (Helton et al. (1997) J Pharmacol Exp Ther 284: 651-660), Parkinson's disease (Bradley et al. (2000) J. Neurosci. 20(9): 3085-94), pain (Simmons et al. (2002) Pharmacol Biochem Behav 73:419-27), sleep disorders (Feinberg et al. (2002) Pharmacol Biochem Behav 73:467-74) and Huntington's disease (Schiefer et al. (2004) Brain Res 1019:246-54).

To date, most of the available pharmacological tools targeting mGluRs are orthosteric ligands which activate several members of the family as they are structural analogs of glutamate (Schoepp et al. (1999) Neuropharmacology, 38:1431-76).

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for several mGluRs (reviewed in Mutel (2002) Expert Opin. Ther. Patents 12:1-8). In particular molecules have been described as mGluR2 positive allosteric modulators (Johnson M P et al. (2003) J Med Chem. 46:3189-92; Pinkerton et al. (2004) J Med Chem. 47:4595-9).

WO2004092135 (NPS & Astra Zeneca), WO04018386 (Merck) and WO0156990 (Eli Lilly) describe respectively phenyl sulfonamid, acetophenone and pyridylmethyl sulfonamide derivatives as mGluR2 positive allosteric modulators. However, none of the specifically disclosed compounds are structurally related to the compounds of the invention.

It was demonstrated that such molecules do not activate the receptor by themselves (Johnson M P et al. (2003) J Med Chem. 46:3189-92; Schaffhauser et al. (2003) Mol Pharmacol. 64:798-810). Rather, they enable the receptor to produce a maximal response to a concentration of glutamate which by itself induces a minimal response. Mutational analysis have demonstrated unequivocally that the binding of mGluR2 positive allosteric modulators does not occur at the orthosteric site, but instead at an allosteric site situated within the seven transmembrane region of the receptor (Schaffhauser et al. (2003) Mol Pharmacol. 64:798-810).

Animal data are suggesting that positive allosteric modulators of mGluR2 have the same effects in anxiety and psychosis models as those obtained with orthosteric agonists. Allosteric modulators of mGluR2 were shown to be active in fear-potentiated startle (Johnson et al. (2003) J Med Chem. 46:3189-92; Johnson et al. (2005) Psychopharmacology 179: 271-83), and in stress-induced hyperthermia (Johnson et al. (2005) Psychopharmacology 179:271-83) models of anxiety. Furthermore, such compounds were shown to be active in reversal of ketamine- (Govek et al. (2005) Bioorg Med Chem Lett 15(18):4068-72) or amphetamine- (Galici et al. (2005) J Pharm Exp Ther Fast Forward, 2005 Aug. 25, Epub ahead of print) induced hyperlocomotion, and in reversal of amphetamine-induced disruption of prepulse inhibition of the acoustic startle effect (Galici et al. J Pharm Exp Ther Fast Forward, 2005 Aug. 25, Epub ahead of print) models of schizophrenia.

Positive allosteric modulators enable potentiation of the glutamate response, but they have also been shown to potentiate the response to orthosteric mGluR2 agonists such as LY379268 (Johnson et al. (2004) Biochem Soc Trans 32:881-87) or DCG-IV (Poisik et al. (2005) Neuropharmacology 49:57-69). These data provide evidence for yet another novel therapeutic approach to treat above mentioned neurological diseases involving mGluR2, which would use a combination of a positive allosteric modulator of mGluR2 together with an orthosteric agonist of mGluR2.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
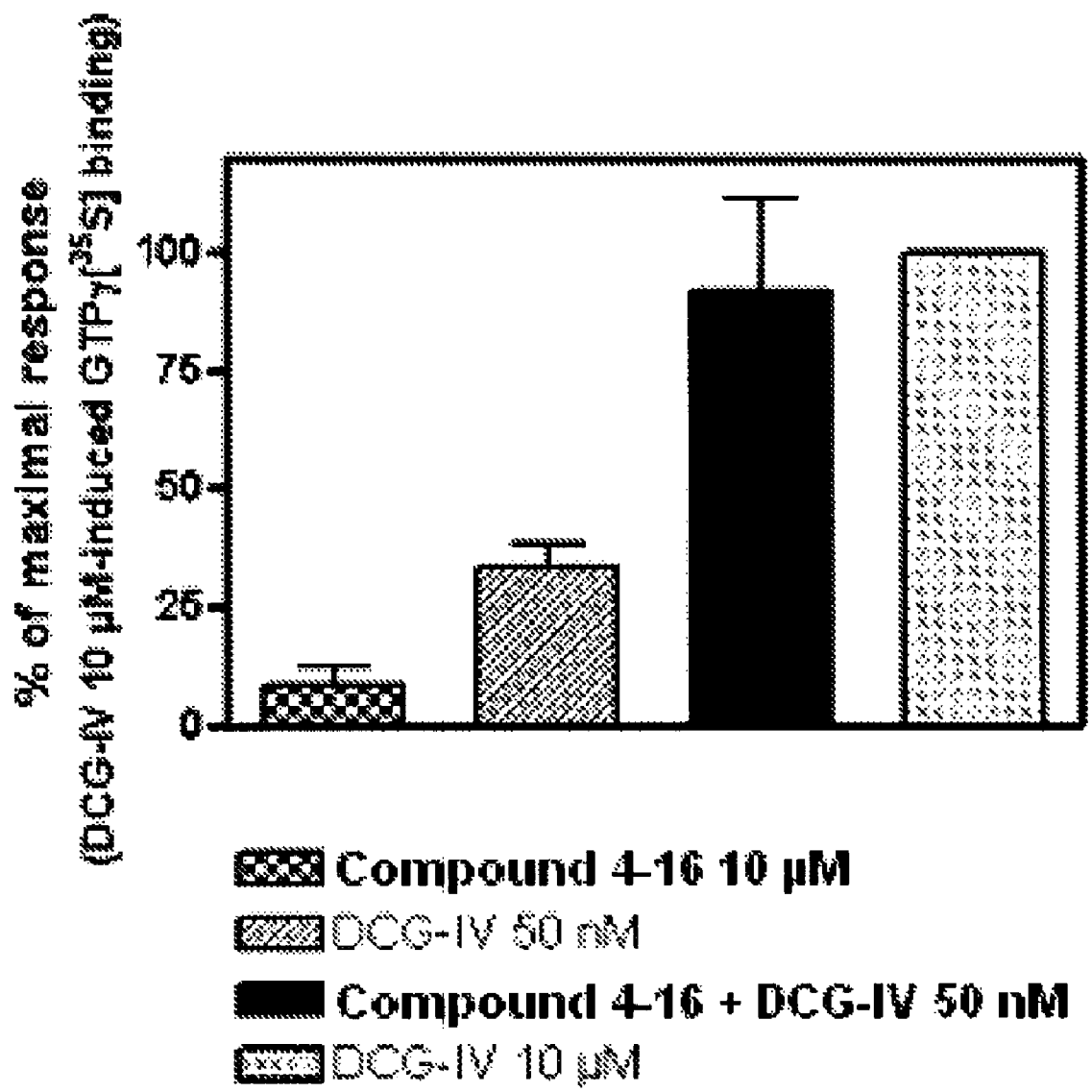
FIG. 1 shows the ability of 10 µM of compound 4-16 to increase the [GTPγ$^{35}$S] binding induced by 50 nM of DCG-IV.

The invention relates to compounds having metabotropic glutamate receptor 2 modulator activity. In its most general compound aspect, the present invention provides a compound according to Formula (I),

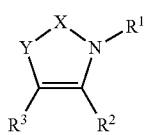

(I)

a pharmaceutically acceptable acid or base addition salt thereof, a stereochemically isomeric form thereof and an N-oxide form thereof, wherein:

X is selected from C(=O), S(O), S(O)$_2$, C(=NR$^6$) and C(=S);

Y is selected from S, —C(R$^4$)=C(R$^5$)—, —C(R$^5$)=N—, —N=C(R$^5$)— and —N(R$^5$)—;

R$^1$ is not hydrogen and is an optionally substituted radical selected from the group of —(C$_1$-C$_6$)alkyl, —(C$_2$-C$_6$)alkynyl, —(C$_2$-C$_6$)alkenyl, —(C$_3$-C$_7$)cycloalkyl, —(C$_3$-C$_8$)cycloalkenyl, —(C$_1$-C$_6$)alkylhalo, —(C$_1$-C$_6$)alkylcyano and a radical —V$_1$-T$_1$-M$_1$;

T$_1$, V$_1$ are each independently a covalent bond or an optionally substituted radical selected from the group of —(C$_1$-C$_6$)alkyl-, —(C$_2$-C$_6$)alkynyl-, —(C$_2$-C$_6$)alkenyl-, —(C$_3$-C$_7$)cycloalkyl-, —(C$_4$-C$_{10}$)alkylcycloalkyl-, —(C$_3$-C$_8$)cycloalkenyl-, —(C$_1$-C$_6$)alkylhalo-, —(C$_1$-C$_6$)alkylcyano-, —(C$_1$-C$_6$)alkyl-C(=O)—(C$_0$-C$_6$)alkyl-, —(C$_1$-C$_6$)alkyl-C(=O)—(C$_2$-C$_6$)-alkynyl-, —(C$_1$-C$_6$)alkyl-C(=O)—(C$_2$-C$_6$)alkenyl-, —(C$_1$-C$_6$)alkyl-C(=O)—(C$_3$-C$_7$)-cycloalkyl-, —(C$_1$-C$_6$)alkyl-C(=O)—(C$_4$-C$_{10}$)alkylcycloalkyl-, —(C$_1$-C$_6$)alkyl-C(=O)O—(C$_0$-C$_6$)alkyl-, —(C$_1$-C$_6$)alkyl-C(=O)O—(C$_2$-C$_6$)alkynyl-, —(C$_1$-C$_6$)alkyl-C(=O)O—(C$_2$-C$_6$)-alkenyl-, —(C$_1$-C$_6$)alkyl-C(=O)O—(C$_3$-C$_7$)cycloalkyl-, —(C$_1$-C$_6$)alkyl-C(=O)O—(C$_4$-C$_{10}$)-alkylcycloalkyl-, —(C$_1$-C$_6$)alkyl-C(=O)NR$^7$—(C$_0$-C$_6$)alkyl-, —(C$_1$-C$_6$)alkyl-C(=O)NR$^7$—(C$_2$-C$_6$)alkynyl-, —(C$_1$-C$_6$)alkyl-C(=O)NR$^7$—(C$_2$-C$_6$)alkenyl-, —(C$_1$-C$_6$)alkyl-C(=O)NR$^7$—(C$_3$-C$_7$)cycloalkyl-, —(C$_1$-C$_6$)alkyl-C(=O)NR$^7$—(C$_4$-C$_{10}$)alkylcycloalkyl-, —(C$_1$-C$_6$)alkyl-O—(C$_0$-C$_6$)alkyl-, —(C$_1$-C$_6$)alkyl-O—(C$_2$-C$_6$)alkynyl-, —(C$_1$-C$_6$)alkyl-O—(C$_2$-C$_6$)alkenyl-, —(C$_1$-C$_6$)alkyl-O—(C$_3$-C$_7$)cycloalkyl-, —(C$_1$-C$_6$)alkyl-O—(C$_4$-C$_{10}$)alkylcycloalkyl-, —(C$_1$-C$_6$)-alkyl-S—(C$_0$-C$_6$)alkyl-, —(C$_1$-C$_6$)alkyl-S—(C$_2$-C$_6$)alkynyl-, —(C$_1$-C$_6$)alkyl-S—(C$_2$-C$_6$)-alkenyl-, —(C$_1$-C$_6$)alkyl-S—(C$_3$-C$_7$)cycloalkyl-, —(C$_1$-C$_6$)alkyl-S—(C$_4$-C$_{10}$)alkylcycloalkyl-, —(C$_1$-C$_6$)alkyl-S(O)—(C$_0$-C$_6$)alkyl-, —(C$_1$-C$_6$)alkyl-S(O)—(C$_2$-C$_6$)alkynyl-, —(C$_1$-C$_6$)alkyl-S(O)—(C$_2$-C$_6$)alkenyl-, —(C$_1$-C$_6$)alkyl-S(O)—(C$_3$-C$_7$)cycloalkyl-, —(C$_1$-C$_6$)alkyl-S(O)—(C$_4$-C$_{10}$)alkylcycloalkyl-, —(C$_1$-C$_6$)alkyl-S(O)$_2$—(C$_0$-C$_6$)alkyl-, —(C$_1$-C$_6$)alkyl-S(O)$_2$—(C$_2$-C$_6$)-alkynyl-, —(C$_1$-C$_6$)alkyl-S(O)$_2$—(C$_2$-C$_6$)alkenyl-, —(C$_1$-C$_6$)alkyl-S(O)$_2$—(C$_3$-C$_7$)cycloalkyl-, —(C$_1$-C$_6$)alkyl-S(O)$_2$—(C$_4$-C$_{10}$)alkylcycloalkyl-, —(C$_1$-C$_6$)alkyl-S(O)$_2$NR$^7$—(C$_0$-C$_6$)alkyl-, —(C$_1$-C$_6$)alkyl-S(O)$_2$NR$^7$—(C$_2$-C$_6$)alkynyl-, —(C$_1$-C$_6$)alkyl-S(O)$_2$NR$^7$—(C$_2$-C$_6$)alkenyl-, —(C$_1$-C$_6$)alkyl-S(O)$_2$NR$^7$—(C$_3$-C$_7$)cycloalkyl-, —(C$_1$-C$_6$)alkyl-S(O)$_2$NR$^7$—(C$_4$-C$_{10}$)alkyl-cycloalkyl-, —(C$_1$-C$_6$)alkyl-NR$^7$—(C$_0$-C$_6$)alkyl-, —(C$_1$-C$_6$)alkyl-NR$^7$—(C$_2$-C$_6$)alkynyl-, —(C$_1$-C$_6$)alkyl-NR$^7$—(C$_2$-C$_6$)alkenyl-, —(C$_1$-C$_6$)alkyl-NR$^7$—(C$_3$-C$_7$)cycloalkyl-, —(C$_1$-C$_6$)alkyl-NR$^7$—(C$_4$-C$_{10}$)alkylcycloalkyl-, —(C$_1$-C$_6$)alkyl-NR$^7$C(=O)—(C$_0$-C$_6$)alkyl-, —(C$_1$-C$_6$)alkyl-NR$^7$C(=O)—(C$_2$-C$_6$)alkynyl-, —(C$_1$-C$_6$)alkyl-NR$^7$C(=O)—(C$_2$-C$_6$)alkenyl-, —(C$_1$-C$_6$)alkyl-NR$^7$C(=O)—(C$_3$-C$_7$)cycloalkyl-, —(C$_1$-C$_6$)alkyl-NR$^7$C(=O)—(C$_4$-C$_{10}$)alkylcycloalkyl-, —(C$_1$-C$_6$)alkyl-NR$^7$C(=O)NR$^8$—(C$_0$-C$_6$)alkyl-, —(C$_1$-C$_6$)alkyl-NR$^7$C(=O)NR$^8$—(C$_2$-C$_6$)-alkynyl-, —(C$_1$-C$_6$)alkyl-NR$^7$C(=O)NR$^8$—(C$_2$-C$_6$)alkenyl-, —(C$_1$-C$_6$)alkyl-NR$^7$C(=O)NR$^8$—(C$_3$-C$_7$)cycloalkyl-, —(C$_1$-C$_6$)alkyl-NR$^7$C(=O)NR$^8$—(C$_4$-C$_{10}$)alkylcycloalkyl-, —(C$_1$-C$_6$)-alkyl-NR$^7$S(O)$_2$—(C$_0$-C$_6$)alkyl-, —(C$_1$-C$_6$)alkyl-NR$^7$S(O)$_2$—(C$_2$-C$_6$)alkynyl-, —(C$_1$-C$_6$)alkyl-NR$^7$S(O)$_2$—(C$_2$-C$_6$)alkenyl-, —(C$_1$-C$_6$)alkyl-NR$^7$S(O)$_2$—(C$_3$-C$_7$)cycloalkyl-, —(C$_1$-C$_6$)alkyl-NR$^7$S(O)$_2$—(C$_4$-C$_{10}$)alkylcycloalkyl-, —(C$_1$-C$_6$)alkyl-NR$^7$C(=S)NR$^8$—(C$_0$-C$_6$)alkyl-, —(C$_1$-C$_6$)alkyl-NR$^7$C(=S)NR$^8$—(C$_2$-C$_6$)alkynyl-, —(C$_1$-C$_6$)alkyl-NR$^7$C(=S)NR$^8$—(C$_2$-C$_6$)alkenyl-, —(C$_1$-C$_6$)alkyl-NR$^7$C(=S)NR$^8$—(C$_3$-C$_7$)cycloalkyl-, —(C$_1$-C$_6$)alkyl-NR$^7$C(=S)NR$^8$—(C$_4$-C$_{10}$)alkylcycloalkyl-, —(C$_1$-C$_6$)alkyl-OC(=O)—(C$_0$-C$_6$)alkyl-, —(C$_1$-C$_6$)alkyl-OC(=O)—(C$_2$-C$_6$)alkynyl-, —(C$_1$-C$_6$)alkyl-OC(=O)—(C$_2$-C$_6$)alkenyl-, —(C$_1$-C$_6$)alkyl-OC(=O)—(C$_3$-C$_7$)-cycloalkyl-, —(C$_1$-C$_6$)alkyl-OC(=O)—(C$_4$-C$_{10}$)alkylcycloalkyl-, —(C$_1$-C$_6$)alkyl-OC(=O)NR$^7$—(C$_0$-C$_6$)alkyl-, —(C$_1$-C$_6$)alkyl-OC(=O)NR$^7$—(C$_2$-C$_6$)alkynyl-, —(C$_1$-C$_6$)alkyl-OC(=O)NR$^7$—(C$_2$-C$_6$)alkenyl-, —(C$_1$-C$_6$)alkyl-OC(=O)NR$^7$—(C$_3$-C$_7$)cycloalkyl-, —(C$_1$-C$_6$)-alkyl-OC(=O)NR$^7$—(C$_4$-C$_{10}$)alkylcycloalkyl-, —(C$_1$-C$_6$)alkyl-NR$^7$C(=O)O—(C$_0$-C$_6$)alkyl-, —(C$_1$-C$_6$)alkyl-NR$^7$C(=O)O—(C$_2$-C$_6$)alkynyl-, —(C$_1$-C$_6$)alkyl-NR$^7$C(=O)O—(C$_2$-C$_6$)-alkenyl-, —(C$_1$-C$_6$)alkyl-NR$^7$C(=O)O—(C$_3$-C$_7$)cycloalkyl-, —(C$_1$-C$_6$)alkyl-NR$^7$C(=O)O—(C$_4$-C$_{10}$)

alkylcycloalkyl-, —(C₁-C₆)alkyl-NR⁷C(=NR⁸)NR⁹—(C₀-C₆)alkyl-, —(C₁-C₆)alkyl-NR⁷C(=NR⁸)NR⁹—(C₂-C₆)alkynyl-, —(C₁-C₆)alkyl-NR⁷C(=NR⁸)NR⁹—(C₂-C₆)alkenyl-, —(C₁-C₆)alkyl-NR⁷C(=NR⁸)NR⁹—(C₃-C₇)cycloalkyl-, —(C₁-C₆)alkyl-NR⁷C(=NR⁸)NR⁹—(C₄-C₁₀)alkylcycloalkyl-, —(C₁-C₆)alkyl-NR⁷C(=NR⁸)—(C₀-C₆)alkyl-, —(C₁-C₆)alkyl-NR⁷C(=NR⁸)—(C₂-C₆)alkynyl-, —(C₁-C₆)alkyl-NR⁷C(=NR⁸)—(C₂-C₆)alkenyl-, —(C₁-C₆)-alkyl-NR⁷C(=NR⁸)—(C₃-C₇)cycloalkyl-, —(C₁-C₆)alkyl-NR⁷C(=NR⁸)—(C₄-C₁₀)-alkylcycloalkyl-, —(C₁-C₆)alkyl-C(=NR⁷)NR⁸—(C₀-C₆)alkyl-, —(C₁-C₆)alkyl-C(=NR⁷)NR⁸—(C₂-C₆)alkynyl-, —(C₁-C₆)alkyl-C(=NR⁷)NR⁸—(C₂-C₆)alkenyl-, —(C₁-C₆)-alkyl-C(=NR⁷)NR⁸—(C₃-C₇)cycloalkyl- and —(C₁-C₆)alkyl-C(=NR⁷)NR⁸—(C₄-C₁₀)-alkylcycloalkyl-;

$R^2$, $R^3$, $R^4$, $R^5$ and $R^6$ are each independently selected from the group of hydrogen, halogen, —CN, —OH, —NO₂, —CF₃, —NH₂, —SH, —C(=NR¹⁰)NR¹¹R¹², —C(=O)R¹⁰, —C(=NR¹⁰)R¹¹, —C(=O)OR¹⁰, —C(=O)NR¹⁰R¹¹, —SR¹⁰, —S(O)R¹¹, —S(O)₂R¹⁰, —NR¹⁰R¹¹, —NR¹⁰C(=O)R¹¹, —NR¹⁰C(=NR¹¹)R¹², —NR¹⁰C(=NR¹¹)NR¹²R¹³, —NR¹⁰C(=O)OR¹¹, —NR¹⁰C(=O)NR¹¹R¹², —NR¹⁰S(O)₂R¹¹, —S(O)₂NR¹⁰R¹¹, —C(=S)NR¹⁰R¹¹, —OC(=O)R¹⁰, —OC(=O)NR¹⁰R¹¹, —OR¹⁰, and an optionally substituted radical selected from the group of —(C₁-C₆)alkyl, —(C₁-C₆)alkylhalo, —(C₂-C₆)alkynyl, —(C₂-C₆)alkenyl, —(C₃-C₇)-cycloalkyl, —(C₃-C₈)cycloalkenyl, —(C₁-C₆)alkylcyano, —(C₁-C₆)alkylaryl, —(C₁-C₆)-alkylheteroaryl, aryl, heteroaryl and a radical —V₂-T₂-M₂;

$T_2$, $V_2$ are each independently a covalent bond or a radical selected from the group of —O—, —C(=O)—, —C(=O)O—, —C(=O)NR¹⁰—, —S—, —S(O)—, —S(O)₂—, —S(O)₂NR¹⁰—, —NR¹⁰—, —NR¹⁰C(=O)—, —NR¹⁰C(=O)NR¹¹—, —NR¹⁰S(O)₂—, —NR¹⁰C(=S)NR¹¹—, —OC(=O)—, —OC(=O)NR¹⁰, —NR¹⁰C(=O)O—, and an optionally substituted radical selected from the group of —(C₁-C₆)alkyl-, —(C₂-C₆)alkynyl-, —(C₂-C₆)alkenyl-, —(C₃-C₇)cycloalkyl-, —(C₃-C₈)cycloalkenyl-, —(C₁-C₆)alkylhalo-, —(C₁-C₆)alkylcyano-, —(C₀-C₆)alkyl-O—(C₁-C₆)-alkyl-, —(C₀-C₆)alkyl-O—(C₂-C₆)alkynyl-, —(C₀-C₆)alkyl-O—(C₂-C₆)alkenyl-, —(C₀-C₆)-alkyl-O—(C₃-C₇)cycloalkyl-, —(C₀-C₆)alkyl-O—(C₄-C₁₀)alkylcycloalkyl-, —(C₀-C₆)alkyl-C(=O)—(C₁-C₆)alkyl-, —(C₀-C₆)alkyl-C(=O)—(C₂-C₆)alkynyl-, —(C₀-C₆)alkyl-C(=O)—(C₂-C₆)alkenyl-, —(C₀-C₆)alkyl-C(=O)—(C₃-C₇)alkylcycloalkyl-, —(C₀-C₆)alkyl-C(=O)—(C₄-C₁₀)cycloalkyl-, —(C₀-C₆)alkyl-C(=O)O—(C₁-C₆)alkyl-, —(C₀-C₆)alkyl-C(=O)O—(C₂-C₆)-alkynyl-, —(C₀-C₆)alkyl-C(=O)O—(C₂-C₆)alkenyl-, —(C₀-C₆)alkyl-C(=O)O—(C₃-C₇)-cycloalkyl-, —(C₀-C₆)alkyl-C(=O)O—(C₄-C₁₀)alkylcycloalkyl-, —(C₀-C₆)alkyl-C(=O)NR¹⁰—(C₁-C₆)alkyl-, —(C₀-C₆)alkyl-C(=O)NR¹⁰—(C₂-C₆)alkynyl-, —(C₀-C₆)alkyl-C(=O)NR¹⁰—(C₂-C₆)alkenyl-, —(C₀-C₆)alkyl-C(=O)NR¹⁰—(C₃-C₇)cycloalkyl-, —(C₀-C₆)-alkyl-C(=O)NR¹⁰—(C₄-C₁₀)alkylcycloalkyl-, —(C₀-C₆)alkyl-S—(C₁-C₆)alkyl-, —(C₀-C₆)-alkyl-S—(C₂-C₆)alkynyl-, —(C₀-C₆)alkyl-S—(C₂-C₆)alkenyl-, —(C₀-C₆)alkyl-S—(C₃-C₇)-cycloalkyl-, —(C₀-C₆)alkyl-S—(C₄-C₁₀)alkylcycloalkyl-, —(C₀-C₆)alkyl-S(O)—(C₁-C₆)alkyl-, —(C₀-C₆)alkyl-O—(C₂-C₆)alkynyl-, —(C₀-C₆)alkyl-S(O)—(C₂-C₆)alkenyl-, —(C₀-C₆)alkyl-S(O)—(C₃-C₇)cycloalkyl-, —(C₀-C₆)alkyl-S(O)—(C₄-C₁₀)alkylcycloalkyl-, —(C₀-C₆)alkyl-S(O)₂—(C₁-C₆)alkyl-, —(C₀-C₆)alkyl-S(O)₂—(C₂-C₆)alkynyl-, —(C₀-C₆)alkyl-S(O)₂—(C₂-C₆)alkenyl-, —(C₀-C₆)alkyl-S(O)₂—(C₃-C₇)cycloalkyl-, —(C₀-C₆)alkyl-S(O)₂—(C₄-C₁₀)alkylcycloalkyl-, —(C₀-C₆)alkyl-S(O)₂NR¹⁰—(C₁-C₆)alkyl-, —(C₀-C₆)alkyl-S(O)₂NR¹⁰—(C₂-C₆)alkynyl-, —(C₀-C₆)alkyl-S(O)₂NR¹⁰—(C₂-C₆)alkenyl-, —(C₀-C₆)alkyl-S(O)₂NR¹⁰—(C₃-C₇)cycloalkyl-, —(C₀-C₆)alkyl-S(O)₂NR¹⁰—(C₄-C₁₀)alkylcycloalkyl-, —(C₀-C₆)alkyl-NR¹⁰—(C₁-C₆)alkyl-, —(C₀-C₆)alkyl-NR¹⁰—(C₂-C₆)alkynyl-, —(C₀-C₆)alkyl-NR¹⁰—(C₂-C₆)alkenyl-, —(C₀-C₆)alkyl-NR¹⁰—(C₃-C₇)cycloalkyl-, —(C₀-C₆)alkyl-NR¹⁰—(C₄-C₁₀)alkylcycloalkyl-, —(C₀-C₆)alkyl-NR¹⁰C(=O)—(C₁-C₆)alkyl-, —(C₀-C₆)alkyl-NR¹⁰C(=O)—(C₂-C₆)alkynyl-, —(C₀-C₆)alkyl-NR¹⁰C(=O)—(C₂-C₆)alkenyl-, —(C₀-C₆)alkyl-NR¹⁰C(=O)—(C₃-C₇)cycloalkyl-, —(C₀-C₆)alkyl-NR¹⁰C(=O)—(C₄-C₁₀)alkylcycloalkyl-, —(C₀-C₆)alkyl-NR¹⁰C(=O)NR¹¹—(C₁-C₆)alkyl-, —(C₀-C₆)alkyl-NR¹⁰C(=O)—NR¹¹—(C₂-C₆)alkynyl-, —(C₀-C₆)alkyl-NR¹⁰C(=O)NR¹¹—(C₂-C₆)alkenyl-, —(C₀-C₆)alkyl-NR¹⁰C(=O)NR¹¹—(C₃-C₇)cycloalkyl-, —(C₀-C₆)alkyl-NR¹⁰C(=O)NR¹¹—(C₄-C₁₀)-alkylcycloalkyl-, —(C₀-C₆)alkyl-NR¹⁰S(O)₂—(C₁-C₆)alkyl-, —(C₀-C₆)alkyl-NR¹⁰S(O)₂—(C₂-C₆)alkynyl-, —(C₀-C₆)alkyl-NR¹⁰S(O)₂—(C₂-C₆)alkenyl-, —(C₀-C₆)alkyl-NR¹⁰S(O)₂—(C₃-C₇)cycloalkyl-, —(C₀-C₆)alkyl-NR¹⁰S(O)₂—(C₄-C₁₀)alkylcycloalkyl-, —(C₀-C₆)alkyl-NR¹⁰C(=S)NR¹¹—(C₁-C₆)alkyl-, —(C₀-C₆)alkyl-NR¹⁰C(=S)NR¹¹—(C₂-C₆)alkynyl-, —(C₀-C₆)alkyl-NR¹⁰C(=S)NR¹¹—(C₂-C₆)alkenyl-, —(C₀-C₆)alkyl-NR¹⁰C(=S)NR¹¹—(C₃-C₇)-cycloalkyl-, —(C₀-C₆)alkyl-NR¹⁰C(=S)NR¹¹—(C₄-C₁₀)alkylcycloalkyl-, —(C₀-C₆)alkyl-OC(=O)—(C₁-C₆)alkyl-, —(C₀-C₆)alkyl-OC(=O)—(C₂-C₆)alkynyl-, —(C₀-C₆)alkyl-OC(=O)—(C₂-C₆)alkenyl-, —(C₀-C₆)alkyl-OC(=O)—(C₄-C₁₀)alkylcycloalkyl-, —(C₀-C₆)alkyl-OC(=O)—(C₃-C₇)cycloalkyl-, —(C₀-C₆)alkyl-OC(=O)NR¹⁰—(C₁-C₆)alkyl-, —(C₀-C₆)alkyl-OC(=O)NR¹⁰—(C₂-C₆)alkynyl-, —(C₀-C₆)alkyl-OC(=O)NR¹⁰—(C₂-C₆)alkenyl-, —(C₀-C₆)-alkyl-OC(=O)NR¹⁰—(C₄-C₁₀)alkylcycloalkyl-, —(C₀-C₆)alkyl-OC(=O)NR¹⁰—(C₃-C₇)-cycloalkyl-, —(C₀-C₆)alkyl-NR¹⁰C(=O)O—(C₁-C₆)alkyl-, —(C₀-C₆)alkyl-NR¹⁰C(=O)O—(C₂-C₆)alkynyl-, —(C₀-C₆)alkyl-NR¹⁰C(=O)O—(C₂-C₆)alkenyl-, —(C₀-C₆)alkyl-NR¹⁰C(=O)O—(C₃-C₇)cycloalkyl-, —(C₀-C₆)alkyl-NR¹⁰C(=O)O—(C₄-C₁₀)alkylcycloalkyl-, —(C₀-C₆)alkyl-NR¹⁰C(=NR¹¹)NR¹²—(C₁-C₆)alkyl-, —(C₀-C₆)alkyl-NR¹⁰C(=NR¹¹)NR¹²—(C₂-C₆)alkynyl-, —(C₀-C₆)alkyl-NR¹⁰C(=NR¹¹)NR¹²—(C₂-C₆)-alkenyl-, —(C₀-C₆)alkyl-NR¹⁰C(=NR¹¹)NR¹²—(C₃-C₇)cycloalkyl-, —(C₀-C₆)alkyl-NR¹⁰C—(=NR¹¹)NR¹²—(C₄-C₁₀)alkylcycloalkyl-, —(C₀-C₆)alkyl-NR¹⁰C(=NR¹¹)—(C₁-C₆)alkyl-, —(C₀-C₆)alkyl-NR¹⁰C(=NR¹¹)—(C₂-C₆)alkynyl-, —(C₀-C₆)alkyl-NR¹⁰C(=NR¹¹)—(C₂-C₆)-alkenyl-, —(C₀-C₆)alkyl-NR¹⁰C(=NR¹¹)—(C₃-C₇)cycloalkyl-, —(C₀-C₆)alkyl-NR¹⁰C(=NR¹¹)—(C₄-C₁₀)alkylcycloalkyl-, —(C₀-C₆)alkyl-C(=NR¹⁰)NR¹¹—(C₁-C₆)alkyl-, —(C₀-C₆)alkyl-C(=NR¹⁰)NR¹¹—(C₂-C₆)alkynyl-, —(C₀-C₆)alkyl-C(=NR¹⁰)NR¹¹—(C₂-C₆)-alkenyl-, —(C₀-C₆)alkyl-C(=NR¹⁰)NR¹¹—(C₃-C₇)cycloalkyl- and —(C₀-C₆)alkyl-C(=NR¹⁰)NR¹¹—(C₄-C₁₀)alkylcycloalkyl-;

($R^2$ and $R^3$) or ($R^4$ and $R^5$) taken together may form an optionally substituted 3 to 10 membered ring selected from the group of aryl, heteroaryl, heterocyclic and cycloalkyl;

$M_1$ and $M_2$ are each independently selected from the group of hydrogen, —CN, —OH, —NO₂, —CF₃, —NH₂, —SH, —C(=NR¹⁴)NR¹⁵R¹⁶, —C(=O)R¹⁴, —C(=NR¹⁴)R¹⁵, —C(=O)OR¹⁴, —C(=O)NR¹⁴R¹⁵, —SR¹⁴, —S(O)R¹⁴, —S(O)₂R¹⁴, —NR¹⁴R¹⁵, —NR¹⁴C(=O)R¹⁵, —NR¹⁴C(=NR¹⁵)R¹⁶, NR⁴C(=NR¹⁵)NR¹⁶R¹⁷, —NR¹⁴C(=O)OR¹⁵, —NR¹⁴C(=O)N15R¹⁶, —NR¹⁴S(O)₂R¹⁵, —C(=S)NR¹⁴R¹⁵, —OC(=O)R¹⁴, —OC(=O)NR¹⁴R¹⁵, —OR¹⁴, —$S(O)_2NR^{14}R^{15}$, and an optionally substituted radical selected from the group of —$(C_1-C_6)$alkyl, —$(C_2-C_6)$alkynyl, —$(C_2-C_6)$alkenyl, —$(C_3-C_8)$cycloalkyl, —$(C_3-C_8)$cycloalkenyl and an optionally substituted 3 to 10 membered ring selected from the group of aryl, heteroaryl, heterocyclic and cycloalkyl;

$R^7$, $R^8$, $R^9$, $R^{10}$, $R^{11}$, $R^{12}$, $R^{13}$, $R^{14}$, $R^{15}$, $R^{16}$, $R^{17}$, are each independently hydrogen or an optionally substituted radical selected from the group of —$(C_1-C_6)$alkylhalo, —$(C_1-C_6)$-alkyl, —$(C_1-C_6)$alkylcyano, —$(C_2-C_6)$alkynyl, —$(C_2-C_6)$alkenyl, —$(C_3-C_7)$cycloalkyl, —$(C_4-C_{10})$alkylcycloalkyl, heteroaryl, —$(C_1-C_6)$alkylheteroaryl, aryl, —$(C_1-C_6)$alkylaryl, —$(C_2-C_6)$alkynyl-$(C_3-C_7)$cycloalkyl, —$(C_2-C_6)$alkynyl-heteroaryl, —$(C_2-C_6)$alkynyl-aryl, —$(C_2-C_6)$alkenyl-$(C_3-C_7)$cycloalkyl, —$(C_2-C_6)$alkenyl-heteroaryl and —$(C_2-C_6)$alkenyl-aryl;

$R^7$, $R^8$ and $R^9$ may be taken together to form an optionally substituted 3 to 10 membered non-aromatic heterocyclic ring or an optionally substituted 5 to 10 membered aromatic heterocyclic ring;

$R^{10}$, $R^{11}$, $R^{12}$ and $R^{13}$ may be taken together to form an optionally substituted 3 to 10 membered non-aromatic heterocyclic ring or an optionally substituted 5 to 10 membered aromatic heterocyclic ring; and $R^{14}$, $R^{15}$, $R^{16}$ and $R^{17}$ may be taken together to form an optionally substituted 3 to 10 membered non-aromatic heterocyclic ring or an optionally substituted 5 to 10 membered aromatic heterocyclic ring.

In a first preferred aspect of Formula (I), the invention concerns a compound according to Formula (II)

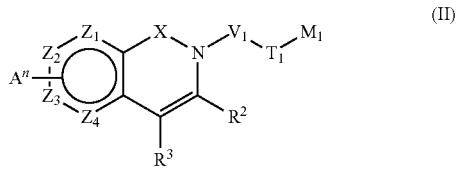

(II)

a pharmaceutically acceptable acid or base addition salt thereof, a stereochemically isomeric form thereof and an N-oxide form thereof, wherein:

X is selected from $C(=O)$ and $S(O)_2$;

$Z_1$, $Z_2$, $Z_3$ and $Z_4$ are each independently, selected from the group of a covalent bond, C, S, N and O, representing a 5 or 6 membered heteroaryl or aryl ring which may further be substituted by 1 to 4 radicals $A^n$;

$A^n$ radicals are each independently selected from the group of hydrogen, halogen, —CN, —OH, —$NO_2$, —$CF_3$, —SH, —$NH_2$, and an optionally substituted radical selected from the group of —$(C_1-C_6)$alkyl, —$(C_1-C_6)$alkylhalo, —$(C_2-C_6)$alkynyl, —$(C_2-C_6)$alkenyl, —$(C_3-C_7)$-cycloalkyl, —$(C_1-C_6)$alkylcyano, —O—$(C_1-C_6)$alkyl, —O—$(C_1-C_6)$alkylhalo, —O—$(C_1-C_6)$-alkylcyano, —O—$(C_3-C_6)$alkynyl, —O—$(C_3-C_7)$cycloalkyl, —O—$(C_2-C_6)$alkenyl, —O—$(C_2-C_6)$-alkyl-$OR^{18}$, —O—$(C_1-C_6)$alkyl-heteroaryl, —O—$(C_0-C_6)$alkylaryl, —$(C_0-C_6)$alkyl-$OR^{18}$, —$(C_3-C_7)$cycloalkyl-$(C_1-C_6)$alkyl, —O—$(C_3-C_7)$cycloalkyl-$(C_1-C_6)$alkyl, —O-heteroaryl, heteroaryl, —$(C_1-C_6)$alkyl-heteroaryl, aryl, —O-aryl, —$(C_1-C_6)$alkylaryl, —$(C_1-C_6)$alkylhalo-$OR^{18}$, —$(C_3-C_6)$alkynyl-$OR^{18}$, —$(C_3-C_6)$alkenyl-$OR^{18}$, —$(C_0-C_6)$alkyl-S—$R^{18}$, —O—$(C_2-C_6)$-alkyl-S—$R^{18}$, —$(C_1-C_6)$alkyl-S(=O)—$R^{18}$, —O—$(C_1-C_6)$alkyl-S(=O)—$R^{18}$, —$(C_0-C_6)$alkyl-S(=O)_2—$R^{18}$, —O—$(C_1-C_6)$alkyl-S(=O)_2—$R^{18}$, —$(C_0-C_6)$alkyl-$NR^{18}R^{19}$, —O—$(C_2-C_6)$alkyl-$NR^{18}R^{19}$, —$(C_0-C_6)$alkyl-S(=O)_2$NR^{18}R^{19}$, —$(C_0-C_6)$alkyl-$NR^{18}$—S(=O)_2$R^{19}$, —O—$(C_1-C_6)$-alkyl-S(=O)_2$NR^{18}R^{19}$, —O—$(C_1-C_6)$alkyl-$NR^{18}$—S(=O)_2$R^{19}$, —$(C_0-C_6)$alkyl-C(=O)—$NR^{18}R^{19}$, —$(C_0-C_6)$alkyl-$NR^{18}$C(=O)—$R^{19}$, —O—$(C_1-C_6)$alkyl-C(=O)—$NR^{18}R^{19}$, —O—$(C_1-C_6)$alkyl-$NR^{18}$C(=O)—$R^{19}$, —$(C_0-C_6)$alkyl-OC(=O)—$R^{18}$, —$(C_0-C_6)$alkyl-C(=O)—$OR^{18}$, —O—$(C_1-C_6)$-alkyl-OC(=O)—$R^{18}$, —O—$(C_1-C_6)$alkyl-C(=O)—$OR^{18}$, —$(C_0-C_6)$alkyl-C(=O)—$R^{18}$, —O—$(C_1-C_6)$alkyl-C(=O)—$R^{18}$, —$(C_0-C_6)$alkyl-$NR^{18}$—C(=O)—$OR^{19}$, —$(C_0-C_6)$alkyl-O—C(=O)—$NR^{18}R^{19}$, —$(C_0-C_6)$alkyl-$NR^{18}$—C(=$NR^{19}$)—$NR^{20}R^{21}$, —$(C_0-C_6)$alkyl-$NR^{18}$—C(=O)—$NR^{19}R^{20}$, —$(C_0-C_6)$alkyl-$NR^{18}$—C(=S)—$NR^{19}R^{20}$ and a —$V_2$-$T_2$-$M_2$ radical;

n is an integer ranging from 1 to 4;

$R^{18}$, $R^{19}$, $R^{20}$ and $R^{21}$ are each independently hydrogen or an optionally substituted radical selected from the group of —$(C_1-C_6)$alkylhalo, —$(C_1-C_6)$alkyl, —$(C_1-C_6)$alkylcyano, —$(C_2-C_6)$alkynyl, —$(C_2-C_6)$alkenyl, —$(C_3-C_7)$cycloalkyl, —$(C_4-C_{10})$alkylcycloalkyl, heteroaryl, —$(C_1-C_6)$alkylheteroaryl, aryl, —$(C_1-C_6)$alkylaryl, —$(C_2-C_6)$alkynyl-$(C_3-C_7)$-cycloalkyl, —$(C_2-C_6)$alkynyl-heteroaryl, —$(C_2-C_6)$alkynyl-aryl, —$(C_2-C_6)$alkenyl-$(C_3-C_7)$-cycloalkyl, —$(C_2-C_6)$alkenyl-heteroaryl and —$(C_2-C_6)$alkenyl-aryl; and $R^{18}$, $R^9$, $R^{20}$ and $R^{21}$ may be taken together to form an optionally substituted 3 to 10 membered non-aromatic heterocyclic ring or an optionally substituted 5 to 10 membered aromatic heterocyclic ring.

Preferred structures according to Formula (II) are indicated in Figure A below.

Figure A

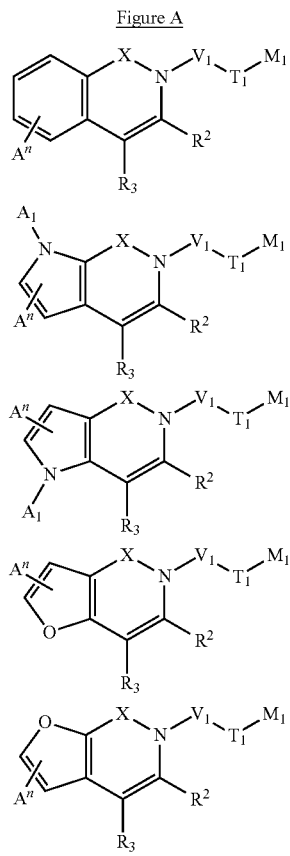

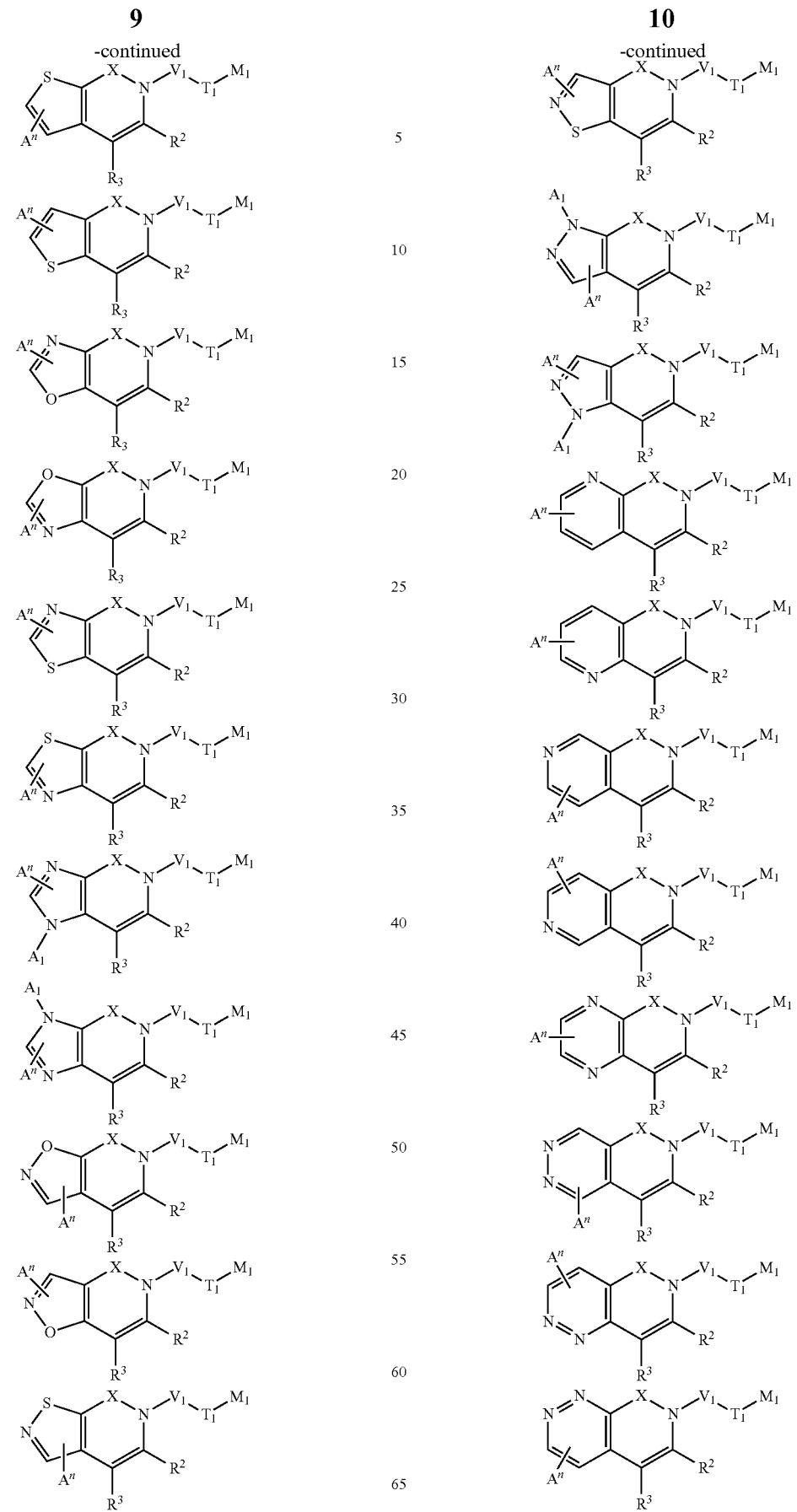

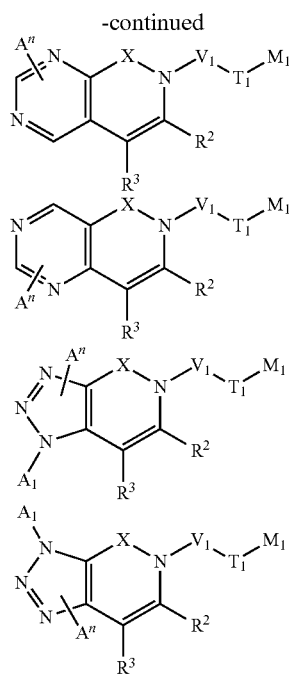

In a more preferred aspect of Formula (II), the invention provides a compound according to Formula (II-a),

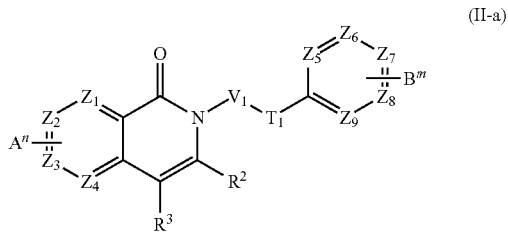

(II-a)

a pharmaceutically acceptable acid or base addition salt thereof, a stereochemically isomeric form thereof and an N-oxide form thereof, wherein:

$Z_5$, $Z_6$, $Z_7$, $Z_8$ and $Z_9$ are each independently selected from the group of a covalent bond, C, S, N and O, representing a 5 or 6 membered heteroaryl or aryl ring which may optionally be substituted by 1 to 5 radicals $B^m$;

$B^m$ radicals are each independently selected from the group of hydrogen, halogen, —CN, —OH, —NO$_2$, —CF$_3$, —SH, —NH$_2$, and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)-cycloalkyl, —(C$_1$-C$_6$)alkylcyano, —O—(C$_1$-C$_6$)alkyl, —O—(C$_1$-C$_6$)alkylhalo, —O—(C$_1$-C$_6$)-alkylcyano, —O—(C$_3$-C$_6$)alkynyl, —O—(C$_3$-C$_7$)cycloalkyl, —O—(C$_2$-C$_6$)alkenyl, —O—(C$_2$-C$_6$)-alkyl-OR$^{22}$, —O—(C$_1$-C$_6$)alkyl-heteroaryl, —O—(C$_0$-C$_6$)alkylaryl, —(C$_0$-C$_6$)alkyl-OR$^{22}$, —(C$_3$-C$_7$)cycloalkyl-(C$_1$-C$_6$)alkyl, —O—(C$_3$-C$_7$)cycloalkyl-(C$_1$-C$_6$)alkyl, —O-heteroaryl, heteroaryl, —(C$_1$-C$_6$)alkyl-heteroaryl, aryl, —O-aryl, —(C$_1$-C$_6$)alkylaryl, —(C$_1$-C$_6$)alkylhalo-OR$^{22}$, —(C$_3$-C$_6$)alkynyl-OR$^{22}$, —(C$_3$-C$_6$)alkenyl-OR$^{22}$, —(C$_0$-C$_6$)alkyl-S—R$^{22}$, —O—(C$_2$-C$_6$)-alkyl-S—R$^{22}$, —(C$_1$-C$_6$)alkyl-S(=O)—R$^{22}$, —O—(C$_1$-C$_6$)alkyl-S(=O)—R$^{22}$, —(C$_0$-C$_6$)alkyl-S(=O)$_2$—R$^{22}$, —O—(C$_1$-C$_6$)alkyl-S(=O)$_2$—R$^{22}$, —(C$_0$-C$_6$)alkyl-NR$^{22}$R$^{23}$, —O—(C$_2$-C$_6$)alkyl-NR$^{22}$R$^{23}$, —(C$_0$-C$_6$)alkyl-S(=O)$_2$NR$^{22}$R$^{23}$, —(C$_0$-C$_6$)alkyl-NR$^{22}$—S(=O)$_2$R$^{23}$, —O—(C$_1$-C$_6$)-alkyl-S(=O)$_2$NR$^{22}$R$^{23}$, —O—(C$_1$-C$_6$)alkyl-NR$^{22}$—S(=O)$_2$R$^{23}$, —(C$_0$-C$_6$)alkyl-C(=O)—NR$^{22}$R$^{23}$, —(C$_0$-C$_6$)alkyl-NR$^{22}$C(=O)—R$^{23}$, —O—(C$_1$-C$_6$)alkyl-C(=O)—NR$^{22}$R$^{23}$, —O—(C$_1$-C$_6$)alkyl-NR$^{22}$C(=O)—R$^{23}$, —(C$_0$-C$_6$)alkyl-OC(=O)—R$^{22}$, —(C$_0$-C$_6$)alkyl-C(=O)—OR$^{22}$, —O—(C$_1$-C$_6$)-alkyl-OC(=O)—R$^{22}$, —O—(C$_1$-C$_6$)alkyl-C(=O)—OR$^{22}$, —(C$_0$-C$_6$)alkyl-C(=O)—R$^{22}$, —O—(C$_1$-C$_6$)alkyl-C(=O)—R$^{22}$, —(C$_0$-C$_6$)alkyl-NR$^{22}$—C(=O)—OR$^{23}$, —(C$_0$-C$_6$)alkyl-O—C(=O)—NR$^{22}$R$^{23}$, —(C$_0$-C$_6$)alkyl-NR$^{22}$—C(=NR$^{23}$)—NR$^{24}$R$^{25}$, —(C$_0$-C$_6$)alkyl-NR$^{22}$—C(=O)—NR$^{23}$R$^{24}$ and —(C$_0$-C$_6$)alkyl-NR$^{22}$—C(=S)—NR$^{23}$R$^{24}$;

m is an integer ranging from 1 to 5;

$R^{22}$, $R^{23}$, $R^{24}$ and $R^{25}$ are each independently selected from hydrogen or an optionally substituted radical selected from the group of —(C$_1$-C$_6$)alkylhalo, —(C$_1$-C$_6$)alkyl, —(C$_1$-C$_6$)alkylcyano, —(C$_2$-C$_6$)alkynyl, —(C$_2$-C$_6$)alkenyl, —(C$_3$-C$_7$)cycloalkyl, —(C$_4$-C$_{10}$)-alkylcycloalkyl, heteroaryl, —(C$_1$-C$_6$)alkylheteroaryl, aryl, —(C$_1$-C$_6$)alkylaryl, —(C$_2$-C$_6$)-alkynyl-(C$_3$-C$_7$)cycloalkyl, —(C$_2$-C$_6$)alkynyl-heteroaryl, —(C$_2$-C$_6$)alkynyl-aryl, —(C$_2$-C$_6$)-alkenyl-(C$_3$-C$_7$)cycloalkyl, —(C$_2$-C$_6$)alkenyl-heteroaryl and —(C$_2$-C$_6$)alkenyl-aryl; and $R^{22}$, $R^{23}$, $R^{24}$ and $R^{25}$ may be taken together to form an optionally substituted 3 to 10 membered non-aromatic heterocyclic ring or an optionally substituted 5 to 10 membered aromatic heterocyclic ring.

In a further preferred aspect of Formula (II-a), the invention provides a compound of Formula (II-b),

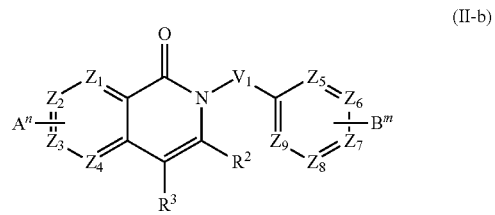

(II-b)

a pharmaceutically acceptable acid or base addition salt thereof, a stereochemically isomeric form thereof and an N-oxide form thereof, wherein:

$V_1$ is an optionally substituted radical selected from the group of —(C$_1$-C$_6$)alkyl-, —(C$_2$-C$_6$)alkynyl-, —(C$_2$-C$_6$)alkenyl-, —(C$_3$-C$_7$)cycloalkyl-, —(C$_3$-C$_8$)cycloalkenyl-, —(C$_1$-C$_6$)-alkylhalo-, —(C$_1$-C$_6$)alkyl-C(=O)—(C$_0$-C$_6$)alkyl-, —(C$_1$-C$_6$)alkyl-C(=O)—(C$_2$-C$_6$)alkynyl-, —(C$_1$-C$_6$)alkyl-C(=O)—(C$_2$-C$_6$)alkenyl-, —(C$_1$-C$_6$)alkyl-C(=O)—(C$_3$-C$_7$)cycloalkyl-, —(C$_1$-C$_6$)alkyl-C(=O)—(C$_4$-C$_{10}$)alkylcycloalkyl-, —(C$_1$-C$_6$)alkyl-C(=O)O—(C$_0$-C$_6$)alkyl-, —(C$_1$-C$_6$)alkyl-C(=O)O—(C$_2$-C$_6$)alkynyl-, —(C$_1$-C$_6$)alkyl-C(=O)O—(C$_2$-C$_6$)alkenyl-, —(C$_1$-C$_6$)-alkyl-C(=O)O—(C$_3$-C$_7$)cycloalkyl-, —(C$_1$-C$_6$)alkyl-C(=O)O—(C$_4$-C$_{10}$)alkylcycloalkyl-, —(C$_1$-C$_6$)alkyl-C(=O)NR$^7$—(C$_0$-C$_6$)alkyl-, —(C$_1$-C$_6$)alkyl-C(=O)NR$^7$—(C$_2$-C$_6$)alkynyl-, —(C$_1$-C$_6$)alkyl-C(=O)NR$^7$—(C$_2$-C$_6$)alkenyl-, —(C$_1$-C$_6$)alkyl-C(=O)NR$^7$—(C$_3$-C$_7$)cycloalkyl-, —(C$_1$-C$_6$)alkyl-C(=O)NR$^7$—(C$_4$-C$_{10}$)alkylcycloalkyl-, —(C$_1$-C$_6$)alkyl-O—(C$_0$-C$_6$)alkyl-, —(C$_1$-C$_6$)alkyl-O—(C$_2$-C$_6$)alkynyl-, —(C$_1$-C$_6$)alkyl-O—(C$_2$-C$_6$)alkenyl-, —(C$_1$-C$_6$)alkyl-O—(C$_3$-C$_7$)cycloalkyl-, —(C$_1$-C$_6$)alkyl-O—(C$_4$-C$_{10}$)alkylcycloalkyl-, —(C$_1$-C$_6$)-alkyl-S—(C$_0$-C$_6$)alkyl-, —(C$_1$-C$_6$)alkyl-S—(C$_2$-C$_6$)alkynyl-, —(C$_1$-C$_6$)alkyl-S—(C$_2$-C$_6$)-alkenyl-, —(C$_1$-C$_6$)alkyl-S—(C$_3$-C$_7$)cycloalkyl-, —(C$_1$-C$_6$)alkyl-S—(C$_4$-

$C_{10}$)alkylcycloalkyl-, —($C_1$-$C_6$)alkyl-S(O)—($C_0$-$C_6$)alkyl-, —($C_1$-$C_6$)alkyl-S(O)—($C_2$-$C_6$)alkynyl-, —($C_1$-$C_6$)alkyl-S(O)—($C_2$-$C_6$)alkenyl-, —($C_1$-$C_6$)alkyl-S(O)—($C_3$-$C_7$)cycloalkyl-, —($C_1$-$C_6$)alkyl-S(O)—($C_4$-$C_{10}$)alkylcycloalkyl-, —($C_1$-$C_6$)alkyl-S(O)$_2$—($C_0$-$C_6$)alkyl-, —($C_1$-$C_6$)alkyl-S(O)$_2$—($C_2$-$C_6$)-alkynyl-, —($C_1$-$C_6$)alkyl-S(O)$_2$—($C_2$-$C_6$)alkenyl-, —($C_1$-$C_6$)alkyl-S(O)$_2$—($C_3$-$C_7$)cycloalkyl-, —($C_1$-$C_6$)alkyl-S(O)$_2$—($C_4$-$C_{10}$)alkylcycloalkyl-, —($C_1$-$C_6$)alkyl-S(O)$_2$NR$^7$—($C_0$-$C_6$)alkyl-, —($C_1$-$C_6$)alkyl-S(O)$_2$NR$^7$—($C_2$-$C_6$)alkynyl-, —($C_1$-$C_6$)alkyl-S(O)$_2$NR$^7$—($C_2$-$C_6$)alkenyl-, —($C_1$-$C_6$)alkyl-S(O)$_2$NR$^7$—($C_3$-$C_7$)cycloalkyl-, —($C_1$-$C_6$)alkyl-S(O)$_2$NR$^7$—($C_4$-$C_{10}$)alkyl-cycloalkyl-, —($C_1$-$C_6$)alkyl-NR$^7$—($C_0$-$C_6$)alkyl-, —($C_1$-$C_6$)alkyl-NR$^7$—($C_2$-$C_6$)alkynyl-, —($C_1$-$C_6$)alkyl-NR$^7$—($C_2$-$C_6$)alkenyl-, —($C_1$-$C_6$)alkyl-NR$^7$—($C_3$-$C_7$)cycloalkyl-, —($C_1$-$C_6$)alkyl-NR$^7$—($C_4$-$C_{10}$)alkylcycloalkyl-, —($C_1$-$C_6$)alkyl-NR$^7$C(=O)—($C_0$-$C_6$)alkyl-, —($C_1$-$C_6$)alkyl-NR$^7$C(=O)—($C_2$-$C_6$)alkynyl-, —($C_1$-$C_6$)alkyl-NR$^7$C(=O)—($C_2$-$C_6$)alkenyl-, —($C_1$-$C_6$)alkyl-NR$^7$C(=O)—($C_3$-$C_7$)cycloalkyl-, —($C_1$-$C_6$)alkyl-NR$^7$C(=O)—($C_4$-$C_{10}$)alkylcycloalkyl-, —($C_1$-$C_6$)alkyl-NR$^7$C(=O)NR$^8$—($C_0$-$C_6$)alkyl-, —($C_1$-$C_6$)alkyl-NR$^7$C(=O)NR$^8$—($C_2$-$C_6$)-alkynyl-, —($C_1$-$C_6$)alkyl-NR$^7$C(=O)NR$^8$—($C_2$-$C_6$)alkenyl-, —($C_1$-$C_6$)alkyl-NR$^7$C(=O)NR$^8$—($C_3$-$C_7$)cycloalkyl-, —($C_1$-$C_6$)alkyl-NR$^7$C(=O)NR$^8$—($C_4$-$C_{10}$)alkylcycloalkyl-, —($C_1$-$C_6$)-alkyl-NR$^7$S(O)$_2$—($C_0$-$C_6$)alkyl-, —($C_1$-$C_6$)alkyl-NR$^7$S(O)$_2$—($C_2$-$C_6$)alkynyl-, —($C_1$-$C_6$)alkyl-NR$^7$S(O)$_2$—($C_2$-$C_6$)alkenyl-, —($C_1$-$C_6$)alkyl-NR$^7$S(O)$_2$—($C_3$-$C_7$)cycloalkyl-, —($C_1$-$C_6$)alkyl-NR$^7$S(O)$_2$—($C_4$-$C_{10}$)alkylcycloalkyl-, —($C_1$-$C_6$)alkyl-NR$^7$C(=S)NR$^8$—($C_0$-$C_6$)alkyl-, —($C_1$-$C_6$)alkyl-NR$^7$C(=S)NR$^8$—($C_2$-$C_6$)alkynyl-, —($C_1$-$C_6$)alkyl-NR$^7$C(=S)NR$^8$—($C_2$-$C_6$)alkenyl-, —($C_1$-$C_6$)alkyl-NR$^7$C(=S)NR$^8$—($C_3$-$C_7$)cycloalkyl-, —($C_1$-$C_6$)alkyl-NR$^7$C(=S)NR$^8$—($C_4$-$C_{10}$)alkylcycloalkyl-, —($C_1$-$C_6$)alkyl-OC(=O)—($C_0$-$C_6$)alkyl-, —($C_1$-$C_6$)alkyl-OC(=O)—($C_2$-$C_6$)alkynyl-, —($C_1$-$C_6$)alkyl-OC(=O)—($C_2$-$C_6$)alkenyl-, —($C_1$-$C_6$)alkyl-OC(=O)—($C_3$-$C_7$)-cycloalkyl-, —($C_1$-$C_6$)alkyl-OC(=O)—($C_4$-$C_{10}$)alkylcycloalkyl-, —($C_1$-$C_6$)alkyl-OC(=O)NR$^7$—($C_0$-$C_6$)alkyl-, —($C_1$-$C_6$)alkyl-OC(=O)NR$^7$—($C_2$-$C_6$)alkynyl-, —($C_1$-$C_6$)alkyl-OC(=O)NR$^7$—($C_2$-$C_6$)alkenyl-, —($C_1$-$C_6$)alkyl-OC(=O)NR$^7$—($C_3$-$C_7$)cycloalkyl-, —($C_1$-$C_6$)-alkyl-OC(=O)NR$^7$—($C_4$-$C_{10}$)alkylcycloalkyl-, —($C_1$-$C_6$)alkyl-NR$^7$C(=O)O—($C_0$-$C_6$)alkyl-, —($C_1$-$C_6$)alkyl-NR$^7$C(=O)O—($C_2$-$C_6$)alkynyl-, —($C_1$-$C_6$)alkyl-NR$^7$C(=O)O—($C_2$-$C_6$)-alkenyl-, —($C_1$-$C_6$)alkyl-NR$^7$C(=O)O—($C_3$-$C_7$)cycloalkyl- and —($C_1$-$C_6$)alkyl-NR$^7$C(=O)O—($C_4$-$C_{10}$)alkylcycloalkyl-;

R$^2$ is selected from the group of hydrogen, halogen, —CN, —CF$_3$, and an optionally substituted radical selected from the group of —($C_1$-$C_6$)alkyl, —($C_2$-$C_6$)alkenyl, —($C_2$-$C_6$)-alkynyl, —($C_1$-$C_6$)alkylhalo, —($C_3$-$C_7$)cycloalkyl, —($C_1$-$C_6$)alkylcyano, —O—($C_1$-$C_6$)alkyl, —O—($C_1$-$C_6$)alkylhalo, —O—($C_1$-$C_6$)alkylcyano, —O—($C_3$-$C_6$)alkynyl, —O—($C_3$-$C_7$)cycloalkyl, —O—($C_2$-$C_6$)alkyl-OR$^{26}$, —O—($C_1$-$C_6$)alkyl-heteroaryl, —O—($C_0$-$C_6$)alkylaryl, —($C_0$-$C_6$)alkyl-OR$^{26}$, —O-heteroaryl, -heteroaryl, —($C_1$-$C_6$)alkyl-heteroaryl, -aryl, —O-aryl, —($C_1$-$C_6$)-alkylaryl, —($C_1$-$C_6$)alkylhalo-OR$^{26}$, —($C_0$-$C_6$)alkyl-SR$^{26}$, —($C_0$-$C_6$)alkyl-S(=O)$_2$—R$^{26}$, —($C_0$-$C_6$)alkyl-NR$^{26}$R$^{27}$, —O—($C_2$-$C_6$)alkyl-NR$^{26}$R$^{27}$, —($C_0$-$C_6$)alkyl-S(=O)$_2$NR$^{26}$R$^{27}$, —($C_0$-$C_6$)-alkyl-NR$^{26}$—S(=O)$_2$R$^{27}$, —($C_0$-$C_6$)alkyl-C(=O)—NR$^{26}$R$^{27}$, —($C_0$-$C_6$)alkyl-NR$^{26}$C(=O)—R$^{27}$, —O—($C_1$-$C_6$)alkylC(=O)—NR$^{26}$R$^{27}$, —O—($C_1$-$C_6$)alkyl-NR$^{26}$C(=O)—R$^{27}$ and —($C_0$-$C_6$)alkyl-C(=O)—R$^{26}$;

R$^{26}$ and R$^{27}$ are each independently hydrogen or an optionally substituted radical selected from the group of —($C_1$-$C_6$)alkylhalo, —($C_1$-$C_6$)alkylcyano, —($C_0$-$C_6$)alkyl, —($C_2$-$C_6$)alkynyl, —($C_2$-$C_6$)alkenyl, —($C_3$-$C_7$)cycloalkyl, —($C_4$-$C_{10}$)alkylcycloalkyl, heteroaryl, —($C_1$-$C_6$)alkylheteroaryl, aryl, —($C_1$-$C_6$)alkylaryl, —($C_2$-$C_6$)alkynyl-($C_3$-$C_7$)cycloalkyl, —($C_2$-$C_6$)alkynyl-heteroaryl, —($C_2$-$C_6$)alkynyl-aryl, —($C_2$-$C_6$)alkenyl-($C_3$-$C_7$)cycloalkyl, —($C_2$-$C_6$)alkenyl-heteroaryl and —($C_2$-$C_6$)alkenyl-aryl; and R$^{26}$ and R$^{27}$ may be taken together to form an optionally substituted 3 to 10 membered non-aromatic heterocyclic ring or an optionally substituted 5 to 10 membered aromatic heterocyclic ring.

In a further preferred aspect of Formula (I-b) the invention provides a compound of Formula (II-c),

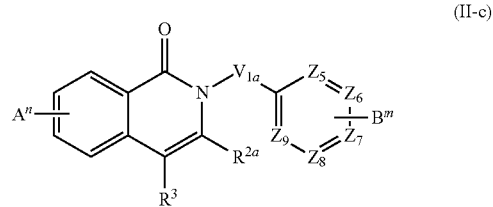

(II-c)

a pharmaceutically acceptable acid or base addition salt thereof, a stereochemically isomeric form thereof and an N-oxide form thereof.

In a further preferred aspect of Formula (II-c) the invention provides a compound according to any one of Formulas (II-c1), (II-c2) and (II-c3),

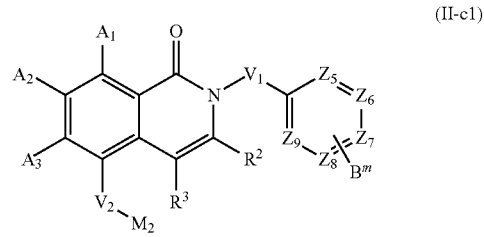

(II-c1)

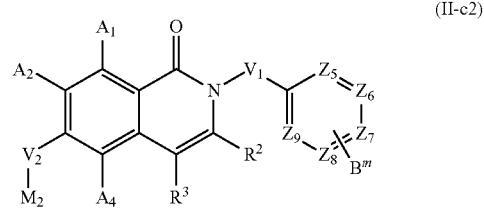

(II-c2)

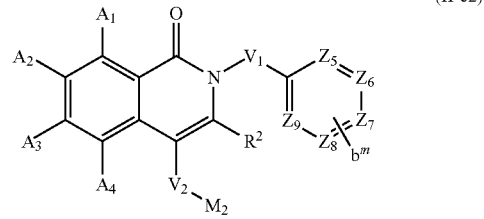

(II-c2)

a pharmaceutically acceptable acid or base addition salt thereof, a stereochemically isomeric form thereof and an N-oxide form thereof, wherein:

$Z_5$, $Z_6$, $Z_7$, $Z_8$ and $Z_9$ are selected from C or N, provided that at least 2 carbons are present and that a free position may further be substituted by 1 to 5 radicals B$^m$; and R$^2$, R$^3$, A$^1$, A$^2$, A$^3$ and A$^4$ are each independently selected from the group of hydrogen, halogen, —CN, —CF$_3$, —OCF₃, and an optionally substituted radical selected from the group of —(C₁-C₆)alkyl, —(C₂-C₆)alkynyl, —(C₂-C₆)alkenyl, —(C₃-C₇)cycloalkyl, —(C₃-C₈)-cycloalkenyl, —(C₁-C₆)alkylhalo, —(C₀-C₃)alkyl-O—(C₁-C₆)alkyl, —(C₀-C₃)alkyl-O—(C₂-C₆)alkynyl, —(C₀-C₃)alkyl-O—(C₂-C₆)alkenyl, —(C₀-C₃)alkyl-O—(C₃-C₇)cycloalkyl, —(C₀-C₃)alkyl-O—(C₄-C₁₀)alkylcycloalkyl, —(C₀-C₃)alkyl-O—(C₁-C₆)alkylhalo, —S—(C₁-C₆)alkyl, —S—(C₂-C₆)alkynyl, —S—(C₂-C₆)alkenyl, —S—(C₃-C₇)cycloalkyl, —S—(C₄-C₁₀)alkyl-cycloalkyl, —(C₀-C₃)alkyl-NR¹⁸R¹⁹, —(C₀-C₃)alkyl-S(O)₂NR¹⁸R¹⁹, —(C₀-C₃)alkyl-NR¹⁸S(O)₂R¹⁹, —(C₀-C₃)alkyl-C(=O)R¹⁸, —(C₀-C₃)alkyl-C(=O)OR¹⁸, —(C₀-C₃)alkyl-C(=O)NR¹⁸R¹⁹, —(C₀-C₃)alkyl-NR¹⁸C(=O)R¹⁹, —O—(C₀-C₃)alkyl-S(O)₂NR¹⁸R¹⁹, —O—(C₀-C₃)alkyl-NR¹⁸S(O)₂R¹⁹, —O—(C₀-C₃)alkyl-C(=O)R¹⁸, —O—(C₀-C₃)alkyl-C(=O)OR¹⁸, —O—(C₀-C₃)alkyl-C(=O)NR¹⁸R¹⁹ and —O—(C₀-C₃)alkyl-NR¹⁸C(=O)R¹⁹.

In a second preferred aspect of Formula (I), the invention provides a compound according to Formula (III),

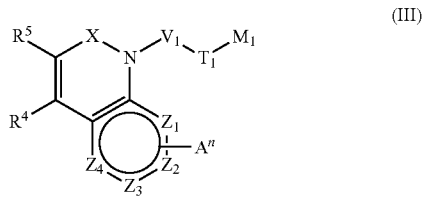

(III)

a pharmaceutically acceptable acid or base addition salt thereof, a stereochemically isomeric form thereof and an N-oxide form thereof, wherein:

X is selected from C(=O) and S(O)₂;

Z₁, Z₂, Z₃ and Z₄ are each independently, selected from the group of a covalent bond, C, S, N and O, representing a 5 or 6 membered heteroaryl or aryl ring which may further be substituted by 1 to 4 radicals A$^n$;

A$^n$ radicals are each independently selected from the group of hydrogen, halogen, —CN, —OH, —NO₂, —CF₃, —SH, —NH₂, and an optionally substituted radical selected from the group of —(C₁-C₆)alkyl, —(C₁-C₆)alkylhalo, —(C₂-C₆)alkynyl, —(C₂-C₆)alkenyl, —(C₃-C₇)-cycloalkyl, —(C₁-C₆)alkylcyano, —(C₁-C₆)alkyl, —O—(C₁-C₆)alkylhalo, —O—(C₁-C₆)-alkylcyano, —O—(C₃-C₆)alkynyl, —O—(C₃-C₇)cycloalkyl, —O—(C₂-C₆)alkenyl, —O—(C₂-C₆)-alkyl-OR¹⁸, —O—(C₁-C₆)alkyl-heteroaryl, —O—(C₀-C₆)alkylaryl, —(C₀-C₆)alkyl-OR¹⁸, —(C₃-C₇)cycloalkyl-(C₁-C₆)alkyl, —O—(C₃-C₇)cycloalkyl-(C₁-C₆)alkyl, —O-heteroaryl, heteroaryl, —(C₁-C₆)alkyl-heteroaryl, aryl, —O-aryl, —(C₁-C₆)alkylaryl, —(C₁-C₆)alkylhalo-OR¹⁸, —(C₃-C₆)alkynyl-OR¹⁸, —(C₃-C₆)alkenyl-OR¹⁸, —(C₀-C₆)alkyl-SR¹⁸, —O—(C₂-C₆)-alkyl-SR¹⁸, —(C₁-C₆)alkyl-S(=O)R¹⁸, —O—(C₁-C₆)alkyl-S(=O)R¹⁸, —(C₀-C₆)alkyl-S(=O)₂R¹⁸, —O—(C₁-C₆)alkyl-S(=O)₂R¹⁸, —(C₀-C₆)alkyl-NR¹⁸R¹⁹, —O—(C₂-C₆)alkyl-NR¹⁸R¹⁹, —(C₀-C₆)alkyl-S(=O)₂NR¹⁸R¹⁹, —(C₀-C₆)alkyl-NR¹⁸—S(=O)₂R¹⁹, —O—(C₁-C₆)alkyl-S(=O)₂NR¹⁸R¹⁹, —O—(C₁-C₆)alkyl-NR¹⁸—S(=O)₂R¹⁹, —(C₀-C₆)alkyl-C(=O)—NR¹⁸R¹⁹, —(C₀-C₆)alkyl-NR¹⁸C(=O)—R¹⁹, —O—(C₁-C₆)alkylC(=O)—NR¹⁸R¹⁹, —O—(C₁-C₆)-alkyl-NR¹⁸C(=O)—R¹⁹, —(C₀-C₆)alkyl-OC(=O)—R¹⁹, —(C₀-C₆)alkyl-C(=O)—OR¹⁸, —O—(C₁-C₆)alkyl-OC(=O)—R¹⁸, —O—(C₁-C₆)alkyl-C(=O)—OR¹⁸, —(C₀-C₆) alkyl-C(=O)—R¹⁸, —O—(C₁-C₆)alkyl-C(=O)—R¹⁸, —(C₀-C₆)alkyl-NR¹⁸—C(=O)—OR¹⁹, —(C₀-C₆)alkyl-O—C(=O)—NR¹⁸R¹⁹, —(C₀-C₆)alkyl-NR¹⁸—C(=NR¹⁹)—NR²⁰R²¹, —(C₀-C₆)alkyl-NR¹⁸—C(=O)—NR¹⁹R²⁰, —(C₀-C₆)alkyl-NR¹⁸—C(=S)—NR¹⁹R²⁰, and a —V₂-T₂-M₂ radical;

n is an integer ranging from 1 to 4;

R¹⁸, R¹⁹, R²⁰ and R²¹ are each independently hydrogen or an optionally substituted radical selected from the group of —(C₁-C₆)alkylhalo, —(C₁-C₆)alkyl, —(C₁-C₆)alkylcyano, —(C₂-C₆)alkynyl, —(C₂-C₆)alkenyl, —(C₃-C₇)cycloalkyl, —(C₄-C₁₀)alkylcycloalkyl, heteroaryl, —(C₁-C₆)alkylheteroaryl, aryl, —(C₁-C₆)alkylaryl, —(C₂-C₆)alkynyl-(C₃-C₇)-cycloalkyl, —(C₂-C₆)alkynyl-heteroaryl, —(C₂-C₆)alkynyl-aryl, —(C₂-C₆)alkenyl-(C₃-C₇)-cycloalkyl, —(C₂-C₆)alkenyl-heteroaryl and —(C₂-C₆)alkenyl-aryl; and R¹⁸, R⁹, R²⁰ and R²¹ may be taken together to form an optionally substituted 3 to 10 membered non-aromatic heterocyclic ring or an optionally substituted 5 to 10 membered aromatic heterocyclic ring.

Preferred structures from Formula (III) are indicated in Figure B below.

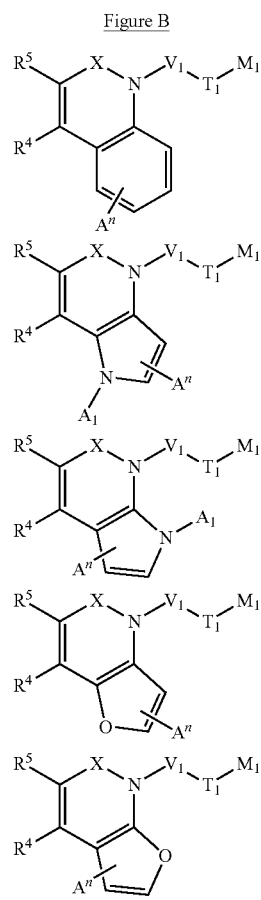

Figure B

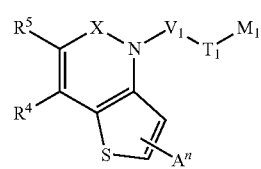

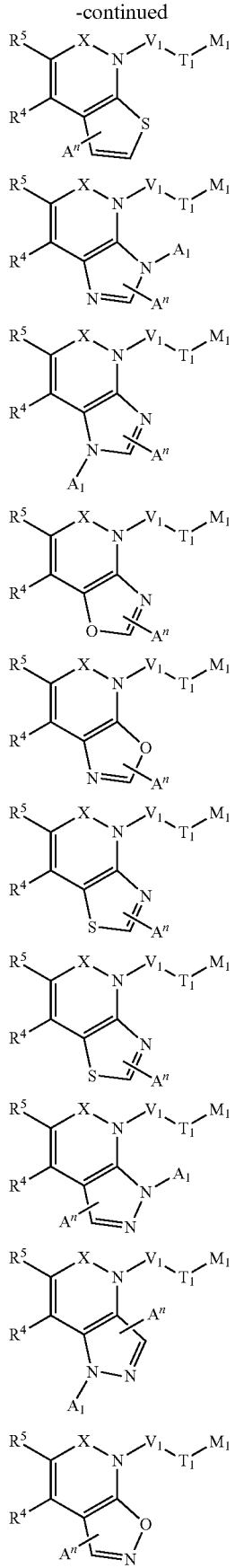
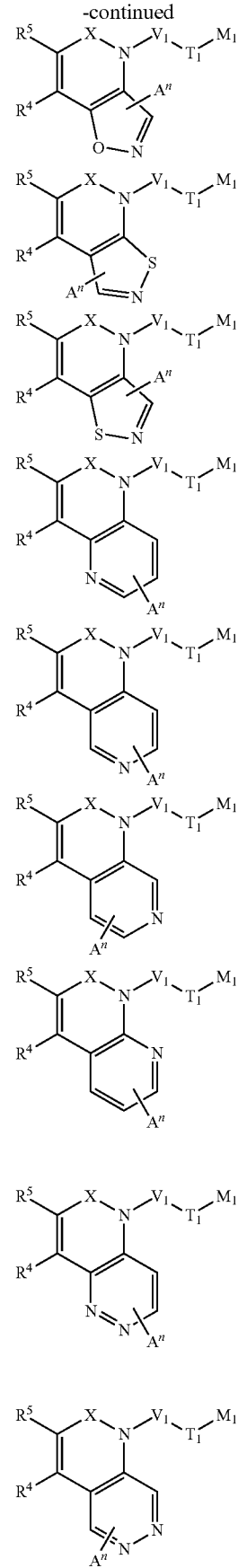

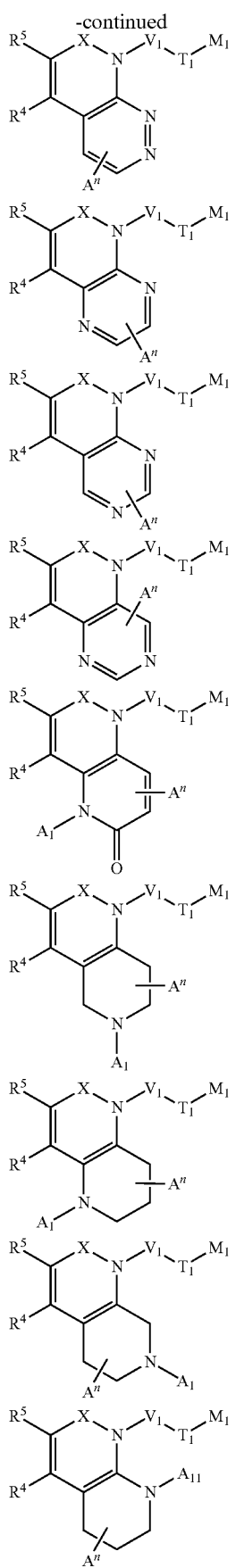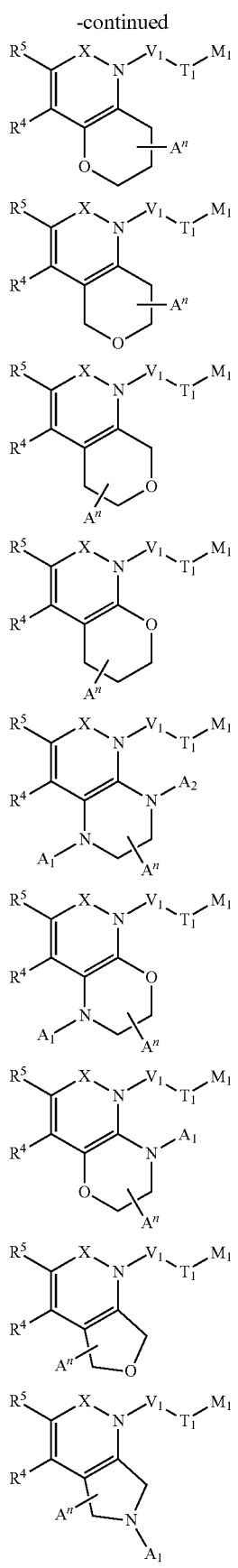

In a preferred aspect of Formula (III) the invention provides a compound of Formula (III-a),

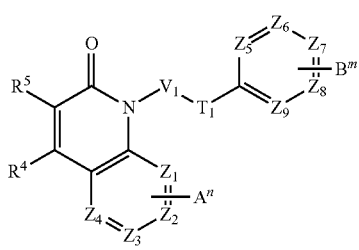
(III-a)

a pharmaceutically acceptable acid or base addition salt thereof, a stereochemically isomeric form thereof and an N-oxide form thereof, wherein:

$Z_5$, $Z_6$, $Z_7$, $Z_8$ and $Z_9$ are each independently selected from the group of a covalent bond, C, S, N and O, representing a 5 or 6 membered heteroaryl or aryl ring which may optionally be substituted by 1 to 5 radicals $B^m$;

$B^m$ radicals are each independently selected from the group of hydrogen, halogen, —CN, —OH, —NO$_2$, —CF$_3$, —SH, —NH$_2$, and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)-cycloalkyl, —(C$_1$-C$_6$)alkylcyano, —O—(C$_1$-C$_6$)alkyl, —O—(C$_1$-C$_6$)alkylhalo, —O—(C$_1$-C$_6$)-alkylcyano, —O—(C$_3$-C$_6$)alkynyl, —O—(C$_3$-C$_7$)cycloalkyl, —O—(C$_2$-C$_6$)alkenyl, —O—(C$_2$-C$_6$)-alkyl-OR$^{22}$, —O—(C$_1$-C$_6$)alkyl-heteroaryl, —O—(C$_0$-C$_6$)alkylaryl, —(C$_0$-C$_6$)alkyl-OR$^{22}$, —(C$_3$-C$_7$)cycloalkyl-(C$_1$-C$_6$)alkyl, —O—(C$_3$-C$_7$)cycloalkyl-(C$_1$-C$_6$)alkyl, —O-heteroaryl, heteroaryl, —(C$_1$-C$_6$)alkyl-heteroaryl, aryl, —O-aryl, —(C$_1$-C$_6$)alkylaryl, —(C$_1$-C$_6$)alkylhalo-OR$^{22}$, —(C$_3$-C$_6$)alkynyl-OR$^{22}$, —(C$_3$-C$_6$)alkenyl-OR$^{22}$, —(C$_0$-C$_6$)alkyl-S—R$^{22}$, —O—(C$_2$-C$_6$)-alkyl-S—R$^{22}$, —(C$_1$-C$_6$)alkyl-S(=O)—R$^{22}$, —O—(C$_1$-C$_6$)alkyl-S(=O)—R$^{22}$, —(C$_0$-C$_6$)alkyl-S(=O)$_2$—R$^{22}$, —O—(C$_1$-C$_6$)alkyl-S(=O)$_2$—R$^{22}$, —(C$_0$-C$_6$)alkyl-NR$^{22}$R$^{23}$, —O—(C$_2$-C$_6$)alkyl-NR$^{22}$R$^{23}$, —(C$_0$-C$_6$)alkyl-S(=O)$_2$NR$^{22}$R$^{23}$, —(C$_0$-C$_6$)alkyl-NR$^{22}$—S(=O)$_2$R$^{23}$, —O—(C$_1$-C$_6$)-alkyl-S(=O)$_2$NR$^{22}$R$^{23}$, —O—(C$_1$-C$_6$)alkyl-NR$^{22}$—S(=O)$_2$R$^{23}$, —(C$_0$-C$_6$)alkyl-C(=O)—NR$^{22}$R$^{23}$, —(C$_0$-C$_6$)alkyl-NR$^{22}$C(=O)—R$^{23}$, —O—(C$_1$-C$_6$)alkyl-C(=O)—NR$^{22}$R$^{23}$, —O—(C$_1$-C$_6$)alkyl-NR$^{22}$C(=O)—R$^{23}$, —(C$_0$-C$_6$)alkyl-OC(=O)—R$^{22}$, —(C$_0$-C$_6$)alkyl-C(=O)—OR$^{22}$, —O—(C$_1$-C$_6$)-alkyl-OC(=O)—R$^{22}$, —O—(C$_1$-C$_6$)alkyl-C(=O)—OR$^{22}$, —(C$_0$-C$_6$)alkyl-C(=O)—R$^{22}$, —O—(C$_1$-C$_6$)alkyl-C(=O)—R$^{22}$, —(C$_0$-C$_6$)alkyl-NR$^{22}$—C(=O)—OR$^{23}$, —(C$_0$-C$_6$)alkyl-O—C(=O)—NR$^{22}$R$^{23}$, —(C$_0$-C$_6$)alkyl-NR$^{22}$C(=NR$^{23}$)—NR$^{24}$R$^{25}$, —(C$_0$-C$_6$)alkyl-NR$^{22}$—C(=O)—NR$^{23}$R$^{24}$ and —(C$_0$-C$_6$)alkyl-NR$^{22}$—C(=S)—NR$^{23}$R$^{24}$;

m is an integer from 1 to 5;

$R^{22}$, $R^{23}$, $R^{24}$ and $R^{25}$ are each independently selected from hydrogen or an optionally substituted radical selected from the group of —(C$_1$-C$_6$)alkylhalo, —(C$_1$-C$_6$)alkyl, —(C$_1$-C$_6$)alkylcyano, —(C$_2$-C$_6$)alkynyl, —(C$_2$-C$_6$)alkenyl, —(C$_3$-C$_7$)cycloalkyl, —(C$_4$-C$_{10}$)-alkylcycloalkyl, heteroaryl, —(C$_1$-C$_6$)alkylheteroaryl, aryl, —(C$_1$-C$_6$)alkylaryl, —(C$_2$-C$_6$)-alkynyl-(C$_3$-C$_7$)cycloalkyl, —(C$_2$-C$_6$)alkynyl-heteroaryl, —(C$_2$-C$_6$)alkynyl-aryl, —(C$_2$-C$_6$)-alkenyl-(C$_3$-C$_7$)cycloalkyl, —(C$_2$-C$_6$)alkenyl-heteroaryl or —(C$_2$-C$_6$)alkenyl-aryl; and $R^{22}$, $R^{23}$, $R^{24}$ and $R^{25}$ may be taken together to form an optionally substituted 3 to 10 membered non-aromatic heterocyclic ring or an optionally substituted 5 to 10 membered aromatic heterocyclic ring.

In a preferred aspect of Formula (III-a), the invention provides a compound according to Formula (III-b),

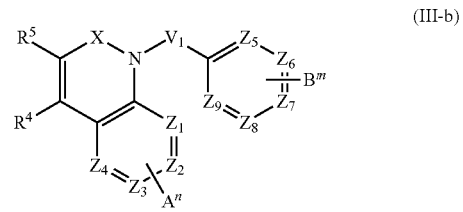
(III-b)

a pharmaceutically acceptable acid or base addition salt thereof, a stereochemically isomeric form thereof and an N-oxide form thereof, wherein:

$V_1$ is an optionally substituted radical selected from the group of —(C$_1$-C$_6$)alkyl-, —(C$_2$-C$_6$)alkynyl-, —(C$_2$-C$_6$)alkenyl-, —(C$_3$-C$_7$)cycloalkyl-, —(C$_3$-C$_8$)cycloalkenyl-, —(C$_1$-C$_6$)-alkylhalo-, —(C$_1$-C$_6$)alkyl-C(=O)—(C$_0$-C$_6$)alkyl-, —(C$_1$-C$_6$)alkyl-C(=O)—(C$_2$-C$_6$)alkynyl-, —(C$_1$-C$_6$)alkyl-C(=O)—(C$_2$-C$_6$)alkenyl-, —(C$_1$-C$_6$)alkyl-C(=O)—(C$_3$-C$_7$)cycloalkyl-, —(C$_1$-C$_6$)alkyl-C(=O)—(C$_4$-C$_{10}$)alkylcycloalkyl-, —(C$_1$-C$_6$)alkyl-C(=O)O—(C$_0$-C$_6$)alkyl-, —(C$_1$-C$_6$)alkyl-C(=O)O—(C$_2$-C$_6$)alkynyl-, —(C$_1$-C$_6$)alkyl-C(=O)O—(C$_2$-C$_6$)alkenyl-, —(C$_1$-C$_6$)-alkyl-C(=O)O—(C$_3$-C$_7$)cycloalkyl-, —(C$_1$-C$_6$)alkyl-C(=O)O—(C$_4$-C$_{10}$)alkylcycloalkyl-, —(C$_1$-C$_6$)alkyl-C(=O)NR$^7$—(C$_0$-C$_6$)alkyl-, —(C$_1$-C$_6$)alkyl-C(=O)NR$^7$—(C$_2$-C$_6$)alkynyl-, —(C$_1$-C$_6$)alkyl-C(=O)NR$^7$—(C$_2$-C$_6$)alkenyl-, —(C$_1$-C$_6$)alkyl-C(=O)NR$^7$—(C$_3$-C$_7$)cycloalkyl-, —(C$_1$-C$_6$)alkyl-C(=O)NR$^7$—(C$_4$-C$_{10}$)alkylcycloalkyl-, —(C$_1$-C$_6$)alkyl-O—(C$_0$-C$_6$)alkyl-, —(C$_1$-C$_6$)alkyl-O—(C$_2$-C$_6$)alkynyl-, —(C$_1$-C$_6$)alkyl-O—(C$_2$-C$_6$)alkenyl-, —(C$_1$-C$_6$)alkyl-O—(C$_3$-C$_7$)cycloalkyl-, —(C$_1$-C$_6$)alkyl-O—(C$_4$-C$_{10}$)alkylcycloalkyl-, —(C$_1$-C$_6$)-alkyl-S—(C$_0$-C$_6$)alkyl-, —(C$_1$-C$_6$)alkyl-S—(C$_2$-C$_6$)alkynyl-, —(C$_1$-C$_6$)alkyl-S—(C$_2$-C$_6$)-alkenyl-, —(C$_1$-C$_6$)alkyl-S—(C$_3$-C$_7$)cycloalkyl-, —(C$_1$-C$_6$)alkyl-S—(C$_4$-C$_{10}$)alkylcycloalkyl-, —(C$_1$-C$_6$)alkyl-S(O)—(C$_0$-C$_6$)alkyl-, —(C$_1$-C$_6$)alkyl-S(O)—(C$_2$-C$_6$)alkynyl-, —(C$_1$-C$_6$)alkyl-S(O)—(C$_2$-C$_6$)alkenyl-, —(C$_1$-C$_6$)alkyl-S(O)—(C$_3$-C$_7$)cycloalkyl-, —(C$_1$-C$_6$)alkyl-S(O)—(C$_4$-C$_{10}$)alkylcycloalkyl-, —(C$_1$-C$_6$)alkyl-S(O)$_2$—(C$_0$-C$_6$)alkyl-, —(C$_1$-C$_6$)alkyl-S(O)$_2$—(C$_2$-C$_6$)-alkynyl-, —(C$_1$-C$_6$)alkyl-S(O)$_2$—(C$_2$-C$_6$)alkenyl-, —(C$_1$-C$_6$)alkyl-S(O)$_2$—(C$_3$-C$_7$)cycloalkyl-, —(C$_1$-C$_6$)alkyl-S(O)$_2$—(C$_4$-C$_{10}$)alkylcycloalkyl-, —(C$_1$-C$_6$)alkyl-S(O)$_2$NR$^7$—(C$_0$-C$_6$)alkyl-, —(C$_1$-C$_6$)alkyl-S(O)$_2$NR$^7$—(C$_2$-C$_6$)alkynyl-, —(C$_1$-C$_6$)alkyl-S(O)$_2$NR$^7$—(C$_2$-C$_6$)alkenyl-, —(C$_1$-C$_6$)alkyl-S(O)$_2$NR$^7$—(C$_3$-C$_7$)cycloalkyl-, —(C$_1$-C$_6$)alkyl-S(O)$_2$NR$^7$—(C$_4$-C$_{10}$)alkyl-cycloalkyl-, —(C$_1$-C$_6$)alkyl-NR$^7$—(C$_0$-C$_6$)alkyl-, —(C$_1$-C$_6$)alkyl-NR$^7$—(C$_2$-C$_6$)alkynyl-, —(C$_1$-C$_6$)alkyl-NR$^7$—(C$_2$-C$_6$)alkenyl-, —(C$_1$-C$_6$)alkyl-NR$^7$—(C$_3$-C$_7$)cycloalkyl-, —(C$_1$-C$_6$)alkyl-NR$^7$—(C$_4$-C$_{10}$)alkylcycloalkyl-, —(C$_1$-C$_6$)alkyl-NR$^7$C(=O)—(C$_0$-C$_6$)alkyl-, —(C$_1$-C$_6$)alkyl-NR$^7$C(=O)—(C$_2$-C$_6$)alkynyl-, —(C$_1$-C$_6$)alkyl-NR$^7$C(=O)—(C$_2$-C$_6$)alkenyl-, —(C$_1$-C$_6$)alkyl-NR$^7$C(=O)—(C$_3$-C$_7$)cycloalkyl-, —(C$_1$-C$_6$)alkyl-NR$^7$C(=O)—(C$_4$-C$_{10}$)alkylcycloalkyl-, —(C$_1$-C$_6$)alkyl-NR$^7$C(=O)NR$^8$—(C$_0$-C$_6$)alkyl-, —(C$_1$-C$_6$)alkyl-NR$^7$C(=O)NR$^8$—(C$_2$-C$_6$)alkynyl-, —(C$_1$-C$_6$)alkyl-NR$^7$C(=O)NR$^8$—(C$_2$-C$_6$)alkenyl-, —(C$_1$-C$_6$)alkyl-NR$^7$C(=O)—NR$^8$—(C$_3$-C$_7$)cycloalkyl-, —(C$_1$-

C$_6$)alkyl-NR$^7$C(=O)NR$^8$—(C$_4$-C$_{10}$)alkylcycloalkyl-, —(C$_1$-C$_6$)alkyl-NR$^7$S(O)$_2$—(C$_0$-C$_6$)alkyl-, —(C$_1$-C$_6$)alkyl-NR$^7$S(O)$_2$—(C$_2$-C$_6$)alkynyl-, —(C$_1$-C$_6$)-alkyl-NR$^7$S(O)$_2$—(C$_2$-C$_6$)alkenyl-, —(C$_1$-C$_6$)alkyl-NR$^7$S(O)$_2$—(C$_3$-C$_7$)cycloalkyl-, —(C$_1$-C$_6$)-alkyl-NR$^7$S(O)$_2$—(C$_4$-C$_{10}$) alkylcycloalkyl-, —(C$_1$-C$_6$)alkyl-NR$^7$C(=S)NR$^8$—(C$_0$-C$_6$) alkyl-, —(C$_1$-C$_6$)alkyl-NR$^7$C(=S)NR$^8$—(C$_2$-C$_6$)alkynyl-, —(C$_1$-C$_6$)alkyl-NR$^7$C(=S)NR$^8$—(C$_2$-C$_6$)-alkenyl-, —(C$_1$-C$_6$)alkyl-NR$^7$C(=S)NR$^8$—(C$_3$-C$_7$)cycloalkyl-, —(C$_1$-C$_6$) alkyl-NR$^7$C(=S)—NR$^8$—(C$_4$-C$_{10}$)alkylcycloalkyl-, —(C$_1$-C$_6$)alkyl-OC(=O)—(C$_0$-C$_6$)alkyl-, —(C$_1$-C$_6$)alkyl-OC(=O)—(C$_2$-C$_6$)alkynyl-, —(C$_1$-C$_6$)alkyl-OC(=O)—(C$_2$-C$_6$)alkenyl-, —(C$_1$-C$_6$)alkyl-OC(=O)—(C$_3$-C$_7$)cycloalkyl-, —(C$_1$-C$_6$)alkyl-OC(=O)—(C$_4$-C$_{10}$) alkylcycloalkyl-, —(C$_1$-C$_6$)-alkyl-OC(=O)NR$^7$—(C$_0$-C$_6$) alkyl-, —(C$_1$-C$_6$)alkyl-OC(=O)NR$^7$—(C$_2$-C$_6$)alkynyl-, —(C$_1$-C$_6$)-alkyl-OC(=O)NR$^7$—(C$_2$-C$_6$)alkenyl-, —(C$_1$-C$_6$)alkyl-OC(=O)NR$^7$—(C$_3$-C$_7$)cycloalkyl-, —(C$_1$-C$_6$) alkyl-OC(=O)NR$^7$—(C$_4$-C$_{10}$)alkylcycloalkyl-, —(C$_1$-C$_6$) alkyl-NR$^7$C(=O)O—(C$_0$-C$_6$)alkyl-, —(C$_1$-C$_6$)alkyl-NR$^7$C(=O)O—(C$_2$-C$_6$)alkynyl-, —(C$_1$-C$_6$)alkyl-NR$^7$C(=O)O—(C$_2$-C$_6$)alkenyl-, —(C$_1$-C$_6$)alkyl-NR$^7$C(=O)O—(C$_3$-C$_7$) cycloalkyl- and —(C$_1$-C$_6$)alkyl-NR$^7$C(=O)O—(C$_4$-C$_{10}$) alkylcycloalkyl-;

R$^2$ is selected from the group of hydrogen, halogen, —CN, —CF$_3$, and an optionally substituted radical selected from the group of —(C$_1$-C$_6$)alkyl, —(C$_2$-C$_6$)alkenyl, —(C$_2$-C$_6$)-alkynyl, —(C$_1$-C$_6$)alkylhalo, —(C$_3$-C$_7$)cycloalkyl, —(C$_1$-C$_6$) alkylcyano, —O—(C$_1$-C$_6$)alkyl, —O—(C$_1$-C$_6$)alkylhalo, —O—(C$_1$-C$_6$)alkylcyano, —O—(C$_3$-C$_6$)alkynyl, —O—(C$_3$-C$_7$)cycloalkyl, —O—(C$_2$-C$_6$)alkyl-OR$^{26}$, —O—(C$_1$-C$_6$)alkyl-heteroaryl, —O—(C$_0$-C$_6$)alkylaryl, —(C$_0$-C$_6$) alkyl-OR$^{26}$, —O-heteroaryl, -heteroaryl, —(C$_1$-C$_6$)alkyl-heteroaryl, -aryl, —O-aryl, —(C$_1$-C$_6$)-alkylaryl, —(C$_1$-C$_6$) alkylhalo-OR$^{26}$, —(C$_0$-C$_6$)alkyl-SR$^{26}$, —(C$_0$-C$_6$)alkyl-S(=O)$_2$—R$^{26}$, —(C$_0$-C$_6$)alkyl-NR$^{26}$R$^{27}$, —O—(C$_2$-C$_6$) alkyl-NR$^{26}$R$^{27}$, —(C$_0$-C$_6$)alkyl-S(=O)$_2$NR$^{26}$R$^{27}$, —(C$_0$-C$_6$)-alkyl-NR$^{26}$—S(=O)$_2$R$^{27}$, —(C$_0$-C$_6$)alkyl-C(=O)—NR$^{26}$R$^{27}$, —(C$_0$-C$_6$)alkyl-NR$^{26}$C(=O)—R$^{27}$, —O—(C$_1$-C$_6$)alkylC(=O)—NR$^{26}$R$^{27}$, —O—(C$_1$-C$_6$)alkyl-NR$^{26}$C(=O)—R$^{27}$ and —(C$_0$-C$_6$)alkyl-C(=O)—R$^{26}$;

R$^{26}$ and R$^{27}$ are each independently hydrogen or an optionally substituted radical selected from the group of —(C$_1$-C$_6$)alkylhalo, —(C$_1$-C$_6$)alkylcyano, —(C$_0$-C$_6$)alkyl, —(C$_2$-C$_6$)alkynyl, —(C$_2$-C$_6$)alkenyl, —(C$_3$-C$_7$)cycloalkyl, —(C$_4$-C$_{10}$) alkylcycloalkyl, heteroaryl, —(C$_1$-C$_6$)alkylheteroaryl, aryl, —(C$_1$-C$_6$)alkylaryl, —(C$_2$-C$_6$)alkynyl-(C$_3$-C$_7$)cycloalkyl, —(C$_2$-C$_6$)alkynyl-heteroaryl, —(C$_2$-C$_6$)alkynyl-aryl, —(C$_2$-C$_6$)alkenyl-(C$_3$-C$_7$)cycloalkyl, —(C$_2$-C$_6$)alkenyl-heteroaryl and —(C$_2$-C$_6$)alkenyl-aryl; and R$^{26}$ and R$^{27}$ may be taken together to form an optionally substituted 3 to 10 membered non-aromatic heterocyclic ring or an optionally substituted 5 to 10 membered aromatic heterocyclic ring.

In a further preferred aspect of Formula (III-b), the invention provides a compound of Formula (III-c),

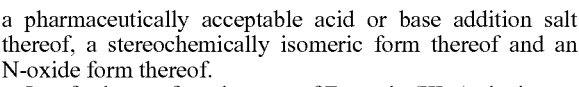

(III-c)

a pharmaceutically acceptable acid or base addition salt thereof, a stereochemically isomeric form thereof and an N-oxide form thereof.

In a further preferred aspect of Formula (III-c), the invention provides a compound according to any one of (III-c1), (III-c2) or (III-c3),

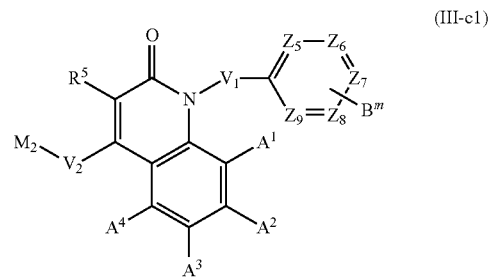

(III-c1)

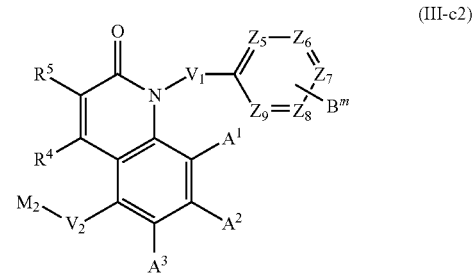

(III-c2)

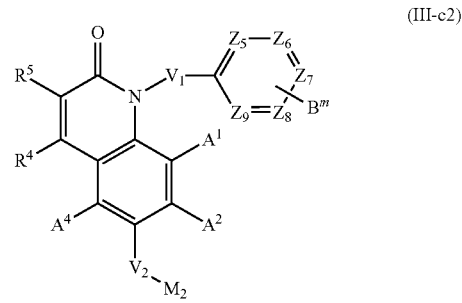

(III-c2)

a pharmaceutically acceptable acid or base addition salt thereof, a stereochemically isomeric form thereof and an N-oxide form thereof, wherein:

Z$_5$, Z$_6$, Z$_7$, Z$_8$ and Z$_9$ are selected from C or N, provided that at least 2 carbons are present and that a free position may further be substituted by 1 to 5 radicals B$^m$; and R$^4$, R$^5$, A$^1$, A$^2$, A$^3$ and A$^4$ are each independently selected from the group of hydrogen, halogen, —CN, —CF$_3$, —OCF$_3$, and an optionally substituted radical selected from the group of —(C$_1$-C$_6$)alkyl, —(C$_2$-C$_6$)alkynyl, —(C$_2$-C$_6$)alkenyl, —(C$_3$-C$_7$)cycloalkyl, —(C$_3$-C$_8$)-cycloalkenyl, —(C$_1$-C$_6$)alkylhalo, —(C$_0$-C$_3$)alkyl-O—(C$_1$-C$_6$)alkyl, —(C$_0$-C$_3$)alkyl-O—(C$_2$-C$_6$)alkynyl, —(C$_0$-C$_3$)alkyl-O—(C$_2$-C$_6$)alkenyl, —(C$_0$-C$_3$)alkyl-O—(C$_3$-C$_7$)cycloalkyl, —(C$_0$-C$_3$)alkyl-O—(C$_4$-C$_{10}$)alkylcycloalkyl, —(C$_0$-C$_3$) alkyl-O—(C$_1$-C$_6$)alkylhalo, —S—(C$_1$-C$_6$)alkyl, —S—(C$_2$-C$_6$)alkynyl, —S—(C$_2$-C$_6$)alkenyl, —S—(C$_3$-C$_7$)cycloalkyl, —S—(C$_4$-C$_{10}$)-alkylcycloalkyl, —(C$_0$-C$_3$)alkyl-NR$^{18}$R$^{19}$, —(C$_0$-C$_3$)alkyl-S(O)$_2$NR$^{18}$R$^{19}$, —(C$_0$-C$_3$)alkyl-NR$^{18}$S(O)$_2$R$^{19}$, —(C$_0$-C$_3$)alkyl-C(=O)R$^{18}$, —(C$_0$-C$_3$) alkyl-C(=O)OR$^{18}$, —(C$_0$-C$_3$)alkyl-C(=O)NR$^{18}$R$^{19}$, —(C$_0$-C$_3$)alkyl-NR$^{18}$C(=O)R$^{19}$, —O—(C$_0$-C$_3$)alkyl-S(O)$_2$NR$^{18}$R$^{19}$, —O—(C$_0$-C$_3$)alkyl-NR$^{18}$S(O)$_2$R$^{19}$, —O—(C$_0$-C$_3$)alkyl-C(=O)R$^{18}$, —O—(C$_0$-C$_3$)alkyl-C(=O)OR$^{18}$, —O—(C$_0$-C$_3$)alkyl-C(=O)NR$^{18}$R$^{19}$ and —O—(C$_0$-C$_3$) alkyl-NR$^{18}$C(=O)R$^{19}$.

In a third preferred aspect of Formula (I), the invention provides a compound according to Formula (IV)

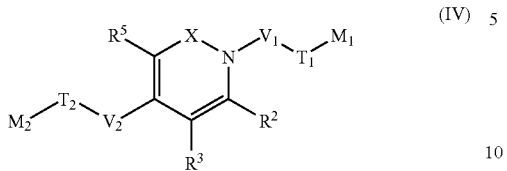

(IV)

a pharmaceutically acceptable acid or base addition salt thereof, a stereochemically isomeric form thereof and an N-oxide form thereof, wherein:

X is selected from C(=O) and S(O)$_2$;

$R^2$, $R^3$ and $R^5$ are each independently selected from the group of hydrogen, halogen, —CN, —OH, —NO$_2$, —CF$_3$, —SH, —NH$_2$, and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_1$-C$_6$)alkylcyano, —O—(C$_1$-C$_6$)alkyl, —O—(C$_1$-C$_6$)alkylhalo, —O—(C$_1$-C$_6$)-alkylcyano, —O—(C$_3$-C$_6$)alkynyl, —O—(C$_3$-C$_7$)cycloalkyl, —O—(C$_2$-C$_6$)alkenyl, —O—(C$_2$-C$_6$)-alkyl-OR$^{18}$, —O—(C$_1$-C$_6$)alkyl-heteroaryl, —O—(C$_0$-C$_6$)alkylaryl, —(C$_0$-C$_6$)alkyl-OR$^{18}$—(C$_3$-C$_7$)cycloalkyl-(C$_1$-C$_6$)alkyl, —O—(C$_3$-C$_7$)cycloalkyl-(C$_1$-C$_6$)alkyl, —O-heteroaryl, heteroaryl, —(C$_1$-C$_6$)alkyl-heteroaryl, aryl, —O-aryl, —(C$_1$-C$_6$)alkylaryl, —(C$_1$-C$_6$)alkylhalo-OR$^{18}$, —(C$_3$-C$_6$)alkynyl-OR$^{18}$, —(C$_3$-C$_6$)alkenyl-OR$^{18}$, —(C$_0$-C$_6$)alkyl-SR$^{18}$, —O—(C$_2$-C$_6$)-alkyl-SR$^{18}$, —(C$_1$-C$_6$)alkyl-S(=O)R$^{18}$, —O—(C$_1$-C$_6$)alkyl-S(=O)R$^{18}$, —(C$_0$-C$_6$)alkyl-S(=O)$_2$R$^{18}$, —O—(C$_1$-C$_6$)alkyl-S(=O)$_2$R$^{18}$, —(C$_0$-C$_6$)alkyl-NR$^{18}$R$^{19}$, —(C$_0$-C$_3$)alkyl-O—(C$_2$-C$_6$)alkyl-NR$^{18}$R$^{19}$, —(C$_0$-C$_6$)alkyl-S(=O)$_2$NR$^{18}$R$^{19}$, —(C$_0$-C$_6$)alkyl-NR$^{18}$—S(=O)$_2$R$^{19}$, —(C$_0$-C$_3$)alkyl-O—(C$_1$-C$_6$)alkyl-S(=O)$_2$NR$^{18}$R$^{19}$, —(C$_0$-C$_3$)alkyl-O—(C$_1$-C$_6$)alkyl-NR$^{18}$—S(=O)$_2$R$^{19}$, —(C$_0$-C$_6$)alkyl-C(=O)—NR$^{18}$R$^{19}$, —(C$_0$-C$_6$)alkyl-NR$^{18}$C(=O)—R$^{19}$, —(C$_0$-C$_3$)-alkyl-O—(C$_1$-C$_6$)alkylC(=O)—NR$^{18}$R$^{19}$, —(C$_0$-C$_3$)alkyl-O—(C$_1$-C$_6$)alkyl-NR$^{18}$C(=O)—R$^{19}$, —(C$_0$-C$_6$)alkyl-OC(=O)—R$^{18}$, —(C$_0$-C$_6$)alkyl-C(=O)—OR$^{18}$, —O—(C$_1$-C$_6$)alkyl-OC(=O)—R$^{18}$, —O—(C$_1$-C$_6$)alkyl-C(=O)—OR$^{18}$, —(C$_0$-C$_6$)alkyl-C(=O)—R$^{18}$, —O—(C$_1$-C$_6$)alkyl-C(=O)—R$^{18}$, —(C$_0$-C$_6$)alkyl-NR$^{18}$—C(=O)—OR$^{19}$, —(C$_0$-C$_6$)alkyl-O—C(=O)—NR$^{18}$R$^{19}$, —(C$_0$-C$_6$)alkyl-NR$^{18}$—C(=NR$^{19}$)—NR$^{20}$R$^{21}$, —(C$_0$-C$_6$)alkyl-NR$^{18}$—C(=O)—NR$^{19}$R$^{20}$ and —(C$_0$-C$_6$)alkyl-NR$^{18}$—C(=S)—NR$^{19}$R$^{20}$;

$R^{18}$, $R^{19}$, $R^{20}$ and $R^{21}$ are each independently selected from hydrogen and an optionally substituted radical selected from the group of —(C$_1$-C$_6$)alkylhalo, —(C$_1$-C$_6$)alkyl, —(C$_1$-C$_6$)alkylcyano, —(C$_2$-C$_6$)alkynyl, —(C$_2$-C$_6$)alkenyl, —(C$_3$-C$_7$)cycloalkyl, —(C$_4$-C$_{10}$)-alkylcycloalkyl, heteroaryl, —(C$_1$-C$_6$)alkylheteroaryl, aryl, —(C$_1$-C$_6$)alkylaryl, —(C$_2$-C$_6$)-alkynyl-(C$_3$-C$_7$)cycloalkyl, —(C$_2$-C$_6$)alkynyl-heteroaryl, —(C$_2$-C$_6$)alkynyl-aryl, —(C$_2$-C$_6$)alkenyl-(C$_3$-C$_7$)cycloalkyl, —(C$_2$-C$_6$)alkenyl-heteroaryl and —(C$_2$-C$_6$)alkenyl-aryl; and $R^{18}$, $R^{19}$, $R^{20}$ and $R^{21}$ may be taken together to form an optionally substituted 3 to 10 membered non-aromatic heterocyclic ring or an optionally substituted 5 to 10 membered aromatic heterocyclic ring.

In a fourth preferred aspect of Formula (I), the invention provides a compound of Formula (V)

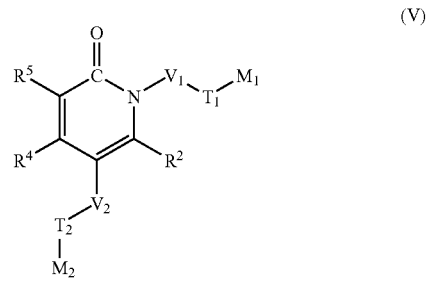

(V)

a pharmaceutically acceptable acid or base addition salt thereof, a stereochemically isomeric form thereof and an N-oxide form thereof, wherein:

$R^2$, $R^4$ and $R^5$ are each independently selected from the group of hydrogen, halogen, —CN, —OH, —NO$_2$, —CF$_3$, —SH, —NH$_2$, and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_1$-C$_6$)alkylcyano, —O—(C$_1$-C$_6$)alkyl, —O—(C$_1$-C$_6$)alkylhalo, —O—(C$_1$-C$_6$)-alkylcyano, —O—(C$_3$-C$_6$)alkynyl, —O—(C$_3$-C$_7$)cycloalkyl, —O—(C$_2$-C$_6$)alkenyl, —O—(C$_2$-C$_6$)alkyl-OR$^{18}$, —O—(C$_1$-C$_6$)alkyl-heteroaryl, —O—(C$_0$-C$_6$)alkylaryl, —(C$_0$-C$_6$)alkyl-OR$^{18}$, —(C$_3$-C$_7$)cycloalkyl-(C$_1$-C$_6$)alkyl, —O—(C$_3$-C$_7$)cycloalkyl-(C$_1$-C$_6$)alkyl, —O-heteroaryl, heteroaryl, —(C$_1$-C$_6$)alkyl-heteroaryl, aryl, —O-aryl, —(C$_1$-C$_6$)alkylaryl, —(C$_1$-C$_6$)alkylhalo-OR$^{18}$, —(C$_3$-C$_6$)alkynyl-OR$^{18}$, —(C$_3$-C$_6$)alkenyl-OR$^{18}$, —(C$_0$-C$_6$)alkyl-SR$^{18}$, —O—(C$_2$-C$_6$)-alkyl-SR$^{18}$, —(C$_1$-C$_6$)alkyl-S(=O)R$^{18}$, —O—(C$_1$-C$_6$)alkyl-S(=O)R$^{18}$, —(C$_0$-C$_6$)alkyl-S(=O)$_2$R$^{18}$, —O—(C$_1$-C$_6$)alkyl-S(=O)$_2$R$^{18}$, —(C$_0$-C$_6$)alkyl-NR$^{18}$R$^{19}$, —(C$_0$-C$_3$)alkyl-O—(C$_2$-C$_6$)alkyl-NR$^{18}$R$^{19}$, —(C$_0$-C$_6$)alkyl-S(=O)$_2$NR$^{18}$R$^{19}$, —(C$_0$-C$_6$)alkyl-NR$^{18}$—S(=O)$_2$R$^{19}$, —(C$_0$-C$_3$)alkyl-O—(C$_1$-C$_6$)alkyl-S(=O)$_2$NR$^{18}$R$^{19}$, —(C$_0$-C$_3$)alkyl-O—(C$_1$-C$_6$)alkyl-NR$^{18}$—S(=O)$_2$R$^{19}$, —(C$_0$-C$_6$)alkyl-C(=O)—NR$^{18}$R$^{19}$, —(C$_0$-C$_6$)alkyl-NR$^{18}$C(=O)—R$^{19}$, —(C$_0$-C$_3$)alkyl-O—(C$_1$-C$_6$)alkylC(=O)—NR$^{18}$R$^{19}$, —(C$_0$-C$_3$)alkyl-O—(C$_1$-C$_6$)alkyl-NR$^{18}$C(=O)—R$^{19}$, —(C$_0$-C$_6$)alkyl-OC(=O)—R$^{18}$, —(C$_0$-C$_6$)alkyl-C(=O)—OR$^{18}$, —O—(C$_1$-C$_6$)alkyl-OC(=O)—R$^{18}$, —O—(C$_1$-C$_6$)alkyl-C(=O)—OR$^{18}$, —(C$_0$-C$_6$)alkyl-C(=O)—R$^{18}$, —O—(C$_1$-C$_6$)alkyl-C(=O)—R$^{18}$, —(C$_0$-C$_6$)alkyl-NR$^{18}$—C(=O)—OR$^{19}$, —(C$_0$-C$_6$)alkyl-O—C(=O)—NR$^{18}$R$^{19}$, —(C$_0$-C$_6$)alkyl-NR$^{18}$—C(=NR$^{19}$)—NR$^{20}$R$^{21}$, —(C$_0$-C$_6$)alkyl-NR$^{18}$—C(=O)—NR$^{19}$R$^{20}$ and —(C$_0$-C$_6$)alkyl-NR$^{18}$—C(=S)—NR$^{19}$R$^{20}$;

$R^{18}$, $R^{19}$, $R^{20}$ and $R^{21}$ are each independently selected from hydrogen and an optionally substituted radical selected from the group of —(C$_1$-C$_6$)alkylhalo, —(C$_1$-C$_6$)alkyl, —(C$_1$-C$_6$)alkylcyano, —(C$_2$-C$_6$)alkynyl, —(C$_2$-C$_6$)alkenyl, —(C$_3$-C$_7$)cycloalkyl, —(C$_4$-C$_{10}$)-alkylcycloalkyl, heteroaryl, —(C$_1$-C$_6$)alkylheteroaryl, aryl, —(C$_1$-C$_6$)alkylaryl, —(C$_2$-C$_6$)-alkynyl-(C$_3$-C$_7$)cycloalkyl, —(C$_2$-C$_6$)alkynyl-heteroaryl, —(C$_2$-C$_6$)alkynyl-aryl, —(C$_2$-C$_6$)-alkenyl-(C$_3$-C$_7$)cycloalkyl, —(C$_2$-C$_6$)alkenyl-heteroaryl and —(C$_2$-C$_6$)alkenyl-aryl; and $R^{18}$, $R^{19}$, $R^{20}$ and $R^{21}$ may be taken together to form an optionally substituted 3 to 10 membered non-aromatic heterocyclic ring or an optionally substituted 5 to 10 membered aromatic heterocyclic ring.

In a further preferred aspect of Formula (V), the invention provides a compound according to Formula (V-a),

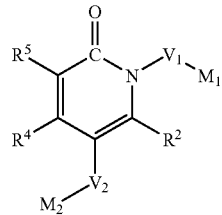

(V-a)

a pharmaceutically acceptable acid or base addition salt thereof, a stereochemically isomeric form thereof and an N-oxide form thereof, wherein:

$V_1$ is not a covalent bond;

$V_2$ is selected from the group of a covalent bond, —O—, —C(=O)—, —C(=O)O—, —C(=O)NR$^{10}$—, —S—, —S(O)—, —S(O)$_2$—, —S(O)$_2$NR$^{10}$—, —NR$^{10}$—, —NR$^{10}$C(=O)—, —NR$^{10}$C(=O)NR$^{11}$—, —NR$^{10}$S(O)$_2$—, —NR$^{10}$C(=S)NR$^{11}$—, —OC(=O)—, —OC(=O)NR$^{10}$, —NR$^{10}$C(=O)O—, and an optionally substituted radical selected from the group of —(C$_1$-C$_6$)alkyl, —(C$_2$-C$_6$)alkynyl, —(C$_2$-C$_6$)alkenyl, —(C$_3$-C$_7$)cycloalkyl, —(C$_3$-C$_8$)-cycloalkenyl, —(C$_1$-C$_6$)alkylhalo, —O—(C$_1$-C$_6$)alkyl, —O—(C$_2$-C$_6$)alkynyl, —O—(C$_2$-C$_6$)-alkenyl, —O—(C$_3$-C$_7$)cycloalkyl, —O—(C$_4$-C$_{10}$)alkylcycloalkyl, —C(=O)—(C$_1$-C$_6$)alkyl, —C(=O)—(C$_2$-C$_6$)alkynyl, —C(=O)—(C$_2$-C$_6$)alkenyl, —C(=O)—(C$_3$-C$_7$)alkylcycloalkyl, —C(=O)—(C$_4$-C$_{10}$)cycloalkyl, —C(=O)O—(C$_1$-C$_6$)alkyl, —C(=O)O—(C$_2$-C$_6$)alkynyl, —C(=O)O—(C$_2$-C$_6$)alkenyl, —C(=O)O—(C$_3$-C$_7$)cycloalkyl, —C(=O)O—(C$_4$-C$_{10}$)-alkylcycloalkyl, —C(=O)NR$^{10}$—(C$_1$-C$_6$)alkyl, —C(=O)NR$^{10}$—(C$_2$-C$_6$)alkynyl, —C(=O)NR$^{10}$—(C$_2$-C$_6$)alkenyl, —C(=O)NR$^{10}$—(C$_3$-C$_7$)cycloalkyl, —C(=O)NR$^{10}$—(C$_4$-C$_{10}$)-alkylcycloalkyl, —S—(C$_1$-C$_6$)alkyl, —S—(C$_2$-C$_6$)alkynyl, —S—(C$_2$-C$_6$)alkenyl, —S—(C$_3$-C$_7$)cycloalkyl, —S—(C$_4$-C$_{10}$)alkylcycloalkyl, —S(O)—(C$_1$-C$_6$)alkyl, —O—(C$_2$-C$_6$)alkynyl, —S(O)—(C$_2$-C$_6$)alkenyl, —S(O)—(C$_3$-C$_7$)cycloalkyl, —S(O)—(C$_4$-C$_{10}$)alkylcycloalkyl, —S(O)$_2$—(C$_1$-C$_6$)alkyl, —S(O)$_2$—(C$_2$-C$_6$)alkynyl, —S(O)$_2$—(C$_2$-C$_6$)alkenyl, —S(O)$_2$—(C$_3$-C$_7$)cycloalkyl, —S(O)$_2$—(C$_4$-C$_{10}$)alkylcycloalkyl, —S(O)$_2$NR$^{10}$—(C$_1$-C$_6$)alkyl, —S(O)$_2$NR$^{10}$—(C$_2$-C$_6$)alkynyl, —S(O)$_2$NR$^{10}$—(C$_2$-C$_6$)alkenyl, —S(O)$_2$NR$^{10}$—(C$_3$-C$_7$)cycloalkyl, —S(O)$_2$NR$^{10}$—(C$_4$-C$_{10}$)alkylcycloalkyl, —NR$^{10}$—(C$_1$-C$_6$)alkyl, —NR$^{10}$—(C$_2$-C$_6$)alkynyl, —NR$^{10}$—(C$_2$-C$_6$)alkenyl, —NR$^{10}$—(C$_3$-C$_7$)cycloalkyl, —NR$^{10}$—(C$_4$-C$_{10}$)alkylcycloalkyl, —NR$^{10}$C(=O)—(C$_1$-C$_6$)alkyl, —NR$^{10}$C(=O)—(C$_2$-C$_6$)alkynyl, —NR$^{10}$C(=O)—(C$_2$-C$_6$)alkenyl, —NR$^{10}$C(=O)—(C$_3$-C$_7$)cycloalkyl, —NR$^{10}$C(=O)—(C$_4$-C$_{10}$)alkylcycloalkyl, —NR$^{10}$C(=O)NR$^{11}$(C$_1$-C$_6$)-alkyl, —NR$^{10}$C(=O)NR$^{11}$—(C$_2$-C$_6$)alkynyl, —NR$^{10}$C(=O)NR$^{11}$—(C$_2$-C$_6$)alkenyl, —NR$^{10}$C(=O)NR$^{11}$—(C$_3$-C$_7$)cycloalkyl, —NR$^{10}$C(=O)NR$^{11}$—(C$_4$-C$_{10}$)alkylcycloalkyl, —NR$^{10}$S(O)$_2$—(C$_1$-C$_6$)alkyl, —NR$^{10}$S(O)$_2$—(C$_2$-C$_6$)alkynyl, —NR$^{10}$S(O)$_2$—(C$_2$-C$_6$)alkenyl, —NR$^{10}$S(O)$_2$—(C$_3$-C$_7$)cycloalkyl, —NR$^{10}$S(O)$_2$—(C$_4$-C$_{10}$)alkylcycloalkyl, —NR$^{10}$C(=S)NR$^{11}$—(C$_1$-C$_6$)alkyl, —NR$^{10}$C(=S)NR$^{11}$—(C$_2$-C$_6$)alkynyl, —NR$^{10}$C(=S)NR$^{11}$—(C$_2$-C$_6$)alkenyl, —NR$^{10}$C(=S)NR$^{11}$—(C$_3$-C$_7$)cycloalkyl, —NR$^{10}$C(=S)NR$^{11}$—(C$_4$-C$_{10}$)alkylcycloalkyl, —OC(=O)—(C$_1$-C$_6$)alkyl, —OC(=O)—(C$_2$-C$_6$)alkynyl, —OC(=O)—(C$_2$-C$_6$)alkenyl, —OC(=O)—(C$_4$-C$_{10}$)alkylcycloalkyl, —OC(=O)—(C$_3$-C$_7$)cycloalkyl, —OC(=O)NR$^{10}$—(C$_1$-C$_6$)alkyl, —OC(=O)NR$^{10}$—(C$_2$-C$_6$)alkynyl, —OC(=O)NR$^{10}$—(C$_2$-C$_6$)alkenyl, —OC(=O)NR$^{10}$—(C$_4$-C$_{10}$)-alkylcycloalkyl, —OC(=O)NR$^{10}$—(C$_3$-C$_7$)cycloalkyl, —NR$^{10}$C(=O)O—(C$_1$-C$_6$)alkyl, —NR$^{10}$C(=O)O—(C$_2$-C$_6$)alkynyl, —NR$^{10}$C(=O)O—(C$_2$-C$_6$)alkenyl, —NR$^{10}$C(=O)O—(C$_3$-C$_7$)-cycloalkyl, —NR$^{10}$C(=O)O—(C$_4$-C$_{10}$)alkylcycloalkyl, —NR$^{10}$C(=NR$^{11}$)NR$^{12}$—(C$_1$-C$_6$)alkyl, —NR$^{10}$C(=NR$^{11}$)NR$^{12}$—(C$_2$-C$_6$)alkynyl, —NR$^{10c}$(=NR$^{11}$)NR$^{12}$—(C$_2$-C$_6$)alkenyl, —NR$^{10}$C(=NR$^{11}$)NR$^{12}$—(C$_3$-C$_7$)cycloalkyl, —NR$^{10}$C(=NR$^{11}$)NR$^{12}$—(C$_4$-C$_{10}$)alkylcycloalkyl, —NR$^{10}$C(=NR$^{11}$)—(C$_1$-C$_6$)alkyl, —NR$^{10}$C(=NR$^{11}$)—(C$_2$-C$_6$)alkynyl, —NR$^{10}$C(=NR$^{11}$)—(C$_2$-C$_6$)alkenyl, —NR$^{10}$C(=NR$^{11}$)—(C$_3$-C$_7$)cycloalkyl, —NR$^{10}$C(=NR$^{11}$)—(C$_4$-C$_{10}$)alkylcycloalkyl, —C(=NR$^{10}$)NR$^{11}$—(C$_1$-C$_6$)alkyl, —C(=NR$^{10}$)NR$^{11}$—(C$_2$-C$_6$)alkynyl, —C(=NR$^{10}$)NR$^{11}$—(C$_2$-C$_6$)alkenyl, —C(=NR$^{10}$)NR$^{11}$—(C$_3$-C$_7$)cycloalkyl and —C(=NR$^{10}$)NR$^{11}$—(C$_4$-C$_{10}$)alkylcycloalkyl; and $R^2$, $R^4$ and $R^5$ are each independently selected from the group of hydrogen, halogen, —CN, —OH, —NO$_2$, —CF$_3$, —SH, —NH$_2$, and an optionally substituted radical selected from the group of —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl, —(C$_1$-C$_6$)alkylcyano, —O—(C$_1$-C$_6$)alkyl, —O—(C$_1$-C$_6$)alkylhalo, —O—(C$_1$-C$_6$)-alkylcyano, —O—(C$_3$-C$_6$)alkynyl, —O—(C$_3$-C$_7$)cycloalkyl, —O—(C$_2$-C$_6$)alkenyl, —O—(C$_2$-C$_6$)-alkyl-OR$^{18}$, —O—(C$_1$-C$_6$)alkyl-heteroaryl, —O—(C$_0$-C$_6$)alkylaryl, —(C$_0$-C$_6$)alkyl-OR$^{18}$, —(C$_3$-C$_7$)cycloalkyl-(C$_1$-C$_6$)alkyl, —O—(C$_3$-C$_7$)cycloalkyl-(C$_1$-C$_6$)alkyl, —O-heteroaryl, —(C$_1$-C$_6$)alkyl-heteroaryl, —O-aryl, —(C$_1$-C$_6$)alkylaryl, —(C$_1$-C$_6$)alkylhalo-OR$^{18}$, —(C$_3$-C$_6$)-alkynyl-OR$^{18}$, —(C$_3$-C$_6$)alkenyl-OR$^{18}$, —(C$_0$-C$_6$)alkyl-SR$^{18}$, —O—(C$_2$-C$_6$)alkyl-SR$^{18}$, —(C$_1$-C$_6$)alkyl-S(=O)R$^{18}$, —O—(C$_1$-C$_6$)alkyl-S(=O)R$^{18}$, —(C$_0$-C$_6$)alkyl-S(=O)$_2$R$^{18}$, —O—(C$_1$-C$_6$)-alkyl-S(=O)$_2$R$^{18}$—(C$_0$-C$_6$)alkyl-NR$^{18}$R$^{19}$, —(C$_0$-C$_3$)alkyl-O—(C$_2$-C$_6$)alkyl-NR$^{18}$R$^{19}$, —(C$_0$-C$_6$)alkyl-S(=O)$_2$NR$^{18}$R$^{19}$, —(C$_0$-C$_6$)alkyl-NR$^{18}$—S(=O)$_2$R$^{19}$, —(C$_0$-C$_3$)alkyl-O—(C$_1$-C$_6$)alkyl-S(=O)$_2$NR$^{18}$R$^{19}$, —(C$_0$-C$_3$)alkyl-O—(C$_1$-C$_6$)alkyl-NR$^{18}$—S(=O)$_2$R$^{19}$, —(C$_0$-C$_6$)alkyl-C(=O)—NR$^{18}$R$^{19}$, —(C$_0$-C$_6$)alkyl-NR$^{18}$C(=O)—R$^{19}$, —(C$_0$-C$_3$)alkyl-O—(C$_1$-C$_6$)alkylC(=O)—NR$^{18}$R$^{19}$, —(C$_0$-C$_3$)alkyl-O—(C$_1$-C$_6$)alkyl-NR$^{18}$C(=O)—R$^{19}$, —(C$_0$-C$_6$)alkyl-OC(=O)—R$^{18}$, —(C$_0$-C$_6$)-alkyl-C(=O)—OR$^{18}$, —O—(C$_1$-C$_6$)alkyl-OC(=O)—R$^{18}$, —O—(C$_1$-C$_6$)alkyl-C(=O)—OR$^{18}$, —(C$_0$-C$_6$)alkyl-C(=O)—R$^{18}$ and —O—(C$_1$-C$_6$)alkyl-C(=O)—R$^{18}$.

In a further preferred aspect of Formula (V-a), the invention provides a compound according to Formula (V-a), wherein:

$V_2$ is selected from the group of a covalent bond, —O—, —C(=O)—, —C(=O)O—, —C(=O)NR$^{10}$—, —S—, —S(O)—, —S(O)$_2$—, —S(O)$_2$NR$^{10}$—, —NR$^{10}$—, —NR$^{10}$C(=O)—, —NR$^{10}$C(=O)NR$^{11}$—, —NR$^{10}$S(O)$_2$—, —NR$^{10}$C(=S)NR$^{11}$—, and an optionally substituted radical selected from the group of —(C$_1$-C$_6$)alkyl, —(C$_2$-C$_6$)alkynyl, —(C$_2$-C$_6$)alkenyl, —(C$_3$-C$_7$)cycloalkyl, —(C$_3$-C$_8$)cycloalkenyl, —(C$_1$-C$_6$)alkylhalo, —O—(C$_1$-C$_6$)alkyl, —O—(C$_3$-C$_7$)cycloalkyl, —C(=O)—(C$_1$-C$_6$)alkyl, —C(=O)—(C$_4$-C$_{10}$)cycloalkyl, —C(=O)O—(C$_1$-C$_6$)-alkyl, —C(=O)O—(C$_3$-C$_7$)cycloalkyl, —C(=O)NR$^{10}$—(C$_1$-C$_6$)alkyl, —C(=O)NR$^{10}$—(C$_3$-C$_7$)-cycloalkyl, —S—(C$_1$-C$_6$)alkyl, —S—(C$_3$-C$_7$)cycloalkyl, —S(O)—(C$_1$-C$_6$)alkyl, —S(O)—(C$_3$-C$_7$)-cycloalkyl, —S(O)$_2$—(C$_1$-C$_6$)alkyl, —S(O)$_2$—(C$_3$-C$_7$)cycloalkyl, —S(O)$_2$NR$^{10}$—(C$_1$-C$_6$)alkyl, —S(O)$_2$NR$^{10}$—(C$_3$-C$_7$)cycloalkyl, —NR$^{10}$—(C$_1$-C$_6$)alkyl, —(C$_3$-C$_7$)cycloalkyl, —NR$^{10}$C(=O)—(C$_1$-C$_6$)alkyl, —NR$^{10}$C(=O)—(C$_3$-C$_7$)cycloalkyl, —NR$^{10}$C(=O) NR$^{11}$—(C$_1$-C$_6$)alkyl, —NR$^{10}$C(=O)NR$^{11}$—(C$_3$-C$_7$)cycloalkyl, —NR$^{10}$S(O)$_2$—(C$_1$-C$_6$)alkyl and —NR$^{10}$S(O)$_2$—(C$_3$-C$_7$)cycloalkyl.

In a further preferred aspect of Formula (V-a), the invention provides a compound of Formula (V-b)

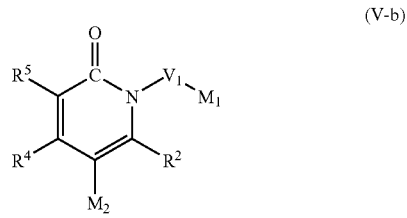
(V-b)

a pharmaceutically acceptable acid or base addition salt thereof, a stereochemically isomeric form thereof and an N-oxide form thereof, wherein:

$V_1$ is an optionally substituted radical selected from the group of —(C$_1$-C$_6$)alkyl, —(C$_2$-C$_6$)alkynyl, —(C$_2$-C$_6$)alkenyl, —(C$_3$-C$_7$)cycloalkyl, —(C$_1$-C$_6$)alkylhalo, —(C$_1$-C$_6$)alkyl-C(=O)—(C$_0$-C$_6$)alkyl, —(C$_1$-C$_6$)alkyl-C(=O)NR$^7$—(C$_0$-C$_6$)alkyl, —(C$_1$-C$_6$)alkyl-O—(C$_0$-C$_6$)-alkyl, —(C$_0$-C$_6$)alkyl-S(O)$_2$—(C$_0$-C$_6$)alkyl, —(C$_1$-C$_6$)alkyl-S(O)$_2$NR$^7$—(C$_0$-C$_6$)alkyl, —(C$_1$-C$_6$)alkyl-NR$^7$—(C$_0$-C$_6$)alkyl, —(C$_1$-C$_6$)alkyl-NR$^7$C(=O)—(C$_0$-C$_6$)alkyl and —(C$_1$-C$_6$)alkyl-NR$^7$S(O)$_2$—(C$_0$-C$_6$)alkyl;

R$^7$ is a radical selected from the group of hydrogen, —(C$_1$-C$_6$)alkyl, —(C$_1$-C$_6$)alkylhalo, —(C$_2$-C$_6$)alkynyl, —(C$_2$-C$_6$)alkenyl, —(C$_3$-C$_7$)cycloalkyl or —(C$_1$-C$_6$)alkylcyano; and M$_1$ and M$_2$ are each independently hydrogen or an optionally substituted radical selected from the group of aryl, heteroaryl and (C$_3$-C$_7$)cycloalkyl.

In a further preferred aspect of Formula (V-b), the invention provides a compound according to Formula (V-b) wherein:

V$_1$ is —(C$_1$-C$_6$)alkyl, optionally substituted by one or more —OCH$_3$, —OCF$_3$, —CF$_3$, fluoro or cyano radicals; and M$_1$ and M$_2$ are each independently an optionally substituted radical selected from hydrogen, aryl, thienyl, pyridyl, thiazolyl, isothiazolyl, oxazolyl, isoxazolyl, benzoimidazolyl, benzooxazolyl, benzothiazolyl, thionaphtyl, indolyl, pyrimidinyl, quinolyl, cyclohexyl and cyclopentyl.

Most preferably, the invention relates to compounds according to Formula (I), a pharmaceutically acceptable acid or base addition salt thereof, a stereochemically isomeric form thereof and an N-oxide form thereof, wherein:

X is C(=O);
Y is selected from —C(R$^4$)=C(R$^5$)—, —C(R$^5$)=N— and —N=C(R$^5$)—;
R$^1$ is an optionally substituted radical selected from the group of —(C$_1$-C$_6$)alkyl, —(C$_1$-C$_6$)alkylhalo and a radical —V$_1$-T$_1$-M$_1$;
T$_1$, V$_1$ are each independently a covalent bond or an optionally substituted radical, preferably substituted with hydroxy, halo and halo(C$_1$-C$_6$)alkyl, selected from the group of —(C$_1$-C$_6$)alkyl-; —(C$_2$-C$_6$)alkenyl-, —(C$_2$-C$_6$)alkynyl-; —(C$_1$-C$_6$)alkyl-C(=O)—(C$_0$-C$_6$)alkyl-; —(C$_1$-C$_6$)alkyl-C(=O)NR$^7$—(C$_0$-C$_6$)alkyl- wherein R$^7$ is hydrogen or —(C$_1$-C$_6$)-alkyl-; and —(C$_1$-C$_6$)alkyl-O—(C$_0$-C$_6$)alkyl-;
R$^2$, R$^3$, R$^4$ and R$^5$ are each independently selected from the group of hydrogen, halogen, —CN, —NO$_2$, —C(=O)OR$^{10}$, —OR$^{10}$, and an optionally substituted radical, preferably substituted with hydroxy, selected from the group of —(C$_1$-C$_6$)alkyl and a radical —V$_2$-T$_2$-M$_2$;

T$_2$, V$_2$ are each independently a covalent bond or a radical selected from the group of —O—; —C(=O)—; —NR$^{10}$— and an optionally substituted radical, preferably substituted with hydroxy, selected from the group of —(C$_1$-C$_6$)alkyl-; —(C$_2$-C$_6$)alkenyl-; —(C$_2$-C$_6$)alkynyl-; —(C$_0$-C$_6$)alkyl-O—(C$_1$-C$_6$)alkyl-; and —(C$_0$-C$_6$)alkyl-NR$^{10}$—(C$_1$-C$_6$)alkyl- wherein R$^{10}$ is preferably hydrogen or (C$_1$-C$_6$)alkyl;

(R$^2$ and R$^3$) or (R$^4$ and R$^5$) taken together may form an aryl optionally substituted with n radicals A″ equal to —V$_2$-M$_2$;

M$_1$ and M$_2$ are each independently selected from the group of hydrogen, an optionally substituted —(C$_1$-C$_6$)alkyl-radical and an optionally substituted 3 to 10 membered ring selected from the group of (C$_{1-6}$)cycloalkyl; aryl, preferably phenyl or naphthyl; heteroaryl and heterocyclic, preferably pyridinyl, indolyl, imidazolyl, oxadiazolyl, isoxazolyl, furyl, thienyl, thiazolyl, benzothiazolyl, pyridinyl, pyrimidinyl, indolyl, quinolinyl, quinoxalinyl, benzoxazolyl, benzodioxolyl, benzotetrahydrofuryl and benzothienyl; wherein the optional substitution on any of the aforementioned rings is selected from the group of (C$_1$-C$_6$)alkyl; (C$_1$-C$_6$)alkyloxy; hydroxy (C$_1$-C$_6$)alkyloxy; (C$_1$-C$_6$)alkyloxy(C$_1$-C$_6$)alkyl; (C$_1$-C$_6$)alkyloxy(C$_1$-C$_6$)alkyloxy; (C$_1$-C$_6$)alkyloxycarbonyl; (C$_1$-C$_6$)alkyloxycarbonyl(C$_1$-C$_6$)alkyl; (C$_1$-C$_6$)alkyloxycarbonyloxy; (C$_1$-C$_6$)alkyloxycarbonyl(C$_1$-C$_6$)alkyloxy; (C$_1$-C$_6$)alkylcarbonyl; (C$_1$-C$_6$)alkylcarbonyl(C$_1$-C$_6$)alkyloxy; (C$_1$-C$_6$)alkylcarbonyloxy; (C$_1$-C$_6$)alkylthieno; (C$_1$-C$_6$)alkylsulfonyl; heterocyclic-sulfonyl, preferably morpholinylsulfonyl and pyrrolidinylsulfonyl; (C$_1$-C$_6$)alkylsulfonylamino; (C$_1$-C$_6$)alkenyl; aryl, preferably phenyl; carboxyl(C$_1$-C$_6$)alkyl; carbonyl(C$_1$-C$_6$)alkyloxy; halo, preferably fluoro and chloro; hydroxy; hydroxy(C$_1$-C$_6$)alkyl; phenyl(C$_1$-C$_6$)alkyloxy; cyano; cyano(C$_1$-C$_6$)alkyloxy; trifluoro(C$_1$-C$_6$)alkyl; trifluoro(C$_1$-C$_6$)alkyloxy; amino; amino (C$_1$-C$_6$)alkyloxy; mono- and di((C$_1$-C$_6$)alkyl)amino; mono- and di((C$_1$-C$_6$)alkylcarbonyl)amino; mono- and di((C$_1$-C$_6$) alkyloxycarbonyl)amino; mono- and di((C$_1$-C$_6$)alkylcarbonyl)amino(C$_1$-C$_6$)alkyl; mono- and di((C$_1$-C$_6$)alkylsulfonyl) amino(C$_1$-C$_6$)alkyloxy; mono- and di((C$_1$-C$_6$)alkyl)amino (C$_1$-C$_6$)alkyloxy; mono- and di((C$_1$-C$_6$)alkylcarbonyl)amino (C$_1$-C$_6$)alkyloxy; mono- and di((C$_1$-C$_6$)alkyl) aminocarbonyl; mono- and di((C$_1$-C$_6$)alkyl)aminocarbonyl (C$_1$-C$_6$)alkyl; mono- and di((C$_1$-C$_6$)alkyl)aminocarbonyl (C$_1$-C$_6$)alkyloxo; mono- and di((C$_1$-C$_6$)alkyl)amino(C$_1$-C$_6$) alkylamino; nitro; tri(C$_1$-C$_6$)alkylsilyl; heterocyclic, preferably morpholinyl; heterocyclic-(C$_1$-C$_6$)alkyl, preferably (C$_1$-C$_6$)alkyltetrazolyl; and heterocyclic-(C$_1$-C$_6$)alkyloxy, the heterocyclic preferably being pyridinyl, morpholinyl, pyrrolidinyl, optionally substituted with oxo, isoxazolyl, imidazolyl, tetrazolyl or thiazolyl;

R$^7$, R$^8$, R$^9$, R$^{10}$, R$^{11}$, R$^{12}$, R$^{13}$, R$^{14}$, R$^{15}$, R$^{16}$, R$^{17}$ are each independently hydrogen or an optionally substituted —(C$_1$-C$_6$)alkyl-radical;

A″ is hydrogen or halo; and
n is an integer equal to 0 or 1.

Particular preferred compounds of the invention are compounds as mentioned in the following list (List of Particular Preferred Compounds), as well as a pharmaceutically acceptable acid or base addition salt thereof, a stereochemically isomeric form thereof and an N-oxide form thereof.

1-(4-methoxybenzyl)-2-oxo-4-phenyl-1,2-dihydropyridine-3-carbonitrile 1-(4-methylbenzyl)-2-oxo-4-phenyl-1,2-dihydropyridine-3-carbonitrile 1-(2-methylbenzyl)-2-oxo-4-(thiophen-2-yl)-1,2-dihydropyridine-3-carbonitrile 1-cinnamyl-2-oxo-4-(thiophen-2-yl)-1,2-dihydropyridine-3-carbonitrile
1-(2,4-difluorobenzyl)-5-(benzofuran-2-yl)pyridin-2(1H)-one
1-benzyl-5-(4-fluorophenyl)pyridin-2(1H)-one
1-(2,4-difluorobenzyl)-5-(4-fluorophenyl)pyridin-2(1H)-one
1-(3-chlorobenzyl)-5-(4-fluorophenyl)pyridin-2(1H)-one
1-benzyl-5-(4-methoxyphenyl)pyridin-2(1H)-one
1-(3-(trifluoromethyl)benzyl)-5-phenylpyridin-2(1H)-one
1-(4-methylbenzyl)-5-phenylpyridin-2(1H)-one
1-(2,4-difluorobenzyl)-5-(thiophen-2-yl)pyridin-2(1H)-one
1-benzyl-5-(4-chlorophenyl)pyridin-2(1H)-one
1-(3-(trifluoromethyl)-5-(4-chlorophenyl)pyridin-2 (1H)-one
1-(2,4-difluorobenzyl)-5-(4-chlorophenyl)pyridin-2(1H)-one
1-(2,4-dichlorobenzyl)-5-(4-methoxyphenyl)pyrimidin-2(1H)-one
1-(3-chlorobenzyl)-5-phenylpyridin-2(1H)-one
1-(3-chlorobenzyl)-5-(4-methoxyphenyl)pyridin-2(1H)-one
1-Benzyl-5-phenylpyridin-2(1H)-one
1-(2,4-difluorobenzyl)-5-phenylpyridin-2(1H)-one
1-Benzyl-5-(3-methoxyphenyl)pyridin-2(1H)-one
1-Benzyl-5-(3-chlorophenyl)pyridin-2(1H)-one
1-Benzyl-5-(4-cyanophenyl)pyridin-2(1H)-one
1-Benzyl-5-(3-nitrophenyl)pyridin-2(1H)-one
1-Benzyl-5-(2-fluorophenyl)pyridin-2(1H)-one
1-Benzyl-5-(3,4-dimethoxyphenyl)pyridin-2(1H)-one
1-Benzyl-5-(naphthalen-2-yl)pyridin-2(1H)-one
1-Benzyl-5-(2-methoxyphenyl)pyridin-2(1H)-one
1-Benzyl-5-m-tolylpyridin-2(1H)-one
1-Benzyl-5-(3-chloro-4-isopropoxyphenyl)pyridin-2(1H)-one
Ethyl-4-(1-benzyl-6-oxo-1,6-dihydropyridin-3-yl)benzoate
1-Benzyl-5-(2-fluoro-5-methoxyphenyl)pyridin-2(1H)-one
1-Benzyl-5-(4-tolyl)pyridin-2(1H)-one
1-Benzyl-5-(4-(trifluoromethoxy)phenyl)pyridin-2(1H)-one
1-Benzyl-5-(4-acetylphenyl)pyridin-2(1H)-one
2-(4-Fluorobenzyl)isoquinolin-1(2H)-one
1-(2-Fluorobenzyl)-5-(4-methoxyphenyl)pyridin-2(1H)-one
1-(4-Fluorobenzyl)-5-(4-methoxyphenyl)pyridin-2(1H)-one
1-(4-Nitrobenzyl)-5-(4-methoxyphenyl)pyridin-2(1H)-one
1-(3,4-Dichlorobenzyl)-5-(4-methoxyphenyl)pyridin-2(1H)-one
1-(3-Nitrobenzyl)-5-(4-methoxyphenyl)pyridin-2(1H)-one
1-(3-Methoxybenzyl)-5-(4-methoxyphenyl)pyridin-2(1H)-one
1-(Benzo[d]thiazol-2-ylmethyl)-5-(4-methoxyphenyl)pyridin-2(1H)-one
1-Benzyl-5-(4-isobutoxyphenyl)pyridin-2(1H)-one
1-Benzyl-5-(2-phenylethynyl)pyridin-2(1H)-one
1-Benzyl-5-(4-hydroxyphenyl)pyridin-2(1H)-one
1-(4-Methoxybenzyl)-5-(4-methoxyphenyl)pyridin-2(1H)-one
1-(4-Chlorobenzyl)-5-(4-methoxyphenyl)pyridin-2(1H)-one
3-((5-(4-Methoxyphenyl)-2-oxopyridin-1(2H)-yl)methyl)benzonitrile
1-(3-Fluorobenzyl)-5-(4-methoxyphenyl)pyridin-2(1H)-one
5-(4-Methoxyphenyl)-1-(1-phenylethyl)pyridin-2(1H)-one
5-(4-Methoxyphenyl)-1-(pyridin-3-ylmethyl)pyridin-2(1H)-one
1-Benzyl-5-(4-ethylphenyl)pyridin-2(1H)-one
1-Benzyl-5-(2,3-dihydro-1-benzofuran-5-yl)pyridin-2(1H)-one
1-Benzyl-5-(4-(dimethylamino)phenyl)pyridin-2(1H)-one
1-Benzyl-5-(3,4-dimethylphenyl)pyridin-2(1H)-one
1-Benzyl-5-(3,4-dichlorophenyl)pyridin-2(1H)-one
1-((3-(4-Fluorophenyl)-1,2,4-oxadiazol-5-yl)methyl)-5-(4-methoxyphenyl)pyridin-2(1H)-one
1-Benzyl-5-(4-tert-butylphenyl)pyridin-2(1H)-one
1-Benzyl-5-(indol-5-yl)pyridin-2(1H)-one
1-Benzyl-5-(4-propoxyphenyl)pyridin-2(1H)-one
1-Benzyl-5-(4-(trimethylsilyl)phenyl)pyridin-2(1H)-one
1-Benzyl-5-(3,5-difluorophenyl)pyridin-2(1H)-one
N-(4-Fluorobenzyl)-2-(5-(4-methoxyphenyl)-2-oxopyridin-1(2H)-yl)-N-methylacetamide
1-((5-Fluorobenzo[d]oxazol-2-yl)methyl)-5-(4-methoxyphenyl)pyridin-2(1H)-one
1-Benzyl-5-(4-methoxyphenyl)-3-methylpyridin-2(1H)-one
1-Benzyl-5-(4-methoxyphenyl)-4-methylpyridin-2(1H)-one
1-Benzyl-5-(6-methoxypyridin-3-yl)pyridin-2(1H)-one
1-Benzyl-5-(4-methoxyphenyl)-3-nitropyridin-2(1H)-one
1-(4-Methylbenzyl)-5-(4-methoxyphenyl)pyridin-2(1H)-one
1-(3,4-Difluorobenzyl)-5-(4-methoxyphenyl)pyridin-2(1H)-one
1-(4-(Trifluoromethyl)benzyl)-5-(4-methoxyphenyl)pyridin-2(1H)-one
1-(3-Fluoro-4-methylbenzyl)-5-(4-methoxyphenyl)pyridin-2(1H)-one
Methyl 4-((5-(4-methoxyphenyl)-2-oxopyridin-1(2H)-yl)methyl)benzoate
4-((5-(4-Methoxyphenyl)-2-oxopyridin-1(2H)-yl)methyl)benzonitrile
5-(4-Methoxyphenyl)-1-(naphthalen-2-ylmethyl)pyridin-2(1H)-one
1-(3-Fluoro-4-(trifluoromethyl)benzyl)-5-(4-methoxyphenyl)pyridin-2(1H)-one
1-(3-Chloro-4-fluorobenzyl)-5-(4-methoxyphenyl)pyridin-2(1H)-one
1-(4-Chloro-3-(trifluoromethyl)benzyl)-5-(4-methoxyphenyl)pyridin-2(1H)-one
1-(2-Fluoro-4-(trifluoromethyl)benzyl)-5-(4-methoxyphenyl)pyridin-2(1H)-one
1-(2-Fluoro-4-chlorobenzyl)-5-(4-methoxyphenyl)pyridin-2(1H)-one
1-(4-Chlorobenzyl)quinolin-2(1H)-one
1-Benzyl-5-phenethylpyridin-2(1H)-one
1-(3-Fluorobenzyl)-3-chloro-5-(4-methoxyphenyl)pyridin-2(1H)-one
5-(4-Methoxyphenyl)-1-((5-methylisoxazol-3-yl)methyl)pyridin-2(1H)-one
1-(4-Chlorobenzyl)-5-(2,5-difluorophenyl)pyridin-2(1H)-one
1-(4-Chlorobenzyl)-5-(3-fluoro-4-methylphenyl)pyridin-2(1H)-one
1-(4-Chlorobenzyl)-5-(2-ethoxyphenyl)pyridin-2(1H)-one
1-(4-Chlorobenzyl)-5-(quinolin-3-yl)pyridin-2(1H)-one
1-(4-Chlorobenzyl)-5-(4-tolyl)pyridin-2(1H)-one
1-(4-Chlorobenzyl)-5-(2-fluorophenyl)pyridin-2(1H)-one
Methyl-3-(4-(1-(4-chlorobenzyl)-1,6-dihydro-6-oxopyridin-3-yl)phenyl) propanoate
1-(4-Chlorobenzyl)-5-(4-isobutylphenyl)pyridin-2(1H)-one
1-(4-Chlorobenzyl)-5-(4-sec-butylphenyl)pyridin-2(1H)-one
1-(4-Chlorobenzyl)-5-(4-vinylphenyl)pyridin-2(1H)-one
1-(4-Chlorobenzyl)-5-(3-methoxyphenyl)pyridin-2(1H)-one
1-(4-Chlorobenzyl)-5-(2,3-dihydrobenzofuran-5-yl)pyridin-2(1H)-one
1-(4-Chlorobenzyl)-5-(4-acetylphenyl)pyridin-2(1H)-one 3-(4-(1-(4-Chlorobenzyl)-1,6-dihydro-6-oxopyridin-3-yl)phenyl)propanoic acid
Methyl 3-(3-(1-(4-chlorobenzyl)-6-oxo-1,6-dihydropyridin-3-yl)phenyl)propanoate
1-(4-Chlorobenzyl)-5-(4-(ethylthio)phenyl)pyridin-2(1H)-one
1-(4-Chlorobenzyl)-5-(3-ethoxyphenyl)pyridin-2(1H)-one
N-(3-(1-(4-Chlorobenzyl)-6-oxo-1,6-dihydropyridin-3-yl)phenyl)methanesulfonamide
1-(4-Chlorobenzyl)-5-(6-methoxypyridin-3-yl)pyridin-2(1H)-one
1-(4-Chlorobenzyl)-5-(4-(methoxymethyl)phenyl)pyridin-2(1H)-one
1-(4-Chlorobenzyl)-5-((3-methoxymethyl)phenyl)pyridin-2(1H)-one
1-(4-Chlorobenzyl)-5-(furan-3-yl)pyridin-2(1H)-one
1-(4-Chlorobenzyl)-5-(1-benzyl-1H-pyrazol-4-yl)pyridin-2(1H)-one
1-(4-Chlorobenzyl)-5-(4-(methylthio)phenyl)pyridin-2(1H)-one
1-(4-Chlorobenzyl)-5-(1-methyl-1H-indol-5-yl)pyridin-2(1H)-one tert-Butyl 2-(1-(4-chlorobenzyl)-6-oxo-1,6-dihydropyridin-3-yl)-1H-pyrrole-1-carboxylate
1-(3-Fluorobenzyl)-5-p-tolylpyridin-2(1H)-one
5-(4-((2H-Tetrazol-5-yl)methyl)phenyl)-1-(4-chlorobenzyl)pyridin-2(1H)-one
1-(3-Fluorobenzyl)-5-(2-(3-methoxyphenyl)ethynyl)pyridine-2(1H)-one
1-(3-Fluorobenzyl)-5-(2-(pyridin-3-yl)ethynyl)pyridin-2(1H)-one hydrochloride
1-(4-Chlorobenzyl)-5-(4-(methylsulfonyl)phenyl)pyridin-2(1H)-one
1-(4-Chlorobenzyl)-5-(1H-indol-5-yl)pyridin-2(1H)-one
1-(4-Chlorobenzyl)-5-(4-methoxyphenyl)-6-methylpyridin-2(1H)-one
1-(3-Fluorobenzyl)-4-phenylpyridin-2(1H)-one
1-(3-Fluorobenzyl)-4-(4-methoxyphenyl)pyridin-2(1H)-one
1-((6-Chloropyridin-3-yl)methyl)-5-(4-methoxyphenyl)pyridin-2(1H)-one
1-(4-Chloro-3-fluorobenzyl)-5-(4-methoxyphenyl)pyridin-2(1H)-one
1-(3,4-Difluorobenzyl)-5-(4-(methoxymethyl)phenyl)pyridin-2(1H)-one
1-(3,4-Difluorobenzyl)-5-(4-acetylphenyl)pyridin-2(1H)-one
1-(3,4-Difluorobenzyl)-5-(2,3-dihydrobenzofuran-5-yl)pyridin-2(1H)-one
1-(4-Methyl-benzyl)-2-oxo-4-thiophen-2-yl-1,2-dihydropyridine-3-carbonitrile
1-(3,4-Difluorobenzyl)-5-(3-methoxyphenyl)pyridin-2(1H)-one
5-(4-Methoxyphenyl)-1-(3-phenylpropyl)pyridin-2(1H)-one
1-(4-Fluorophenethyl)-5-(4-methoxyphenyl)pyridin-2(1H)-one
5-(4-Methoxyphenyl)-1-(4-phenylbutyl)pyridin-2(1H)-one
1-(4-Chlorobenzyl)-5-(4-hydroxyphenyl)pyridin-2(1H)-one
1-(4-Chlorobenzyl)-5-((methyl(phenyl)amino)methyl)pyridin-2(1H)-one
1-(4-Chlorobenzyl)-5-((benzyl(methyl)amino)methyl)pyridin-2(1H)-one
1-(4-Chlorobenzyl)-5-((phenylamino)methyl)pyridin-2(1H)-one
(Z)-5-(3-Methoxystyryl)-1-(4-chlorobenzyl)pyridin-2(1H)-one
(E)-5-(3-Methoxystyryl)-1-(4-chlorobenzyl)pyridin-2(1H)-one
1-(3-Fluorobenzyl)-4-phenethoxypyridin-2(1H)-one
1-(4-Chlorobenzyl)-5-(4-isopropoxyphenyl)pyridin-2(1H)-one
Ethyl 2-(4-(1-(4-chlorobenzyl)-6-oxo-1,6-dihydropyridin-3-yl)phenoxy)acetate
1-(4-Chlorobenzyl)-5-((4-fluorophenyl)(hydroxy)methyl)pyridine-2(1H)-one
1-(4-Chlorobenzyl)-5-(4-fluorobenzyl)pyridin-2(1H)-one
1-(4-Chlorobenzyl)-5-(hydroxy(3-methoxyphenyl)methyl)pyridin-2(1H)-one
5-(4-Methoxyphenyl)-1-(2-oxo-2-phenylethyl)-1H-pyridin-2-one
1-((4-Chlorophenoxy)methyl)-5-(4-methoxyphenyl)pyridin-2(1H)-one
5-(4-Methoxyphenyl)-1-(2-phenoxyethyl)pyridin-2(1H)-one
1-(4-Chlorobenzyl)-5-(4-sec-butoxyphenyl)pyridin-2(1H)-one
1-(4-Chlorobenzyl)-5-(3-methoxybenzoyl)pyridin-2(1H)-one
5-(3-Methoxyphenethyl)-1-(4-chloro-3-fluorobenzyl)pyridin-2(1H)-one
1-(3,4-Difluorobenzyl)-5-(3-methoxyphenethyl)pyridine-2(1H)-one
5-(3-Methoxybenzyl)-1-(4-chlorobenzyl)pyridin-2(1H)-one
1-(4-Chloro-3-fluorobenzyl)-5-(4-methoxyphenethyl)pyridine-2(1H)-one
1-(4-Chloro-2-fluorobenzyl)-5-(4-methoxyphenyl)-4-methylpyridin-2(1H)-one
1-(4-Chloro-2-fluorobenzyl)-4-methyl-5-phenylpyridin-2(1H)-one
1-(4-Chloro-3-fluorobenzyl)-5-(benzo[d]thiazol-2-yl)pyridin-2(1H)-one
1-(3,4-Difluorobenzyl)-5-(phenoxymethyl)pyridin-2(1H)-one
1-(4-Chlorobenzyl)-5-((4-methoxyphenoxy)methyl)pyridin-2(1H)-one
1-(4-Chlorobenzyl)-5-((4-fluorophenyl)(methyl)amino)pyridin-2(1H)-one
1-(4-Chloro-2-fluorobenzyl)-5-(phenoxymethyl)pyridin-2(1H)-one
1-(3,4-Difluorobenzyl)-5-(thiophen-2-yl)pyridin-2(1H)-one
4-(1-(3,4-Difluorobenzyl)-6-oxo-1,6-dihydropyridin-3-yl)benzonitrile
N-(4-(1-(3,4-Difluorobenzyl)-6-oxo-1,6-dihydropyridin-3-yl)phenyl)methanesulfonamide
N-(3-Chlorobenzyl)-2-(5-(4-methoxyphenyl)-2-oxopyridin-1(2H)-yl)-N-methylacetamide
N-Benzyl-2-(5-(4-methoxyphenyl)-2-oxopyridin-1(2H)-yl)-N-methylacetamide
N-(3-Methoxybenzyl)-2-(5-(4-methoxyphenyl)-2-oxopyridin-1(2H)-yl)-N-methylacetamide
1-(3,4-Difluorobenzyl)-5-(6-methoxypyridin-3-yl)pyridine-2(1H)-one
1-(3,4-Difluorobenzyl)-5-(benzo[d][1,3]dioxol-5-yl)pyridin-2(1H)-one
1-(4-Chloro-2-fluorobenzyl)-5-(4-(trifluoromethyl)phenyl)pyridin-2(1H)-one
1-(4-Chloro-2-fluorobenzyl)-5-(3-fluoro-4-methoxyphenyl)pyridin-2(1H)-one
1-(4-(Trifluoromethoxy)benzyl)-5-(4-methoxyphenyl)pyridin-2(1H)-one
1-(2,4-Difluorobenzyl)-5-(4-methoxyphenyl)pyridin-2(1H)-one
1-(2-Methylphenylmethyl)-5-(4-methoxyphenyl)pyridin-2(1H)-one
1-(2,3-Difluorobenzyl)-5-(4-methoxyphenyl)pyridin-2(1H)-one 1-(4-Chlorobenzyl)-4-methylquinolin-2(1H)-one
N-(4-Nitrobenzyl)-2-(5-(4-methoxyphenyl)-2-oxopyridin-1(2H)-yl)-N-methylacetamide
N-(4-Methylbenzyl)-2-(5-(4-methoxyphenyl)-2-oxopyridin-1(2H)-yl)-N-methylacetamide
N-(4-(Trifluoromethyl)benzyl)-2-(5-(4-methoxyphenyl)-2-oxopyridin-1(2H)-yl)-N-methylacetamide
1-(4-Chlorobenzyl)-5-phenylpyridin-2(1H)-one
1-(4-Chloro-2-fluorobenzyl)-5-(benzo[b]thiophen-5-yl)pyridin-2(1H)-one
1-(2,4,6-Trifluorobenzyl)-5-(4-methoxyphenyl)pyridin-2(1H)-one
1-(2-Chlorobenzyl)-5-(4-methoxyphenyl)pyridin-2(1H)-one
5-(4-Methoxyphenyl)-1-((6-(trifluoromethyl)pyridin-3-yl)methyl)pyridin-2(1H)-one hydrochloride
4-(1-(4-Methoxybenzyl)-6-oxo-1,6-dihydropyridin-3-yl)benzonitrile
1-(4-Methoxybenzyl)-5-(4-acetylphenyl)pyridin-2(1H)-one
5-(4-Methoxyphenyl)-1-((6-methoxypyridin-3-yl)methyl)pyridin-2(1H)-one hydrochloride
1-(4-Chloro-2-fluorobenzyl)-5-(3,4-dimethoxyphenyl)pyridin-2(1H)-one
5-(4-Methoxyphenyl)-1-((5-phenyl-1,2,4-oxadiazol-3-yl)methyl)pyridin-2(1H)-one
1-(4-Chloro-2-fluorobenzyl)-5-(4-hydroxyphenyl)pyridin-2(1H)-one
1-(4-Chloro-2-fluorobenzyl)-5-(4-(pyrrolidin-1-ylsulfonyl)phenyl)pyridin-2(1H)-one
1-(4-Chloro-2-fluorobenzyl)-5-(4-(morpholinosulfonyl)phenyl)pyridin-2(1H)-one
1-((4-Fluorobenzo[d]thiazol-2-yl)methyl)-5-(4-methoxyphenyl)pyridin-2(1H)-one
1-(4-Chloro-2-fluorobenzyl)-5-(4-(2-methoxyethoxy)phenyl)pyridin-2(1H)-one
1-(4-Chloro-2-fluorobenzyl)-5-bromopyridin-2(1H)-one
Methyl 1-(4-chlorobenzyl)-2-oxo-5-phenyl-1,2-dihydropyridine-3-carboxylate
1-(4-Chlorobenzyl)-3-(hydroxymethyl)-5-(4-methoxyphenyl)pyridin-2(1H)-one
1-(4-Chloro-2-fluorobenzyl)-5-(4-(2-morpholinoethoxy)phenyl)pyridin-2(1H)-one
1-(Benzo[d]thiazol-2-ylmethyl)-5-phenylpyridin-2(1H)-one
1-(4-Chloro-2-fluorobenzyl)-5-(4-(2-(dimethylamino)ethoxy)phenyl)pyridin-2(1H)-one
2-(4-(1-(4-Chloro-2-fluorobenzyl)-6-oxo-1,6-dihydropyridin-3-yl)phenoxy)acetonitrile
5-(4-((2H-Tetrazol-5-yl)methoxy)phenyl)-1-(4-chloro-2-fluorobenzyl)pyridin-2(1H)-one
1-Butyl-5-(4-methoxyphenyl)pyridin-2(1H)-one
1-(4-Chloro-2-fluorobenzyl)-5-(4-(3-morpholinopropoxy)phenyl)pyridin-2(1H)-one hydrochloride
1-(4-Chloro-2-fluorobenzyl)-5-(4-(3-(dimethylamino)propoxy)phenyl)pyridin-2(1H)-one
4-(1-(4-Chloro-2-fluorobenzyl)-6-oxo-1,6-dihydropyridin-3-yl)phenyl methyl carbonate
1-(4-Chloro-2-fluorobenzyl)-5-(4-(2-oxopropoxy)phenyl)pyridin-2(1H)-one
1-(4-Chloro-2-fluorobenzyl)-5-(4-isobutoxyphenyl)pyridin-2(1H)-one
1-(4-Chloro-2-fluorobenzyl)-5-(4-methoxy-3-methylphenyl)pyridin-2(1H)-one
Methyl 2-(4-(1-(4-chloro-2-fluorobenzyl)-6-oxo-1,6-dihydropyridin-3-yl)phenoxy)acetate
5-(4-(1H-Tetrazol-5-yl)phenyl)-1-(4-chloro-2-fluorobenzyl)pyridin-2(1H)-one
1-(4-Chloro-2-fluorobenzyl)-5-(4-aminophenyl)pyridin-2(1H)-one hydrochloride
1-(4-Chloro-2-fluorobenzyl)-5-(3-aminophenyl)pyridin-2(1H)-one
1-(4-Chloro-2-fluorobenzyl)-5-(4-(hydroxymethyl)phenyl)pyridin-2(1H)-one
1-(4-Chloro-2-fluorobenzyl)-3-fluoro-5-(4-methoxyphenyl)pyridin-2(1H)-one
1-(4-Chloro-2-fluorobenzyl)-5-(4-methoxy-3,5-dimethylphenyl)pyridin-2(1H)-one
1-Isobutyl-5-(4-methoxyphenyl)pyridin-2(1H)-one
1-Isopentyl-5-(4-methoxyphenyl)pyridin-2(1H)-one
5-(4-Methoxyphenyl)-1-(pent-4-ynyl)pyridin-2(1H)-one
1-(Cyclohexylmethyl)-5-(4-methoxyphenyl)pyridin-2(1H)-one
N-(4-(1-(4-Chloro-2-fluorobenzyl)-6-oxo-1,6-dihydropyridin-3-yl)phenyl)acetamide
1-(4-Chloro-2-fluorobenzyl)-5-(4-((2-methylthiazol-4-yl)methoxy)phenyl)pyridin-2(1H)-one
1-(4-Chloro-2-fluorobenzyl)-5-(4-((1-methyl-1H-imidazol-2-yl)methoxy)phenyl)pyridin-2(1H)-one
1-(4-Chloro-2-fluorobenzyl)-5-(3,4-dihydro-2H-benzo[b][1,4]dioxepin-7-yl)pyridin-2(1H)-one
1-(4-Chloro-2-fluorobenzyl)-5-(4-(2-aminoethoxy)phenyl)pyridin-2(1H)-one
1-(4-Chloro-2-fluorobenzyl)-5-(4-((5-methylisoxazol-3-yl)methoxy)phenyl)pyridin-2(1H)-one
tert-Butyl 4-(1-(4-chloro-2-fluorobenzyl)-6-oxo-1,6-dihydropyridin-3-yl)benzylcarbamate
1-(4-Chloro-2-fluorobenzyl)-5-(4-propoxyphenyl)pyridin-2(1H)-one
1-(4-Chloro-2-fluorobenzyl)-4-methoxy-5-(4-methoxyphenyl)pyridin-2(1H)-one
N-(3-(1-(4-Chloro-2-fluorobenzyl)-6-oxo-1,6-dihydropyridin-3-yl)phenyl)acetamide
1-(4-Chloro-2-fluorobenzyl)-5-(4-(aminomethyl)phenyl)pyridin-2(1H)-one
1-(4-Chlorobenzyl)-5-(3-hydroxyphenyl)pyridin-2(1H)-one
N-(4-(1-(4-Chloro-2-fluorobenzyl)-6-oxo-1,6-dihydropyridin-3-yl)benzyl)acetamide
N-(4-(1-(4-Chloro-2-fluorobenzyl)-6-oxo-1,6-dihydropyridin-3-yl)benzyl)methanesulfonamide
N-(3-(1-(4-Chloro-2-fluorobenzyl)-6-oxo-1,6-dihydropyridin-3-yl)benzyl)acetamide
N-(3-(1-(4-Chloro-2-fluorobenzyl)-6-oxo-1,6-dihydropyridin-3-yl)benzyl)methanesulfonamide
1-(4-Chlorobenzyl-3-fluorobenzyl)-5-bromo-4-methylpyridin-2(1H)-one
5-(4-Methoxyphenyl)-1-((5-(trifluoromethyl)furan-2-yl)methyl)pyridin-2(1H)-one
1-(4-(Methoxymethyl)benzyl)-5-(4-methoxyphenyl)pyridin-2(1H)-one
1-(4-Chloro-3-fluorobenzyl)-5-bromo-4-methylpyridin-2(1H)-one
1-(4-Chloro-2-fluorobenzyl)-5-(4-(2-(2-oxopyrrolidin-1-yl)ethoxy)phenyl)pyridin-2(1H)-one
2-(4-(1-(4-Chloro-2-fluorobenzyl)-6-oxo-1,6-dihydropyridin-3-yl)phenoxy)-N-methylacetamide
1-(4-Chloro-2-fluorobenzyl)-5-(4-(3-aminopropoxy)phenyl)pyridin-2(1H)-one
1-(4-(Ethoxymethyl)benzyl)-5-(4-methoxyphenyl)pyridin-2(1H)-one
1-(4-chlorobenzyl)-5-(4-(ethoxymethyl)phenyl)pyridin-2(1H)-one
N-(2-(4-(1-(4-Chloro-2-fluorobenzyl)-6-oxo-1,6-dihydropyridin-3-yl)phenoxy)ethyl)acetamide N-Acetyl-N-(2-(4-[1-(4-chloro-2-fluorobenzyl)-6-oxo-1,6-dihydropyridin-3-yl]phenoxy)ethyl)acetamide
N-(2-(4-(1-(4-Chloro-2-fluorobenzyl)-6-oxo-1,6-dihydropyridin-3-yl)phenoxy)ethyl)methanesulfonamide
N-(3-(4-(1-(4-Chloro-2-fluorobenzyl)-6-oxo-1,6-dihydropyridin-3-yl)phenoxy)propyl)methanesulfonamide
N-Acetyl-N-(3-(4-(1-(4-chloro-2-fluorobenzyl)-6-oxo-1,6-dihydropyridin-3-yl)phenoxy)propyl)acetamide
N-(3-(4-(1-(4-Chloro-2-fluorobenzyl)-6-oxo-1,6-dihydropyridin-3-yl)phenoxy)propyl)acetamide
1-(4-Chloro-2-fluorobenzyl)-5-isopropylpyridin-2(1H)-one
1-(4-Chlorobenzyl)-5-(6-(dimethylamino)pyridin-3-yl)pyridin-2(1H)-one
1-(4-Chlorobenzyl)-5-(3-amino-4-methoxyphenyl)pyridin-2(1H)-one
1-(4-Chlorobenzyl)-5-(4-morpholinophenyl)pyridin-2(1H)-one
1-(4-Chlorobenzyl)-5-(5-methylthiophen-2-yl)pyridin-2(1H)-one
1-(4-Chlorobenzyl)-5-(6-morpholinopyridin-3-yl)pyridin-2(1H)-one
1-(4-Chloro-2-fluorobenzyl)-5-(6-methoxypyridin-3-yl)pyridin-2(1H)-one
5-(6-Methoxypyridin-3-yl)-1-((6-(trifluoromethyl)pyridin-3-yl)methyl)pyridin-2(1H)-one
1-(4-Chlorobenzyl)-5-(4-(ethoxymethyl)phenyl)pyridin-2(1H)-one
1-(4-Chlorobenzyl)-5-(4-(benzyloxymethyl)phenyl)pyridin-2(1H)-one
1-(4-Chlorobenzyl)-5-(4-(hydroxymethyl)phenyl)pyridin-2(1H)-one
1-(4-Chlorobenzyl)-5-(4-(dimethylamino)phenyl)pyridin-2(1H)-one
1-(4-Chlorobenzyl)-5-(quinoxalin-6-yl)pyridin-2(1H)-one
Methyl 4-(1-(4-chlorobenzyl)-6-oxo-1,6-dihydropyridin-3-yl)benzoate
1-(4-Chlorobenzyl)-5-(4-(3-hydroxypropyl)phenyl)pyridin-2(1H)-one
4-(1-Isopentyl-6-oxo-1,6-dihydropyridin-3-yl)benzonitrile
N-(3-(1-Isopentyl-6-oxo-1,6-dihydropyridin-3-yl)phenyl)methanesulfonamide
3-(1-(4-Chloro-2-fluorobenzyl)-6-oxo-1,6-dihydropyridin-3-yl)benzonitrile
1-(4-Chlorobenzyl)-5-(4-methoxyphenyl)pyrazin-2(1H)-one
1-(4-Chlorobenzyl)-5-(6-chloropyridin-3-yl)pyridin-2(1H)-one
N-(5-(1-(4-Chlorobenzyl)-6-oxo-1,6-dihydropyridin-3-yl)-2-methoxyphenyl)methanesulfonamide
5-(4-Methoxyphenyl)-1-pentylpyridin-2(1H)-one
1-(Cyclopropylmethyl)-5-(4-methoxyphenyl)pyridin-2(1H)-one
5-(4-Methoxyphenyl)-1-(4,4,4-trifluorobutyl)pyridin-2(1H)-one
1-(Cyclopentylmethyl)-5-(4-methoxyphenyl)pyridin-2(1H)-one
Methyl 2-(4-(1-(4-chlorobenzyl)-6-oxo-1,6-dihydropyridin-3-yl)phenyl)acetate
1-(4-Chlorobenzyl)-5-cyclohexylpyridin-2(1H)-one
1-(4-Chlorobenzyl)-5-(quinolin-7-yl)pyridin-2(1H)-one
1-(4-Chloro-2-fluorobenzyl)-5-(4-(furan-2-ylmethoxy)phenyl)pyridin-2(1H)-one
5-(3-(2H-Tetrazol-5-yl)phenyl)-1-(4-chloro-2-fluorobenzyl)pyridin-2(1H)-one
1-(4-Chlorobenzyl)-5-(4-(2-hydroxypropan-2-yl)phenyl)pyridin-2(1H)-one
1-(4-Chlorobenzyl)-5-(4-(isobutoxymethyl)phenyl)pyridin-2(1H)-one
1-(4-Chlorobenzyl)-5-phenylpyrazin-2(1H)-one
1-(4-Chlorobenzyl)-5-(4-((2-(dimethylamino)ethoxy)methyl)phenyl)pyridin-2(1H)-one
1-(4-Chlorobenzyl)-5-(4-((2-morpholinoethoxy)methyl)phenyl)pyridin-2(1H)-one
2-(4-(1-(4-Chlorobenzyl)-6-oxo-1,6-dihydropyridin-3-yl)phenyl)acetic acid
4-(1-(4-Chlorobenzyl)-6-oxo-1,6-dihydropyridin-3-yl)-N,N-dimethylbenzamide
2-(4-(1-(4-Chlorobenzyl)-6-oxo-1,6-dihydropyridin-3-yl)phenyl)-N,N-dimethylacetamide
N-(2-(4-(1-(4-chlorobenzyl)-6-oxo-1,6-dihydropyridin-3-yl)benzyloxy)ethyl)acetamide
1-(4-Chlorobenzyl)-5-(4-((2-methoxyethoxy)methyl)phenyl)pyridin-2(1H)-one
1-(4-Fluorobenzyl)-4-(furan-2-yl)-2-oxo-1,2-dihydropyridine-3-carbonitrile
2-(4-(1-(4-Chlorobenzyl)-6-oxo-1,6-dihydropyridin-3-yl)phenyl)-N-methylacetamide
3-(4-(1-(4-Chlorobenzyl)-6-oxo-1,6-dihydropyridin-3-yl)phenyl)-N-methylpropanamide
3-(4-(1-(4-Chlorobenzyl)-6-oxo-1,6-dihydropyridin-3-yl)phenyl)-N,N-dimethylpropanamide
1-(4-Chloro-2-fluorobenzyl)-5-(4-(2-hydroxypropoxy)phenyl)pyridin-2(1H)-one
1-Isopentyl-2-oxo-4-(thiophen-2-yl)-1,2-dihydropyridine-3-carbonitrile
2-Oxo-1-(3-phenylpropyl)-4-(thiophen-2-yl)-1,2-dihydropyridine-3-carbonitrile
4-(Furan-2-yl)-1-isopentyl-2-oxo-1,2-dihydropyridine-3-carbonitrile
4-(Furan-2-yl)-2-oxo-1-(3-phenylpropyl)-1,2-dihydropyridine-3-carbonitrile
1-(4-Methylphenylmethyl)-4-(furan-2-yl)-2-oxo-1,2-dihydropyridine-3-carbonitrile
1-(4-Chloro-2-fluorobenzyl)-5-(3-phenylpropyl)pyridin-2(1H)-one
1-(4-Chloro-2-fluorobenzyl)-5-(4-(3-methoxyphenyl)butyl)pyridin-2(1H)-one
1-(4-Chloro-2-fluorobenzyl)-5-(4-phenylbutyl)pyridin-2(1H)-one
1-(4-Chlorobenzyl)-5-butylpyridin-2(1H)-one
1-(4-Chlorobenzyl)-5-(4-methoxyphenyl)pyrimidin-2 (H)-one
1-Benzyl-5-(4-methoxyphenyl)pyrimidin-2(1H)-one
1-Isopentyl-5-(4-methoxyphenyl)pyrazin-2(1H)-one
1-(4-Chlorobenzyl)-5-(4-(2-(dimethylamino)ethylamino)phenyl)pyridin-2(1H)-one
1-(4-Chlorobenzyl)-5-(4-(2-methoxyethylamino)phenyl)pyridin-2(1H)-one
1-(4-Chlorobenzyl)-5-(4-(propylamino)phenyl)pyridin-2(1H)-one
1-(3,3-Dimethylbutyl)-5-(4-methoxyphenyl)pyridin-2(1H)-one
1-(4-Chloro-2-fluorobenzyl)-5-(4-(pyridin-3-ylmethoxy)phenyl)pyridin-2(1H)-one
1-(4-Chlorobenzyl)-4-(2-hydroxyethyl)-5-(4-methoxyphenyl)pyridin-2(1H)-one
1-(4-Chloro-2-fluorobenzyl)-5-(4-(4-methoxyphenyl)butyl)pyridin-2(1H)-one
1-(4-Chloro-2-fluorobenzyl)-5-(4-methoxybenzyl)pyridin-2(1H)-one
1-(4-Chloro-2-fluorobenzyl)-5-(3-phenoxypropyl)pyridin-2(1H)-one
1-Isopentyl-4-methylquinolin-2(1H)-one 1-(4-Chlorobenzyl)-5-(4-methoxyphenoxy)pyridin-2(1H)-one
1-(4-Chlorobenzyl)-5-propoxypyridin-2(1H)-one
1-(4-Chlorobenzyl)-5-(cyclohexylmethoxy)pyridin-2(1H)-one
1-(4-Chlorobenzyl)-5-(4-fluorobenzyloxy)pyridin-2(1H)-one
1-(4-Chlorobenzyl)-5-(4-methoxybenzyloxy)pyridin-2(1H)-one
1-(4-Chlorobenzyl)-5-phenethoxypyridin-2(1H)-one
1-(4-Chlorobenzyl)-5-(4-fluorophenoxy)pyridin-2(1H)-one
1-(4-Chlorobenzyl)-5-(2-methoxyethoxy)pyridin-2(1H)-one
1-(4-Chlorobenzyl)-5-(5-methylpyridin-2-yl)pyridin-2(1H)-one
1-(4-Chloro-2-fluorobenzyl)-5-(4-(pyridin-2-ylmethoxy)phenyl)pyridin-2(1H)-one
1-(4-Chloro-2-fluorobenzyl)-4-(methoxymethyl)-5-(4-methoxyphenyl)pyridin-2(1H)-one
1-(4-Chlorobenzyl)-4-(2-methoxyethyl)-5-(4-methoxyphenyl)pyridin-2(1H)-one
1-(4-Chlorobenzyl)-3-chloro-5-phenylpyridin-2(1H)-one
1-(4-Chloro-2-fluorobenzyl)-3-methoxy-5-(4-methoxyphenyl)pyridin-2(1H)-one
5-(2-Methoxybenzyl)-1-(4-chloro-2-fluorobenzyl)pyridin-2(1H)-one
N-(3-(1-(4-Chlorobenzyl)-5-chloro-6-oxo-1,6-dihydropyridin-3-yl)phenyl)acetamide
5-(4-Methoxyphenethylamino)-2-propylisoquinolin-1(2H)-one
5-(4-Hydroxyphenethylamino)-2-propylisoquinolin-1(2H)-one
1-(4-Chlorobenzyl)-6-methoxy-4-methylquinolin-2(1H)-one
1-Isobutyl-2-oxo-4-(thiophen-2-yl)-1,2-dihydropyridine-3-carbonitrile
1-(Cyclohexylmethyl)-2-oxo-4-(thiophen-2-yl)-1,2-dihydropyridine-3-carbonitrile
2-Oxo-4-(thiophen-2-yl)-1-((6-(trifluoromethyl)pyridin-3-yl)methyl)-1,2-dihydropyridine-3-carbonitrile
5-(4-Methoxyphenyl)-1-((6-(4-methoxyphenyl)pyridin-3-yl)methyl)pyridin-2(1H)-one
1-((6-Ethynylpyridin-3-yl)methyl)-5-(4-methoxyphenyl)pyridin-2(1H)-one
1-((6-Ethylpyridin-3-yl)methyl)-5-(4-methoxyphenyl)pyridin-2(1H)-one
2-Oxo-1-(pentan-2-yl)-4-(thiophen-2-yl)-1,2-dihydropyridine-3-carbonitrile
5-(4-Methoxyphenyl)-1-((2-methylthiazol-5-yl)methyl)pyridin-2(1H)-one
5-(4-Methoxyphenyl)-1-((5-methylpyrazin-2-yl)methyl)pyridin-2(1H)-one
5-(Phenoxymethyl)-1-((6-(trifluoromethyl)pyridin-3-yl)methyl)pyridin-2(1H)-one
mixture of isomers of 1-(4-chloro-2-fluorobenzyl)-5-(4-((2-methyl-2H-tetrazol-5-yl)methoxy)phenyl)pyridin-2(1H)-one
1-(4-Chlorobenzyl)-3-chloro-5-(4-methoxyphenyl)pyridin-2(1H)-one
N-(3-(5-Chloro-1-isopentyl-6-oxo-1,6-dihydropyridin-3-yl)phenyl)methanesulfonamide
1-(4-Chlorobenzyl)-5-(4-fluorophenyl)pyridin-2(1H)-one
5-(4-Methoxyphenyl)-1-(pentan-2-yl)pyridin-2(1H)-one
5-(4-Methoxyphenyl)-1-((4-methylcyclohexyl)methyl)pyridin-2(1H)-one
1-Isopentyl-2-oxo-4-phenyl-1,2-dihydropyridine-3-carbonitrile
4-(Benzo[d][1,3]dioxol-5-yl)-1-isopentyl-2-oxo-1,2-dihydropyridine-3-carbonitrile
1-(4-Ethoxybenzyl)-5-(4-methoxyphenyl)pyridin-2(1H)-one
1-Isopentyl-5-(4-methoxyphenyl)pyrimidin-2(1H)-one
1-Isopentyl-5-((4-methoxyphenoxy)methyl)pyridin-2(1H)-one
1-(4-Chloro-2-fluorobenzyl)-5-((3-methoxyphenoxy)methyl)pyridin-2(1H)-one
1-(4-Chlorobenzyl)-5-(2-fluoro-4-methoxyphenyl)pyridin-2(1H)-one
1-(4-Chlorobenzyl)-5-(2-methoxypyrimidin-5-yl)pyridin-2(1H)-one
2-Oxo-1-propyl-4-(thiophen-2-yl)-1,2-dihydropyridine-3-carbonitrile
1-Butyl-2-oxo-4-(thiophen-2-yl)-1,2-dihydropyridine-3-carbonitrile
1-(2-Methylbutyl)-2-oxo-4-phenyl-1,2-dihydropyridine-3-carbonitrile
1-(4-Chlorobenzyl)-2-oxo-4-(thiophen-2-yl)-1,2-dihydropyridine-3-carbonitrile
6-Chloro-1-isopentylquinolin-2(1H)-one
4-(4-Methoxyphenethyl)-2-propylisoquinolin-1(2H)-one
5-(4-Methoxyphenethoxy)-2-propylisoquinolin-1(2H)-one.

Definition of Terms

Listed below are definitions of various terms used in the specification and claims to describe the present invention.

For the avoidance of doubt it is to be understood that in this specification "$(C_1\text{-}C_6)$" means a carbon radical having 1, 2, 3, 4, 5 or 6 carbon atoms. "$(C_0\text{-}C_6)$" means a carbon radical having 0, 1, 2, 3, 4, 5 or 6 carbon atoms. In this specification "C" means a carbon atom, "N" means a nitrogen atom and "S" means a sulphur atom.

In the case where a subscript is the integer 0 (zero) the radical to which the subscript refers, indicates that the radical is absent, i.e. there is a direct bond between the radicals.

When two or more bonds are adjacent to one another, they are assumed to be equal to one bond. For example, a radical -A-B—, wherein both A and B may be a bond, the radical is depicting a single bond.

In this specification, unless stated otherwise, the term "bond" refers to a saturated covalent bond.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term "$(C_0\text{-}C_3)$alkyl" refers to an alkyl radical having 0, 1, 2 or 3 carbon atoms, and may be methyl, ethyl, n-propyl and i-propyl.

In this specification, unless stated otherwise, the term "cycloalkyl" refers to an optionally substituted carbocycle containing no heteroatoms, including mono-, bi-, and tricyclic saturated carbocycles, as well as fused ring systems. Such fused ring systems can include one ring that is partially or fully unsaturated such as a benzene ring to form fused ring systems such as benzo-fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl, 1,2,3,4-tetrahydronaphthalene and the like. The term "$(C_3\text{-}C_7)$cycloalkyl" may be cyclopropyl, cyclobutyl, cyclopentyl, cyclohexyl, cycloheptyl and the like.

In this specification, unless stated otherwise, the term "alkenyl" includes both straight and branched chain alkenyl radicals. The term "$(C_2\text{-}C_6)$alkenyl" refers to an alkenyl radical having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl radicals. The term ($C_2$-$C_6$)alkynyl having 2 to 6 carbon atoms and one or two triple bonds, and may be, but is not limited to ethynyl, propargyl, butynyl, ibutynyl, pentynyl, i-pentynyl and hexynyl.

The term "aryl" refers to an optionally substituted monocyclic or bicyclic hydrocarbon ring system containing at least one unsaturated aromatic ring. Examples and suitable values of the term "aryl" are phenyl, naphtyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thiophene, thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, benzothiazolyl, tetrahydrotriazolopyridyl, tetrahydrotriazolopyrimidinyl, benzofuryl, thionaphtyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazolopyridyl, thiazolopyridyl, pyridyl, imidazopyridazinyl, oxazolopyridazinyl, thiazolopyridazinyl, cynnolyl, pteridinyl, furazanyl, benzotriazolyl, pyrazolopyridinyl, purinyl and the like.

In this specification, unless stated otherwise, the term "alkylaryl", "alkylheteroaryl" and "alkylcycloalkyl" refers respectively to a substituent that is attached via the alkyl radical to an aryl, heteroaryl or cycloalkyl radical, respectively. The term "($C_1$-$C_6$)alkylaryl" includes aryl-$C_1$-$C_6$-alkyl radicals such as benzyl, 1-phenylethyl, 2-phenylethyl, 1-phenylpropyl, 2-phenylpropyl, 3-phenylpropyl, 1-naphtylmethy, 2-naphtylmethyl, or the like. The term "($C_1$-$C_6$)alkyheteroaryl" includes heteroaryl-$C_1$-$C_3$-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 2-thiazolylmethyl, 2-pyridylmethyl, 3-pyridylmethyl, 1-quinolylmethyl, or the like.

In this specification, unless stated otherwise, the term "heterocycle" refers to an optionally substituted, monocyclic or bicyclic saturated, partially saturated or unsaturated ring system containing at least one heteroatom selected independently from N, O and S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl, cyclohexenyl, and the like.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, cyclopentyl, cyclopentenyl, cyclohexyl, cyclohexenyl, cycloheptyl, cycloheptenyl, cyclooctyl, cyclooctenyl, and the like.

In this specification, unless stated otherwise, the term "halo" may be fluoro, chloro, bromo or iodo.

In this specification, unless stated otherwise, the term "alkylhalo" means an alkyl radical as defined above, substituted with one or more halo radicals. The term "($C_1$-$C_6$) alkylhalo" may include, but is not limited to, fluoromethyl, difluoromethyl, trifluoromethyl, fluoroethyl and difluoroethyl. The term "O—$C_1$-$C_6$-alkylhalo" may include, but is not limited to, fluoromethoxy, difluoromethoxy, trifluoromethoxy and fluoroethoxy.

In this specification, unless stated otherwise, the term "alkylcyano" means an alkyl radical as defined above, substituted with one or more cyanos.

(This Paragraph Will be Cleaned Up Tomorrow)

In this specification, unless stated otherwise, the term "optionally substituted" refers to radicals further bearing one or more substituents which are preferably selected from the group of ($C_1$-$C_6$)alkyl; ($C_1$-$C_6$)alkyloxy; hydroxy($C_1$-$C_6$) alkyloxy; ($C_1$-$C_6$)alkyloxy($C_1$-$C_6$)alkyl; ($C_1$-$C_6$)alkyloxy ($C_1$-$C_6$)alkyloxy; ($C_1$-$C_6$)alkyloxycarbonyl; ($C_1$-$C_6$)alkyloxy-carbonyl($C_1$-$C_6$)alkyl; ($C_1$-$C_6$)alkyloxycarbonyloxy; ($C_1$-$C_6$)alkyloxycarbonyl($C_1$-$C_6$)-alkyloxy; ($C_1$-$C_6$)alkylcarbonyl; ($C_1$-$C_6$)alkylcarbonyl($C_1$-$C_6$)alkyloxy; ($C_1$-$C_6$) alkyl-carbonyloxy; ($C_1$-$C_6$)alkylthieno; ($C_1$-$C_6$)alkylsulfonyl; heterocyclic-sulfonyl, preferably morpholinylsulfonyl and pyrrolidinylsulfonyl; ($C_1$-$C_6$)alkylsulfonylamino; ($C_1$-$C_6$)alkenyl; aryl, preferably phenyl; carboxyl($C_1$-$C_6$)alkyl; carbonyl($C_1$-$C_6$)-alkyloxy; halo, preferably fluoro and chloro; hydroxy; hydroxy($C_1$-$C_6$)alkyl; phenyl($C_1$-$C_6$)alkyloxy; cyano; cyano($C_1$-$C_6$)alkyloxy; trifluoro($C_1$-$C_6$)alkyl; trifluoro($C_1$-$C_6$)-alkyloxy; amino; amino($C_1$-$C_6$)alkyloxy; mono- and di(($C_1$-$C_6$)alkyl)amino; mono- and di(($C_1$-$C_6$) alkylcarbonyl)amino; mono- and di(($C_1$-$C_6$)alkyloxycarbonyl)amino; mono- and di(($C_1$-$C_6$)alkylcarbonyl)amino($C_1$-$C_6$)alkyl; mono- and di(($C_1$-$C_6$)alkyl-sulfonyl)amino($C_1$-$C_6$) alkyloxy; mono- and di(($C_1$-$C_6$)alkyl)amino($C_1$-$C_6$) alkyloxy; mono- and di(($C_1$-$C_6$)alkylcarbonyl)amino($C_1$-$C_6$) alkyloxy; mono- and di(($C_1$-$C_6$)-alkyl)aminocarbonyl; mono- and di(($C_1$-$C_6$)alkyl)aminocarbonyl($C_1$-$C_6$)alkyl; mono- and di(($C_1$-$C_6$)alkyl)aminocarbonyl($C_1$-$C_6$)alkyloxo; mono- and di(($C_1$-$C_6$)alkyl)-amino($C_1$-$C_6$)alkylamino; nitro; tri($C_1$-$C_6$)alkylsilyl; heterocyclic, preferably morpholinyl; heterocyclic-($C_1$-$C_6$)alkyl, preferably ($C_1$-$C_6$)alkyltetrazolyl; and heterocyclic-($C_1$-$C_6$)alkyloxy, the heterocyclic preferably being pyridinyl, morpholinyl, pyrrolidinyl, optionally substituted with oxo, isoxazolyl, imidazolyl, tetrazolyl or thiazolyl.

In this specification, the term "solvate" refers to a complex of variable stoichiometry formed by a solute (e.g. a compound of Formula (I)) and a solvent. The solvent is a pharmaceutically acceptable solvent as preferably water; such solvent may not interfere with the biological activity of the solute.

In this specification, unless stated otherwise, the term "positive allosteric modulator of mGluR2" or "allosteric modulator of mGluR2" refers also to a pharmaceutically acceptable acid or base addition salt thereof, a stereochemically isomeric form thereof and an N-oxide form thereof.

Pharmaceutical Compositions

Positive allosteric modulators of mGluR2 described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The positive allosteric modulators of mGluR2 will be present in such pharmaceutical compositions in amounts sufficient to provide the desired dosage amount in the range described herein. Techniques for Formulation and administration of the compounds of the instant invention can be found in Remington: the Science and Practice of Pharmacy, 19$^{th}$ edition, Mack Publishing Co., Easton, Pa. (1995).

The amount of positive allosteric modulators of mGluR2, administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used CNS drugs are well known to the skilled person. The total daily dose usually ranges from about 0.05-2000 mg.

The present invention relates to pharmaceutical compositions which provide from about 0.01 to 1000 mg of the active ingredient per unit dose. The compositions may be administered by any suitable route. For example orally in the form of capsules, etc. . . . , parenterally in the form of solutions for injection, topically in the form of onguents or lotions, ocularly in the form of eye-drops, rectally in the form of suppositories, intranasally or transcutaneously in the form of delivery system like patches.

For oral administration, the positive allosteric modulators of mGluR2 thereof can be combined with a suitable solid or liquid carrier or diluent to form capsules, tablets, pills, powders, syrups, solutions, suspensions and the like.

The tablets, pills, capsules, and the like contain from about 0.01 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parenteral administration the disclosed positive allosteric modulators of mGluR2 can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

Preferably disclosed positive allosteric modulators of mGluR2 or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmacology

The compounds provided in this invention are positive allosteric modulators of metabotropic receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor. Hence, the present invention relates to a compound for use as a medicine, as well as to the use of a compound according to the invention or a pharmaceutical composition according to the invention for the manufacture of a medicament for treating or preventing a condition in a mammal, including a human, the treatment or prevention of which is affected or facilitated by the neuromodulatory effect of mGluR2 allosteric modulators, in particular positive mGluR2 allosteric modulators.

Also, the present invention relates to the use of a compound according to the invention or a pharmaceutical composition according to the invention for the manufacture of a medicament for treating, or preventing, ameliorating, controlling or reducing the risk of various neurological and psychiatric disorders associated with glutamate dysfunction in a mammal, including a human, the treatment or prevention of which is affected or facilitated by the neuromodulatory effect of mGluR2 positive allosteric modulators.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. a treatment, an effective amount of a compound or composition according to the invention.

In particular, the neurological and psychiatric disorders associated with glutamate dysfunction, include one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Methods of Synthesis

The compounds according to the invention, in particular the compounds according to the Formula (I), (II), (II-a), (II-b), (II-c), (II-c1), (II-c2), (II-c3), (III), (III-a), (III-b), (III-c), (III-c1), (III-c2), (III-c3), (IV), (V), (V-a) and (V-b), may be prepared by methods known in the art of organic synthesis or by the following synthesis schemes. In all of the schemes described below it is understood that protecting groups for sensitive or reactive groups are employed where necessary in accordance with the general principles of organic chemistry. Protecting groups are manipulated according to standard methods (T. W. Green and P. G. M. Wuts, 1991, *Protecting Groups in Organic Synthesis*, John Wiley & Sons, Inc.). These groups are then removed at a convenient stage of the synthesis using methods that are readily apparent to those skilled in the art.

The compounds according to the invention may be represented as a mixture of enantiomers which may be resolved into their individual R- or S-enantiomers. If for instance, a particular enantiomer is required it may be prepared by asymmetric synthesis or by derivation with a chiral auxiliary and the resulting diastereomeric mixture separated. The auxiliary group can then be cleaved to provide the desired pure enantiomers. Alternatively, where the molecule contains a basic functional group such as an amino or an acidic functional group such as a carboxyl functional group, resolution may be performed by fractional crystallization from various solvents as the salt of an optical active acid or by other methods known in the literature (e.g. chiral column chromatography).

Resolution of the final product, an intermediate or a starting material may be performed by any suitable method known in the art (E. L. Eliel, S. H. Wilen and L. N. Mander, 1984, *Stereochemistry of Organic Compounds*, Wiley-Interscience).

Many of the heterocyclic compounds of Formula (I) to (V-b) where $M_1$ or $M_2$ is a heteroaromatic or heterocyclic group may be prepared using synthetic routes well known in the art (A. R. Katrizky and C. W. Rees, 1984, *Comprehensive Heterocyclic Chemistry*, Pergamon Press).

The synthesis of mGluR2 modulators disclosed herein are shown in the following synthetic schemes. Specific conditions for carrying out these reactions are provided in the examples. In one embodiment, the invention provides compounds of Formula V, where the $V_1T_1M_1$ group can be introduced by alkylation (N—C, bond formation) using the appropriate starting materials (i.e. pyridine derivatives or pyridinone derivatives). The $V_1T_1M_1$ group can be introduced by an alkylation (O—C or N—C, bond formation), a reductive amination (C—N, bond formation), or by displacement of a leaving group Cl, Br, I or OP, where OP is defined as a leaving group (e.g. tosylate, and mesylate) (C—N or C—O, bond formation). C—N, C—O and C—C bond formation are well understood by a person skilled in the art of organic chemistry. The synthetic schemes described below show exemplified approaches to compounds of the present invention but these routes should not be taken as the only possible synthetic routes to compounds of the present invention.

Pyridinones g1 are commercially available or may be synthesized in ways described in the literature (Synthesis, 2002, 79-82; Tetrahedron Asymmetry, 1998, 2027; J. Heterocycl. Chem., 1974, 251; Synth. Commun., 1994, 1367). Selective bromination of a suitably substituted pyridine g1 leads to bromopyridine g2. It is well known that such brominations can lead to isomers (Bioorg. Med. Chem. Lett., 2002, 197-202) which can be separated by crystallization or column chromatography. The group $V_1T_1M_1$ can then be introduced in one step by alkylation using an elaborated W—$V_1T_1M_1$ group (where W is Cl, Br or OP) or alternatively, a HO—$V_1T_1M_1$ group using Mitsunobu conditions (Tetrahedron Letters, 1994, 2819-2822). It is described in the literature that this procedure may give undesired O-alkylated product which can be separated by crystallization or column chromatography.

Scheme 1

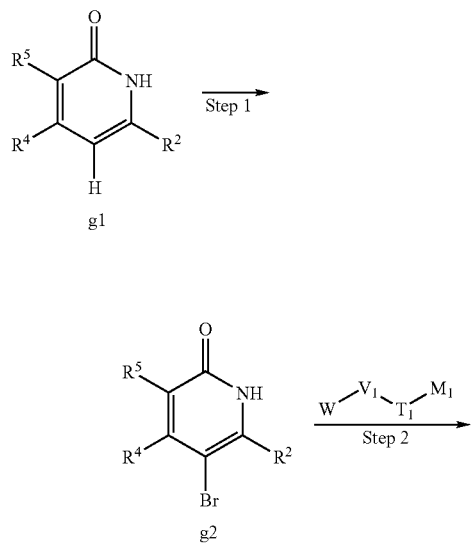

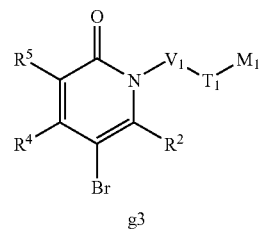

Alternatively, the group $V_1T_1M_1$ can be introduced by reaction of a suitably substituted 2-methoxypyridine with an elaborated W—$V_1T_1M_1$ where W is Cl, Br or OP (Scheme 2).

Scheme 2

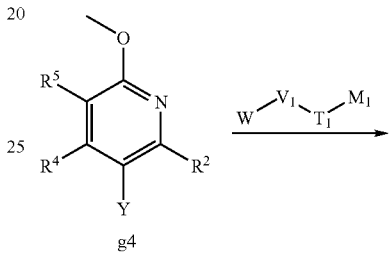

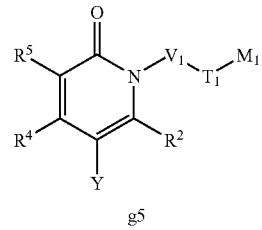

Y = Br, COOMe, CN, CHO

Suitably substituted, means in the context of the invention, substituents as defined in the list of preferred substituents or substituent which can be precursor of the aforementioned preferred substituents and are therefore protected in a manner that a person skilled in the art would recognize.

The introduction of the $V_2T_2M_2$ can be done through carbon-carbon bond formation (Scheme 3).

- Using a boronic acid under Suzuki-Miyaura conditions (Chem. Rev., 1995, 95, 54, 263) where $V_2T_2$ are bonds and $M_2$ is aryl, heteroaryl, cycloalkenearyl or cycloalkeneheteroaryl (Method A).
- Using a suitable alkylidinyl group under Sonogashira condition (J. Med. Chem., 2000, 43, 4288-4312) where $V_2T_2$ is an alkylidinyl group and $M_2$ is aryl, alkylaryl, heteroaryl or alkylheteroaryl (Method B).
- Using a suitable alkylidenyl group under Heck condition where $V_2T_2$ is alkylidenyl group and $M_2$ is aryl, alkylaryl, heteroaryl or alkylheteroaryl.

Scheme 3

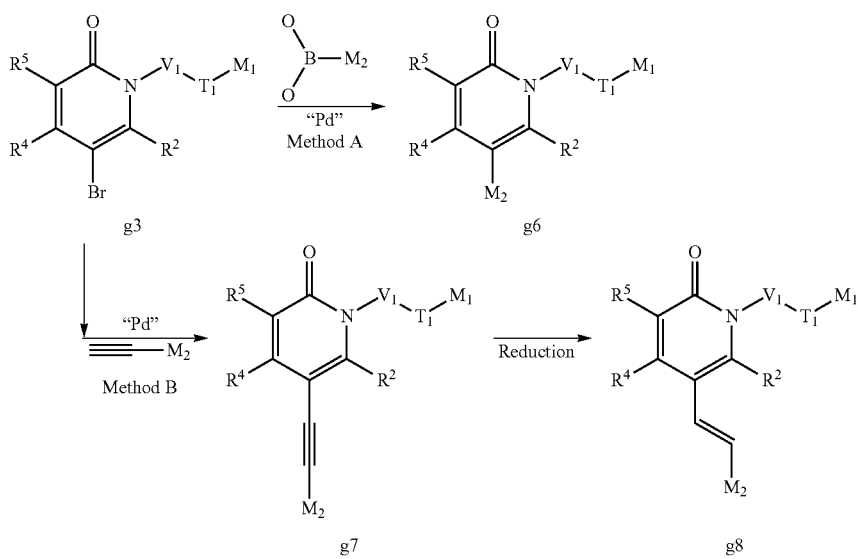

The Suzuki-Miyaura (Method A, Scheme 3) carbon-carbon coupling reaction requires a catalyst such as $PdCl_2(PPh_3)_2$, $Pd(PPh_3)_4$, $Pd_2(dba)_3$, $Pd_2(dppf)$ or $Pd(OAc)_2$ and an aqueous or non-aqueous base such as sodium carbonate, potassium carbonate, sodium hydroxide or cesium fluoride in a suitable solvent such as dioxane, toluene, dimethoxyethane or DMF. The Sonogashira (Method B, Scheme 3) carbon-carbon coupling reaction requires a catalyst such as $PdCl_2(PPh_3)_2$, $Pd(PPh_3)_4$ or $Pd(OAc)_2$ in a suitable solvent such as DMF, acetonitrile or benzene. Typically, a co-catalyst such as copper (I) iodide and a base such as triethylamine, diisopropylamine, or KOAc will also be present in the reaction mixture. The Suzuki-Miyaura and Sonogashira reactions typically react at temperatures ranging from 0° C. to 150° C. Typically, the reaction is maintained for 1 to 24 hours, with 12 hours usually being sufficient. The product of the reaction can be isolated and purified using standard techniques such as solvent extraction, column chromatography, crystallization, distillation and sublimation.

For a person skilled in the art of organic chemistry it is well understood that compound g7 can be hydrogenated under catalytic conditions using for example Pd/C and $H_2$ or ammonium formate (as hydrogen source) to afford the partially reduced analogs g8 which are also part of this invention. It is noteworthy that a full hydrogenated version cannot be achieved under these conditions and therefore another approach should be envisaged to achieve fully reduced compounds (Scheme 8).

The inventors are aware that some chemical groups within $V_1T_1M_1$ may not be compatible with the aforementioned carbon-carbon bond forming reaction (i.e. Sonogashira, Heck or Suzuki-Miyaura). Therefore, the $V_1T_1M_1$ group can be introduced later in the synthesis (Scheme 4, Method A) and for example the Sonogashira reaction could be performed in the first step on a suitably substituted 2-methoxypyridine 5-boronic acid g9. The synthesis of such boronic acid is well described in the literature (J. Org. Chem., 2002, 67, 7541-7543) from commercial precursors with aryl and heteroaryl triflates or bromides. Aryl and heteroaryl bromides are available from commercial sources. The synthesis can also be performed from a suitably substituted 2-methoxypyridine having in position 5 an halide or a triflate reacting in a Suzuki-Miyaura reaction with a boronic compound $Q-M_2$ where Q is $B(OR)_2$. (Method B)

Scheme 4

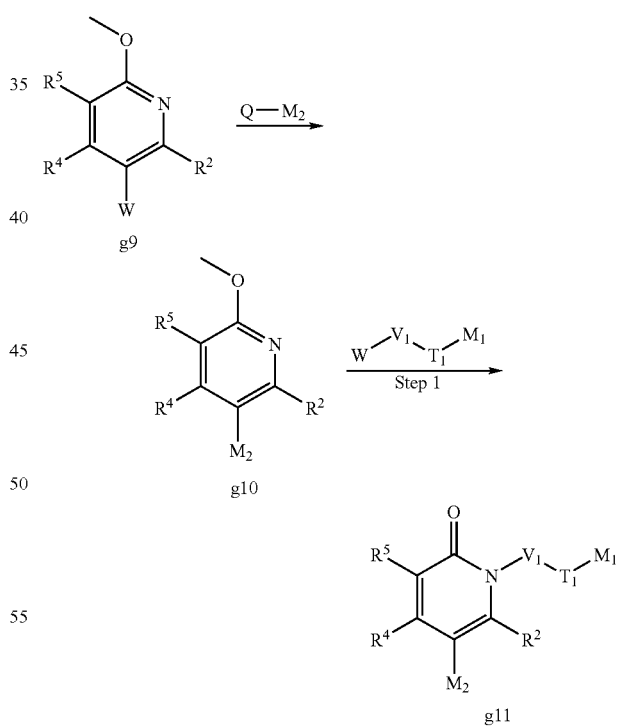

Method A: $W = B(OR)_2$, $Q = OSO_2CF_3$, Br
Method B: $W = OSO_2CF_3$, Br, $Q = B(OR)_2$ Likewise, the $V_2T_2M_2$ (in this case $V_2$ and $T_2$ are bonds and $M_2$ is aryl, alkenearyl, aryl or heteroaryl) group can be introduced onto g2 in the first step (Scheme 5), to yield compound g12 which is then subjected to $W-V_1T_1M_1$ under conditions similar to those described in Scheme 1, Step 2.

Scheme 5

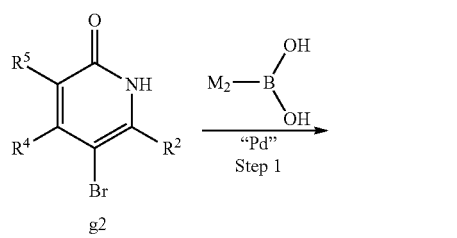

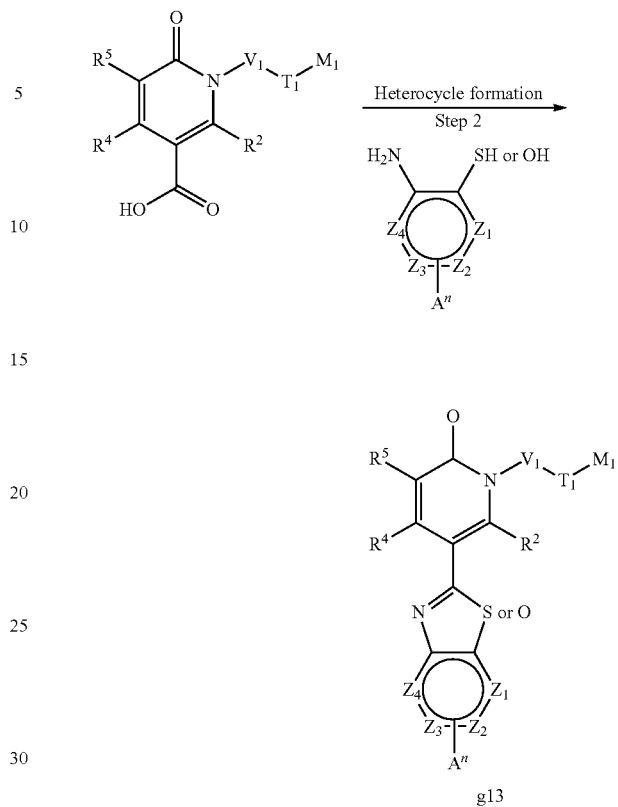

For a person skilled in the art of organic chemistry it is well understood that functionalities present in compound g5 (where Y is COOMe, CN or CHO) may be further transformed into compound g13 as exemplified where Y is COOMe (Scheme 6).

Scheme 6

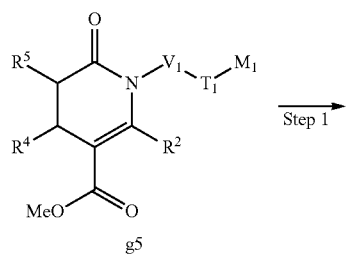

The acid compound generated from the ester g5 is an excellent anchoring point for heterocycle formation such as benzothiazole, oxadiazole, benzoxazole or isoxazole. The composition of the invention is not limited only to the aforementioned heterocycles but extends to our preferred list of heterocycles which may be synthesized through a similar scheme. (A. R. Katrizky and C. W. Rees, 1984, *Comprehensive Heterocyclic Chemistry*, Pergamon Press).

For one skilled in the art of organic chemistry it is well understood that functionalities present in compound g5 (where Y is COOMe, CN or CHO) may be further transformed into compounds g14, g15, g16 and g17 (Scheme 7).

Scheme 7

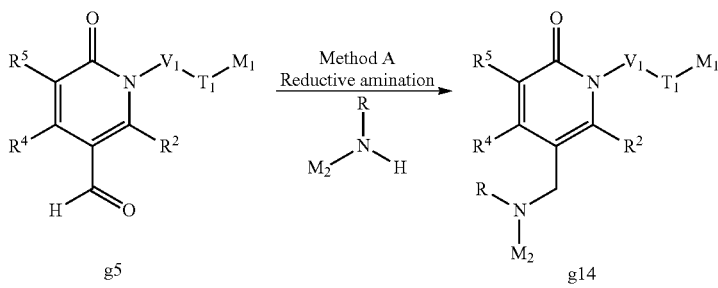

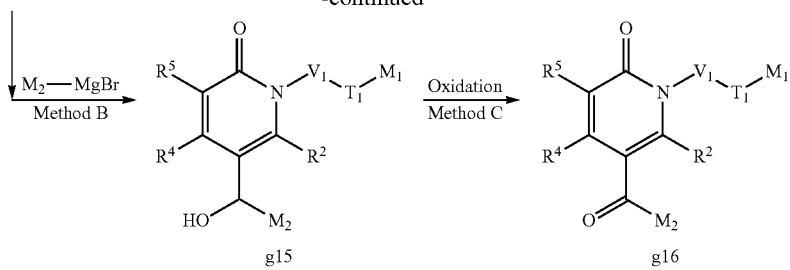

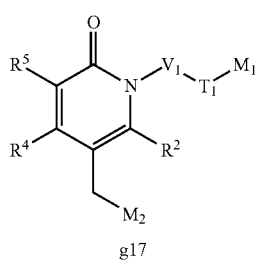

The reductive amination to afford compound g14 is well documented in the literature (Helv. Chim. Acta, 1998, 81, 1754). The synthesis of alcohol g15 may utilize organometallic reagents such as the Grignard reagent exemplified here. However, many alternative organometallic reagents may be used and their preparation and use is well exemplified in the literature (M. Schlosser, 1994, *Organometallics in Synthesis*, John Wiley & Sons, Inc.). Compound g15 can be subsequently transformed into ketone g16 via oxidation or into alkyl g17 via reductive elimination.

The inventors are aware that for specific compounds of the invention for instance compound g19 neither compound g5 nor compound g3 are compatible intermediates, therefore, compound g4 would be a suitable starting material (Scheme 8).

Scheme 8

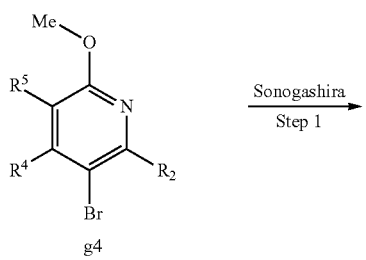

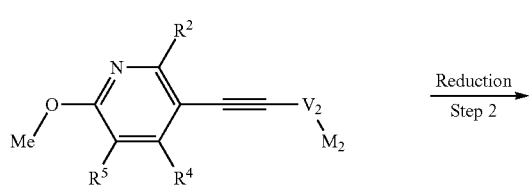

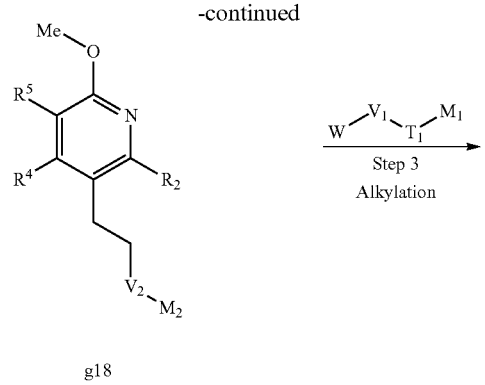

All the methods used in Scheme 8 have been described in previous schemes.

A person skilled in the art of organic chemistry would recognise that the $V_1T_1M_1$ group assembly may be constructed stepwise to afford compounds g20 and g22 (Scheme 9).

Scheme 9

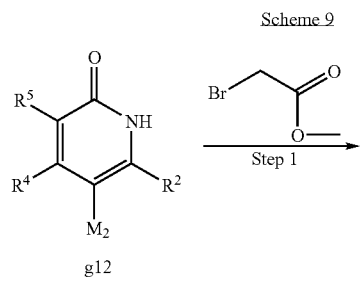

The acid moiety present in g21 is an excellent anchoring point for heterocycle formation such as benzothiazole g23, benzoxazole g24, oxadiazole g25 and isoxazole (Scheme 10) which are also compounds of this invention. The composition of the invention is not limited only to the aforementioned heterocycles but extend to our preferred list of heterocycles which can be synthesized through a similar scheme (A. R. Katrizky and C. W. Rees, 1984, *Comprehensive Heterocyclic Chemistry*, Pergamon Press; Chem. Pharm. Bull., 1999, 47, 120-122).

Scheme 10

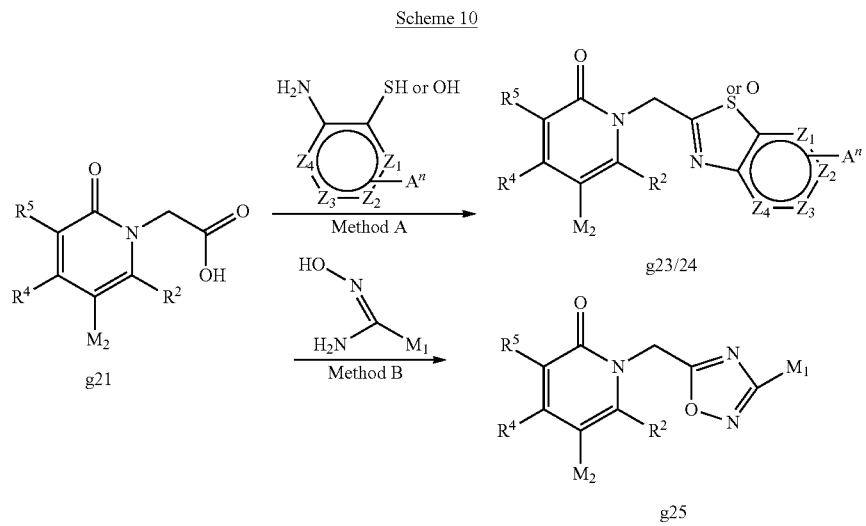

-continued

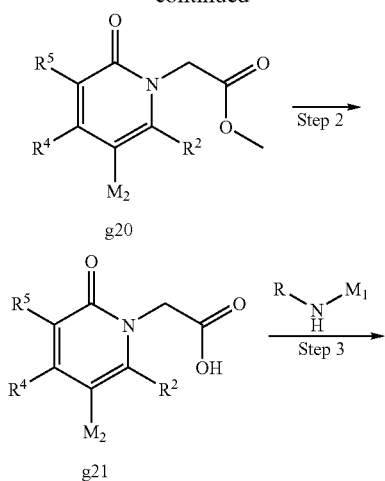

In another embodiment, the invention provides compounds of Formula (II) (Scheme 11). The synthesis of starting materials (i.e. isoquinolin-1-one derivatives) when not commercially available are well described in the literature (Chem. Ber., 1972, 3726-3747; Chem. Pharm. Bull., 1982, 1680-1691, Chem. Pharm. Bull., 1986, 2754-2759). For a person skilled in the art of organic chemistry it is well understood that the preferred substituents as defined in the claims can be introduced using similar chemistry. $V_1T_1M_1$ may be introduced using an elaborated $W—V_1T_1M_1$ (where W is Cl, Br or OP) in the presence of base such as NaH, $K_2CO_3$ or NaHMDS in a suitable solvent such as THF or DMF. It is noteworthy that these procedures may lead to undesired O-alkylated product which can be separated by crystallization or column chromatography.

Scheme 11

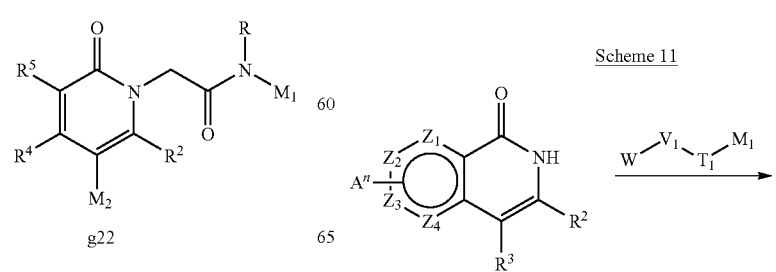

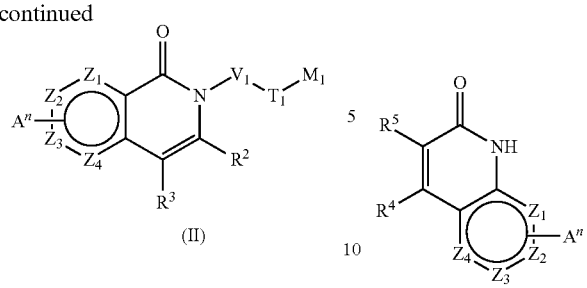

(II)

Scheme 12

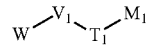

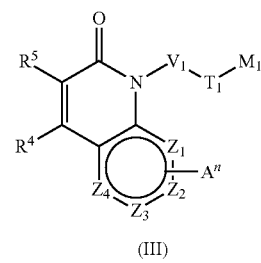

(III)

In another embodiment, the invention provides compounds of Formula (III) (Scheme 12). The syntheses of similar compounds are well described in the literature (Magn. Reson. Chem., 26, 1988, 511-517; J. Chem. Soc. Perkin Trans., 1, 1980, 197-202; J. Heterocycl. Chem., 1983, 1707-1708, Heterocycles, 1997, 483-492). For a person skilled in the art of organic chemistry it is well understood that preferred substituents as defined in the claims can be introduced using similar chemistry. $V_1T_1M_1$ can be introduced using an elaborated $W-V_1T_1M_1$ (where W is Cl, Br or OP) in presence of base such as NaH or $K_2CO_3$ or alternatively, with HO—$V_1T_1M_1$ using Mitsunobu condition (Tetrahedron Letters, 1994, 2819-2822) It is noteworthy that this procedure may lead to undesired O-alkylated product which can be separated by crystallization or column chromatography.

In another embodiment of the invention provides compounds of Formula (IV) (Scheme 13).

Scheme 13

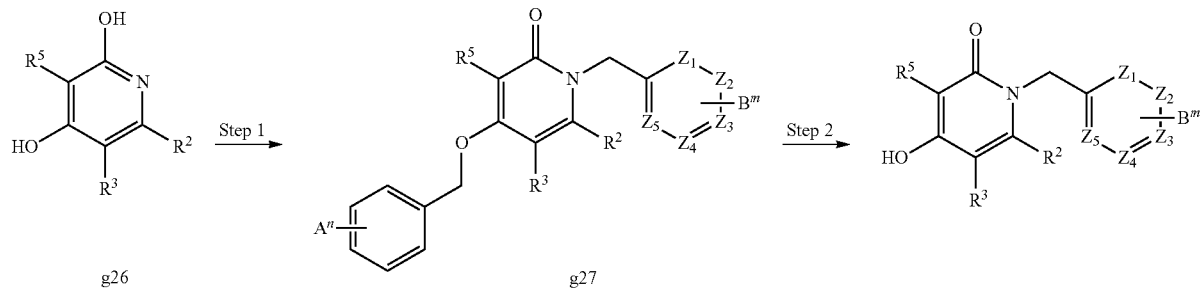

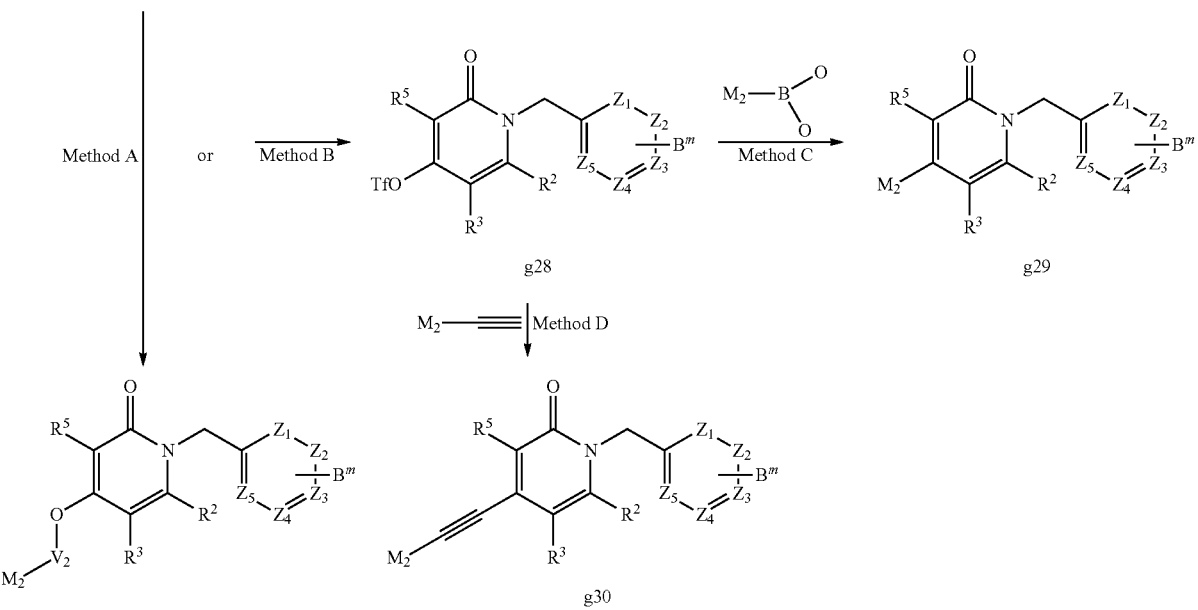

Alkylation of 2,4-dihydroxypyridine (commercially available) with a substituted benzyl halide is achieved using a base such as $K_2CO_3$ in a suitable solvent such as THF, $CH_3CN$ or DMF under heating at 80° C. This transformation may lead to a mixture of products which can then be separated to isolate intermediate g27. The deprotection of the hydroxybenzyl moiety can be selectively achieved using Pd/C and $H_2$ or ammonium formate (as hydrogen source). The subsequent alcohol can either be alkylated as described previously or transformed into a triflate. Triflate g28 is a rather sensitive molecule and is used in the carbon-carbon bond formation (exemplified here with a Suzuki-Miyaura reaction or Sonogashira coupling, Scheme 3).

In another embodiment of the present invention compounds of Formula (V) may be prepared in accordance with Scheme 14. Compound g31 can be deprotected in the presence of $BBr_3$ (J. Med. Chem., 1997, 40, 2085-2101). The resulting alcohol g32 can be alkylated by $XCH_2R$ where X may be a good leaving group such as Cl, Br, I or OP in the presence of a base such as $K_2CO_3$, $Cs_2CO_3$ or NaH in a suitable solvent such as DMF, acetone or tetrahydrofuran at an appropriate temperature or acylated by XCOR where X is Cl in the presence of a base such as $Et_3N$ or DIEA in a suitable solvent.

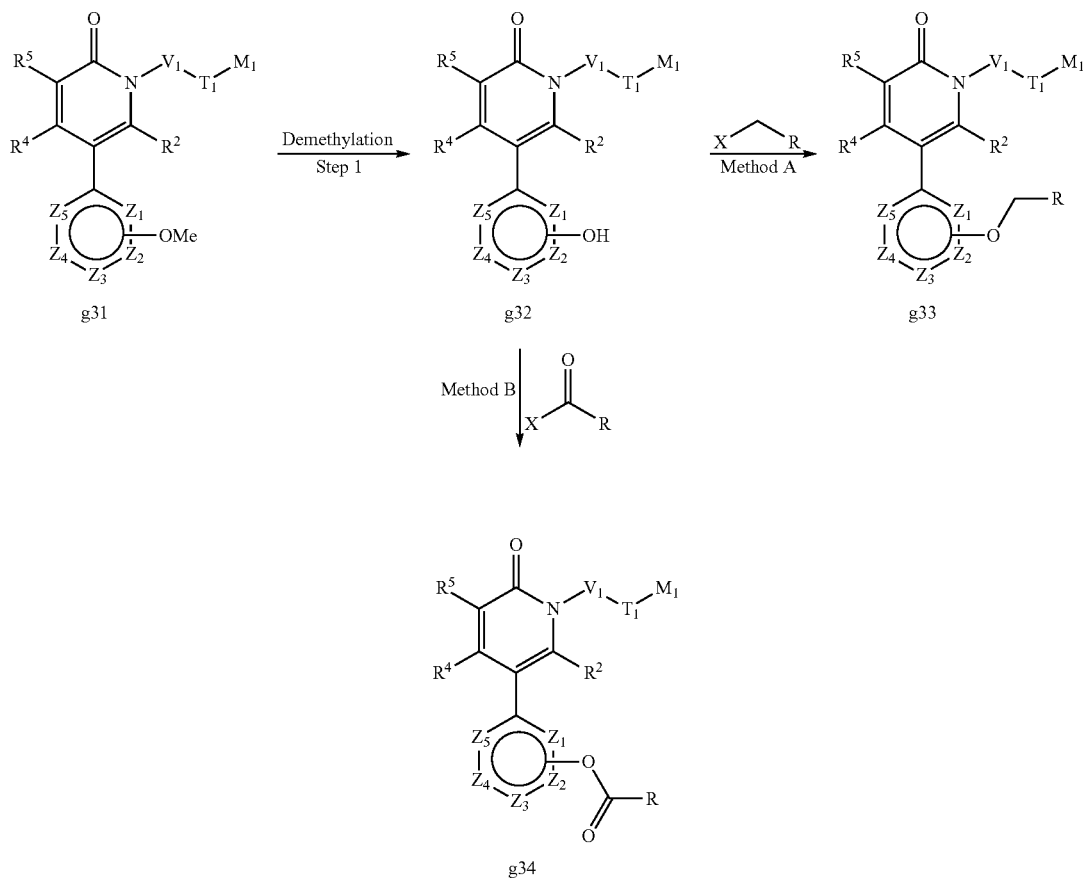

In another embodiment of the present invention, the compounds of Formula (V) may be prepared according to the synthetic sequences illustrated in Scheme 15. Compound g35 may be hydrolyzed by standard procedures followed by reaction with a primary or secondary amine in order to lead to compound g37 (Scheme 6). Compounds g36 and g38 represent an excellent anchoring point (acid, nitrile or amide) for heterocycle formation such as thiazole, oxadiazole, oxazole or isoxazole. The composition of the invention is not limited only to the aforementioned heterocycles but extends to our preferred list of heterocycles which can be synthesized through a similar scheme (A. R. Katrizky and C. W. Rees, 1984, *Comprehensive Heterocyclic Chemistry*, Pergamon Press).

Scheme 15

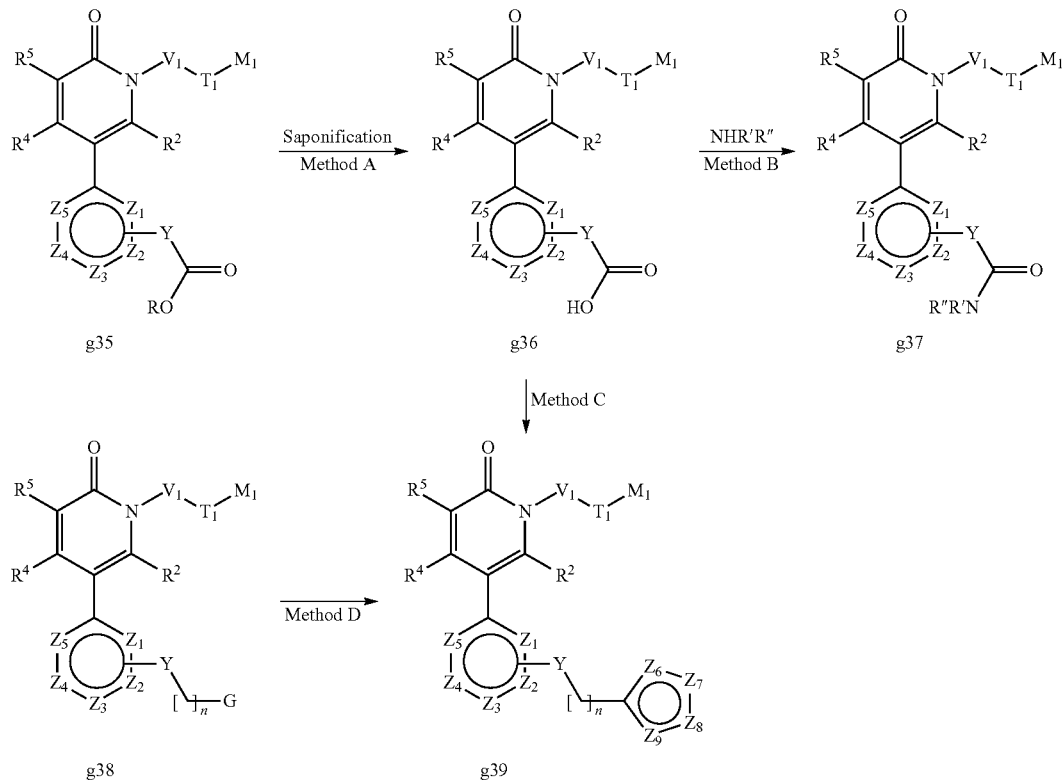

Y = bond, CHR, O, N
G = CN, CONH$_2$
n = 0, 1, 2, 3

In another embodiment of the present invention, compounds of Formula (V) may be prepared in accordance with Scheme 16. For a person skilled in the art of organic chemistry it is well understood that aldehyde g4 can be reduced using LiAlH$_4$ to afford the alcohol g40 which can be alkylated using either R'X (where X is Cl, Br or OP) in the presence of a base such as K$_2$CO$_3$, Cs$_2$CO$_3$ or NaH in a suitable solvent such as DMF, acetone or tetrahydrofuran or alternatively, using R'OH with Mitsunobu conditions as described in Scheme 1. Another way to synthesize compound g42 is to first alkylate compound g4 then reduce and finally to alkylate a second time.

Scheme 16

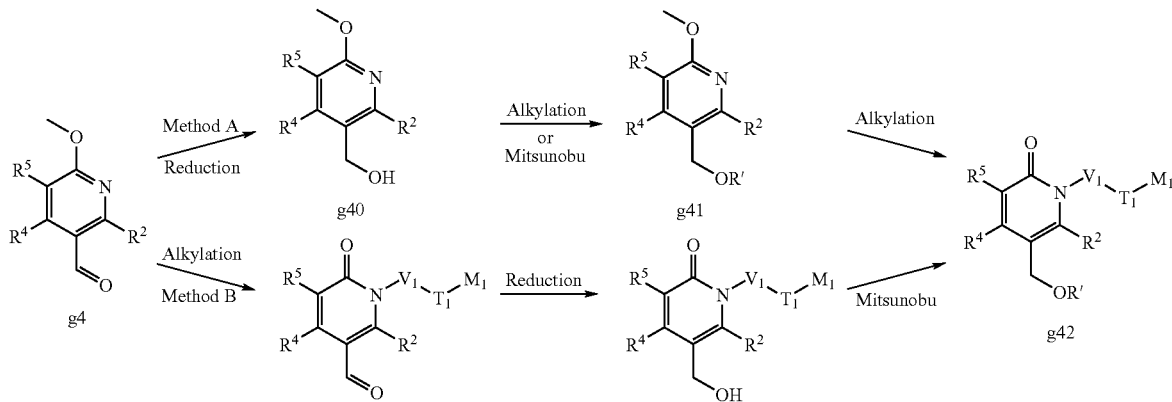

In one embodiment of the present invention compounds of Formula (V-b) may be prepared according to the synthetic sequences illustrated in Scheme 17. Compound g3 can be transformed into boronic esters via metal-halogen exchange in the presence of $Pd(PPh_3)_4$. The resulting boronic esters can be coupled to $M_2$ via Suzuki-Miyaura coupling as described in Scheme 3.

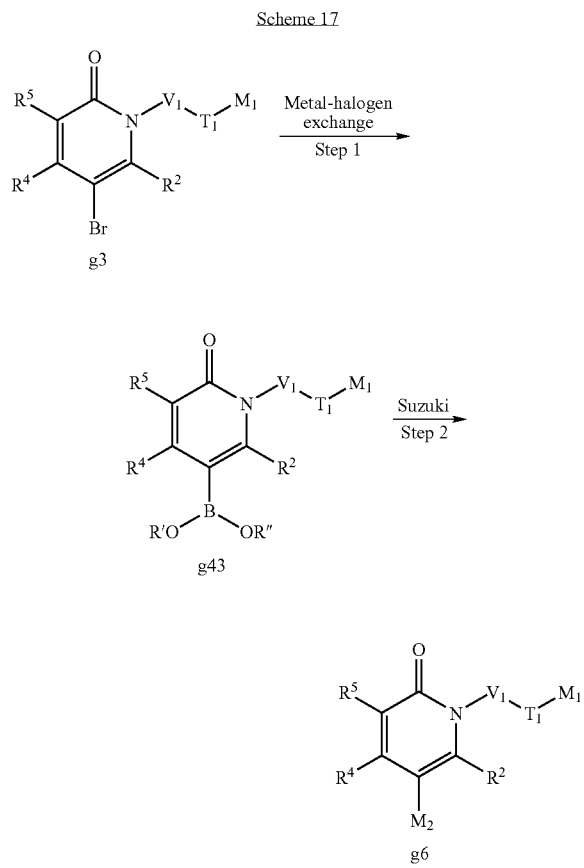

In another embodiment of the present invention, compounds of Formula (V) may be prepared in accordance with Scheme 18. For one skilled in the art of organic chemistry it is well understood that ester g44 can be reduced using $LiAlH_4$ to afford the alcohol g45.

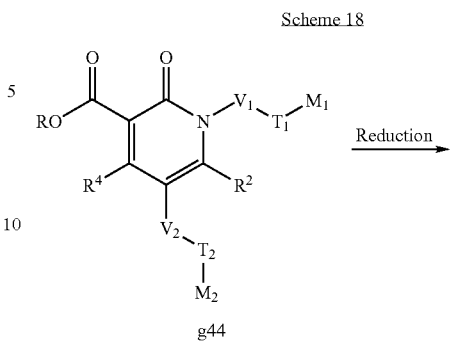

In another embodiment of the present invention, the compounds of Formula (V) may be also prepared according to the synthetic sequences illustrated in Scheme 19. Compound g3 can be submitted to Suzuki-Miyaura coupling with boronic compounds being substituted by a protected amino moiety. Then in Method A, the removal of the Boc group in compound g46 may be achieved under classical conditions well known in the art such as HCl or TFA. The resulting primary amine can then be either acylated by standard procedure or submitted to reductive amination (Scheme 7). And in Method B, compound g46 can be submitted first to alkylation using preferentially NaH as base and tetrahydrofurane as organic solvent followed by deprotection under acidic conditions (for example the reaction can be done in an organic solvent such as DCM with an acid such as TFA typically at room temperature to give compound g48b.

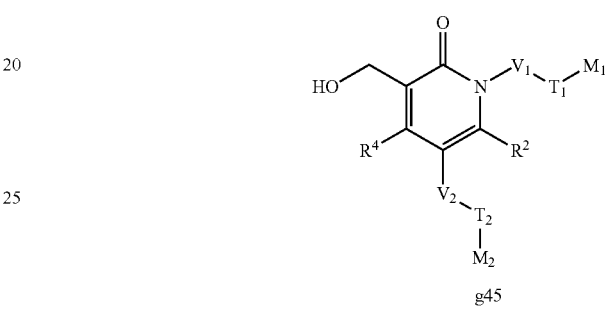

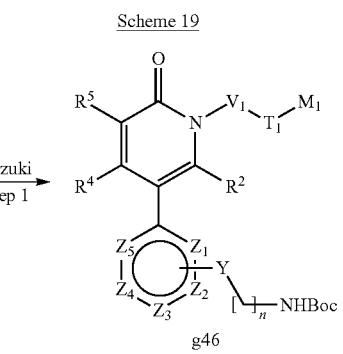

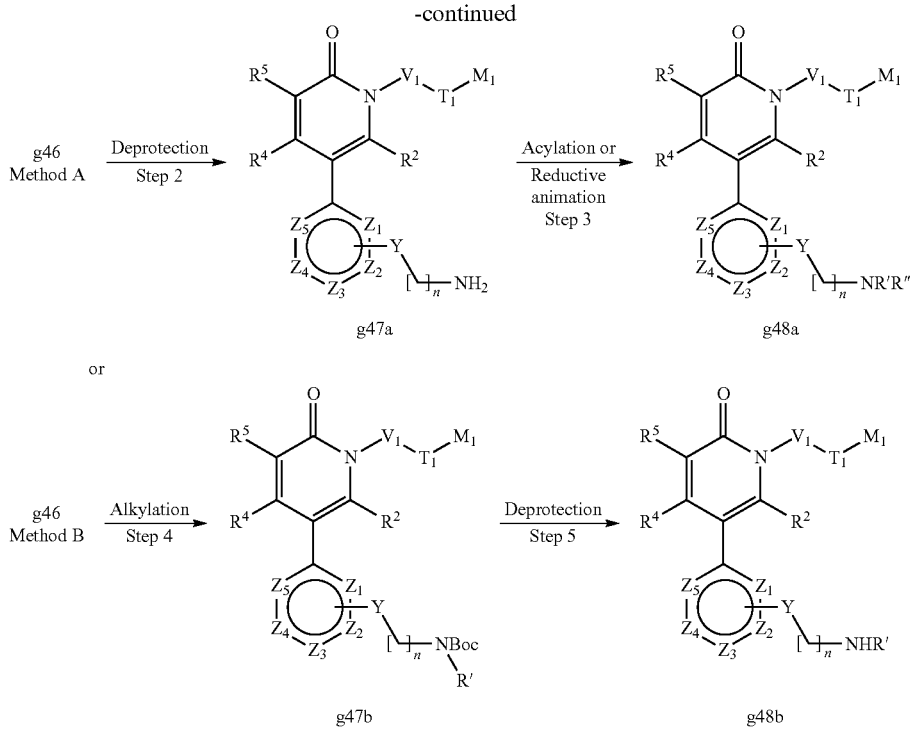

Y = bond, CHR, O, N
n = 0, 1, 2, 3

The synthesis of alcohol g50 may requires organometallic reagents such as the Grignard reagent exemplified here (Scheme 20). However, many alternative organometallic reagents may be used and their preparation and use is well exemplified in the literature (M. Schlosser, 1994, *Organometallics in Synthesis*, John Wiley & Sons, Inc.).

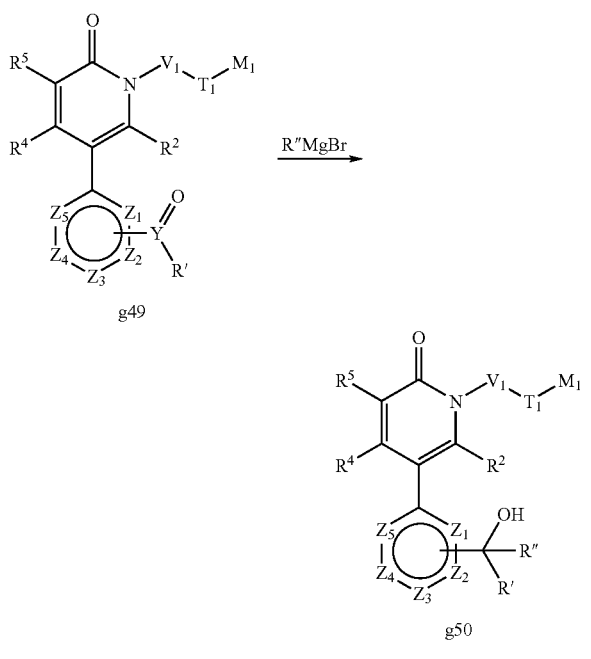

Another embodiment of the invention provides compounds of Formula (IV) (exemplified in Scheme 21). Substituted 3-bromo-pyridine or 3-iodopyridine g51 can be subjected to directed ortho metalation at low temperatures (e.g. −78° C.) in a solvent such as. THF or diethyl ether with lithium diisopropylamide and subsequently quenched with an electrophilic halogen source (e.g. $Br_2$ or $I_2$). 4-halopyridine g52 can then be functionalized by carbon-carbon bond forming reaction (Step 2, exemplified here by Suzuki-Miyaura or Stille reaction) under condition similar to those described in Scheme 3. Displacement of 2-halopyridine g53 by sodium methoxide in methanol yielded 2-methoxypyridine g54. Subsequent alkylation was then performed as described in Scheme 2 to yield pyridinone g55.

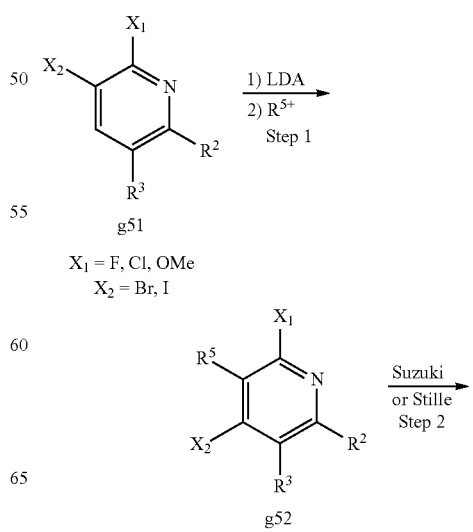

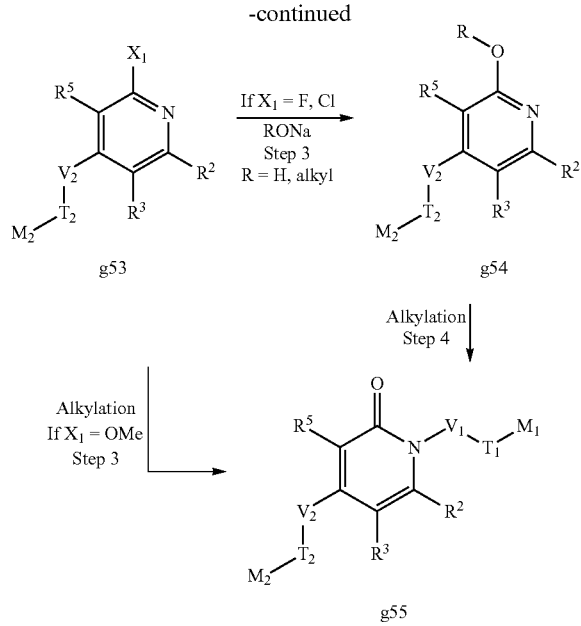

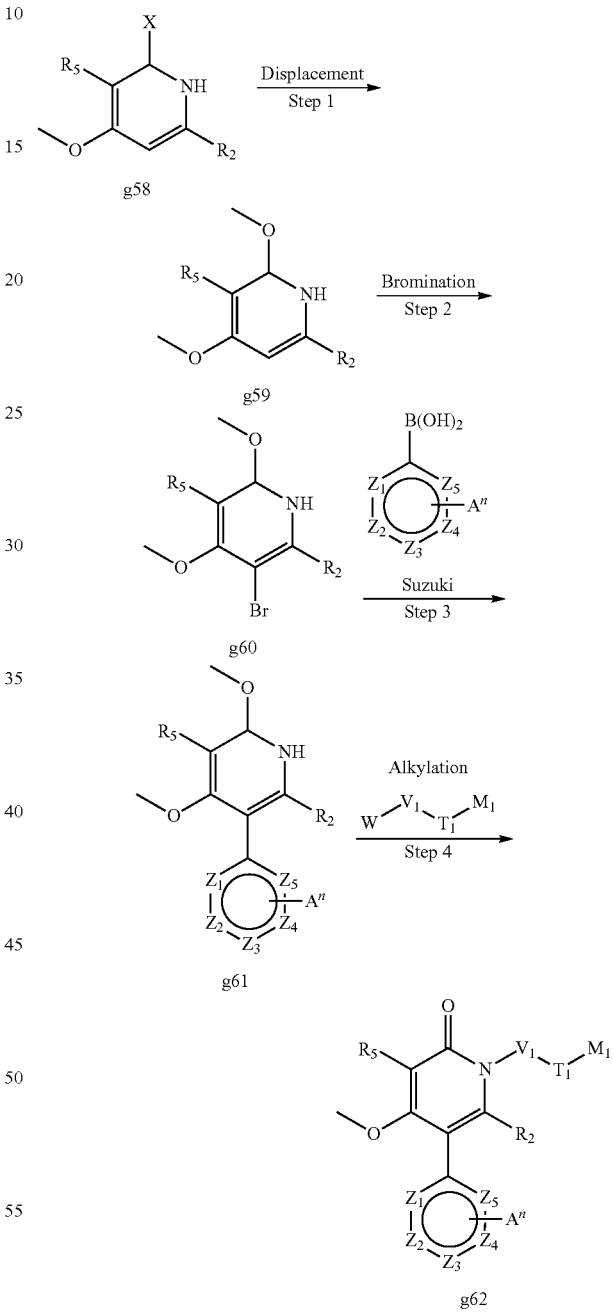

potassium bromide, potassium hydroxide and water (Step 2). The bromopyridine g60 was then functionalized by carbon-carbon bond forming reaction (Step 3, exemplified here by Suzuki-Miyaura reaction) under conditions similar to those described in Scheme 3. Step 4, alkylation was then performed as described in Scheme 2 to give compound g62.

Another embodiment of the invention provides compounds of Formula (V) (exemplified in Scheme 22). Method A, substituted 5-bromo-2-methoxy-pyridine g4 was subjected to lithium-halogen exchange at −78° C. in an a solvent such as THF or diethyl ether with butyl lithium and quenched with a substituted alkyl bromide ($M_2V_2T_2X$) to give compound g56. Alkylation was then performed as described in example 1 to give compound g57.

In a similar manner, compound g4 can be involved in a Buchwald reaction (Method B) with an amine in conditions known in the art using palladium, a suitable catalyst and a ligand to afford after alkylation compound g57 (where $V_2$=NH or N-alkyl).

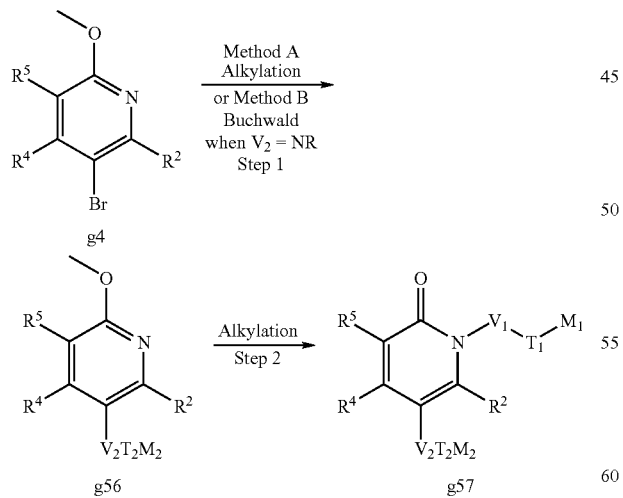

Another embodiment of the invention provides compounds of Formula (V-b) (Scheme 23). Step 1, nucleophilic displacement of 2-halopyridine g58 (where X=I, Br, Cl or F) by sodium methoxide in methanol yielded 2-methoxypyridine g59. Bromination was achieved using bromine, aqueous Another embodiment of the invention provides compounds of Formula (V-b) (Scheme 24). Step 1, substituted pyridine g2 (where X=Br, I or TfO) was first functionalized by carbon-carbon bond forming reaction (Step 1, exemplified here by Suzuki-Miyaura reaction) under conditions similar to those described in Scheme 3. Alkylation was performed with alkyl halides (W—$R_1$), NaI in MeCN at 70° C. (Step 2). The resulting alcohol g63 was alkylated using standard Williamson ether synthesis (Step 3, NaH, DMF and alkyl halide at 0° C.) to yield compound g64.

Scheme 24

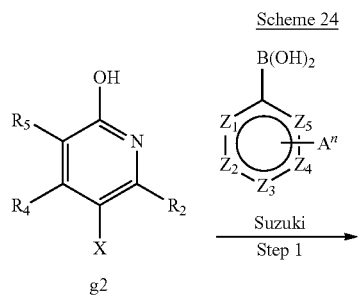

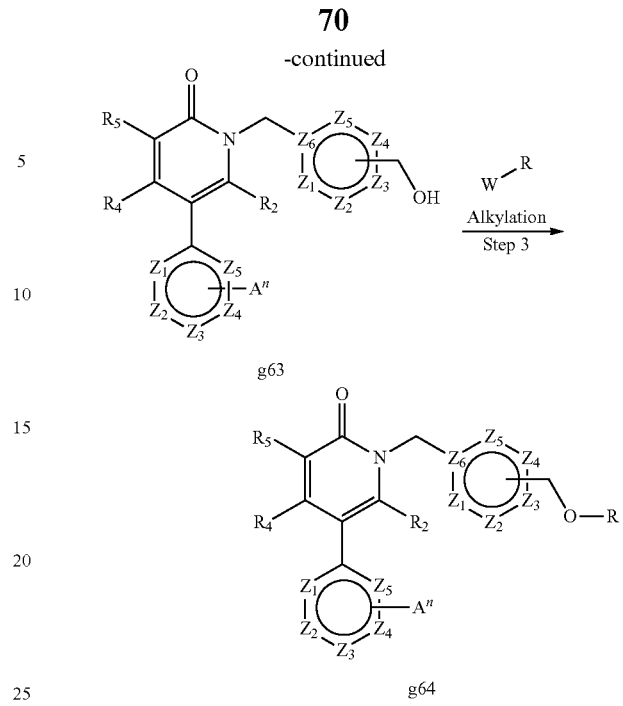

Another embodiment of the invention provides compounds of Formula (V-b) (Scheme 25). Alkylation of 2-hydroxypyridine g2 was performed as described in example 1. Step 2, bromopyridine 3 was first functionalized by carbon-carbon bond forming reaction (exemplified here by Suzuki-Miyaura reaction) under conditions similar to those described in Scheme 3. The alcohol g65 was then alkylated to obtain compound g66. Or bromination of compound g65 was achieved using $PPh_3$, NBS and $Et_2O$ at $-20°$ C. (Step 3). The resulting bromide was alkylated using standard Williamson ether synthesis to yield ether g66 (Step 4, alkyl alcohol, NaH and DMF at 0° C.).

Scheme 25

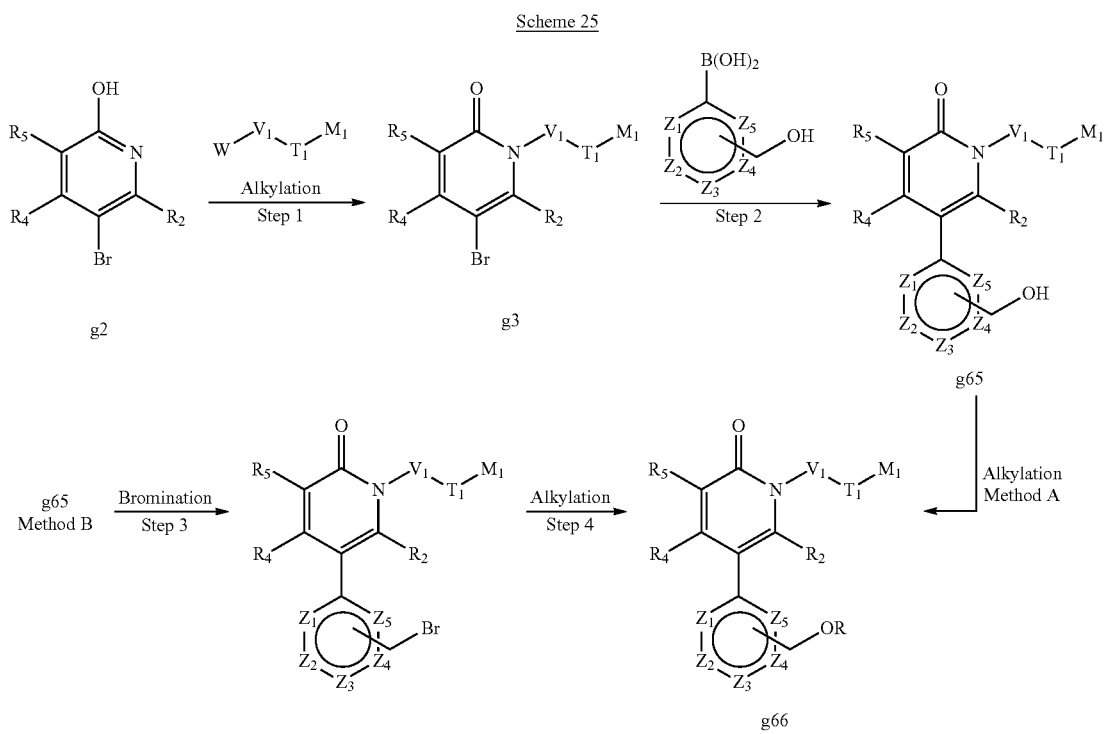

Another embodiment of the invention provides compounds of Formula (V-b) (Scheme 26). Step 1, lithium-halogen exchange on substituted 5-bromo-2-methoxy-pyridine g4 at −78° C. in THF with butyl lithium was reacted with a substituted carbonyl compounds. The resulting alcohol g67 was then eliminated using MsCl, TEA and DCM at room temperature (Step 2). The olefin g68 was then hydrogenated using standard conditions ($H_2$, Pd/C in EtOH). Finally, the compound was alkylated as described for Scheme 2 to give compound g70.

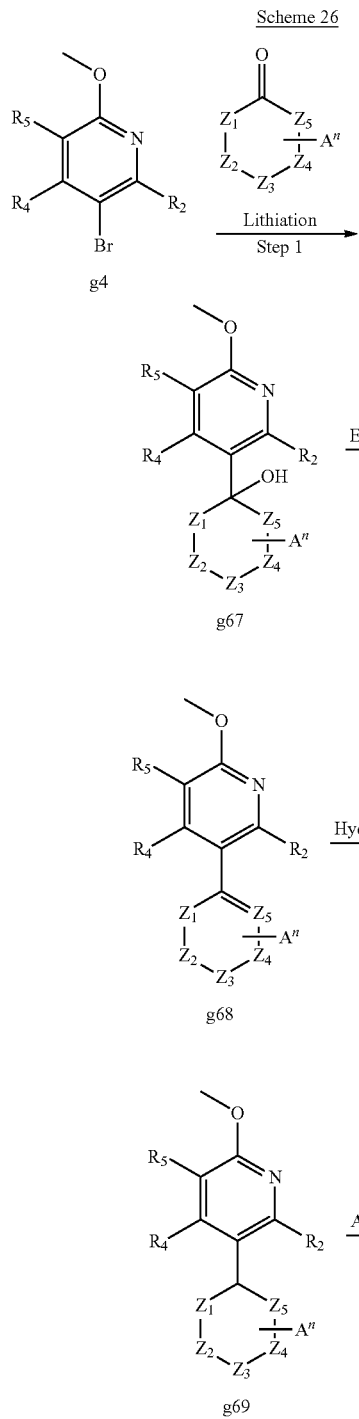

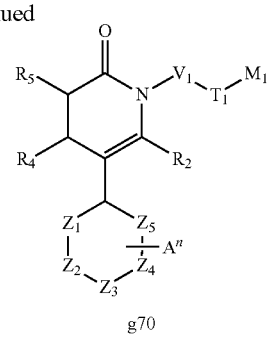

Another embodiment of the invention provides compounds of Formula (I) (Scheme 27). Where W is Cl, Br, I and OTf, pyrazine g71 was alkylated using standard conditions (Step 1). NaH, DMF or $K_2CO_3$, MeCN, at room temperature, elevated temperatures or with microwave irradiation. Alternatively, where W is OH, alkylation could be performed by Mitsunobu reaction using, DEAD, $PPh_3$, THF at room temperature or 60° C. The bromopyrazine g72 was then subjected to a carbon-carbon bond forming reaction (Step 2, exemplified here by Suzuki-Miyaura reaction) under conditions similar to those described in Scheme 3 to give compound g73.

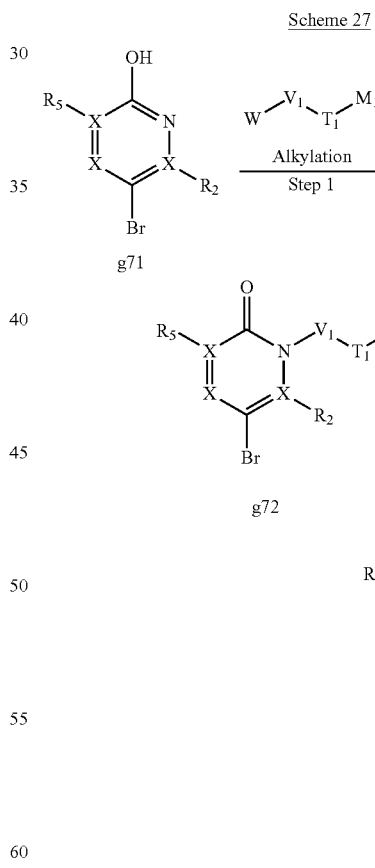

Where X = C or N

In another embodiment of the present invention, the compounds of Formula (II) may be prepared according to the synthetic sequences illustrated in Scheme 28. Isoquinoline g74 can be converted into isoquinolone g76 (Heterocycles, 1996, 42, 415) via oxidation with mCPBA followed by rearrangement of the N-oxide in the presence of acetic anhydride and then by basic sodium hydroxide cleavage. Finally, the resulting isoquinolone g76 can be alkylated as described in Scheme 1 and submitted to Buchwald coupling (if $V_2$=NR) as in Scheme 22. It is obvious that introduction of $V_1T_1M_1$ or $V_2T_2M_2$ groups can be done through the same process as described earlier.

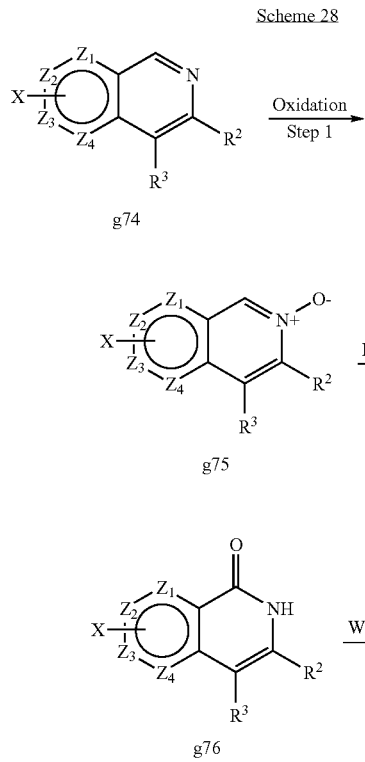

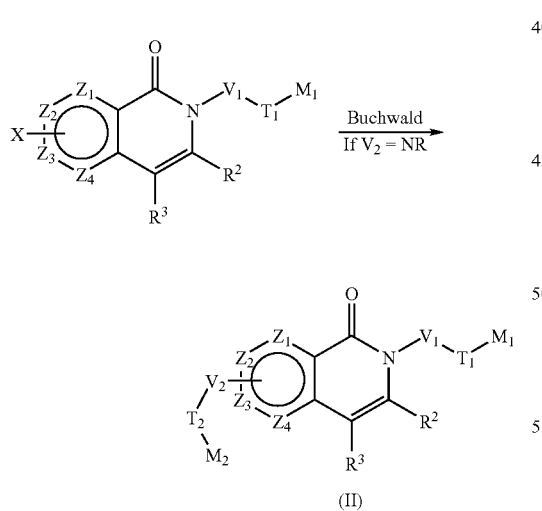

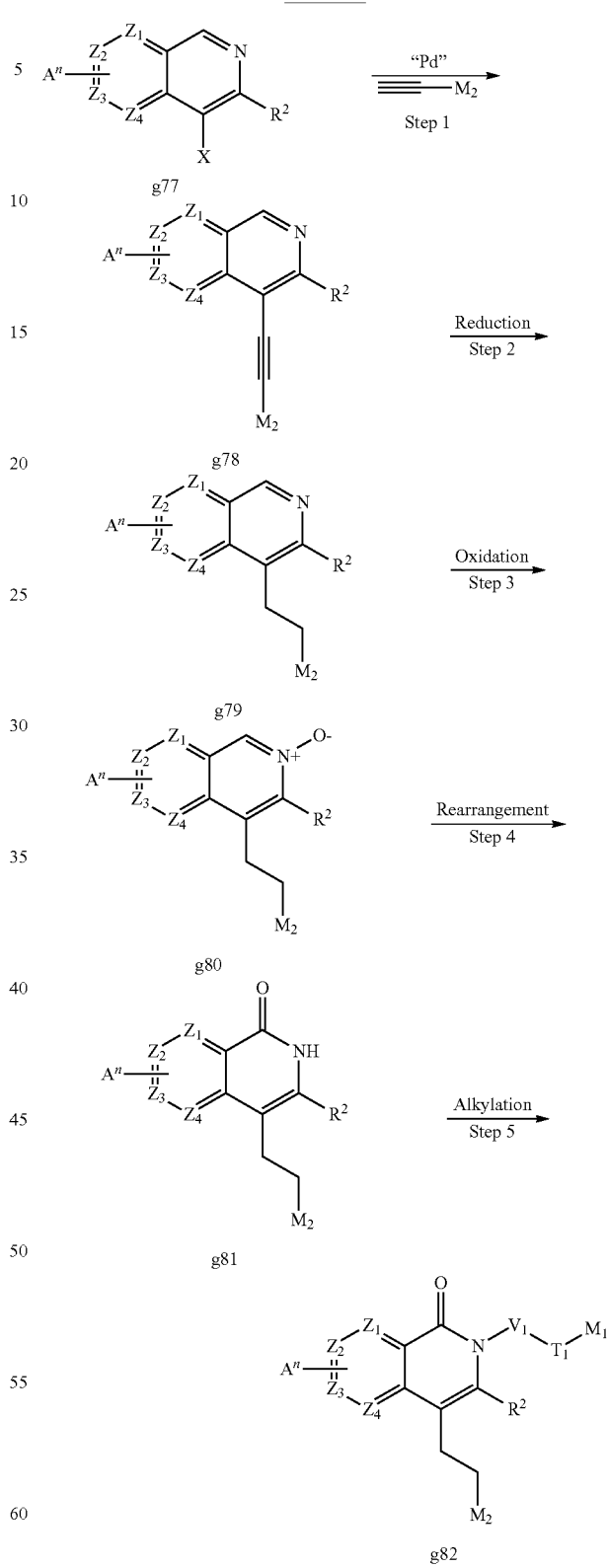

In another embodiment of the present invention, the compounds of Formula (II) may be prepared according to the synthetic sequences illustrated in Scheme 29. Compound g77 can be submitted to a Sonogashira coupling and reduced (Scheme 8) to yield compound g79. Then the isoquinoline may be transformed into alkylated isoquinolone g82 as presented in Scheme 29.

In another embodiment of the present invention, compounds of Formula (V-b) can be prepared in accordance with Scheme 30. Bromopyridine g83 can be functionalized by carbon-carbon bond forming reaction (exemplified here by Suzuki-Miyaura reaction) under condition similar to those described in Scheme 3. The resulting pyridine g84 can be lithiated by strong base such as butyl lithium or LDA in THF at low temperatures (e.g. −78° C.) and subsequently quenched with paraformaldehyde to give alcohol g86 after workup. N-Alkylation by NaI in acetonitrile at elevated temperatures using W—$V_1T_1M_1$ yields compound g86. The resulting alcohol g86 can be alkylated by the methods described in Scheme 24, step 3.

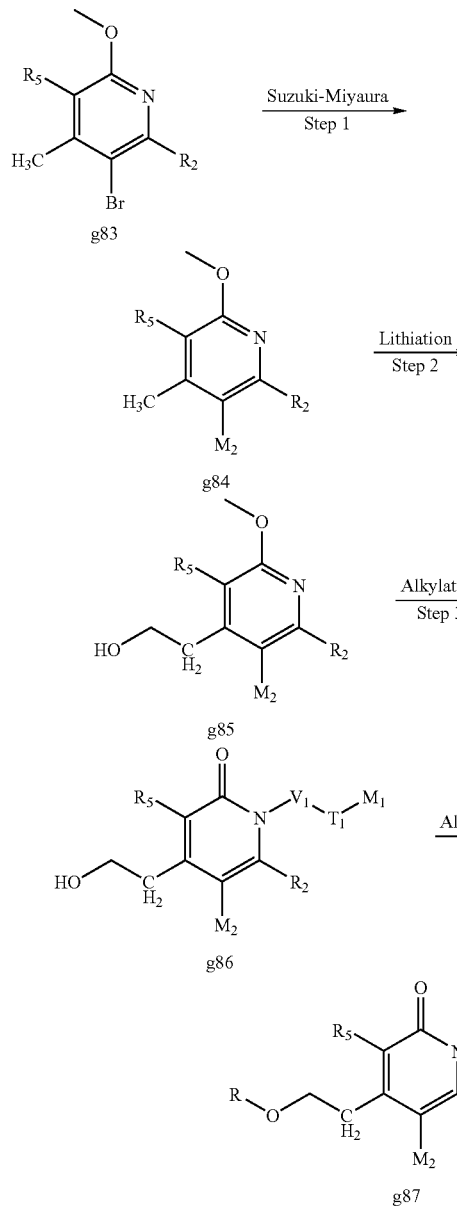

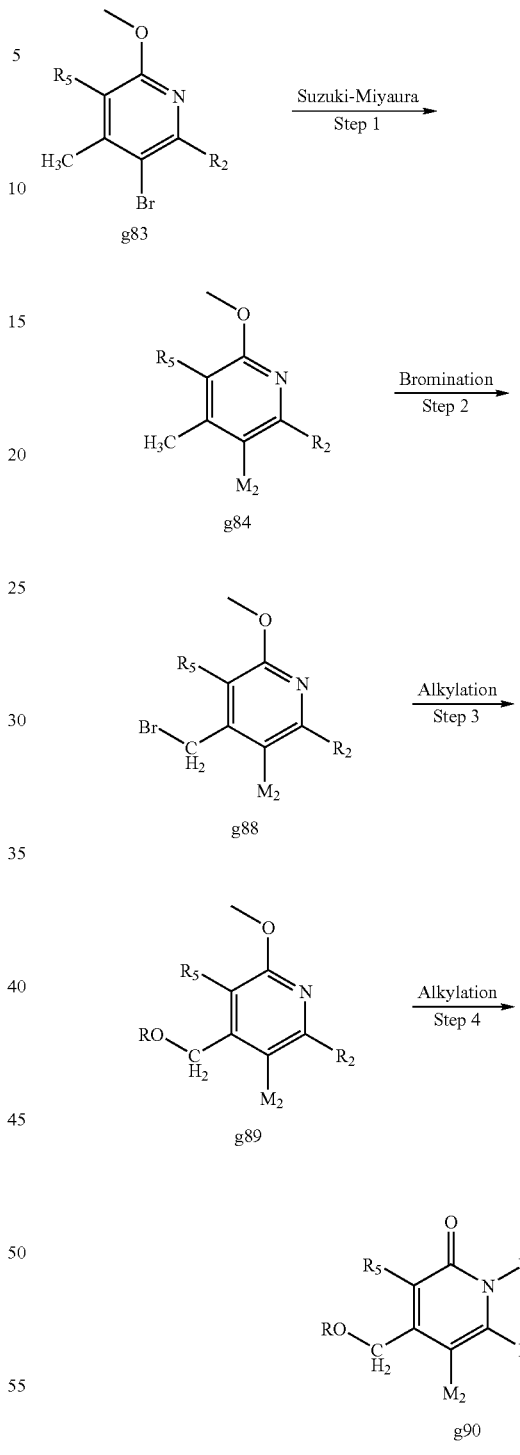

In another embodiment of the present invention, compounds of Formula (V-b) can be prepared in accordance with Scheme 31. Pyridine g84 was prepared as described in Scheme 30. Bromination with NBS under UV light in $CCl_4$ at reflux gave compound g88. Alkylation using ROH and sodium methoxide at reflux gave compound g89. The resulting alcohol g89 can then be alkylated by the methods described in Scheme 1.

Compound g93 (Scheme 32) can be synthesized from either bromide g91 or alcohol g92 using any one of the procedures known in the art, for example, using a copper catalyzed coupling reaction conditions when R is aryl or via a Mitsunobu reaction conditions when R is alkyl respectively. Finally, the resulting ether g93 can be alkylated with for example alkyl halide, in an organic solvent such as acetonitrile or dimethylformamide and with a base such as $K_2CO_3$.

Scheme 32

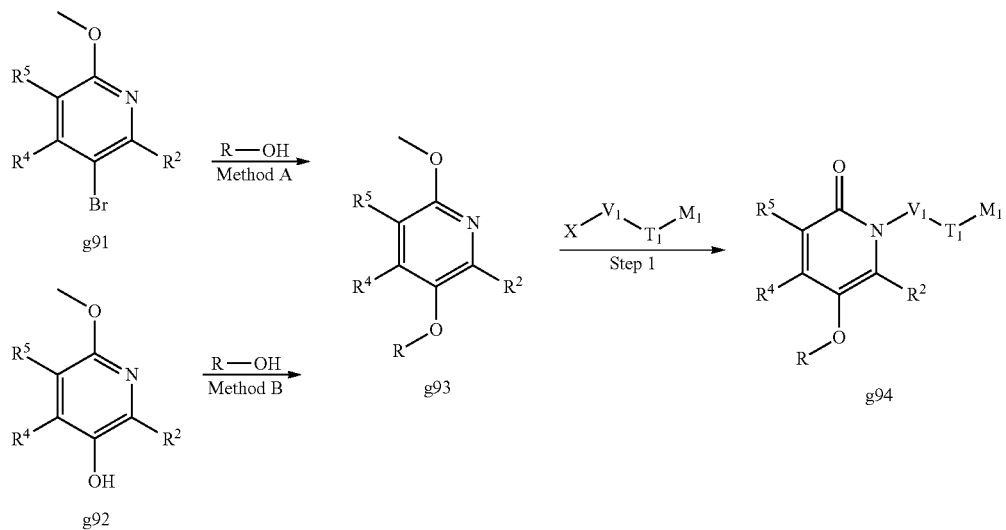

Compound g96 (Scheme 33) can be synthesized from pyridine g95 (prepared as described in Schemes 1 and 3) via halogen exchange. Then the iodopyridine may be coupled through Sonogashira or Heck conditions to alkynes or alkenes respectively. The resulting insaturated compound g97 can then be reduced as exemplified earlier by hydrogenation to give compound g98.

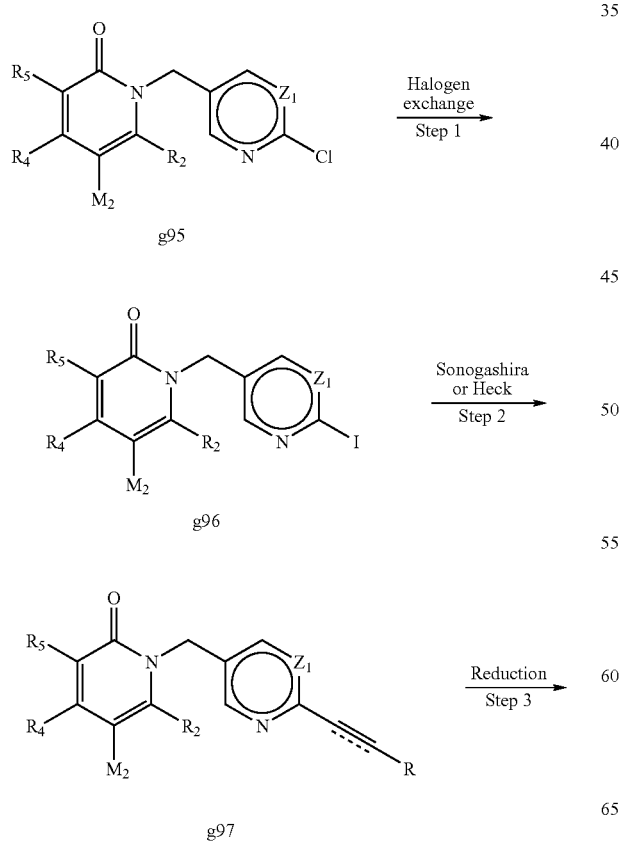

-continued

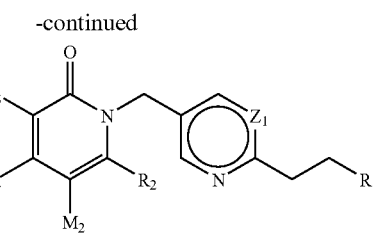

In another embodiment of the present invention, the compounds of Formula (II) may be prepared according to the synthetic sequences illustrated in Scheme 34. Isoquinoline g99 can be converted into his N-oxide g100 via oxidation in the presence of MCPBA followed by standard alkylation. Rearrangement of N-oxide g101 in the presence of acetic anhydride and basic sodium hydroxide cleavage yielded isoquinolone g102. Finally, the resulting isoquinolone g102 can be alkylated as described in Scheme 1. It is obvious that introduction of $V_1T_1M_1$ or $V_2T_2M_2$ groups can be done through the same process as described earlier.

Scheme 34

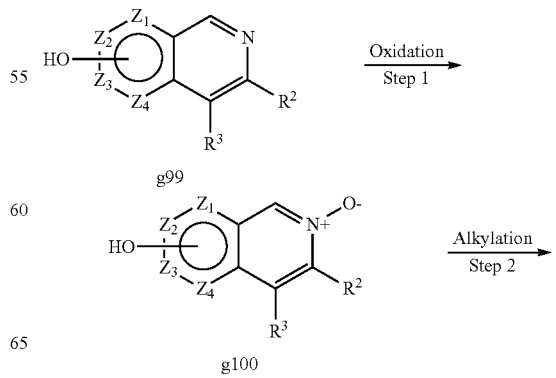

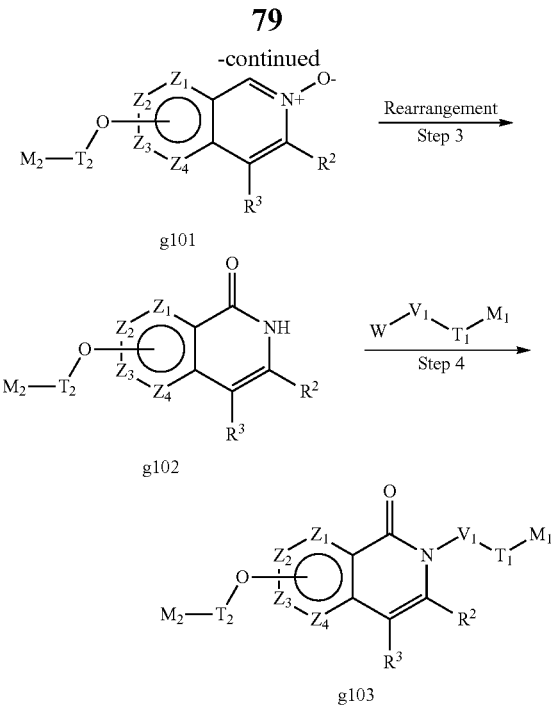

EXPERIMENTAL

Several methods for preparing the compounds of this invention are illustrated in the following Examples.

Unless otherwise noted, all starting materials were obtained from commercial suppliers and used without further purification.

Specifically, the following abbreviations may be used in the examples and throughout the specification.

AcOEt (ethyl acetate)
AcOH (acetic acid)
$BBr_3$ (boron tribromide)
BINAP (±-1,1'-Bi(2-naphthol))
$Br_2$ (bromine)
$CDCl_3$ (deuterated chloroform)
$CCl_4$ (carbon tetrachloride)
$CH_2Cl_2$ (dichloromethane)
MCPBA (3-chloroperbenzoic acid)
DEAD (diethyl azodicarboxylate)
DIBAL (diisobutyl aluminium hydride)
DME (dimethoxyethane)
DMF (dimethylformamide)
DMSO (dimethyl sulfoxide)
Dppf (1,1'-bis(diphenylphosphanyl)ferrocene)
EDCI.HCl (1-3(dimethylaminopropyl)-3-ethylcarbodiimide, hydrochloride)
$Et_3N$ (triethylamine)
$Et_2O$ (diethyl ether)
EtOH (ethanol)
g (grams)
$^1H$ (proton)
$H_2$ (hydrogen)
HCl (hydrochloric acid)
HPLC (High Pressure Liquid Chromatography)
Hz (Hertz)
KBr (potassium bromide)
$K_2CO_3$ (potassium carbonate)
KOAc (potassium acetate)
KI (potassium iodide)
KOtBu (potassium tert-butoxide)
KOH (potassium hydroxide)
$K_3PO_4$ (potassium phosphate)

LCMS (Liquid Chromatography Mass Spectrum)
$LiAlH_4$ (lithium aluminium hydride)
M (molar)
MeOH (methanol)
mg (milligrams)
$MgSO_4$ (magnesium sulphate)
MHz (megahertz)
min (minutes)
μL (microliters)
mL (milliliters)
mmol (millimoles)
M.p. (melting point)
$NaBH(OAc)_3$ (sodium borohydride triacetate)
$Na_2CO_3$ (sodium carbonate)
NaH (sodium hydride)
$NaHCO_3$ (sodium hydrogenocarbonate)
NaHMDS (sodium hexamethyldisilazane)
NaI (sodium iodide)
$NaO^tBu$ (sodium tert-butoxide)
$Na_2SO_4$ (sodium sulphate)
NBS (N-bromosuccinimide)
$NH_4Cl$ (ammonium chloride)
$NH_4OH$ (ammonium hydroxide)
NMR (Nuclear Magnetic Reasonance)
$Pd_2(dba)_3$ (palladium (II)dibenzylideneacetone)
$PdCl_2(dppf)_2$ (Bis(1,1'-bis(diphenylphosphanyl)ferrocene palladium (II) dichloride
$PdCl_2(PPh_3)_2$ (Bis(triphenylphosphine) palladium (II) dichloride
$Pd(OAc)_2$
$Pd(PPh_3)_4$ (tetrakis(triphenylphosphine)palladium(0))
$PPh_3$ (triphenylphosphine)
Rf
RT (Retention Time)
TFA (trifluoroacetic acid)
THF (tetrahydrofuran)
TLC (thin layer chromatography)

All references to brine refer to a saturated aqueous solution of NaCl. Unless otherwise indicated, all temperatures are expressed in ° C. (degrees Celsius). All reactions are conducted not under an inert atmosphere at room temperature unless otherwise noted.

The microwave oven used is an apparatus from Biotage (Optimizer™) equipped with an internal probe that monitors reaction temperature and pressure, and maintains the desired temperature by computer control.

EXAMPLES

Example 1

1-(4-Chloro-2-fluorobenzyl)-5-(6-methoxypyridin-3-yl)pyridin-2(1H)-one (Final Compound 6-51)

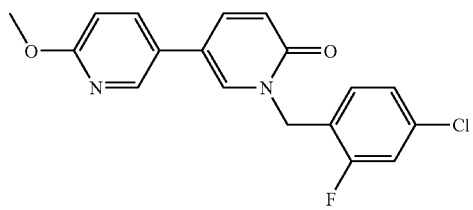 [SMILES: COc1ccc(-c2ccc(=O)n(Cc3ccc(Cl)cc3F)c2)cn1]

Step 1: 5-Bromopyridin-2(1H)-one

According to Scheme 1 Step 1: A mixture of 2-hydroxypyridine (1 eq, 100 mmol, 10.0 g) in AcOH (100 mL) was treated with NBS (1.06 eq, 110 mmol, 19.8 g) at room temperature for 4 hours. The mixture was concentrated, azeotroped twice with EtOH then the solid was taken up in hot EtOH (100 mL). After cooling to room temperature, the precipitate was removed by filtration and recrystallized from EtOH to provide 5-bromopyridin-2(1H)-one (51.7 mmol, 9.00 g, 49%) as a pale brown solid. Rf=0.60 (AcOEt/MeOH/NEt$_3$ 100/15/1); LC (XTerra RP$_{18}$, 3.5 µm, 3.0×50 mm Column): RT=0.59-2.46 min; MS m/z (CI) [MH]$^+$=174, 176.

Step 2: 1-(4-Chloro-2-fluorobenzyl)-5-bromopyridin-2(1H)-one

According to Scheme 1 Step 2: K$_2$CO$_3$ (10 eq, 0.11 mmol, 16.0 g) and 1-(bromomethyl)-4-chloro-2-fluorobenzene (1.5 eq, 17.0 mmol, 3.90 g) was added to a solution of 5-bromopyridin-2(1H)-one (1 eq, 11.0 mmol, 2.00 g), in THF (100 mL). The suspension was stirred for 2 hours at room temperature and 17 hours at 60° C. The reaction mixture was filtered and the mother liquor was concentrated under reduced pressure. The crude product was purified by flash chromatography over silica gel (AIT Flashsmart prepacked column 70 g SiO$_2$) using CH$_2$Cl$_2$/AcOEt 80/20 as eluent to afford the title compound 1-(4-chloro-2-fluorobenzyl)-5-bromopyridin-2(1H)-one (9.10 mmol, 2.87 g, 79%) as a white solid.

LC (XTerra RP$_{18}$, 3.5 µm, 3.0×50 mm Column): RT=4.12 min; MS m/z (CI) [MH]$^+$=316, 318.

Step 3: 1-(4-Chloro-2-fluorobenzyl)-5-(6-methoxypyridin-3-yl)pyridin-2(1H)-one According to Scheme 3 Method A: To a mixture of 1-(4-chloro-2-fluorobenzyl)-5-bromopyridin-2(1H)-one (1 eq, 1.00 mmol, 0.40 g) in dioxane/K$_3$PO$_4$ (2M, 10 mL), were added Pd(PPh$_3$)$_4$ (0.3 eq, 0.4 mmol, 0.4 g) and 6-methoxypyridin-3-ylboronic acid (1.5 eq, 2.00 mmol, 0.30 g) then the reaction mixture was heated at 80° C. for 17 hours. The mixture was diluted with AcOEt. The organic fraction washed with brine, dried over Na$_2$SO$_4$, filtered and concentrated under reduced pressure. The crude product was purified by silica gel chromatography (AIT Flashsmart prepacked column 25 g SiO$_2$, CH$_2$Cl$_2$/AcOEt 70/30) and by crystallization in pentane/Et$_2$O to afford 1-(4-chloro-2-fluorobenzyl)-5-(6-methoxypyridin-3-yl)pyridin-2(1H)-one (0.91 mmol, 0.40 g, 91%) as a white solid.

M.p.: 136° C.; LC (XTerra RP$_{18}$, 3.5 µm, 3.0×50 mm Column): RT=4.13 min; MS m/z (CI) [MH]$^+$=345, 347; $^1$H NMR (300 MHz, DMSO-d$^6$) δ 3.87 (s, 3H), 5.17 (s, 2H), 6.53 (d, J=9.5 Hz, 1H), 6.89 (d, J=8.7 Hz, 1H), 7.17-7.24 (m, 1H), 7.27 (dd, J=2.0 Hz and 8.4 Hz, 1H), 7.46 (dd, J=2.0 Hz and 10.2 Hz, 1H), 7.84-7.94 (m, 2H), 8.20 (d, J=2.6 Hz, 1H), 8.38 (d, J=2.3 Hz, 1H).

Example 2

1-(4-Chlorobenzyl)-5-(4-(3-hydroxypropyl)phenyl)pyridin-2(1H)-one (Final Compound 2-16)

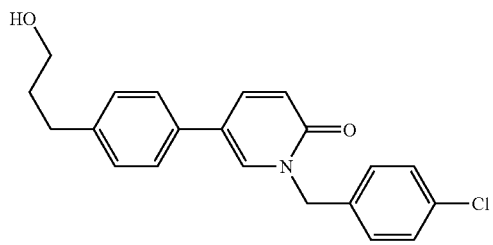 [SMILES: O=c1ccc(-c2ccc(CCCO)cc2)cn1Cc1ccc(Cl)cc1]

Step 1: 1-(4-Chlorobenzyl)-5-bromopyridin-2(1H)-one

According to Scheme 1 Step 2: The title compound was prepared from 5-bromopyridin-2(1H)-one (1 eq, 29.0 mmol, 5.00 g, Example 1 Step 1) and 4-chlorobenzyl bromide (1.2 eq, 34.0 mmol, 7.10 g) according to the procedure described for Example 1 Step 2. After concentration of the solvent, water was added. The aqueous phase was extracted with AcOEt and the combined organic fractions were dried over Na$_2$SO$_4$, filtered and concentrated under reduced pressure. The crude product was recrystallized with pentane/Et$_2$O 50/50 to afford 1-(4-chlorobenzyl)-5-bromopyridin-2(1H)-one (26.2 mmol, 7.82 g, 91%) as a white solid.

LC (XTerra RP$_{18}$, 3.5 µm, 3.0×50 mm Column): RT=4.18 min; MS m/z (CI) [MH]$^+$=299, 301.

Step 2: 1-(4-Chlorobenzyl)-5-(4-(3-hydroxypropyl)phenyl)pyridin-2(1H)-one

According to Scheme 3 Method A: To a solution of 1-(4-chlorobenzyl)-5-bromopyridin-2(1H)-one (1 eq, 0.33 mmol, 0.10 g) in dioxane/saturated aqueous NaHCO$_3$ (1:1, 6 mL) was added Pd(PPh$_3$)$_4$ (0.15 eq, 0.05 mmol, 58 mg) and 4-(3-hydroxypropyl)phenylboronic acid (1.5 eq, 0.50 mmol, 90.0 mg). The reaction was then stirred at 90° C. for 4.5 hours. The reaction was allowed to cool and diluted with AcOEt. The reaction washed with saturated NH$_4$Cl solution, brine and the organic phase extracted (×3). The combined organic fractions were dried (Na$_2$SO$_4$), filtered and concentrated under reduced pressure. The crude product was purified by flash chromatography over silica gel (AIT Flashsmart prepacked column 15 g SiO$_2$) using pure AcOEt as the eluent to afford 1-(4-chlorobenzyl)-5-(4-(3-hydroxypropyl)phenyl)pyridin-2(1H)-one (0.22 mmol, 78 mg, 66%) as a white solid. M.p.: 165° C.; Rf=0.05 (CH$_2$Cl$_2$/AcOEt 80/20); LC (XTerra RP$_{18}$, 3.5 µm, 3.0×50 mm Column): RT=3.78 min; MS m/z (CI) [MH]$^+$=354, 356; $^1$H NMR (300 MHz, DMSO-d$^6$) δ 1.64-1.77 (m, 2H), 2.61 (t, J=7.3 Hz, 2H), 3.32-3.46 (m, 2H), 4.48 (t, J=5.1 Hz, 1H), 5.15 (s, 2H), 6.52 (d, J=9.5 Hz, 1H), 7.24 (d, J=8.1 Hz, 2H), 7.35-7.44 (4H), 7.47 (d, J=8.1 Hz, 2H), 7.83 (dd, J=2.6 Hz, 9.5 Hz, 1H), 8.23 (d, J=2.6 Hz, 1H).

Example 3

N-(3-(1-Isopentyl-6-oxo-1,6-dihydropyridin-3-yl)phenyl)methane-sulfonamide (Final Compound 8-02)

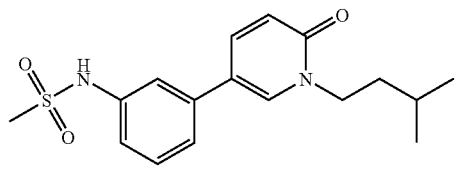 [SMILES: CC(C)CCn1cc(-c2cccc(NS(C)(=O)=O)c2)ccc1=O]

Step 1: 5-Bromo-1-isopentylpyridin-2(1H)-one

According to Scheme 1 Step 2: The title compound was prepared from 5-bromopyridin-2(1H)-one (1 eq, 0.01 mol, 1.73 g) and 1-isopentylbromide (1 eq, 0.01 mmol, 1.51 g) according to the procedure described for Example 1 Step 2. Reaction conditions: 3 hours under reflux in acetonitrile. The crude product was purified by flash chromatography over silica gel (AIT Flashsmart prepacked column SiO$_2$) using CH$_2$Cl$_2$/AcOEt (80/20) as the eluent to afford 5-bromo-1-isopentylpyridin-2(1H)-one (6.23 mmol, 1.52 g, 62%) as a brown oil.

Step 2: N-(3-(1-Isopentyl-6-oxo-1,6-dihydropyridin-3-yl)phenyl)methanesulfonamide According to scheme 3 Method A: The title compound was prepared from 5-bromo-1-isopentylpyridin-2(1H)-one (1 eq, 0.41 mmol, 0.10 g) and 3-(methylsulfonamido)phenylboronic acid (1.5 eq, 0.61 mmol, 0.13 g) according to the procedure described for Example 2 Step 2. The crude product was purified by flash chromatography over silica gel (AIT Flashsmart prepacked column 15 g SiO$_2$) using CH$_2$Cl$_2$/AcOEt (80/20) as the eluent to afford N-(3-(1-isopentyl-6-oxo-1,6-dihydropyridin-3-yl)phenyl)methanesulfonamide (0.32 mmol, 0.11 g, 77%) as a white solid.

M.p.: 159° C.; Rf=0.42 (CH$_2$Cl$_2$/AcOEt 50/50); LC (XTerra RP$_{18}$, 3.5 µm, 3.0×50 mm Column): RT=3.49 min; MS m/z (CI) [MH]$^+$=335; $^1$H NMR (300 MHz, DMSO-d$^6$) δ 0.93 (d, 6H), 1.49-1.62 (m, 3H), 3.02 (s, 3H), 3.91-4.00 (m, 2H), 6.48 (d, J=9.4 Hz, 1H), 7.10-7.18 (m, 1H), 7.28-7.42 (m, 3H), 7.70 (dd, J=2.6 Hz, 9.4 Hz, 1H), 8.03 (d, J=2.6 Hz, 1H), 9.78 (s, 1H).

Example 4

N-(5-(1-(4-Chlorobenzyl)-6-oxo-1,6-dihydropyridin-3-yl)-2-methoxyphenyl)methanesulfonamide (Final Compound 2-56)

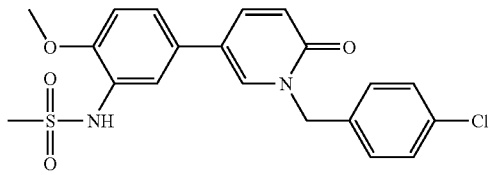 [SMILES: COc1ccc(-c2ccc(=O)n(Cc3ccc(Cl)cc3)c2)cc1NS(C)(=O)=O]

Step 1: 4-Methoxy-3-(methylsulfonamido)phenylboronic acid

To a solution of 3-amino-4-methoxyphenylboronic acid (1 eq, 2.10 mmol, 0.35 g) in CH$_2$Cl$_2$ (5 mL) at −78° C. was added Et$_3$N (6 eq, 13.0 mmol, 1.7 mL). The reaction was stirred for 30 minutes then methanesulfonyl chloride (1.1 eq, 2.30 mmol, 0.26 g) was added. The reaction was then stirred at −78° C. for 1 hour. The reaction was allowed to warm to room temperature and diluted with CH$_2$Cl$_2$. The reaction washed with 1.0N aqueous HCl and the organic phase was extracted (×3). The combined organic fractions were dried (Na$_2$SO$_4$), filtered and concentrated under reduced pressure to afford 4-methoxy-3-(methylsulfonamido)phenylboronic acid (1.92 mmol, 0.49 g, 96%) as a white solid.

LC (XTerra RP$_{18}$, 3.5 µm, 3.0×50 mm Column): RT=2.11 min; MS m/z (CI) [MH]$^+$=246.

Step 2: N-(5-(1-(4-Chlorobenzyl)-6-oxo-1,6-dihydropyridin-3-yl)-2-methoxyphenyl)methane sulphonamide According to Scheme 3 Method A: The title compound was prepared from 1-(4-chlorobenzyl)-5-bromopyridin-2(1H)-one (1 eq, 1.80 mmol, 0.55 g, Example 2 Step 1) and 4-methoxy-3-(methylsulfonamido)phenylboronic acid (1.1 eq, 2.00 mmol, 0.49 g) according to the procedure described for Example 1 Step 3. Reaction conditions: 4 hours at 80° C. The crude product was purified by flash chromatography over silica gel (AIT Flashsmart prepacked column 25 g SiO$_2$) using CH$_2$Cl$_2$/AcOEt (90/10) then recrystallized from pentane/Et$_2$O to afford N-(5-(1-(4-chlorobenzyl)-6-oxo-1,6-dihydropyridin-3-yl)-2-methoxyphenyl)methanesulphonamide (0.31 mmol, 0.32 g, 41%) as a white solid.

M.p.: 151° C.; LC (XTerra RP$_{18}$, 3.5 µm, 3.0×50 mm Column): RT=3.75 min; MS m/z (CI) [MH]$^+$=419, 421; $^1$H NMR (300 MHz, DMSO-d$^6$) δ 2.88 (s, 3H), 3.76 (s, 3H), 5.08 (s, 2H), 6.44 (d, J=10.9 Hz, 1H), 7.05 (d, J=10.9 Hz, 1H), 7.27-7.35 (m, 3H), 7.42-7.60 (m, 3H), 7.68 (dd, J=3.5 Hz, J=10.9 Hz, 1H), 8.08 (d, J=3.5 Hz, 1H), 8.94 (s, 1H).

Example 5

1-(3-Fluorobenzyl)-5-(2-(pyridin-3-yl)ethynyl)pyridin-2(1H)-one hydrochloride (Final Compound 7-02)

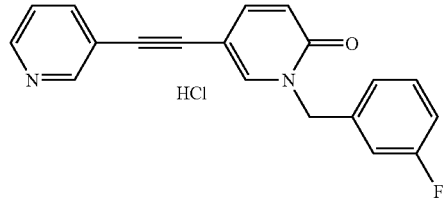 [SMILES: O=c1ccc(C#Cc2cccnc2)cn1Cc1cccc(F)c1 ; Cl]

Step 1: 1-(3-Fluorobenzyl)-5-bromopyridin-2(1H)-one

According to Scheme 1 Step 2: 1-(3-Fluorobenzyl)-5-bromopyridin-2(1H)-one was prepared from 5-bromopyridin-2(1H)-one (Example 1 Step 1) and 3-fluorobenzyl bromide according to the procedure described for Example 2 Step 1. The crude product washed with pentane/Et$_2$O 50/50 to afford 1-(3-fluorobenzyl)-5-bromopyridin-2(1H)-one (10.7 mmol, 3.00 g, 62%) as a white solid.

LC (XTerra RP$_{18}$, 3.5 µm, 3.0×50 mm Column): RT=4.05 min; MS m/z (CI) [MH]$^+$=283.

Step 2: 1-(3-Fluorobenzyl)-5-(2-(pyridin-3-yl)ethynyl)pyridin-2(1H)-one hydrochloride According to Scheme 3 Method B: Copper iodide (0.1 eq, 6.7 mg, 35 µmol) and Et$_3$N (20 eq, 7.09 mmol, 1.00 mL) in DMF (5 mL) were stirred under nitrogen for 10 min. PdCl$_2$(PPh$_3$)$_2$ (0.1 eq, 35 µmol, 25 mg) was added to the reaction mixture and the reaction mixture was stirred for a further 15 min at room temperature. 1-(3-Fluorobenzyl)-5-bromopyridin-2(1H)-one (1 eq, 0.35 mmol, 0.10 g) and 3-ethynylpyridine (1.2 eq, 0.43 mmol, 0.04 g) were successively added to the reaction mixture. After stirring at 80° C. for 4 hours, the reaction mixture was quenched with water and the aqueous layer washed with AcOEt (3×30 mL). The combined organic layers were dried over Na$_2$SO$_4$, filtered and evaporated under reduced pressure. The crude product was purified by chromatography on silica gel using CH$_2$Cl$_2$/AcOEt 90/10+1% HCl 2M in dioxane as eluent. 1-(3-Fluorobenzyl)-5-(2-(pyridin- 3-yl)ethynyl)pyridin-2(1H)-one hydrochloride was obtained as a beige solid (32 μmol, 11 mg, 9%).

M.p.: 179° C.; LC (XTerra RP$_{18}$, 3.5 μm, 3.0×50 mm Column): RT=3.68 min; MS m/z (CI) [MH]$^+$=305; $^1$H NMR (500 MHz, DMSO-d$^6$) δ 5.12 (s, 2H), 6.50 (d, J=9.4 Hz, 1H), 7.11-7.20 (3H), 7.37-7.43 (m, 1H), 7.51 (dd, J=5.0 Hz and 8.0 Hz, 1H), 7.58 (dd, J=2.5 Hz and 9.4 Hz, 1H), 7.96-8.00 (m, 1H), 8.37 (d, J=2.4 Hz, 1H), 8.59 (dd, J=1.6 Hz and 5.0 Hz, 1H), 8.73 (d, J=2.1 Hz, 1H).

Example 6

1-(4-Chloro-3-fluorobenzyl)-5-(benzo[d]thiazol-2-yl)pyridin-2(1H)-one (Final Compound 6-19)

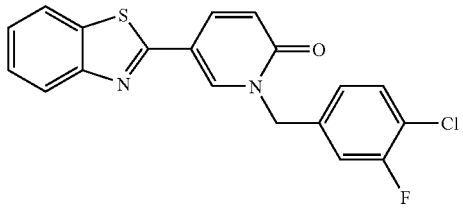 [SMILES: O=c1ccc(-c2nc3ccccc3s2)cn1Cc1ccc(Cl)c(F)c1]

Step 1: 2-(6-Methoxypyridin-3-yl)benzo[d]thiazole

According to Scheme 4 Method A: The title compound was prepared from 2-bromobenzo[d]thiazole (1 eq, 0.91 mmol, 0.20 g) and 6-methoxypyridin-3-ylboronic acid (1.5 eq, 1.36 mmol, 0.21 g) according to the procedure described for Example 2 Step 2. The crude product was purified by silica gel chromatography (AIT Flashsmart prepacked column 25 g SiO$_2$) using cyclohexane/AcOEt 95/5 as eluent to afford 2-(6-methoxypyridin-3-yl)benzo[d]thiazole (0.74 mmol, 0.18 g, 82%) as a white solid.

Step 2: 1-(4-Chloro-3-fluorobenzyl)-5-(benzo[d]thiazol-2-yl)pyridin-2(1H)-one

According to Scheme 4, Step 1: A mixture of 2-(6-methoxypyridin-3-yl)benzo[d]thiazole (1 eq, 0.25 mmol, 60 mg), NaI (5 eq, 1.20 mmol, 0.19 g) and 4-chloro-3-fluorobenzyl-bromide (5 eq, 1.20 mmol, 0.28 g) in acetonitrile (10 mL) was stirred for 14 hours at 90° C. The crude residue was partitioned between CH$_2$Cl$_2$ and water. The aqueous layer was extracted with CH$_2$Cl$_2$. The combined organic layers were dried over MgSO$_4$, filtered and evaporated. The crude product was purified by silica gel chromatography (AIT Flashsmart prepacked column 25 g SiO$_2$) using CH$_2$Cl$_2$/AcOEt 95/5 as eluent to afford 1-(4-chloro-3-fluorobenzyl)-5-(benzo[d]thiazol-2-yl)pyridin-2(1H)-one (0.14 mmol, 0.05 g, 58%) as a beige solid.

M.p.: 164° C.; LC (XTerra RP$_{18}$, 3.5 μm, 3.0×50 mm Column): RT=4.89 min; MS m/z (CI) [MH]$^+$=371, 373; $^1$H NMR (500 MHz, CDCl$_3$) δ 5.26 (s, 2H), 6.61 (d, J=9.5 Hz, 1H), 7.22-7.25 (m, 1H), 7.41-7.45 (m, 1H), 7.45-7.48 (m, 1H), 7.50-7.54 (m, 1H), 7.56-7.60 (m, 1H), 7.96 (d, J=7.7 Hz, 1H), 8.11 (dd, J=2.7 Hz and 9.5 Hz, 1H), 8.11-8.13 (m, 1H), 8.81 (d, J=2.6 Hz, 1H).

Example 7

5-(4-Methoxyphenyl)-1-(2-phenoxyethyl)pyridin-2(1H)-one (Final Compound 5-18)

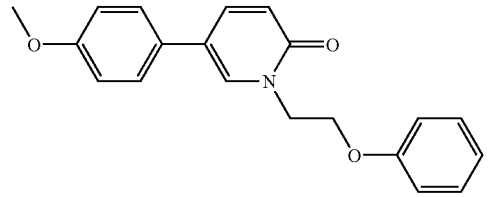 [SMILES: COc1ccc(-c2ccc(=O)n(CCOc3ccccc3)c2)cc1]

Step 1: 5-(4-Methoxyphenyl)-(1H)-pyridin-2-one

According to Scheme 5 Step 1: The title compound was prepared from 5-bromopyridin-2(1H)-one (1 eq, 17.2 mmol, 3.00 g, Example 1 Step 1) and 4-methoxyphenylboronic acid (1.5 eq, 25.9 mmol, 3.93 g) according to the procedure described for Example 2 Step 2. Reaction conditions: 4.5 hours at 120° C. The crude product was purified by flash chromatography over silica gel (AIT Flashsmart prepacked column 70 g SiO$_2$) using pure AcOEt then AcOEt/MeOH 95/5 as eluent to afford 5-(4-methoxyphenyl)-(1H)-pyridin-2-one (11.9 mmol, 2.40 g, 69%) as a white solid.

Rf=0.48 (AcOEt/MeOH 90/10); LC (XTerra RP$_{18}$, 3.5 μm, 3.0×50 mm Column): RT=2.56 min; MS m/z (CI) [MH]$^+$=202.

Step 2: 5-(4-Methoxyphenyl)-1-(2-phenoxyethyl)pyridin-2(1H)-one

According to Scheme 5 Step 2: To a solution of 5-(4-methoxyphenyl)-(1H)-pyridin-2-one (1 eq, 0.30 mmol, 60 mg) in THF (3 mL) was added K$_2$CO$_3$ (10 eq, 3.00 mmol, 0.41 g). The reaction was stirred at room temperature for 30 minutes then 1-(2-bromoethoxy)benzene (3 eq, 0.90 mmol, 0.18 g) was added. The reaction was stirred at 60° C. for 12 hours. After concentration of the solvent, acetonitrile (3 mL) was added followed by K$_2$CO$_3$ (10 eq, 3.00 mmol, 0.41 g) and 1-(2-bromoethoxy)benzene (10 eq, 3.00 mmol, 0.60 g) then the reaction was microwaved for 5 minutes at 180° C. The reaction was filtered and concentrated under reduced pressure. The crude product was purified by flash chromatography over silica gel (AIT Flashsmart prepacked column 10 g SiO$_2$) using CH$_2$Cl$_2$/AcOEt (80/20) as the eluent to afford 5-(4-methoxyphenyl)-1-(2-phenoxyethyl)pyridin-2(1H)-one (0.13 mmol, 42 mg, 44%) as a yellow oil.

Rf=0.29 (CH$_2$Cl$_2$/AcOEt 90/10); LC (XTerra RP$_{18}$, 3.5 μm, 3.0×50 mm Column): RT=4.31 min; MS m/z (CI) [MH]$^+$=322; $^1$H NMR (500 MHz, CDCl$_3$) δ 3.86 (s, 3H), 4.33-4.37 (m, 2H), 4.38-4.43 (m, 2H), 6.67 (d, J=10.1 Hz, 1H), 6.87-6.90 (m, 2H), 6.95-6.99 (m, 3H), 7.25-7.30 (m, 2H), 7.32-7.35 (m, 2H), 7.59-7.62 (m, 2H).

Example 8

5-(4-Methoxyphenyl)-1-((6-(trifluoromethyl)pyridin-3-yl)methyl)-pyridin-2(1H)-one hydrochloride (Final Compound 4-47)

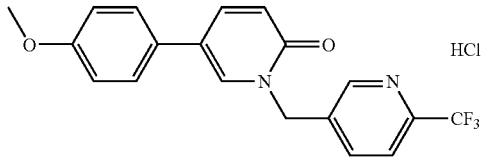 [SMILES: COc1ccc(-c2ccc(=O)n(Cc3ccc(C(F)(F)F)nc3)c2)cc1 ; Cl]

According to Scheme 5 Step 2: The title compound was prepared from 5-(4-methoxyphenyl)-(1H)-pyridin-2-one (1 eq, 0.50 mmol, 0.10 g, Example 7 Step 1) and 5-(chloromethyl)-2-(trifluoromethyl)pyridine (1.5 eq, 0.74 mmol, 0.15 g) according to the procedure described for Example 1 Step 2. Reaction conditions: 6 hours at 70° C. and 48 hours at room temperature. The crude product was purified by silica gel chromatography (AIT Flashsmart prepacked column 10 g SiO$_2$, CH$_2$Cl$_2$/AcOEt 90/10). The purified oil was dissolved in Et$_2$O and HCl (4M in dioxane) was added. The resulting precipitate was filtered, dried to afford 5-(4-methoxyphenyl)-1-((6-(trifluoromethyl)pyridin-3-yl)methyl)pyridin-2(1H)-one hydrochloride (83 µmol, 30 mg, 17%) as a white solid.

M.p.: 168° C.; LC (XTerra RP$_{18}$, 3.5 µm, 3.0×50 mm Column): RT=4.06 min; MS m/z (CI) [MH]$^+$=361; $^1$H NMR (500 MHz, CDCl$_3$) δ 3.76 (s, 3H), 5.27 (s, 2H), 6.51 (d, J=9.4 Hz, 1H), 6.98 (d, J=6.7 Hz, 2H), 7.51 (d, J=6.7 Hz, 2H), 7.83 (dd, J=2.7 Hz and 9.4 Hz, 1H), 7.88 (d, J=8.2 Hz, 1H), 8.00 (dd, J=1.7 Hz and 8.2 Hz, 1H), 8.28 (d, J=2.5 Hz, 1H), 8.81 (d, J=1.7 Hz, 1H).

Example 9

1-(Cyclohexylmethyl)-5-(4-methoxyphenyl)pyridin-2(1H)-one (Final Compound 4-03)

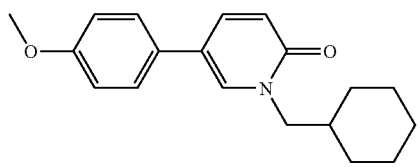 [SMILES: COc1ccc(-c2ccc(=O)n(CC3CCCCC3)c2)cc1]

According to Scheme 5 Step 2: To a solution of 5-(4-methoxyphenyl)pyridin-2(1H)-one (1 eq, 0.35 mmol, 70 mg, Example 7 Step 1) in acetonitrile (2 mL) were added K$_2$CO$_3$ (10 eq, 3.50 mmol, 0.48 g) and (bromomethyl)cyclohexane (10 eq, 3.50 mmol, 0.49 mL). The reaction was microwaved for 10 minutes at 180° C. The reaction was allowed to cool. The reaction was then filtered and concentrated under reduced pressure. The crude product was purified by flash chromatography over silica gel (AIT Flashsmart prepacked column 15 g SiO$_2$) using CH$_2$Cl$_2$/AcOEt (80/20, Rf=0.3). The product was further purified by reverse phase C$_{18}$ column using water/acetonitrile 60/40 to afford 1-(cyclohexylmethyl)-5-(4-methoxyphenyl)pyridin-2(1H)-one (0.11 mmol, 32 mg, 31%) as a colorless oil.

LC (XTerra RP$_{18}$, 3.5 µm, 3.0×50 mm Column): RT=4.72 min; MS m/z (CI) [MH]$^+$=298; $^1$H NMR (300 MHz, CDCl$_3$) δ 0.85-1.09 (m, 2H), 1.09-1.32 (m, 3H), 1.53-1.78 (m, 5H), 1.78-2.00 (m, 1H), 3.74 (d, J=7.3 Hz, 2H), 3.77 (s, 3H), 6.57 (d, J=9.4 Hz, 1H), 6.88 (d, J=8.7 Hz, 2H), 7.29-7.35 (3H), 7.49 (dd, J=2.7 Hz, 9.4 Hz, 1H).

Example 10

1-(4-Chlorobenzyl)-5-((methyl(phenyl)amino)methyl)pyridin-1-2(1H)-one (Final Compound 3-07)

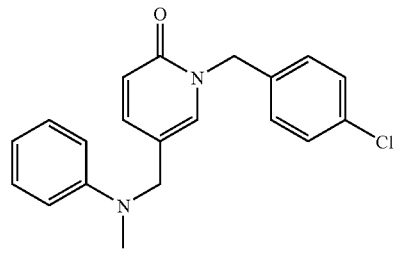 [SMILES: CN(Cc1ccc(=O)n(Cc2ccc(Cl)cc2)c1)c1ccccc1]

Step 1: 1-(4-Chlorobenzyl)-6-oxo-1,6-dihydropyridine-3-carbaldehyde

According to Scheme 2: The title compound was prepared from 6-methoxynicotinaldehyde (1 eq, 13.4 mmol, 1.83 g) and 4-chloro-benzylbromide (2 eq, 26.8 mmol, 5.50 g) according to the procedure described for Example 6 Step 2. Reaction conditions: 17 hours under reflux. The crude product was purified by silica gel chromatography (AIT Flashsmart prepacked column 25 g SiO$_2$) using CH$_2$Cl$_2$/AcOEt 95/5 as eluent to afford 1-(4-chlorobenzyl)-6-oxo-1,6-dihydropyridine-3-carbaldehyde (9.08 mmol, 2.25 g, 68%) as an orange solid.

LC (XTerra RP$_{18}$, 3.5 µm, 3.0×50 mm Column): RT=3.51 min; MS m/z (CI) [MH]$^+$=248.

Step 2: 1-(4-Chlorobenzyl)-5-((methyl(phenyl)amino)methyl)pyridin-2(1H)-one

According to Scheme 7 Method A: A solution of N-methylbenzenamine (1 eq, 0.40 mmol, 0.04 mL) and 1-(4-chlorobenzyl)-6-oxo-1,6-dihydropyridine-3-carbaldehyde (1 eq, 0.40 mmol, 0.10 g) in CH$_2$Cl$_2$ (8 mL) was stirred for 10 min. at room temperature then AcOH (1 eq, 0.40 mmol, 0.02 mL) and NaBH(OAc)$_3$ (1.5 eq, 0.60 mmol, 0.10 g) were added. The reaction mixture was stirred 3 hours at room temperature, was quenched with water and the aqueous phase was extracted with CH$_2$Cl$_2$. The organic layer was dried over Na$_2$SO$_4$, filtered and evaporated. The crude product was purified by silica gel chromatography (AIT Flashsmart prepacked column 25 g SiO$_2$) using CH$_2$Cl$_2$/MeOH 95/5 followed by crystallization in pentane/diisopropyl ether to afford 1-(4-chlorobenzyl)-5-((methyl(phenyl)amino)methyl)pyridin-2(1H)-one (0.12 mmol, 0.04 g, 29%) as a white solid.

M.p.: 106° C.; LC (XTerra RP$_{18}$, 3.5 µm, 3.0×50 mm Column): RT=4.43 min; MS m/z (CI) [MH]$^+$=339, 341; $^1$H NMR (500 MHz, DMSO-d$^6$) δ 2.88 (s, 3H), 4.25 (s, 2H), 5.03 (s, 2H), 6.37 (d, J=9.3 Hz, 1H), 6.61-6.66 (m, 1H), 6.75 (dd, J=0.9 Hz and 8.8 Hz, 2H), 7.11-7.17 (m, 2H), 7.21-7.25 (m, 2H), 7.30 (dd, J=2.6 Hz and 9.3 Hz, 1H), 7.33-7.38 (m, 2H), 7.67 (d, J=2.0 Hz, 1H).

Example 11

1-(4-Chlorobenzyl)-5-(3-methoxybenzoyl)pyridin-2 (1H)-one (Final Compound 3-12)

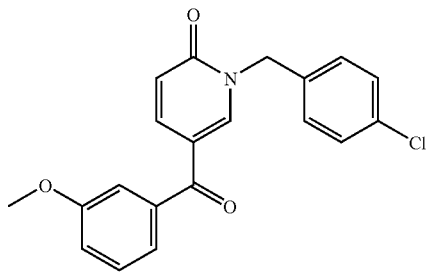 [SMILES: COc1cccc(C(=O)c2ccc(=O)n(Cc3ccc(Cl)cc3)c2)c1]

According to Scheme 7 Method C: 1-(4-Chlorobenzyl)-5-(hydroxy(3-methoxyphenyl)-methyl)pyridin-2(1H)-one (1 eq, 0.28 mmol, 0.10 g, Example 41) and manganese dioxide (30 eq, 8.43 mmol, 0.73 g) were stirred overnight at room temperature in $CH_2Cl_2$ (10 mL). Upon completion, the crude mixture was filtered through a pad of celite and the filtrate was concentrated. The crude residue was partitioned between water and $CH_2Cl_2$. The aqueous layer was extracted with $CH_2Cl_2$. The combined organic layers were washed with brine, dried over $MgSO_4$ and concentrated under vacuum to afford the title compound as a white solid (0.28 mmol, 0.10 g, 100%).

M.p.: 104° C.; LC (XTerra $RP_{18}$, 3.5 μm, 3.0×50 mm Column): RT=4.41 min; MS m/z $ES^+$=354, 356; $^1$H NMR (500 MHz, $CDCl_3$) δ 3.83 (s, 3H), 5.13 (s, 2H), 6.65 (d, J=9.6 Hz, 1H), 7.11-7.17 (3H), 7.26-7.29 (m, 2H), 7.33-7.39 (3H), 7.89 (dd, J=2.6 Hz and 9.6 Hz, 1H), 7.97 (d, J=2.6 Hz, 1H).

Example 12

5-(3-Methoxybenzyl)-1-(4-chlorobenzyl)pyridin-2 (1H)-one (Final Compound 3-02)

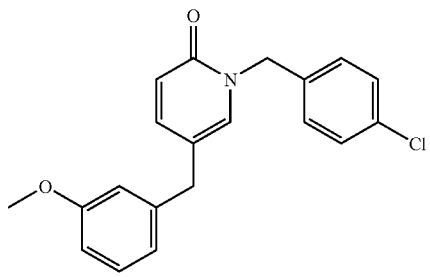 [SMILES: COc1cccc(Cc2ccc(=O)n(Cc3ccc(Cl)cc3)c2)c1]

According to Scheme 7 Method D: Triethylsilane (3 eq, 0.84 mmol, 0.10 g) was added to a solution of 1-(4-chlorobenzyl)-5-(hydroxy(3-methoxyphenyl)methyl)pyridin-2(1H)-one (1 eq, 0.28 mmol, 0.10 g, Example 41) in TFA (2 mL). The mixture was stirred 1 hour at room temperature. Upon completion, MeOH was added and the solution was evaporated. The crude residue was partitioned between water and $CH_2Cl_2$. The aqueous layer was extracted with $CH_2Cl_2$. The combined organic layers were successively washed with brine, dried over $MgSO_4$ and concentrated under vacuum to afford the crude product. Purification by flash chromatography (AIT Flashsmart prepacked column 10 g $SiO_2$) ($CH_2Cl_2$/AcOEt 95/5 to 90/10) of the crude product afford the title compound 5-(3-methoxybenzyl)-1-(4-chlorobenzyl)pyridin-2(1H)-one (0.20 mmol, 0.07 g, 71%) as a yellow oil.

LC (XTerra $RP_{18}$, 3.5 μm, 3.0×50 mm Column): RT=4.49 min; MS m/z $ES^+$=340, 342; $^1$H NMR (500 MHz, $CDCl_3$) δ 3.65 (s, 2H), 3.78 (s, 3H), 5.08 (s, 2H), 6.57 (d, J=9.3 Hz, 1H), 6.63-6.66 (m, 1H), 6.70-6.73 (m, 1H), 6.76-6.80 (m, 1H), 7.02 (d, J=1.9 Hz, 1H), 7.18 (dd, J=2.5 Hz and 9.3 Hz, 1H), 7.21-7.25 (3H), 7.32 (d, J=8.5 Hz, 2H).

Example 13

5-(3-Methoxyphenethyl)-1-(4-chloro-3-fluorobenzyl)pyridin-2(1H)-one (Final Compound 7-06)

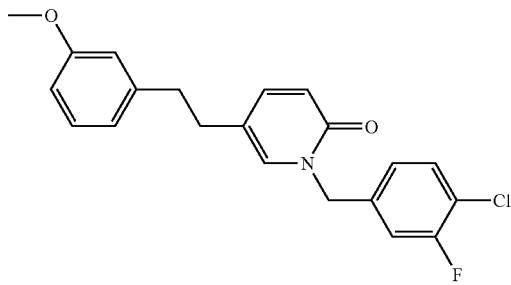 [SMILES: COc1cccc(CCc2ccc(=O)n(Cc3ccc(Cl)c(F)c3)c2)c1]

Step 1:
5-(3-Methoxyphenethynyl)-2-methoxypyridine

According to Scheme 8 Step 1: $Et_3N$ (15 eq, 12.0 mmol, 1.68 mL), $PdCl_2(PPh_3)_2$ (0.05 eq, 0.04 mmol, 17.5 mg), $PPh_3$ (0.2 eq, 0.16 mmol, 41.8 mg) and 5-bromo-2-methoxypyridine (1 eq, 0.80 mmol, 0.15 g) were added to a stirred solution of copper iodide (0.05 eq, 0.04 mmol, 7.6 mg) in DMF (8 mL). Then 1-ethynyl-3-methoxybenzene (1.1 eq, 0.88 mmol, 0.12 g) was added and the mixture was heated under microwaves (120° C./25 min) and was stirred overnight at room temperature. The resulting solution was poured onto water and extracted with AcOEt. The combined organic layers were dried over $MgSO_4$, filtered and evaporated under reduced pressure. The crude product was purified by flash chromatography over silica gel (AIT Flashsmart prepacked column 25 g $SiO_2$) using pentane/$Et_2O$ 98/2 as eluent to afford 5-(3-methoxyphenethynyl)-2-methoxypyridine (0.64 mmol, 154 mg, 81%) as a colorless oil.

LC (XTerra $RP_{18}$, 3.5 μm, 3.0×50 mm Column): RT=5.13 min; MS m/z $ES^+$=240.

Step 2:
2-Methoxy-5-(2-(3-methoxyphenyl)ethyl)pyridine

According to Scheme 8 Step 2: A suspension of 5-(3-methoxyphenethynyl)-2-methoxypyridine (1 eq, 0.64 mmol, 154 mg) and Pd/C (15 mg) in MeOH (10 mL) was stirred overnight at room temperature under $H_2$ at atmospheric pressure. The resulting mixture was then filtered on a pad of celite and washed with MeOH. The filtrate was concentrated under reduced pressure to afford 2-methoxy-5-(2-(3-methoxyphenyl)ethyl)pyridine (0.49 mmol, 0.12 g, 77%) as a colorless oil.

LC (XTerra RP$_{18}$, 3.5 μm, 3.0×50 mm Column): RT=4.66 min; MS m/z ES$^+$=244.

Step 3: 5-(3-Methoxyphenethyl)-1-(4-chloro-3-fluorobenzyl)pyridin-2(1H)-one

According to Scheme 8 Step 3: The title compound was prepared from 2-methoxy-5-(2-(3-methoxyphenyl)ethyl)pyridine (1 eq, 0.25 mmol, 0.06 g) and 4-chloro-3-fluorobenzylbromide (2 eq, 0.49 mmol, 0.11 g) according to the procedure described for Example 6 Step 2. Reaction conditions: 12 hours at 100° C. The resulting dark brown oil was purified by flash chromatography (AIT Flashsmart prepacked column 25 g SiO$_2$, CH$_2$Cl$_2$/MeOH 98/2) to afford 5-(3-methoxyphenethyl)-1-(4-chloro-3-fluorobenzyl)pyridin-2(1H)-one (0.14 mmol, 55.0 mg, 60%) as a yellow oil.

LC (XTerra RP$_{18}$, 3.5 μm, 3.0×50 mm Column): RT=4.68 min; MS m/z ES$^+$=372, 374; $^1$H NMR (500 MHz, CDCl$_3$) δ 2.65 (t, J=7.4 Hz, 2H), 2.79 (t, J=7.4 Hz, 2H), 3.76 (s, 3H), 4.98 (s, 2H), 6.59 (d, J=9.2 Hz, 1H), 6.60-6.65 (2H), 6.72-6.75 (m, 1H), 6.79-6.82 (m, 1H), 6.90-6.94 (m, 1H), 6.99 (d, J=2.0 Hz and 9.6 Hz, 1H), 7.13-7.18 (m, 1H), 7.23 (dd, J=2.5 Hz and 9.2 Hz, 1H), 7.31-7.36 (m, 1H).

Example 14

N-(3-Chlorobenzyl)-2-(5-(4-methoxyphenyl)-2-oxopyridin-1(2H)-yl)-N-methylacetamide (Final Compound 5-24)

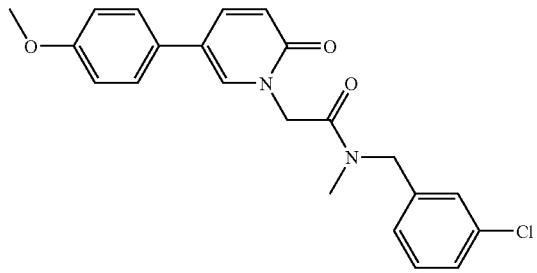 [SMILES: COc1ccc(-c2ccc(=O)n(CC(=O)N(C)Cc3cccc(Cl)c3)c2)cc1]

Step 1: Ethyl 2-(5-(4-methoxyphenyl)-2-oxopyridin-1(2H)-yl)acetate

According to Scheme 9 Step 1: The title compound was prepared from 5-(4-methoxyphenyl)pyridin-2(1H)-one (1 eq, 3.73 mmol, 0.75 g, Example 7 Step 1) and ethylbromoacetate (1.2 eq, 4.47 mmol, 0.50 mL) according to the procedure described for Example 1 Step 2. The reaction was stirred at 60° C. for 12 hours. The reaction was filtered and concentrated under reduced pressure to yield a yellow oil. The product was triturated from diisopropyl ether to afford ethyl 2-(5-(4-methoxyphenyl)-2-oxopyridin-1(2H)-yl)acetate (3.38 mmol, 0.97 g, 91%) as a white solid.

LC (XTerra RP$_{18}$, 3.5 μm, 3.0×50 mm Column): RT=3.53 min; MS m/z (CI) [MH]$^+$=288.

Step 2: 2-(5-(4-Methoxyphenyl)-2-oxopyridin-1(2H)-yl)acetic acid

According to Scheme 9 Step 2: To a solution of ethyl 2-(5-(4-methoxyphenyl)-2-oxopyridin-1(2H)-yl)acetate (1 eq, 3.38 mmol, 0.97 g) in water/EtOH (1:1, 20 mL) at 0° C. was added lithium hydroxide (10 eq, 33.8 mmol, 1.44 g). The reaction was then allowed to warm to room temperature and stirred for 2 hours. The reaction was then cooled to 0° C. and acidified with HCl 1M solution till pH=2. The resulting precipitate was filtered under reduced pressure to yield 2-(5-(4-methoxyphenyl)-2-oxopyridin-1(2H)-yl)acetic acid (2.56 mmol, 0.66 g, 76%) as a white solid.

LC (XTerra RP$_{18}$, 3.5 μm, 3.0×50 mm Column): RT=2.89 min; MS m/z (CI) [MH]$^+$=260.

Step 3: N-(3-Chlorobenzyl)-2-(5-(4-methoxyphenyl)-2-oxopyridin-1(2H)-yl)-N-methyl-acetamide According to Scheme 9 Step 3: To a solution of (3-chlorophenyl)-N-methylmethanamine (1 eq, 0.19 mmol, 0.03 g), 2-(5-(4-methoxyphenyl)-2-oxopyridin-1(2H)-yl)acetic acid (1 eq, 0.19 mmol, 0.05 g) and hydroxybenzotriazole (1.1 eq, 0.21 mmol, 0.03 g) in CH$_2$Cl$_2$ (2 mL) at room temperature was added EDCI.HCl (1.5 eq, 0.29 mmol, 55 mg). The reaction was stirred at room temperature for 12 hours then diluted with AcOEt. The reaction washed with brine and the organic phase extracted (×3). The combined organic fractions were dried (Na$_2$SO$_4$), filtered and concentrated under reduced pressure. The crude product was purified by flash chromatography over silica gel (AIT Flashsmart prepacked column 10 g SiO$_2$) using CH$_2$Cl$_2$/AcOEt (50/50) as eluent to afford the N-(3-chlorobenzyl)-2-(5-(4-methoxyphenyl)-2-oxopyridin-1(2H)-yl)-N-methylacetamide (0.11 mmol, 44 mg, 57%) as a yellow oil.

LC (XTerra RP$_{18}$, 3.5 μm, 3.0×50 mm Column): RT=4.06 min; MS m/z (CI) [MH]$^+$=397, 399; $^1$H NMR (500 MHz, CDCl$_3$) mixture 2:1 of isomers δ 2.79 (s, 3Hb), 3.05 (s, 3Ha), 3.77 (s, 3Ha, 3Hb), 4.54 (s, 2Ha), 4.70 (s, 2Hb), 4.93 (s, 2Hb), 4.93 (s, 2Ha), 6.47 (d, J=9.5 Hz, 1Hb), 6.49 (d, J=9.5 Hz, 1Ha), 7.00 (d, J=8.5 Hz, 2Ha, 2Hb), 7.23 (d, J=7.6 Hz, 1Ha), 7.30-7.35 (m, 2Ha, 2Hb), 7.35-7.41 (m, 1Ha, 2Hb), 7.41-7.51 (m, 2Ha, 2Hb), 7.82 (dd, J=2.8 Hz and 9.5 Hz, 1Ha, 1Hb), 7.96 (d, J=2.5 Hz, 1Ha), 7.98 (d, J=2.5 Hz, 1Hb).

Example 15

1-((5-Fluorobenzo[d]oxazol-2-yl)methyl)-5-(4-methoxyphenyl)-pyridin-2(1H)-one (Final Compound 4-51)

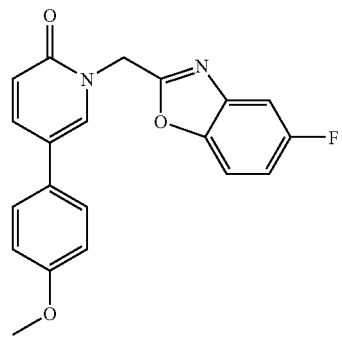 [SMILES: COc1ccc(-c2ccc(=O)n(Cc3nc4cc(F)ccc4o3)c2)cc1]

According to Scheme 10 Method A: A solution of PPh$_3$ (3 eq, 1.04 mmol, 0.27 g) in 1:1 acetonitrile/pyridine (3 mL) was added dropwise over a period of 1 hour to a mixture of 2-(5-(4-methoxyphenyl)-2-oxopyridin-1(2H)-yl)acetic acid (1 eq, 0.35 mmol, 0.09 g, Example 14 Step 2), 2-amino-4- fluorophenol (1 eq, 0.35 mmol, 0.04 g), Et$_3$N (3 eq, 1.04 mmol, 0.15 mL) and CCl$_4$ (4 eq, 1.39 mmol, 0.13 mL) in 1:1 mixture of acetonitrile/pyridine (3 mL). The reaction mixture was stirred at room temperature for 2 days. The solvent was removed under reduced pressure and the residue was dissolved in CH$_2$Cl$_2$ and NH$_4$OH. The aqueous phase was extracted 3 times with CH$_2$Cl$_2$. The combined organic fractions were washed with brine, dried over Na$_2$SO$_4$, filtered and concentrated under reduced pressure. The crude product was purified by flash chromatography over silica gel (AIT Flashsmart prepacked column 15 g SiO$_2$) using CH$_2$Cl$_2$/AcOEt 90/10 as eluent to afford 1-((5-fluorobenzo[d]oxazol-2-yl)methyl)-5-(4-methoxyphenyl)pyridin-2(1H)-one (0.06 mmol, 0.02 g, 16%) as a brown solid.

M.p.: 115° C.; Rf=0.21 (CH$_2$Cl$_2$/AcOEt 90/10); LC (XTerra RP$_{18}$, 3.5 µm, 3.0×50 mm Column): RT=4.06 min; MS m/z (CI) [MH]$^+$=351; $^1$H NMR (500 MHz, CDCl$_3$) δ 3.84 (s, 3H), 5.46 (s, 2H), 6.74 (d, J=9.5 Hz, 1H), 6.96 (d, J=8.8 Hz, 2H), 7.05-7.12 (m, 1H), 7.35 (d, J=8.8 Hz, 2H), 7.40 (dd, J=8.3 Hz and 2.6 Hz, 1H), 7.46 (dd, J=9.1 Hz and 4.2 Hz, 1H), 7.58 (d, J=2.6 Hz, 1H), 7.66 (dd, J=9.5 Hz and 2.6 Hz, 1H).

Example 16

1-((3-(4-Fluorophenyl)-1,2,4-oxadiazol-5-yl)methyl)-5-(4-methoxyphenyl)pyridin-2(1H)-one (Final Compound 4-42)

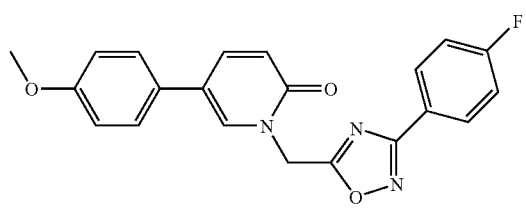 [SMILES: COc1ccc(-c2ccc(=O)n(Cc3nc(-c4ccc(F)cc4)no3)c2)cc1]

According to Scheme 10 Method B: A mixture of 2-(5-(4-methoxyphenyl)-2-oxopyridin-1(2H)-yl)acetic acid (1 eq, 0.23 mmol, 60 mg, Example 14 Step 2), 4-fluorophenylamidoxime (1.2 eq, 0.28 mmol, 43 mg), 1-hydroxybenzotriazole (1 eq, 0.23 mmol, 35 mg), EDCI.HCl (1.5 eq, 0.35 mmol, 67 mg) in dioxane (2 mL) was stirred at room temperature for 12 hours, then heated at 100° C. for 3 days. The solution was poured onto brine and AcOEt and the aqueous phase was extracted twice with AcOEt. The combined organic fractions were washed once with brine, dried over Na$_2$SO$_4$, filtered and concentrated under reduced pressure. The crude product was purified by flash chromatography over silica gel (AIT Flashsmart prepacked column 15 g SiO$_2$) using CH$_2$Cl$_2$/AcOEt 90/10 as eluent to afford the title compound (0.12 mmol, 44 mg, 50%) as a yellow solid.

M.p.: 123° C.; Rf=0.25 (CH$_2$Cl$_2$/AcOEt 90/10); LC (XTerra RP$_{18}$, 3.5 µm, 3.0×50 mm Column): RT=4.39 min; MS m/z (CI) [MH]$^+$=378; $^1$H NMR (500 MHz, CDCl$_3$) δ 3.85 (s, 3H), 5.46 (s, 2H), 6.73 (d, J=9.5 Hz, 1H), 6.98 (d, J=8.8 Hz, 2H), 7.13-7.18 (m, 2H), 7.36 (d, J=8.8 Hz, 2H), 7.53 (d, J=2.3 Hz, 1H), 7.68 (dd, J=9.5 Hz and 2.3 Hz, 1H), 8.05-8.08 (m, 2H).

Example 17

2-(4-Fluorobenzyl)isoquinolin-1(2H)-one (Final Compound 13-01)

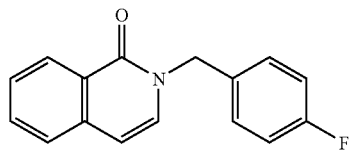 [SMILES: O=c1c2ccccc2ccn1Cc1ccc(F)cc1]

According to Scheme 11: To a solution of NaHMDS (2 eq, 3.00 mmol, 0.50 g) in THF (3 mL) at 0° C. was added isoquinolin-1(2H)-one (1 eq, 1.00 mmol, 0.20 g) dissolved in THF (3 mL) and DMF (5 mL). The reaction mixture was stirred for 10 min at 0° C. then cooled at −70° C. The 1-(bromomethyl)-4-fluorobenzene (4 eq, 4.00 mmol, 0.80 g) was added in one portion to the reaction mixture. The reaction mixture was allowed to warm to room temperature, for one hour. Upon completion the reaction mixture was concentrated under vacuum and the crude residue partitioned between water and AcOEt, the aqueous layer was extracted with AcOEt. The combined organic layers were successively washed with water (2.30 mL), HCl (1M, 2.30 mL), brine (2.20 mL), dried over Na$_2$SO$_4$, filtered and evaporated to afford a yellow oil. The crude compound was purified on silica gel using cyclohexane/AcOEt 80/20 as eluent to afford 2-(4-fluorobenzyl)isoquinolin-1(2H)-one as a white solid (0.70 mmol, 0.26 g, 74%).

M.p.: 107° C.; LC (XTerra RP$_{18}$, 3.5 µm, 3.0×50 mm Column): RT=3.76 min; MS m/z (CI) [MH]$^+$=254; $^1$H NMR (DMSO-d$^6$) δ 5.16 (s, 2H), 6.67 (d, J=7.2 Hz, 1H), 7.14-7.18 (m, 2H), 7.37-7.39 (m, 2H), 7.51 (m, 1H), 7.60 (d, J=7.2 Hz, 1H), 7.66 (m, 1H), 7.71 (m, 1H), 8.23 (m, 1H).

Example 18

1-(4-Chlorobenzyl)quinolin-2(1H)-one (Final Compound 15-04)

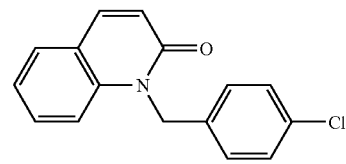

According to Scheme 12: The title compound was prepared from quinolin-2-ol (1 eq, 0.69 mmol, 0.10 g) and 1-(bromomethyl)-4-chlorobenzene (1.5 eq, 1.03 mmol, 0.21 g) according to the procedure described for Example 1, Step 2. Reaction conditions: 17 hours under reflux. The residue was purified by flash chromatography on silica gel using pure CH$_2$Cl$_2$ as eluent to afford 1-(4-chlorobenzyl)quinolin-2 (1H)-one as a white solid (0.55 mmol, 0.15 g, 79%).

M.p.: 139° C.; LC (XTerra RP$_{18}$, 3.5 µm, 3.0×50 mm Column): RT=4.40 min; MS m/z (CI) [MH]$^+$=270, 272. $^1$H NMR (300 MHz, CDCl$_3$) δ 5.52 (s, 2H), 6.80 (d, J=9.5 Hz, 1H), 7.13-7.24 (4H), 7.25-7.30 (m, 2H), 7.40-7.48 (m, 1H), 7.58 (dd, J=1.5 Hz and 7.9 Hz, 1H), 7.75 (d, J=9.5 Hz, 1H).

Example 19

1-(3-Fluorobenzyl)-4-(4-methoxyphenyl)pyridin-2(1H)-one (Final Compound 11-03)

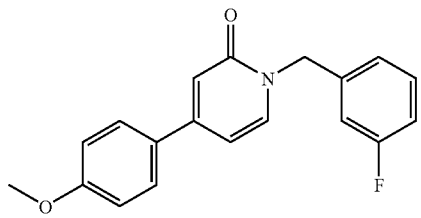 [SMILES: COc1ccc(-c2ccn(Cc3cccc(F)c3)c(=O)c2)cc1]

Step 1: 1-(3-Fluorobenzyl)-4-(3-fluorobenzyloxy)pyridin-2(1H)-one

According to Scheme 13 Step 1: The title compound was prepared from pyridine-2,4-diol (1 eq, 2.52 mmol, 0.28 g) and 1-(bromomethyl)-3-fluorobenzene (3 eq, 7.56 mmol, 0.93 mL) according to the procedure described for Example 1 Step 2. Reaction conditions: 17 h under reflux in DMF. The crude product was purified by flash chromatography on silica gel (CH$_2$Cl$_2$/AcOEt 90/10) to afford 1-(3-fluorobenzyl)-4-(3-fluorobenzyloxy)pyridin-2(1H)-one as a white solid (0.95 mmol, 0.29 g, 36%).

M.p.: 121° C.; LC (XTerra RP$_{18}$, 3.5 μm, 3.0×50 mm Column): RT=4.33 min; MS m/z (CI) [MH]$^+$=328; $^1$H NMR (DMSO-d$^6$) δ 7.72 (d, 1H, J=7.88 Hz); 7.47-7.42 (m, 1H); 7.40-7.38 (m, 1H); 7.28-7.26 (m, 2H); 7.18 (m, 1H); 7.10-7.07 (m, 3H); 6.08-6.06 (dd, 1H, J=2.8 Hz, J=7.56 Hz); 5.93 (d, 1H, J=2.83 Hz); 5.09 (s, 2H); 5.02 (s, 2H).

Step 2: 1-(3-Fluorobenzyl)-4-hydroxypyridin-2(1H)-one

According to Scheme 13 Step 2: A suspension of 1-(3-fluorobenzyl)-4-(3-fluorobenzyloxy)pyridin-2(1H)-one (1 eq, 0.95 mmol, 0.29 g) and Pd/C (0.3 eq, 0.29 mmol, 30.3 mg) in MeOH (3 mL) was hydrogenated until complete (30 min). The suspension was filtered through celite and the filtrate concentrated under vacuum to afford 1-(3-fluorobenzyl)-4-hydroxypyridin-2(1H)-one (0.75 mmol, 0.16 g, 79%) as a white powder.

LC (XTerra RP$_{18}$, 3.5 μm, 3.0×50 mm Column): RT=2.88 min; MS m/z (CI) [MH]$^+$=220.

Step 3: 1-(3-Fluorobenzyl)-1,2-dihydro-2-oxopyridin-4-yl trifluoromethanesulfonate According to Scheme 13 Method B: To a solution of 1-(3-fluorobenzyl)-4-hydroxypyridin-2(1H)-one (1 eq, 1.00 mmol, 0.30 g) and pyridine (3 eq, 4.00 mmol, 0.30 mL) in CH$_2$Cl$_2$ (10 mL) at −78° C. was added dropwise a solution of trifluoromethanesulfonic anhydride (2 eq, 3.00 mmol, 0.50 mL). The solution was allowed to warm to room temperature and further stirred for 1 hour. The mixture was quenched with cold water. The aqueous layer was extracted with CH$_2$Cl$_2$. The combined organic layers were dried over Na$_2$SO$_4$, filtered and evaporated under reduced pressure to afford the crude product 1-(3-fluorobenzyl)-1,2-dihydro-2-oxopyridin-4-yl trifluoromethanesulfonate as a viscous oil (0.90 mmol, 0.41 g, 90%). The crude product is used in the next step without further purification.

LC (XTerra RP$_{18}$, 3.5 μm, 3.0×50 mm Column): RT=4.34 min; MS m/z (CI) [MH]$^+$=352.

Step 4: 1-(3-Fluorobenzyl)-4-(4-methoxyphenyl)pyridin-2(1H)-one

According to Scheme 13 Method C: The title compound was prepared from 1-(3-fluorobenzyl)-1,2-dihydro-2-oxopyridin-4-yl trifluoromethanesulfonate (1 eq, 0.28 mmol, 0.10 g) and 4-methoxyphenyl boronic acid (1.5 eq, 0.43 mmol, 65 mg) according to the procedure described for Example 1 Step 3. The crude product was purified by flash chromatography on silica gel using cyclohexane/AcOEt 70/30 as eluent to afford the title compound (0.17 mmol, 52 mg, 59%) was obtained as a white solid.

M.p.: 114° C.; LC (XTerra RP$_{18}$, 3.5 μm, 3.0×50 mm Column): RT=4.18 min; MS m/z (CI) [MH]$^+$=310; $^1$H NMR (500 MHz, DMSO-d$^6$) δ 3.80 (s, 3H), 5.11 (s, 2H), 6.62 (dd, J=2.1 Hz and 7.2 Hz, 1H), 6.66 (d, J=2.0 Hz, 1H), 7.02 (d, J=8.9 Hz, 2H), 7.09-7.17 (m, 3H), 7.36-7.42 (m, 1H), 7.70 (dd, J=2.1 Hz and 6.8 Hz, 2H), 7.85 (d, J=7.1 Hz, 1H).

Example 20

2-(4-(1-(4-Chloro-2-fluorobenzyl)-6-oxo-1,6-dihydropyridin-3-yl)-phenoxy)acetonitrile (Final Compound 6-46)

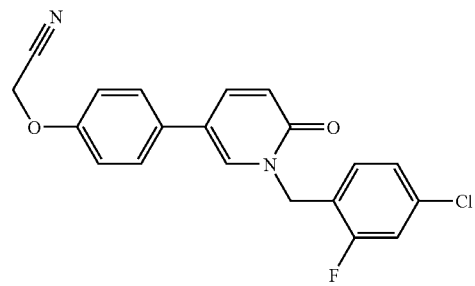 [SMILES: N#CCOc1ccc(-c2ccc(=O)n(Cc3ccc(Cl)cc3F)c2)cc1]

Step 1: 1-(2-Fluoro-4-chlorobenzyl)-5-(4-methoxyphenyl)pyridin-2(1H)-one

According to Scheme 3 Method A: The title compound was prepared from 1-(4-chloro-2-fluorobenzyl)-5-bromopyridin-2(1H)-one (1 eq, 16.4 mmol, 5.20 g, Example 1 Step 2) and 4-methoxyphenylboronic acid (1.5 eq, 25.0 mmol, 3.80 g) according to the procedure described for Example 1 Step 3. The crude product was purified by flash chromatography over silica gel using CH$_2$Cl$_2$/AcOEt 95/5 to 80/20 as eluent to afford 1-(2-fluoro-4-chlorobenzyl)-5-(4-methoxyphenyl)pyridin-2(1H)-one (16.4 mmol, 5.64 g, 100%) as a white solid.

Rf=0.29 (CH$_2$Cl$_2$/AcOEt 90/10); LC (XTerra RP$_{18}$, 3.5 μm, 3.0×50 mm Column): RT=4.58 min; MS m/z (CI) [MH]$^+$=344, 346.

Step 2: 1-(4-Chloro-2-fluorobenzyl)-5-(4-hydroxyphenyl)pyridin-2(1H)-one

According to Scheme 14 Step 1: BBr$_3$ (4 eq, 65.6 mmol, 6.56 mL) was added to a solution of 1-(2-fluoro-4-chlorobenzyl)-5-(4-methoxyphenyl)pyridin-2(1H)-one (16.4 mmol, 5.64 g) in $CH_2Cl_2$ at −50° C. The reaction mixture was stirred 1.5 hour at −40° C., overnight at room temperature then $BBr_3$ (20 mL) was added at −30° C. and the reaction mixture was stirred 4 hours at room temperature. The reaction mixture was cooled down to −40° C. then MeOH (50 mL) was added dropwise and the crude mixture was stirred at room temperature. After evaporation, the crude mixture was purified by silica gel chromatography (300 g $SiO_2$) using $CH_2Cl_2$/MeOH 95/5 to afford 1-(4-chloro-2-fluorobenzyl)-5-(4-hydroxyphenyl)pyridin-2(1H)-one (14.9 mmol, 4.80 g, 83%) as an orange solid.

M.p.: 207° C.; LC (XTerra $RP_{18}$, 3.5 μm, 3.0×50 mm Column): RT=3.67 min; MS m/z (CI) $[MH]^+$=330; $^1H$ NMR (500 MHz, $CDCl_3$) δ 5.16 (s, 2H), 6.47 (d, J=9.5 Hz, 1H), 6.79 (d, J=8.7 Hz, 2H), 7.15-7.20 (m, 1H), 7.25 (dd, J=2.1 Hz and 8.7 Hz, 1H), 7.34 (d, J=6.6 Hz, 2H), 7.45 (dd, J=2.1 Hz and 10.1 Hz, 1H), 7.77 (dd, J=2.7 Hz and 9.5 Hz, 1H), 8.03 (d, J=2.7 Hz, 1H), 9.51 (s, 1H).

Step 3: 2-(4-(1-(4-Chloro-2-fluorobenzyl)-6-oxo-1,6-dihydropyridin-3-yl)phenoxy)-acetonitrile According to Scheme 14 Method A: A suspension of 1-(4-chloro-2-fluorobenzyl)-5-(4-hydroxyphenyl)pyridin-2(1H)-one (1 eq, 1.21 mmol, 0.40 g), $K_2CO_3$ (10 eq, 12.1 mmol, 1.68 g) and 2-bromoacetonitrile (1 eq, 1.21 mmol, 0.15 g) in acetonitrile (10 mL) was heated in a microwave at 180° C. during 5 min. The reaction mixture was filtered, the filtrate was concentrated and the resulting crude residue was dissolved in $CH_2Cl_2$. The organic phase washed with water, dried over $MgSO_4$, filtered and evaporated. The crude oil was purified by flash chromatography over silica gel (AIT Flashsmart prepacked column 25 g $SiO_2$) using $CH_2Cl_2$/MeOH 98/2 as eluent followed by trituration in acetonitrile to afford 2-(4-(1-(4-chloro-2-fluorobenzyl)-6-oxo-1,6-dihydropyridin-3-yl)phenoxy)acetonitrile (0.51 mmol, 0.19 g, 42%) as a white solid.

M.p.: 160° C.; LC (XTerra $RP_{18}$, 3.5 μm, 3.0×50 mm Column): RT=4.20 min; MS m/z (CI) $[MH]^+$=369, 371; $^1H$ NMR (300 MHz, $CDCl_3$) δ 5.19 (s, 2H), 5.20 (s, 2H), 6.52 (d, J=9.5 Hz, 1H), 7.11-7.16 (m, 2H), 7.18-7.23 (m, 1H), 7.27 (dd, J=2.0 Hz and 8.4 Hz, 1H), 7.46 (dd, J=2.0 Hz and 10.1 Hz, 1H), 7.55-7.60 (m, 2H), 7.86 (dd, J=2.7 Hz and 9.5 Hz, 1H), 8.16 (d, J=2.7 Hz, 1H).

Example 21

1-(4-Chloro-2-fluorobenzyl)-5-(4-(2-oxopropoxy)phenyl)pyridin-2(1H)-one (Final Compound 6-40)

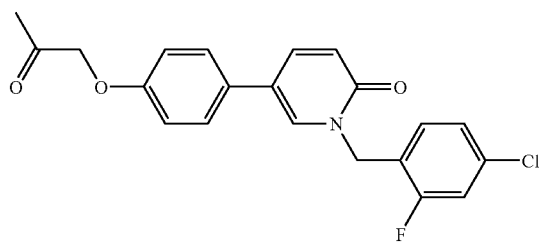 [SMILES: CC(=O)COc1ccc(-c2ccc(=O)n(Cc3ccc(Cl)cc3F)c2)cc1]

According to Scheme 14 Method A: A suspension of 1-(4-chloro-2-fluorobenzyl)-5-(4-hydroxyphenyl)pyridin-2(1H)-one (1 eq, 0.61 mmol, 0.20 g, Example 20 Step 2), $K_2CO_3$ (10 eq, 6.10 mmol, 0.84 g) and chloroacetone (4 eq, 2.43 mmol, 0.20 mL) in THF (10 mL) was heated in a microwave at 110° C. during 30 min. After filtration and evaporation, the resulting crude oil was purified by flash chromatography over silica gel (AIT Flashsmart prepacked column 25 g $SiO_2$) using $CH_2Cl_2$/AcOEt 80/20 then washed with $Et_2O$ and was dried to afford 1-(4-chloro-2-fluorobenzyl)-5-(4-(2-oxopropoxy)phenyl)pyridin-2(1H)-one (0.12 mmol, 46 mg, 20%) as a white solid.

M.p.: 127° C.; LC (XTerra $RP_{18}$, 3.5 μm, 3.0×50 mm Column): RT=4.02 min; MS m/z (CI) $[MH]^+$=386, 388; $^1H$ NMR (300 MHz, $CDCl_3$) δ 2.16 (s, 3H), 4.83 (s, 2H), 5.18 (s, 2H), 6.50 (d, J=9.3 Hz, 1H), 6.93-7.02 (m, 2H), 7.15-7.24 (m, 1H), 7.27 (dd, J=2.1 Hz and 8.7 Hz, 1H), 7.42-7.51 (3H), 7.83 (dd, J=2.4 Hz and 9.3 Hz, 1H), 8.11 (d, J=2.4 Hz, 1H).

Example 22

2-(4-(1-(4-Chlorobenzyl)-1,6-dihydro-6-oxopyridin-3-yl)phenyl)-N-methylacetamide (Final Compound 2-44)

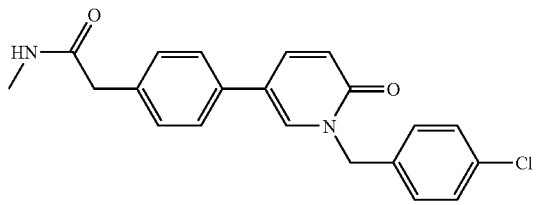 [SMILES: CNC(=O)Cc1ccc(-c2ccc(=O)n(Cc3ccc(Cl)cc3)c2)cc1]

Step 1: 2-(4-(1-(4-Chlorobenzyl)-1,6-dihydro-6-oxopyridin-3-yl)phenyl)acetic acid According to Scheme 3 Method A: The title compound was prepared according to Example 2 Step 2, from 1-(4-chlorobenzyl)-5-bromopyridin-2(1H)-one (1 eq, 0.67 mmol, 0.20 g, Example 2 Step 1) and 2-(4-(4,4,5,5-tetramethyl-1,3,2-dioxaborolan-2-yl)phenyl)acetic acid (1.5 eq, 1.00 mmol, 0.26 g). Reaction conditions: 4.5 hours at 90° C. The reaction mixture was made acidic then extracted with AcOEt. The organic layer washed with brine, dried over $Na_2SO_4$, filtered and concentrated. The residue was purified by chromatography over silicagel (AIT Flashsmart prepacked column 25 g $SiO_2$, AcOEt/MeOH 95/5), yielding the title compound (0.24 g, 100%) as a white solid. LC (XTerra $RP_{18}$, 3.5 μm, 3.0×50 mm Column): RT=3.53 min; MS m/z (CI) $[MH]^+$=354, 356.

Step 2: 2-(4-(1-(4-Chlorobenzyl)-1,6-dihydro-6-oxopyridin-3-yl)phenyl)-N-methyl acetamide Scheme 15 Method B: The title compound was prepared according to Example 14 Step 3, from 2-(4-(1-(4-chlorobenzyl)-1,6-dihydro-6-oxopyridin-3-yl)phenyl)acetic acid (1 eq, 0.10 mmol, 50 mg) and methylamine (2M in MeOH, 0.10 mmol, 0.07 mL), then purified by chromatography over silicagel (AIT Flashsmart prepacked column 10 g $SiO_2$, $CH_2Cl_2$/AcOEt 50/50), yielding the title compound (0.07 mmol, 34 mg, 66%) as a white solid.

M.p.: 183° C.; LC (XTerra $RP_{18}$, 3.5 μm, 3.0×50 mm Column): RT=3.32 min; MS m/z (CI) $[MH]^+$=367, 369; $^1H$ NMR (300 MHz, DMSO-$d^6$) δ 2.56 (d, J=4.6 Hz, 3H), 3.36 (s, 2H), 5.15 (s, 2H), 6.52 (d, J=9.5 Hz, 1H), 7.29 (d, J=8.2 Hz, 2H), 7.33-7.45 (4H), 7.49 (d, J=8.2 Hz, 2H), 7.83 (dd, J=J=2.6 Hz, 9.45 Hz, 1H), 7.92-8.01 (m, 1H), 8.24 (d, J=2.6 Hz, 1H).

Example 23

5-(4-((2H-Tetrazol-5-yl)methyl)phenyl)-1-(4-chlorobenzyl)pyridin-2(1H)-one (Final Compound 2-51)

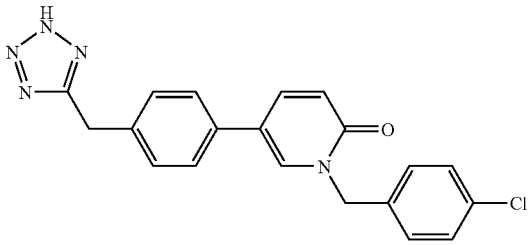 [SMILES: O=c1ccc(-c2ccc(Cc3nn[nH]n3)cc2)cn1Cc1ccc(Cl)cc1]

Step 1: 2-(4-(1-(4-Chlorobenzyl)-1,6-dihydro-6-oxopyridin-3-yl)phenyl)acetonitrile According to Scheme 3 Method A: The title compound was synthesized as described in Example 2 Step 2 using 4-(cyanomethyl)phenyl boronic acid (1.5 eq, 0.50 mmol, 80.9 mg) and 1-(4-chlorobenzyl)-5-bromopyridin-2(1H)-one (1 eq, 0.33 mmol, 0.10 g, Example 2 Step 1) as substrates. The crude product was purified by flash chromatography over silica gel (AIT Flashsmart prepacked column 25 g $SiO_2$) using $CH_2Cl_2$/AcOEt to afford 2-(4-(1-(4-chlorobenzyl)-1,6-dihydro-6-oxopyridin-3-yl)phenyl)acetonitrile as a yellow solid (0.33 mmol, 110 mg, 98%).

M.p.: 172° C.; LC (XTerra RP18, 3.5 μm, 3.0×50 mm Column): RT=4.18 min, MS m/z (CI) [MH]$^+$=335, 337.

Step 2: 5-(4-((2H-Tetrazol-5-yl)methyl)phenyl)-1-(4-chlorobenzyl)pyridin-2(1H)-one According to Scheme 15 Method D: 2-(4-(1-(4-Chlorobenzyl)-1,6-dihydro-6-oxopyridin-3-yl)phenyl)acetonitrile (1 eq, 0.24 mmol, 0.08 g) was heated at 110° C. under nitrogen overnight with dibutyltin oxide (0.22 eq, 0.05 mmol, 0.01 g) and azidotrimethylsilane (6.0 eq, 1.43 mmol, 0.19 mL) in toluene (4 mL). The suspension was filtered and the filtrate concentrated under vacuo. The crude product was purified by chromatography on silica gel using MeOH/AcOEt 20/80 as eluent and recrystallised in diisopropyl ether to afford the title compound as a white solid (0.09 mmol, 35 mg, 39%).

M.p.: 231° C.; LC (XTerra $RP_{18}$, 3.5 μm, 3.0×50 mm Column): RT=3.56 min; MS m/z (CI) [MH]$^+$=376, 378; $^1$H NMR (500 MHz, DMSO-d$^6$) δ 3.99 (s, 2H), 5.13 (s, 2H), 6.48 (d, J=9.5 Hz, 1H), 7.25 (d, J=8.4 Hz, 2H), 7.35-7.40 (4H), 7.42 (d, J=8.4 Hz, 2H), 7.80 (dd, J=2.7 Hz and 9.5 Hz, 1H), 8.21 (d, J=2.5 Hz, 1H).

Example 24

5-(4-((2H-Tetrazol-5-yl)methoxy)phenyl)-1-(4-chloro-2-fluoro benzyl)pyridin-2(1H)-one (Final Compound 6-65)

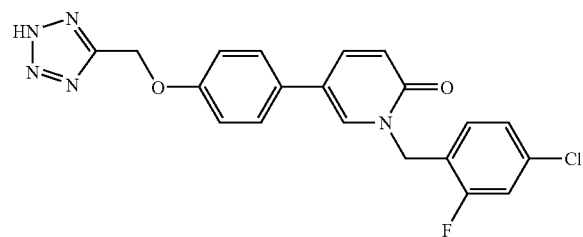 [SMILES: O=c1ccc(-c2ccc(OCc3nn[nH]n3)cc2)cn1Cc1ccc(Cl)cc1F]

According to Scheme 15 Method D: The title compound was prepared from 2-(4-(1-(4-chloro-2-fluorobenzyl)-6-oxo-1,6-dihydropyridin-3-yl)phenoxy)acetonitrile (1 eq, 0.35 mmol, 0.13 g, Example 20 Step 3) according to the procedure described for Example 23 Step 2. The crude product was purified by silica gel chromatography (AIT Flashsmart prepacked column 10 g $SiO_2$) using $CH_2Cl_2$/MeOH 95/5 as eluent followed by trituration in $Et_2O$ to afford 5-(4-((2H-tetrazol-5-yl)methoxy)phenyl)-1-(4-chloro-2-fluorobenzyl)pyridin-2(1H)-one (85 μmol, 35 mg, 24%) as a white solid.

M.p.: 197° C.; LC (XTerra $RP_{18}$, 3.5 μm, 3.0×50 mm Column): RT=3.57 min; MS m/z (CI) [MH]$^+$=412, 414; $^1$H NMR (300 MHz, CDCl$_3$) δ 3.00-3.60 (br. s, 1H), 5.18 (s, 2H), 5.35 (s, 2H), 6.50 (d, J=9.5 Hz, 1H), 7.11-7.17 (m, 2H), 7.18-7.23 (m, 1H), 7.27 (dd, J=2.0 Hz and 8.4 Hz, 1H), 7.45 (dd, J=2.0 Hz and 10.2 Hz, 1H), 7.47-7.60 (m, 2H), 7.84 (dd, J=2.7 Hz and 9.5 Hz, 1H), 8.13 (d, J=2.7 Hz, 1H).

Example 25

1-(3,4-Difluorobenzyl)-5-(phenoxymethyl)pyridin-2(1H)-one (Final Compound 16-03)

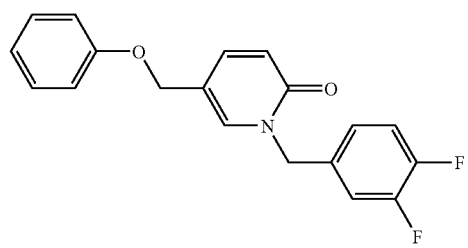 [SMILES: O=c1ccc(COc2ccccc2)cn1Cc1ccc(F)c(F)c1]

Step 1: (6-Methoxypyridin-3-yl)methanol

According to Scheme 16 Method A: A solution of 6-methoxynicotinaldehyde (1 eq, 2.19 mmol, 0.30 g) and LiAlH$_4$ (0.5 eq, 1.05 mmol, 0.04 g) in THF (10 mL) was stirred for 30 min. at 0° C. and overnight at room temperature. After the addition of AcOEt, the reaction mixture was diluted with water. The organic layer washed with saturated NH$_4$Cl solution, dried over Na$_2$SO$_4$, filtered and evaporated. The resulting crude residue was purified by silica gel chromatography (AIT Flashsmart prepacked column 25 g SiO$_2$) using CH$_2$Cl$_2$/AcOEt 80/20 to afford (6-methoxypyridin-3-yl)methanol (1.80 mmol, 0.26 g, 90%) as a pale oil.

LC (XTerra $RP_{18}$, 3.5 μm, 3.0×50 mm Column): RT=1.86 min; MS m/z (CI) [MH]$^+$=140.

Step 2: 2-Methoxy-5-(phenoxymethyl)pyridine

According to Scheme 16 Method A: Phenol (1.5 eq, 2.80 mmol, 0.26 g), PPh$_3$ (2 eq, 3.70 mmol, 1.20 g) and DEAD (2 eq, 3.70 mmol, 1.60 g) were added to a solution of (6-methoxypyridin-3-yl)methanol (1 eq, 1.87 mmol, 0.26 g) in THF (6 mL). The reaction mixture was stirred overnight at room temperature. After evaporation of the solvent, the reaction mixture was diluted with water. The organic layer washed with saturated NaHCO$_3$ solution, dried over Na$_2$SO$_4$, filtered and evaporated. The resulting crude residue was purified by silica gel chromatography (AIT Flashsmart prepacked column 25 g SiO$_2$) using cyclohexane/AcOEt 85/15 to afford 2-methoxy-5-(phenoxymethyl)pyridine (0.93 mmol, 0.20 g, 49%) as a pale oil.

LC (XTerra $RP_{18}$, 3.5 μm, 3.0×50 mm Column): RT=4.46 min; MS m/z (CI) [MH]$^+$=216.

Step 3: 1-(3,4-Difluorobenzyl)-5-(phenoxymethyl)pyridin-2(1H)-one

According to Scheme 16 Method A: The title compound was prepared from 2-methoxy-5-(phenoxymethyl)pyridine (1 eq, 0.46 mmol, 0.10 g) and 4-(bromomethyl)-1,2-difluorobenzene (3 eq, 1.39 mmol, 0.18 mL) according to the procedure described for Example 1 Step 2. Reaction conditions: under reflux for 3 days in DMF (5 mL). The crude oil was purified by flash chromatography over silica gel (AIT Flashsmart prepacked column 25 g SiO$_2$) using CH$_2$Cl$_2$/AcOEt 90/10 followed by recrystallization in diisopropyl ether to afford 1-(3,4-difluorobenzyl)-5-(phenoxymethyl)pyridin-2(1H)-one (0.14 mmol, 0.04 g, 29%) as a white solid.

M.p.: 89° C.; LC (XTerra RP$_{18}$, 3.5 µm, 3.0×50 mm Column): RT=4.29 min; MS m/z (CI) [MH]$^+$=328; $^1$H NMR (500 MHz, DMSO-d$^6$) δ 4.80 (s, 2H), 5.06 (s, 2H), 6.45 (d, J=9.3 Hz, 1H), 6.91-6.96 (m, 1H), 6.96-6.99 (m, 2H), 7.12-7.17 (m, 1H), 7.25-7.30 (m, 2H), 7.36-7.43 (m, 2H), 7.53 (dd, J=2.5 Hz and 9.3 Hz, 1H), 7.99 (d, J=2.3 Hz, 1H).

Example 26

1-(4-Chloro-2-fluorobenzyl)-5-(benzo[b]thiophen-5-yl)pyridin-2(1H)-one (Final Compound 6-69)

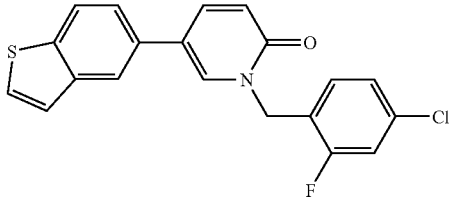 [SMILES: O=c1ccc(-c2ccc3sccc3c2)cn1Cc1ccc(Cl)cc1F]

Step 1: 1-(4-Chloro-2-fluorobenzyl)-5-(4,4,5,5-tetramethyl-1,3,2-dioxaborolan-2-yl)pyridin-2(1H)-one According to Scheme 17 Step 1: To a solution of 1-(4-chloro-2-fluorobenzyl)-5-bromopyridin-2(1H)-one (1 eq, 1.26 mmol, 0.40 g, Example 1 Step 2) in degazed dioxane (20 mL) was added under nitrogen 4,4,5,5-tetramethyl-2-(4,4,5,5-tetramethyl-1,3,2-dioxaborolan-2-yl)-1,3,2-dioxaborolane (1.3 eq, 1.64 mmol, 0.42 g), PdCl$_2$(dppf)$_2$ (0.03 eq, 38 µmol, 28 mg), dppf (0.06 eq, 76 µmol, 42 mg) and KOAc (3 eq, 3.79 mmol, 0.37 g). The reaction mixture was stirred at 80° C. for 4 hours, was quenched with water and the aqueous phase was extracted with AcOEt. The organic phase was dried over Na$_2$SO$_4$, filtered and concentrated. The crude product was purified by silica gel chromatography (AIT Flashsmart prepacked column 25 g SiO$_2$) using CH$_2$Cl$_2$/AcOEt 90/10 as eluent to afford 1-(4-chloro-2-fluorobenzyl)-5-(4,4,5,5-tetramethyl-1,3,2-dioxaborolan-2-yl)pyridin-2(1H)-one (0.74 mmol, 0.27 g, 59%) as a pale oil.

LC (XTerra RP$_{18}$, 3.5 µm, 3.0×50 mm Column): RT=3.03 min; MS m/z (CI) [MH]$^+$=364, 366.

Step 2: 1-(4-Chloro-2-fluorobenzyl)-5-(benzo[b]thiophen-5-yl)pyridin-2(1H)-one According to Scheme 17 Step 2: The title compound was prepared from 1-(4-chloro-2-fluorobenzyl)-5-(4,4,5,5-tetramethyl-1,3,2-dioxaborolan-2-yl)pyridin-2(1H)-one (1 eq, 1.26 mmol, 0.40 g) and 5-bromobenzo[b]thiophene (1.5 eq, 0.29 mmol, 0.06 g) according to the procedure described for Example 1 Step 2. The crude product was purified by flash chromatography over silica gel (AIT Flashsmart prepacked column 25 g SiO$_2$) using CH$_2$Cl$_2$/AcOEt 90/10 and by crystallization with diisopropyl ether/pentane to afford the title compound (17 µmol, 6.4 mg, 9%) as a white solid.

M.p.: 110° C.; LC (XTerra RP$_{18}$, 3.5 µm, 3.0×50 mm Column): RT=5.03 min; MS m/z (CI) [MH]$^+$=370, 372; $^1$H NMR (500 MHz, DMSO-d$^6$) δ 5.21 (s, 2H), 6.55 (d, J=9.5 Hz, 1H), 7.19-7.24 (m, 1H), 7.26-7.30 (m, 1H), 7.43-7.49 (m, 2H), 7.57 (dd, J=1.8 Hz and 8.6 Hz, 1H), 7.80 (d, J=5.4 Hz, 1H), 7.95 (dd, J=2.7 Hz and 9.4 Hz, 1H), 8.05 (d, J=8.4 Hz, 1H), 8.07 (d, J=1.6 Hz, 1H), 8.28 (d, J=2.3 Hz, 1H).

Example 27

1-(4-Chlorobenzyl)-3-(hydroxymethyl)-5-(4-methoxyphenyl)pyridin-2(1H)-one (Final Compound 9-08)

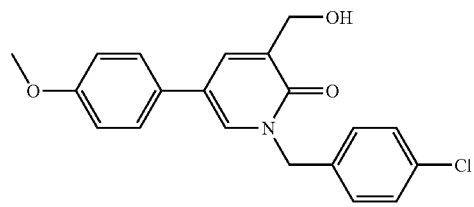 [SMILES: COc1ccc(-c2cc(CO)c(=O)n(Cc3ccc(Cl)cc3)c2)cc1]

Step 1: Methyl 1-(4-chlorobenzyl)-5-bromo-2-oxo-1,2-dihydropyridine-3-carboxylate According to Scheme 1 Step 2: The title compound was prepared from methyl 5-bromo-2-oxo-1,2-dihydropyridine-3-carboxylate (1 eq, 10.0 mmol, 3.00 g) and 1-(bromomethyl)-4-chlorobenzene (1.5 eq, 20.0 mmol, 4.00 g) according to the procedure described for Example 1 Step 2. Reaction conditions: 3 hours at 50° C. in THF/DMF (2:1, 300 mL). The crude product was purified by flash chromatography over silica gel (AIT Flashsmart prepacked 130 g column SiO$_2$) using CH$_2$Cl$_2$/AcOEt 85/15 as the eluent and recrystallized from Et$_2$O to afford the title compound (9.00 mmol, 4.17 g, 90%) as a white solid.

LC (XTerra RP$_{18}$, 3.5 µm, 3.0×50 mm Column): RT=4.05 min; MS m/z (CI) [MH]$^+$=357, 359.

Step 2: Methyl 1-(4-chlorobenzyl)-5-(4-methoxyphenyl)-2-oxo-1,2-dihydropyridine-3-carboxylate According to Scheme 3 Method A: The title compound was prepared from methyl 1-(4-chlorobenzyl)-5-bromo-2-oxo-1,2-dihydropyridine-3-carboxylate (1 eq, 7.00 mmol, 2.50 g) and 4-methoxyphenyl boronic acid (1.5 eq, 11.0 mmol, 1.60 g) according to the procedure described for Example 1 Step 3. Reaction conditions: 4 hours at 80° C. The crude product was purified by flash chromatography over silica gel (AIT Flashsmart prepacked column 80 g SiO$_2$) using CH$_2$Cl$_2$/AcOEt 80/20 and by recrystallization with Et$_2$O/pentane to afford methyl 1-(4-chlorobenzyl)-5-(4-methoxyphenyl)-2-oxo-1,2-dihydropyridine-3-carboxylate (5.74 mmol, 2.22 g, 82%) as a beige solid.

LC (XTerra RP$_{18}$, 3.5 µm, 3.0×50 mm Column): RT=4.38 min; MS m/z (CI) [MH]$^+$=384, 386.

Step 3: 1-(4-Chlorobenzyl)-3-(hydroxymethyl)-5-(4-methoxyphenyl)pyridin-2(1H)-one According to Scheme 18: To a solution of methyl 1-(4-chlorobenzyl)-5-(4-methoxyphenyl)-2-oxo-1,2-dihydropyridine-3-carboxylate (1 eq, 0.52 mmol, 0.20 g) in Et$_2$O (7 mL) at −78° C. was added DIBAL (3 eq, 1.60 mmol, 1.11 g). The reaction was stirred at −78° C. for 30 minutes and 0° C. for 1 hour. The reaction was then allowed to warm to room temperature and quenched with saturated aqueous NH$_4$Cl solution. The aqueous phase was extracted 3 times with AcOEt and the combined organic fractions were washed twice with water, dried over Na$_2$SO$_4$, filtered and concentrated under reduced pressure. The crude product was purified by flash chromatography over silica gel (AIT Flashsmart prepacked 50 g column SiO$_2$) using CH$_2$Cl$_2$/AcOEt 80/20 as eluent which was then recrystallized from pentane/Et$_2$O to afford the title compound (0.04 mmol, 16.0 mg, 9%) as a beige solid.

M.p.: 128° C.; LC (XTerra RP$_{18}$, 3.5 μm, 3.0×50 mm Column): RT=3.98 min; MS m/z (CI) [MH]$^+$=356, 358; $^1$H NMR (300 MHz, DMSO-d$^6$) δ 3.77 (s, 3H), 4.37 (d, J=5.8 Hz, 2H), 5.12-5.19 (3H), 7.00 (d, J=8.9 Hz, 2H), 7.35-7.43 (m, 4H), 7.44-7.52 (m, 2H), 7.72-7.76 (m, 1H), 8.07-8.10 (m, 1H).

Example 28

1-(4-Chloro-2-fluorobenzyl)-5-(4-aminophenyl)pyridin-2(1H)-one hydrochloride (Final Compound 6-23)

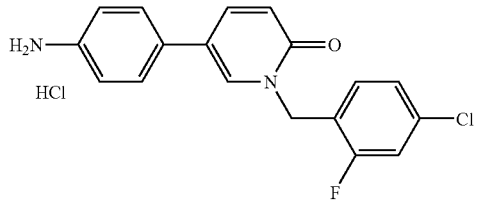 [SMILES: Nc1ccc(-c2ccc(=O)n(Cc3ccc(Cl)cc3F)c2)cc1 ; Cl]

Step 1: tert-Butyl 4-(1-(4-chloro-2-fluorobenzyl)-6-oxo-1,6-dihydropyridin-3-yl)phenylcarbamate According to Scheme 19 Step 1: The title compound was prepared from 1-(4-chloro-2-fluorobenzyl)-5-bromopyridin-2(1H)-one (1 eq, 2.81 mmol, 0.89 g, Example 1 Step 2) and 4-(tert-butoxycarbonyl)aminophenylboronic acid (1.5 eq, 4.20 mmol, 1.00 g) according to the procedure described for Example 1 Step 3. Reaction conditions: 2 hours at 80° C. The crude product was purified by silica gel chromatography (AIT Flashsmart prepacked column 50 g SiO$_2$, CH$_2$Cl$_2$/AcOEt 90/10). The resulting brown solid washed twice with acetonitrile to afford tert-butyl 4-(1-(4-chloro-2-fluorobenzyl)-6-oxo-1,6-dihydropyridin-3-yl)phenylcarbamate (2.11 mmol, 0.90 g, 75%) as a beige solid.

M.p.: 208° C.; LC (XTerra RP$_{18}$, 3.5 μm, 3.0×50 mm Column): RT=4.82 min; MS m/z (CI) [MH]$^+$=429, 431.

Step 2: 1-(4-Chloro-2-fluorobenzyl)-5-(4-aminophenyl)pyridin-2(1H)-one hydrochloride According to Scheme 19 Step 2: HCl/dioxane (10 eq, 4M, 5.00 mL) was added to a solution of tert-butyl 4-(1-(4-chloro-2-fluorobenzyl)-6-oxo-1,6-dihydropyridin-3-yl)phenylcarbamate (1 eq, 2.00 mmol, 1.00 g) in MeOH (20 mL) at 0° C. The reaction was stirred for 2 days at 80° C., then the solvent was concentrated and Et$_2$O was added. The solid was filtered and dried to yield 1-(4-chloro-2-fluorobenzyl)-5-(4-aminophenyl)pyridin-2(1H)-one hydrochloride (1.78 mmol, 0.76 g, 89%) as a beige solid.

M.p.: 266° C.; LC (XTerra RP$_{18}$, 3.5 μm, 3.0×50 mm Column): RT=3.18 min; MS m/z (CI) [MH]$^+$=329, 331; $^1$H NMR (300 MHz, DMSO-d$^6$) δ 3.10-3.70 (br s, 3H), 5.19 (s, 2H), 6.53 (d, J=9.5 Hz, 1H), 7.16-7.24 (m, 1H), 7.24-7.37 (3H), 7.46 (dd, J=1.8 Hz and 10.2 Hz, 1H), 7.63 (dd, J=8.2 Hz, 2H), 7.87 (dd, J=2.6 Hz and 9.5 Hz, 1H), 8.23 (s, 1H).

Example 29

N-(2-(4-(1-(4-Chloro-2-fluorobenzyl)-6-oxo-1,6-dihydropyridin-3-yl)phenoxy)ethyl)acetamide (Final Compound 6-53)

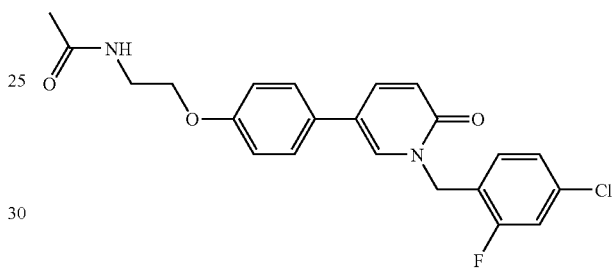

Step 1: tert-Butyl 2-(4-(1-(4-chloro-2-fluorobenzyl)-6-oxo-1,6-dihydropyridin-3-yl)phenoxy)ethylcarbamate The title compound was prepared from 1-(4-chloro-2-fluorobenzyl)-5-(4-hydroxyphenyl)pyridin-2(1H)-one (1 eq, 0.60 mmol, 0.20 g, Example 20 Step 2) and tert-butyl 2-hydroxyethylcarbamate (1.5 eq, 0.90 mmol, 0.10 g) according to the procedure described for Example 25 Step 2. The crude product was purified by crystallization in pentane/Et$_2$O followed by silica gel chromatography (AIT Flashsmart prepacked column 25 g SiO$_2$, CH$_2$Cl$_2$/AcOEt 80/20) to afford tert-butyl 2-(4-(1-(4-chloro-2-fluorobenzyl)-6-oxo-1,6-dihydropyridin-3-yl)phenoxy)ethylcarbamate (0.40 mmol, 0.19 g, 66%) as a yellow oil.

LC (XTerra RP$_{18}$, 3.5 μm, 3.0×50 mm Column): RT=4.73 min; MS m/z (CI) [MH]$^+$=473, 475.

Step 2: 1-(4-Chloro-2-fluorobenzyl)-5-(4-(2-aminoethoxy)phenyl)pyridin-2(1H)-one According to Scheme 19 Step 2: The title compound was prepared from tert-butyl 2-(4-(1-(4-chloro-2-fluorobenzyl)-6-oxo-1,6-dihydropyridin-3-yl)phenoxy)ethylcarbamate (1 eq, 0.40 mmol, 0.19 g) according to the procedure described for Example 28 Step 2. Reaction conditions: room temperature overnight. After trituration with Et$_{2O}$, 1-(4-chloro-2-fluorobenzyl)-5-(4-(2-aminoethoxy)phenyl)pyridin-2(1H)-one (0.40 mmol, 0.16 g, 100%) was obtained as a white solid.

M.p.: 226° C.; LC (XTerra RP$_{18}$, 3.5 μm, 3.0×50 mm Column): RT=2.63 min; MS m/z (CI) [MH]$^+$=373, 375.

Step 3: N-(2-(4-(1-(4-Chloro-2-fluorobenzyl)-6-oxo-1,6-dihydropyridin-3-yl)phenoxy)ethyl)acetamide According to Scheme 19 Step 3: To a solution of 1-(4-chloro-2-fluorobenzyl)-5-(4-(2-aminoethoxy)phenyl)pyridin-2(1H)-one (1 eq, 0.18 mmol, 0.07 g) in CH$_2$Cl$_2$ (5 mL) at 0° C. were added Et$_3$N (6 eq, 1.10 mmol, 0.15 mL) and 30 min. later acetyl chloride (1.5 eq, 0.27 mmol, 19 μL) and. The reaction mixture was stirred 1 hour at room temperature. The reaction mixture was quenched with water and extracted with CH$_2$Cl$_2$. The organic phase was dried over Na$_2$SO$_4$, filtered and evaporated. The crude product was purified by silica gel chromatography (AIT Flashsmart prepacked column 25 g SiO$_2$, CH$_2$Cl$_2$/AcOEt 70/30) to afford N-(2-(4-(1-(4-chloro-2-fluorobenzyl)-6-oxo-1,6-dihydropyridin-3-yl)phenoxy)ethyl)acetamide (0.08 mmol, 0.04 g, 47%) as a white solid.

M.p.: 153° C.; LC (XTerra RP$_{18}$, 3.5 μm, 3.0×50 mm Column): RT=3.51 min; MS m/z (CI) [MH]$^+$=415, 417; $^1$H NMR (300 MHz, DMSO-d$^6$) δ 3.16 (s, 3H), 3.99 (t, J=5.6 Hz, 2H), 5.18 (s, 2H), 5.75 (s, 1H), 6.51 (d, J=9.5 Hz, 1H), 7.00 (d, J=8.7 Hz, 2H), 7.15-7.23 (m, 1H), 7.23-7.29 (m, 1H), 7.43-7.53 (m, 3H), 7.84 (dd, J=2.8 Hz and 9.5 Hz, 1H), 8.09-8.20 (m, 1H).

Example 30

1-(4-Chlorobenzyl)-5-(4-(2-hydroxypropan-2-yl)phenyl)pyridin-2(1H)-one (Final Compound 2-15)

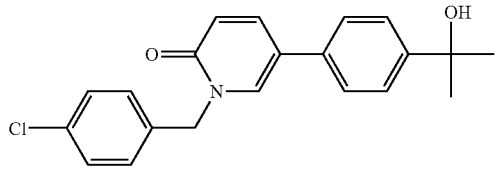 [SMILES: CC(C)(O)c1ccc(-c2ccc(=O)n(Cc3ccc(Cl)cc3)c2)cc1]

Step 1: 1-(4-Chlorobenzyl)-5-(4-acetylphenyl)pyridin-2(1H)-one

According to Scheme 3 Method A: The title compound was prepared from 1-(4-chlorobenzyl)-5-bromopyridin-2(1H)-one (Example 2 Step 1) and 4-acetylphenylboronic acid according to the procedure described for Example 2 Step 2. Reaction conditions: 4 hours at 80° C. The crude product was purified by silica gel chromatography (AIT Flashsmart prepacked column 25 g SiO$_2$) using CH$_2$Cl$_2$/AcOEt 50/50 as eluent to afford 1-(4-chlorobenzyl)-5-(4-acetylphenyl)pyridin-2(1H)-one (0.29 mmol, 0.10 g, 86%) as a yellow solid.

M.p.: 162° C.; LC (XTerra RP$_{18}$, 3.5 μm, 3.0×50 mm Column): RT=4.21 min; MS m/z (CI) [MH]$^+$=338, 340; $^1$H NMR (500 MHz, DMSO-d$^6$) δ 2.58 (s, 3H), 5.17 (s, 2H), 6.55 (d, J=9.4 Hz, 1H), 7.37-7.42 (4H), 7.74 (d, J=2.6 Hz, 2H), 7.95 (dd, J=2.6 Hz and 9.4 Hz, 1H), 7.99 (d, J=8.6 Hz, 2H), 8.45 (d, J=2.6 Hz, 1H).

Step 2: 1-(4-Chlorobenzyl)-5-(4-(2-hydroxypropan-2-yl)phenyl)pyridin-2(1H)-one According to Scheme 20: To a solution of 1-(4-chlorobenzyl)-5-(4-acetylphenyl)pyridin-2(1H)-one (1 eq, 0.20 mmol, 80 mg) in THF (5 mL) at −50° C. was added a solution of methyl magnesium bromide (3M, 1.3 eq, 0.30 mmol, 0.04 g) and the reaction stirred at −50° C. for 1 hour. The reaction was quenched at −78° C. with saturated aqueous NH$_4$Cl. The reaction was allowed to warm to room temperature and diluted with AcOEt and the organic phase extracted (×3). The combined organic fractions were dried (Na$_2$SO$_4$), filtered and concentrated under reduced pressure. The crude product was purified by flash chromatography over silica gel (AIT Flashsmart prepacked column 25 g SiO$_2$) using CH$_2$Cl$_2$/AcOEt 80/20 and was recrystallized from pentane/Et$_2$O to afford 1-(4-chlorobenzyl)-5-(4-(2-hydroxypropan-2-yl)phenyl)pyridin-2(1H)-one (0.08 mmol, 30 mg, 36%) as a white solid.

M.p.: 157° C. LC (XTerra RP$_{18}$, 3.5 μm, 3.0×50 mm Column): RT=3.86 min; MS m/z (CI) [MH]$^+$=354, 356. $^1$H NMR (300 MHz, DMSO-d$^6$) δ 1.42 (s, 6H), 5.05 (s, 1H), 5.15 (s, 2H), 6.52 (d, J=9.7 Hz, 1H), 7.32-7.43 (m, 4H), 7.43-7.52 (m, 3H), 7.84 (dd, J=1.8 Hz, 9.5 Hz, 1H), 8.22 (d, J=1.8 Hz, 1H).

Example 31

1,2-Dihydro-1-isopentyl-2-oxo-4-(thiophen-2-yl)pyridine-3-carbonitrile (Final Compound 10-28)

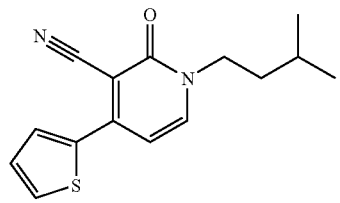 [SMILES: CC(C)CCn1ccc(-c2cccs2)c(C#N)c1=O]

According to Scheme 21: The title compound was prepared according to Example 1 Step 2 from 1,2-dihydro-2-oxo-4-(thiophen-2-yl)pyridine-3-carbonitrile (1 eq, 0.50 mmol, 0.10 g) and 1-bromo-3-methylbutane (1.5 eq, 0.70 mmol, 0.10 g). Reaction conditions: 17 hours at 60° C. in acetonitrile (10 mL). The crude product was purified by chromatography over silicagel (AIT Flashsmart prepacked column SiO$_2$, cyclohexane/AcOEt 80/20) and recrystallized in pentane/Et$_2$O yielding the title compound (88 mg, 0.30 mmol, 65%) as a yellow solid. M.p.: 123° C.; LC (XTerra RP$_{18}$, 3.5 μm, 3.0×50 mm Column): RT=4.29 min; MS m/z (CI) [MH]$^+$=273; $^1$H NMR (300 MHz, DMSO-d$^6$) δ 0.92 (d, J=5.6 Hz, 6H), 1.48-1.63 (m, 3H), 3.90-4.02 (m, 2H), 6.72 (d, J=7.2 Hz, 1H), 7.32 (d, J=8.4 Hz, 1H), 7.96-8.04 (m, 2H), 8.08 (d, J=7.2 Hz, 1H).

Example 32

1-(4-Chloro-2-fluorobenzyl)-5-(3-phenylpropyl)pyridin-2(1H)-one (Final Compound 7-08)

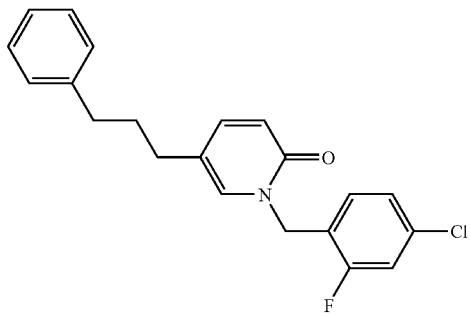 [SMILES: O=c1ccc(CCCc2ccccc2)cn1Cc1ccc(Cl)cc1F]

Step 1: 2-Methoxy-5-(3-phenylpropyl)pyridine

According to Scheme 22 Method A: To a solution of 5-bromo-2-methoxypyridine (1 eq, 2.70 mmol, 0.50 g) in THF (4.4 mL) at −78° C. under nitrogen was added dropwise n-butyl lithium (1 eq, 2.5M in hexanes, 2.70 mmol, 1.10 mL). The reaction mixture was stirred at −78° C. for 30 min. and 1-(3-bromopropyl)benzene (1 eq, 2.70 mmol, 0.40 mL) in solution in THF (1 mL) was added dropwise. The reaction mixture was stirred at −78° C. for 30 min. and then allowed to warm to room temperature for 1 hour. The reaction was quenched at 0° C. with water and extracted with $Et_2O$. The organic phase was dried over $Na_2SO_4$, filtered and solvent was removed under reduced pressure leaving an orange oil. This residue was purified by flash chromatography over silicagel (AIT Flashsmart prepacked column $SiO_2$, cyclohexane/AcOEt 97.5/2.5), yielding the title compound (0.46 mmol, 0.10 g, 17%) as a colorless semi-solid.

LC (XTerra $RP_{18}$, 3.5 µm, 3.0×50 mm Column): RT=5.08 min; MS m/z (CI) $[MH]^+$=228.

Step 2: 1-(4-Chloro-2-fluorobenzyl)-5-(3-phenylpropyl)pyridin-2(1H)-one

According to Scheme 22 Step 2: The title compound was prepared according to Example 6 Step 2, from 2-methoxy-5-(3-phenylpropyl)pyridine (1 eq, 0.44 mmol, 0.10 g) and 1-(bromomethyl)-4-chloro-2-fluorobenzene (2 eq, 0.88 mmol, 0.20 g). Reaction conditions: overnight at 90° C. The residue was purified by flash chromatography over silicagel (AIT Flashsmart prepacked column $SiO_2$, cyclohexane/AcOEt 70/30) yielding the title compound (75 mg, 0.21 mmol, 48%) as a yellow oil.

LC (XTerra $RP_{18}$, 3.5 µm, 3.0×50 mm Column): RT=5.07 min; MS m/z (CI) $[MH]^+$=356, 358; $^1H$ NMR (300 MHz, $CDCl_3$) δ 1.76-1.93 (m, 2H), 2.30-2.46 (m, 2H), 2.52-2.70 (m, 2H), 5.09 (s, 2H), 6.54 (d, J=9.2 Hz, 1H), 7.04-7.35 (9H), 7.35-7.50 (m, 1H).

Example 33

1-(4-Chloro-2-fluorobenzyl)-4-methoxy-5-(4-methoxyphenyl)pyridin-2(1H)-one (Final Compound 9-18)

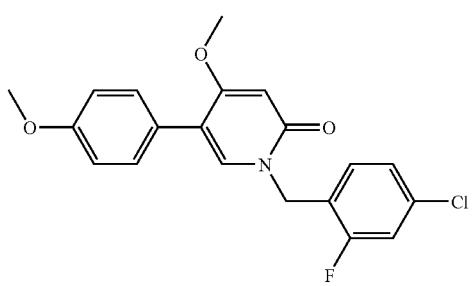 [SMILES: COc1ccc(-c2cn(Cc3ccc(Cl)cc3F)c(=O)cc2OC)cc1]

Step 1: 2,4-Dimethoxypyridine

According to Scheme 23 Step 1: To a solution of sodium methoxide (30% in MeOH, 2 eq, 35 mmol) was added 2-chloro-4-methoxypyridine (1 eq, 17.0 mmol, 2.50 g). The reaction was refluxed overnight. The reaction was allowed to cool, poured onto water (10 mL) and extracted with $CH_2Cl_2$ (3×10 mL). The combined organic fractions were dried ($Na_2SO_4$), filtered and concentrated under reduced pressure to afford 2,4-dimethoxypyridine (10.1 mmol, 1.40 g, 58%) as a colorless oil. The crude product was reacted on.

LC (XTerra $RP_{18}$, 3.5 µm, 3.0×50 mm Column): RT=1.40 min; MS m/z (CI) $[MH]^+$=140.

Step 2: 5-Bromo-2,4-dimethoxypyridine

According to Scheme 23 Step 2: To a solution of KOH (0.5 eq, 0.8 mmol, 40 mg) in water (75 mL) was added 2,4-dimethoxypyridine (1 eq, 2.00 mmol, 0.21 g) followed by the dropwise addition of $Br_2$ (1 eq, 2.00 mmol, 0.20 g) in 1M aqueous KBr solution (75 mL). The reaction was stirred at room temperature for 5 hours and then poured onto water (10 mL) and extracted with $CH_2Cl_2$ (3×10 mL). The combined organic fractions were dried ($MgSO_4$), filtered and concentrated under reduced pressure to afford 5-bromo-2,4-dimethoxypyridine (1.40 mmol, 0.30 g, 70%) as a colorless oil. The crude product was reacted on.

LC (XTerra $RP_{18}$, 3.5 µm, 3.0×50 mm Column): RT=3.92 min; MS m/z (CI) $[MH]^+$=219, 221.

Step 3: 2,4-Dimethoxy-5-(4-methoxyphenyl)pyridine

According to Scheme 23 Step 3: The title compound was prepared from 5-bromo-2,4-dimethoxypyridine (1 eq, 1.40 mmol, 0.30 g) and 4-methoxyphenylboronic acid (1.5 eq, 2.10 mmol, 0.32 g) according to the procedure described for Example 1 Step 3. The crude product was purified by flash chromatography over silica gel (AIT Flashsmart prepacked column 25 g $SiO_2$) using $CH_2Cl_2$/MeOH 98/2 to afford 2,4-dimethoxy-5-(4-methoxyphenyl)pyridine (1.39 mmol, 0.34 g, 99%) as a brown oil.

LC (XTerra $RP_{18}$, 3.5 µm, 3.0×50 mm Column): RT=3.85 min; MS m/z (CI) $[MH]^+$=246, 248.

Step 4: 1-(4-Chloro-2-fluorobenzyl)-4-methoxy-5-(4-methoxyphenyl)pyridin-2(1H)-one According to Scheme 23 Step 4: The title compound was prepared from 2,4-dimethoxy-5-(4-methoxyphenyl)pyridine (1 eq, 0.20 mmol, 0.05 g) and 4-chlorobenzyl-2-fluorobenzyl bromide (1.5 eq, 0.30 mmol, 68 mg) according to the procedure described for Example 6 Step 2. Reaction conditions: 80° C. for 2 days. The crude product was purified by flash chromatography over silica gel (AIT Flashsmart prepacked column 25 g $SiO_2$) using $CH_2Cl_2$/MeOH 98/2 to afford 1-(4-chloro-2-fluorobenzyl)-4-methoxy-5-(4-methoxyphenyl)pyridin-2(1H)-one (0.10 mmol, 36 mg, 48%).

LC (XTerra $RP_{18}$, 3.5 µm, 3.0×50 mm Column): RT=4.62 min; MS m/z (CI) $[MH]^+$=374, 376; $^1H$ NMR (300 MHz, $CDCl_3$) δ 3.78 (s, 3H), 3.82 (s, 3H), 5.11 (s, 2H), 5.99 (s, 1H), 6.88-6.95 (m, 2H), 7.08-7.15 (m, 2H), 7.20-7.30 (m, 3H), 7.40-7.50 (m, 1H).

Example 34

1-(4-(Methoxymethyl)benzyl)-5-(4-methoxyphenyl)pyridin-2(1H)-one (Final Compound 4-25)

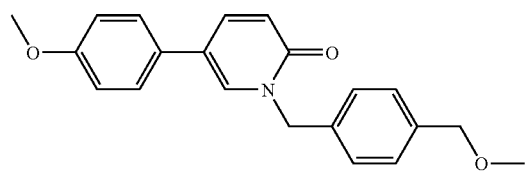

Step 1: 2-Methoxy-5-(4-methoxyphenyl)pyridine

According to Scheme 4 Method B: The title compound was prepared according to Example 1 Step 3 from 5-bromo-2-methoxypyridine (12.1 mmol, 2.30 g) and 4-methoxyphenylboronic acid (18.2 mmol, 2.76 g), then purified by flash chromatography over silica gel (AIT Flashsmart prepacked column 25 g SiO$_2$, CH$_2$Cl$_2$/MeOH 100/0 to 95/5), yielding the title compound (1.60 g, 61%).

LC (XTerra RP18, 3.5 μm, 3.0×50 mm Column): RT=3.03 min; MS m/z (CI) [MH]$^+$=216.

Step 2: 1-(4-(Hydroxymethyl)benzyl)-5-(4-methoxyphenyl)pyridin-2(1H)-one

According to Scheme 4 Step 1: The title compound was prepared according to Example 6 Step 2, from 2-methoxy-5-(4-methoxyphenyl)pyridine (1 eq, 4.60 mmol, 1.00 g) and (4-(bromomethyl)phenyl)methanol (1.1 eq, 5.10 mmol 1.00 g). Reaction conditions: 5 hours at 70° C. and room temperature overnight. The residue was triturated with pentane, yielding the title compound (3.70 mmol, 1.20 g, 80%).

LC (XTerra RP$_{18}$, 3.5 μm, 3.0×50 mm Column): RT=3.23 min; MS m/z (CI) [MH]$^+$=322.

Step 3: 1-(4-(Methoxymethyl)benzyl)-5-(4-methoxyphenyl)pyridin-2(1H)-one

According to Scheme 24 Step 3: A mixture of 1-(4-(hydroxymethyl)benzyl)-5-(4-methoxyphenyl)pyridin-2(1H)-one (1 eq, 0.25 mmol, 0.08 g), NaH (55%, 1.5 eq, 0.37 mmol, 18 mg) and iodomethane (3 eq, 0.75 mmol, 0.11 g) in DMF (2 mL) was stirred at room temperature overnight. The crude was diluted with AcOEt. The organic layer washed with water, dried over Na$_2$SO$_4$, filtered and evaporated under reduced pressure. The residue was purified by flash chromatography over silica gel (AIT Flashsmart prepacked column 5 g SiO$_2$, CH$_2$Cl$_2$/MeOH 99/1), yielding the title compound (0.14 mmol, 46 mg, 55%) as white solid.

M.p.: 72° C.; LC (Zorbax C$_{18}$, 3.5 μm, 4.6×50 mm Column): RT=3.92 min; MS m/z (CI) [MH]$^+$=336; $^1$H NMR (300 MHz, CDCl$_3$) δ 3.25 (s, 3H), 3.77 (s, 3H), 4.36 (s, 2H), 5.15 (s, 2H), 6.50 (d, J=9.3 Hz, 1H), 6.98 (d, J=9.0 Hz, 2H), 7.25-7.39 (m, 4H), 7.49 (d, J=9.0 Hz, 2H), 7.80 (dd, J=2.7 Hz and 9.6 Hz, 1H), 8.15 (d, J=2.7 Hz, 1H).

Example 35

1-(4-Chlorobenzyl)-5-(4-(ethoxymethyl)phenyl)pyridin-2(1H)-one (Final Compound 2-25)

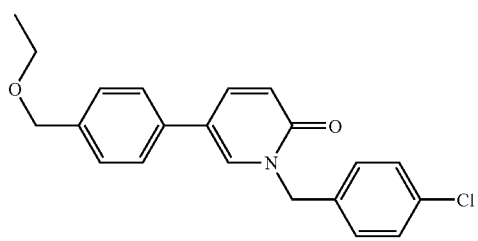 [SMILES: CCOCc1ccc(-c2ccc(=O)n(Cc3ccc(Cl)cc3)c2)cc1]

Step 1: 1-(4-Chlorobenzyl)-5-(4-(hydroxymethyl)phenyl)pyridin-2(1H)-one

According to Scheme 25 Step 2: The title compound was prepared from 1-(4-chlorobenzyl)-5-bromopyridin-2(1H)-one (1 eq, 3.30 mmol, 1.00 g, Example 2 Step 1) and 4-(hydroxymethyl)phenylboronic acid (1.5 eq, 5.00 mmol, 0.76 g) according to the procedure described for Example 1 Step 3. Reaction conditions: overnight at 80° C. The crude product was purified by flash chromatography over silica gel (AIT Flashsmart prepacked column 70 g SiO$_2$) using CH$_2$Cl$_2$/MeOH 98/2 as the eluent to afford 1-(4-chlorobenzyl)-5-(4-(hydroxymethyl)phenyl)pyridin-2(1H)-one (1.72 mmol, 0.62 g, 52%) as a brown oil LC (XTerra RP$_{18}$, 3.5 μm, 3.0×50 mm Column): RT=3.47 min; MS m/z (CI) [MH]$^+$=326, 328.

Step 2: 1-(4-Chlorobenzyl)-5-(4-(ethoxymethyl)phenyl)pyridin-2(1H)-one

According to Scheme 25 Method A: The title compound was prepared from 1-(4-chlorobenzyl)-5-(4-(hydroxymethyl)phenyl)pyridin-2(1H)-one (1 eq, 2.50 mmol, 0.80 g) and iodoethane (3 eq, 7.40 mmol, 1.10 g)) according to the procedure described for Example 34 Step 3. The crude product was purified by flash chromatography over silica gel (AIT Flashsmart prepacked column 5 g SiO$_2$) using CH$_2$Cl$_2$/MeOH 99/1 as eluent to afford 1-(4-chlorobenzyl)-5-(4-(ethoxymethyl)phenyl)pyridin-2(1H)-one (1.02 mmol, 0.36 g, 41%) as a yellow solid.

M.p.: 109° C.; LC (Zorbax C$_{18}$, 3.5 μm, 4.6×50 mm Column): RT=4.62 min; MS m/z (CI) [MH]$^+$=354, 356; $^1$H NMR (300 MHz, DMSO-d$^6$) δ 1.15 (t, J=6.9 Hz, 3H), 3.47 (q, J=6.9 Hz, 2H), 4.45 (s, 2H), 5.16 (s, 2H), 6.53 (d, J=9.6 Hz, 1H), 7.32-7.40 (4H), 7.55 (d, J=8.4 Hz, 2H), 7.85 (dd, J=2.7 Hz and 9.3 Hz, 1H), 8.28 (d, J=2.7 Hz, 1H).

Example 36

1-(4-Chlorobenzyl)-5-cyclohexylpyridin-2(1H)-one (Final Compound 2-01)

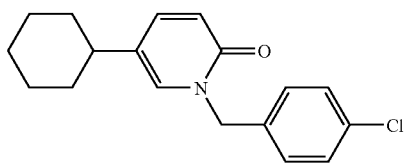 [SMILES: O=c1ccc(C2CCCCC2)cn1Cc1ccc(Cl)cc1]

Step 1: 1-(6-Methoxypyridin-3-yl)cyclohexanol

According to Scheme 26 Step 1: To a stirred solution of 4-bromo-2-methoxypyridine (1 eq, 5.30 mmol, 1.00 g) in anhydrous THF (30 mL) at −78° C. under nitrogen was added dropwise a solution of butyl lithium (1.3 eq, 2.5M solution in hexane, 6.90 mmol, 2.8 mL). The reaction was then stirred at −78° C. for 2 hours. Cyclohexanone (5 eq, 27.0 mmol, 2.8 mL) was then added dropwise over 5 minutes. The reaction was stirred at −78° C. for two hours then allowed to warm to room temperature. The reaction was stirred for a further 16 hours then quenched with water. The reaction was evaporated in vacuo, redissolved in CH$_2$Cl$_2$ (100 mL) and washed with brine (100 mL). The organic phase was extracted, dried over MgSO$_4$, filtered and evaporated to leave a yellow oil. The oil was purified by column chromatography (AIT Flashsmart prepacked column 25 g SiO$_2$, pure AcOEt), yielding the title compound (4.10 mmol, 0.86 g, 78%) as a colorless oil which solidified on standing.

LC (Zorbax C$_{18}$, 3.5 μm, 4.6×50 mm Column): RT=3.33 min; MS m/z (CI) [MH]$^+$=208.

Step 2: 5-Cyclohexenyl-2-methoxypyridine

According to Scheme 26 Step 2: The title compound was prepared from 1-(6-methoxypyridin-3-yl)cyclohexanol (1 eq, 1.21 mmol, 0.25 g) and methanesulfonyl chloride (4 eq, 4.82 mmol, 0.37 mL) according to the procedure described for Example 4 Step 1. The crude residue was purified by chromatography over silicagel (AIT Flashsmart prepacked column 10 g $SiO_2$, AcOEt/pentane 30/10 to pure AcOEt), yielding the title compound (0.76 mmol, 0.14 g, 63%) as a colorless oil.

LC (Zorbax $C_{18}$, 3.5 µm, 4.6×50 mm Column): RT=5.08 min; MS m/z (CI) [MH]$^+$=190.

Step 3: 5-Cyclohexyl-2-methoxypyridine

According to Scheme 26 Step 3: The title compound was prepared according to Example 19 Step 2, from 5-cyclohexenyl-2-methoxypyridine (1 eq, 0.74 mmol, 0.14 g). Reaction conditions: 32 hours at room temperature. The residue was purified by chromatography over silicagel (AIT Flashsmart prepacked column 10 g $SiO_2$, $CH_2Cl_2$/AcOEt 95/5), yielding the title compound (0.33 mmol, 63 mg, 45%) as a colorless oil.

LC (Zorbax $C_{18}$, 3.5 µm, 4.6×50 mm Column): RT=5.15 min; MS m/z (CI) [MH]$^+$=192.

Step 4: 1-(4-Chlorobenzyl)-5-cyclohexylpyridin-2(1H)-one

According to Scheme 26 Step 4: The title compound was prepared according to Example 6 Step 2, from 5-cyclohexyl-2-methoxypyridine (1 eq, 0.30 mmol. 57 mg) and 1-(bromomethyl)-4-chlorobenzene (1.5 eq, 0.44 mmol, 92 mg), then purified by chromatography over silicagel (AIT Flashsmart prepacked column 5 g $SiO_2$, $CH_2Cl_2$/MeOH 98/2) then recrystallized in pentane/diisopropyl ether, yielding the title compound (0.20 mmol, 0.09 g, 68%) as a beige solid.

M.p.: 72° C.; LC (Zorbax $C_{18}$, 3.5 µm, 4.6×50 mm Column): RT=5.07 min; MS m/z (CI) [MH]$^+$=302, 304; $^1$H NMR (300 MHz, $CDCl_3$) δ 1.07-1.43 (5H), 1.63-1.86 (5H), 2.13-2.28 (m, 1H), 5.08 (s, 2H), 6.58 (d, J=9.5 Hz, 1H), 6.99 (d, J=2.6 Hz, 1H), 7.20-7.25 (m, 2H), 7.26-7.30 (m, 2H), 7.31-7.33 (m, 1H).

Example 37

1-(4-Chlorobenzyl)-5-(4-methoxyphenyl)pyrazin-2 (1H)-one (Final Compound 12-06)

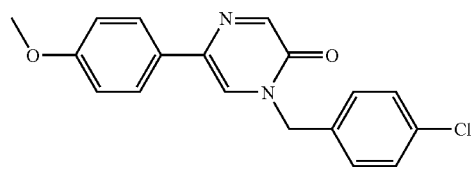 [SMILES: COc1ccc(-c2cn(Cc3ccc(Cl)cc3)c(=O)cn2)cc1]

Step 1: 1-(4-Chlorobenzyl)-5-bromopyrazin-2(1H)-one

According to Scheme 27 Step 1: The title compound was prepared from 5-bromopyrazin-2(1H)-one (1 eq, 2.86 mmol, 0.50 g) and 1-(bromomethyl)-4-chlorobenzene (1.5 eq, 4.29 mmol, 0.88 g) according to the procedure described for Example 1 Step 2. Reaction conditions: 3 hours at 70° C. in acetonitrile. The crude product was purified by flash chromatography over silica gel (AIT Flashsmart prepacked column 25 g $SiO_2$) using pure AcOEt as eluent to afford 1-(4-chlorobenzyl)-5-bromopyrazin-2(1H)-one (2.48 mmol, 0.74 g, 87%) as a white solid.

LC (XTerra $RP_{18}$, 3.5 µm, 3.0×50 mm Column): RT=3.91 min; MS m/z (CI) [MH]$^+$=300, 302.

Step 2: 1-(4-Chlorobenzyl)-5-(4-methoxyphenyl) pyrazin-2(1H)-one

According to Scheme 27 Step 2: The title compound was prepared from 1-(4-chlorobenzyl)-5-bromopyrazin-2(1H)-one (1 eq, 0.67 mmol, 0.20 g) and 4-methoxyphenylboronic acid (1.5 eq, 1.00 mmol, 0.15 g) according to the procedure described for Example 1 Step 3. Reaction conditions: 1 hour at 80° C. The crude product was purified by flash chromatography over silica gel (AIT Flashsmart prepacked column 10 g $SiO_2$) using $CH_2Cl_2$/MeOH (98/2) as the eluent to afford 1-(4-chlorobenzyl)-5-(4-methoxyphenyl)pyrazin-2(1H)-one (0.47 mmol, 0.15 g, 71%) as a beige solid.

M.p.: 133° C.; LC (XTerra $RP_{18}$, 3.5 cm, 3.0×50 mm Column): RT=4.41 min; MS m/z (CI) [MH]$^+$=327, 329. $^1$H NMR (300 MHz, DMSO-d$^6$) δ 3.78 (s, 3H), 5.12 (s, 2H), 7.00 (d, J=9.0 Hz 2H), 7.40-7.50 (m, 4H), 7.77 (d, J=9.0 Hz, 2H), 8.14 (s, 1H), 8.39 (s, 1H).

Example 38

5-(4-Hydroxyphenethylamino)-2-propylisoquinolin-1(2H)-one (Final Compound 13-05)

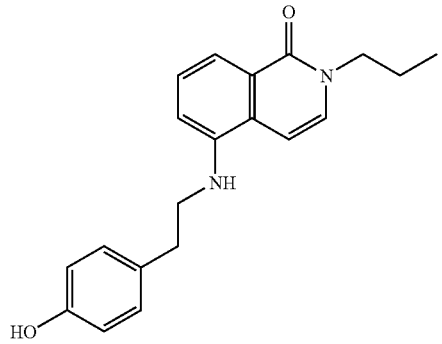 [SMILES: CCCn1ccc2c(NCCc3ccc(O)cc3)cccc2c1=O]

Step 1: 5-Chloroisoquinoline N-oxide

According to Scheme 28 Step 1: A solution of MCPBA (1.9, 15.0 mmol, 3.6 g) and 5-chloroisoquinoline (1 eq, 7.80 mmol, 1.27 g) in $CH_2Cl_2$ (30 mL) was stirred for 2 hours at room temperature. The reaction mixture was diluted with $CH_2Cl_2$ (20 mL) and MeOH (10 mL) and the organic phase washed with 2M NaOH solution. The aqueous layer was extracted with $CH_2Cl_2$. The organic fractions were combined, dried over $MgSO_4$, filtered and evaporated to yield the title compound (6.20 mmol, 1.12 g, 79%) as an orange solid.

Step 2: 5-Chloroisoquinolin-1(2H)-one

According to Scheme 28 Step 2: A solution of 5-chloroisoquinoline N-oxide (1 eq, 6.88 mmol, 1.25 g) in anhydride acetic (20 mL) was stirred for 3 hours under reflux and overnight at room temperature. After distillation of anhydride acetic, a solution of NaOH (2M, 10 mL) was added and the reaction mixture was stirred for 1 hour at 50-60° C. Then the reaction mixture was acidified (pH=6) with citric acid (5% in water). The precipitate was filtered, washed with water, dried under vacuum. The crude residue was taken up in $CH_2Cl_2$ (20 mL). The organic phase washed with brine, dried over $MgSO_4$, filtered and evaporated to yield the title compound (3.73 mmol, 0.67 g, 100%) as a brown solid.

Step 3: 5-Chloro-2-propylisoquinolin-1(2H)-one

According to Scheme 28 Step 3: The title compound was prepared from 5-chloroisoquinolin-1(2H)-one (1 eq, 2.66 mmol, 0.48 g) and 1-bromopropyl (1.1 eq, 2.93 mmol, 0.27 mL) according to the procedure described for Example 1 Step 2. Reaction conditions: microwaved at 150° C. for 60 min. in acetone. The crude product was purified by flash chromatography over silica gel (AIT Flashsmart prepacked column 25 g $SiO_2$) using pure $CH_2Cl_2$ to afford 5-chloro-2-propylisoquinolin-1(2H)-one (1.06 mmol, 0.24 g, 40%) as an orange solid.

Step 4: 5-(4-Methoxyphenethylamino)-2-propylisoquinolin-1(2H)-one

According to Scheme 28 Step 4: To a mixture of 5-chloro-2-propylisoquinolin-1(2H)-one (1 eq, 1.08 mmol, 0.24 g), NaOtBu (1.5 eq, 1.62 mmol, 0.16 g), $Pd_2(dba)_3$ (0.05 eq, 54 µmol, 50 mg), BINAP (0.05 eq, 54 µmol, 34 mg) in degassed and dried toluene (4 mL) was added (1.5 eq, 1.62 mmol, 0.25 g). The reaction mixture was microwaved at 180° C. for 2 hours and 1 hour at 200° C. The reaction mixture was quenched with water and the aqueous phase was extracted with $CH_2Cl_2$. The organic fraction washed with saturated $NH_4OH$ solution, brine, dried over $Na_2SO_4$, filtered and concentrated under reduced pressure. The crude product was purified by silica gel chromatography (AIT Flashsmart prepacked column $SiO_2$, cyclohexane/AcOEt 90/10) to afford 5-(4-methoxyphenethylamino)-2-propylisoquinolin-1(2H)-one (0.39 mmol, 0.13 g, 36%) as a white solid.

Rf=0.05 (cyclohexane/AcOEt 80/20); M.p.: 109-110° C.; LC (XTerra $RP_{18}$, 3.5 µm, 3.0×50 mm Column): RT=4.60 min; MS m/z (CI) [MH]$^+$=337.

Step 5: 5-(4-Hydroxyphenethylamino)-2-propylisoquinolin-1(2H)-one

The title compound was prepared from 5-(4-methoxyphenethylamino)-2-propylisoquinolin-1(2H)-one (1 eq, 0.20 mmol, 66 mg) according to the procedure described for Example 20 Step 2. The crude product was purified by trituration in diisopropyl ether to yield after filtration 5-(4-hydroxyphenethylamino)-2-propylisoquinolin-1(2H)-one (64 µmol, 20 mg, 32%) as a brown powder M.p.: 170-171° C.; LC (XTerra $RP_{18}$, 3.5 µm, 3.0×50 mm Column): RT=3.78 min; MS m/z (CI) [MH]$^+$=323; $^1$H NMR (300 MHz, DMSO-d$^6$) δ 0.96 (t, J=7.4 Hz, 3H), 1.40-1.72 (br. s, 1H), 1.72-1.87 (m, 2H), 2.99 (t, J=7.2 Hz, 2H), 3.47 (t, J=6.9 Hz, 2H), 3.95 (t, J=7.4 Hz, 2H), 6.35-6.47 (m, 1H), 6.79 (d, J=8.4 Hz, 2H), 6.99-7.12 (m, 4H), 7.34-7.42 (m, 1H), 7.91-8.02 (m, 1H).

Example 39

4-(4-Methoxyphenethyl)-2-propylisoquinolin-1(2H)-one (Final Compound 14-01)

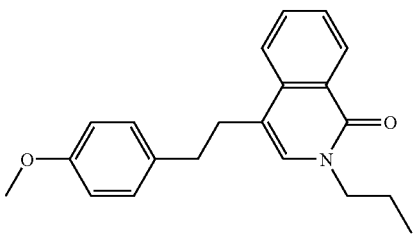 [SMILES: CCCn1cc(CCc2ccc(OC)cc2)c2ccccc2c1=O]

Step 1: 4-(2-(4-Methoxyphenyl)ethynyl)isoquinoline

According to Scheme 29 Step 1: The title compound was prepared from 4-bromoisoquinoline (1 eq, 5.30 mmol, 1.10 g) and 1-ethynyl-4-methoxybenzene (1 eq, 5.30 mmol, 0.70 g) according to the procedure described for Example 13 Step 1. Reaction conditions: 70° C. for 4 hours. The crude product was purified by silica gel chromatography (AIT Flashsmart prepacked column $SiO_2$, cyclohexane/AcOEt 90/10 to 80/20) to afford 4-(2-(4-methoxyphenyl)ethynyl)isoquinoline (3.11 mmol, 0.81 g, 59%) as a white solid.

LC (XTerra $RP_{18}$, 3.5 µm, 3.0×50 mm Column): RT=5.19 min; MS m/z (CI) [MH]$^+$=260.

Step 2: 4-(4-Methoxyphenethyl)isoquinoline

According to Scheme 29 Step 2: The title compound was prepared from 4-(2-(4-methoxyphenyl)ethynyl)isoquinoline (1 eq, 3.11 mmol, 0.81 g) according to the procedure described for Example 13 Step 2. Reaction conditions: overnight at 50° C. The crude product was purified by silica gel chromatography (AIT Flashsmart prepacked column $SiO_2$ 30 g, cyclohexane/AcOEt 85/15) to afford 4-(4-methoxyphenethyl)isoquinoline (1.33 mmol, 0.35 g, 43%) as a yellow oil.

LC (XTerra $RP_{18}$, 3.5 µm, 3.0×50 mm Column): RT=3.26 min; MS m/z (CI) [MH]$^+$=264.

Step 3: 4-(4-Methoxyphenethyl)isoquinoline-N-oxide

According to Scheme 29 Step 3: The title compound was prepared from 4-(4-methoxyphenethyl)isoquinoline (1 eq, 1.33 mmol, 0.35 g) according to the procedure described for Example 38 Step 1. The crude product was used without being purified and yielded 4-(4-methoxyphenethyl)isoquinoline-N-oxide (1.33 mmol, 0.37 g, 100%) as an orange solid.

Step 4: 4-(4-Methoxyphenethyl)isoquinolin-1(2H)-one

According to Scheme 29 Step 4: The title compound was prepared from 4-(4-methoxyphenethyl)isoquinoline-N-oxide (1 eq, 1.33 mmol, 0.37 g) according to the procedure described for Example 38 Step 2. The crude product was used without being purified and yielded 4-(4-methoxyphenethyl) isoquinolin-1(2H)-one (0.36 mmol, 0.10 g, 27%) as a brown solid.

Step 5: 4-(4-Methoxyphenethyl)-2-propylisoquinolin-1(2H)-one

According to Scheme 29 Step 5: The title compound was prepared from 4-(4-methoxyphenethyl)isoquinolin-1(2H)-one (1 eq, 0.36 mmol, 0.10 g) 1-bromopropane (1.5 eq, 0.54 mmol, 49 µL) according to the procedure described for Example 1 Step 2. Reaction conditions: microwaved at 180° C. for 15 min. The crude product was purified by flash chromatography over silica gel (AIT Flashsmart prepacked column 25 g $SiO_2$) using $CH_2Cl_2$/MeOH 99.5/0.5 to afford 4-(4-methoxyphenethyl)-2-propylisoquinolin-1(2H)-one (47 µmol, 15 mg, 13%) as an orange oil.

LC (XTerra $RP_{18}$, 3.5 µm, 3.0×50 mm Column): RT=4.89 min; MS m/z (CI) [MH]$^+$=322; $^1$H NMR (300 MHz, $CDCl_3$) δ 0.83 (t, J=7.4 Hz, 3H), 1.55-1.70 (m, 2H), 2.75-2.90 (4H), 3.72 (s, 3H), 3.81 (t, J=7.3 Hz, 2H), 6.60 (s, 1H), 6.75 (d, J=8.7 Hz, 2H), 6.97 (d, J=8.6 Hz, 2H), 7.40-7.50 (m, 1H), 7.62-7.68 (m, 2H), 8.40-8.45 (m, 1H).

Example 40

1-(4-Chloro-2-fluorobenzyl)-3-methoxy-5-(4-methoxyphenyl)pyridin-2(1H)-one (Final Compound 9-10)

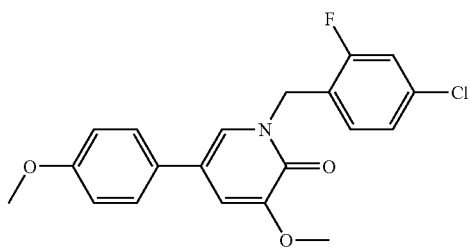 [SMILES: COc1ccc(-c2cc(OC)c(=O)n(Cc3ccc(Cl)cc3F)c2)cc1]

Step 1: 5-Bromo-2,3-dimethoxypyridine

The title compound was prepared from 2,3-dimethoxypyridine (1 eq, 7.19 mmol, 1.00 g) according to the procedure described for Example 1 Step 1. Reaction conditions: 48 hours at room temperature. The crude product was purified by flash chromatography over silica gel (AIT Flashsmart prepacked column 25 g $SiO_2$) using cyclohexane/AcOEt 96/4 to afford 5-bromo-2,3-dimethoxypyridine (3.81 mmol, 0.83 g, 53%).

Step 2: 2,3-Dimethoxy-5-(4-methoxyphenyl)pyridine

According to Scheme 4 Method B: The title compound was prepared from 5-bromo-2,3-dimethoxypyridine (1 eq, 1.83 mmol, 0.40 g) and 4-methoxyphenyl boronic acid (1 eq, 1.83 mmol, 0.28 g) according to the procedure described for Example 1 Step 3. The crude product was purified by flash chromatography on silica gel using cyclohexane/AcOEt 90/10 as eluent to afford the title compound 2,3-dimethoxy-5-(4-methoxyphenyl)pyridine (0.82 mmol, 0.20 g, 45%) was obtained.

LC (XTerra $RP_{18}$, 3.5 µm, 3.0×50 mm Column): RT=4.27 min; MS m/z (CI) [MH]$^+$=246.

Step 3: 1-(4-Chloro-2-fluorobenzyl)-3-methoxy-5-(4-methoxyphenyl)pyridin-2(1H)-one According to Scheme 4 Step 1: The title compound was prepared from 2,3-dimethoxy-5-(4-methoxyphenyl)pyridine (1 eq, 0.41 mol, 0.10 g) and 1-(bromomethyl)-4-chloro-2-fluorobenzene (2 eq, 0.82 mmol, 0.18 g) according to the procedure described for Example 6 Step 2. Reaction conditions: 14 hours at 80° C. in acetonitrile. The crude product was purified by silica gel chromatography (AIT Flashsmart prepacked column 10 g $SiO_2$) using cyclohexane/AcOEt 70/30 to 50/50 as eluent to afford 1-(4-Chloro-2-fluorobenzyl)-3-methoxy-5-(4-methoxyphenyl)pyridin-2(1H)-one (0.24 mmol, 0.09 g, 59%).

LC (XTerra $RP_{18}$, 3.5 µm, 3.0×50 mm Column): RT=4.53 min; MS m/z (CI) [MH]$^+$=374, 376; $^1$H NMR (300 MHz, $CDCl_3$) δ 3.83 (s, 3H), 3.87 (s, 3H), 5.22 (s, 2H), 6.82 (d, J=2.3 Hz, 1H), 6.95 (d, J=8.7 Hz, 2H), 7.07-7.12 (m, 2H), 7.13-7.15 (m, 1H), 7.32 (d, J=9.0 Hz, 2H), 7.47-7.55 (m, 1H).

Example 41

1-(4-Chlorobenzyl)-5-(hydroxy(3-methoxyphenyl)methyl)pyridin-2(1H)-one (Final Compound 3-10)

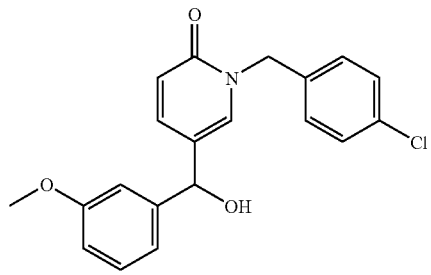 [SMILES: COc1cccc(C(O)c2ccc(=O)n(Cc3ccc(Cl)cc3)c2)c1]

According to Scheme 7 Method B: A solution of 3-methoxybenzylmagnesium bromide (1.2 eq, 1.00 mmol, 1.00 mL) was added dropwise to a solution of 1-(4-chlorobenzyl)-1,6-dihydro-6-oxopyridine-3-carbaldehyde (1 eq, 1.21 mmol, 0.30 g, Example 10 Step 1) in THF (15 mL) at −78° C. under a nitrogen atmosphere. The reaction mixture was stirred for 14 hours at room temperature. The resulting mixture was poured onto ice and extracted with $CH_2Cl_2$. The organic layer was dried over $MgSO_4$, filtered and evaporated. Purification by flash chromatography (AIT Flashsmart prepacked column 25 g $SiO_2$, $CH_2Cl_2$/AcOEt 80/20 to 70/30) afford 1-(4-chlorobenzyl)-5-(hydroxy(3-methoxyphenyl)methyl)pyridin-2(1H)-one (0.64 mmol, 0.28 g, 64%) as a yellow semi-solid.

LC (XTerra $RP_{18}$, 3.5 cm, 3.0×50 mm Column): RT=3.76 min; MS m/z ES$^+$=356, 358; $^1$H NMR (500 MHz, $CDCl_3$) δ 2.13 (d, J=3.4 Hz, 1H), 3.80 (s, 3H), 5.09 (s, 2H), 5.56 (d, J=3.5 Hz, 1H), 6.57 (d, J=9.4 Hz, 1H), 6.84-6.90 (3H), 7.22-7.35 (5H).

Example 42

1-(3-Fluorobenzyl)-4-phenethoxypyridin-2(1H)-one (Final Compound 7-03)

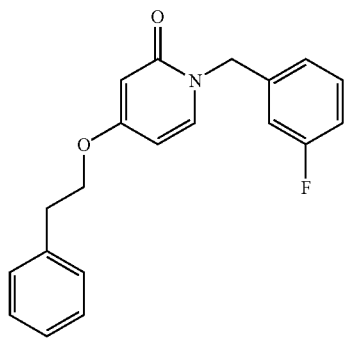 [SMILES: O=c1cc(OCCc2ccccc2)ccn1Cc1cccc(F)c1]

According to Scheme 13 Method A: The title compound was prepared from 1-(3-fluorobenzyl)-4-hydroxypyridin-2(1H)-one (1 eq, 0.23 mmol, 0.05 g, Example 19 Step 2) and 1-(2-bromoethyl)benzene (2 eq, 0.46 mmol, 0.06 mL) according to the procedure described for Example 1 Step 2. Microwave conditions: 180° C. for 900s in acetonitrile (2 mL). The crude product was purified by flash chromatography over silica gel (AIT Flashsmart prepacked column 25 g $SiO_2$) using $CH_2Cl_2$/AcOEt 80/20 and by recrystallization in pentane to afford 1-(3-fluorobenzyl)-4-phenethoxypyridin-2(1H)-one (0.13 mmol, 43 mg, 58%) as a white solid.

M.p.: 93° C.; LC (XTerra $RP_{18}$, 3.5 µm, 3.0×50 mm Column): RT=4.41 min; MS m/z (CI) $[MH]^+$=324; $^1H$ NMR (500 MHz, DMSO-$d^6$) δ 3.00 (t, J=6.7 Hz, 2H), 4.18 (t, J=6.7 Hz, 2H), 5.01 (s, 2H), 5.84 (d, J=2.7 Hz, 1H), 5.95 (dd, J=2.7 Hz and 7.6 Hz, 1H), 7.03-7.11 (3H), 7.18-7.25 (m, 1H), 7.29 (d, J=4.7 Hz, 4H), 7.32-7.38 (m, 1H), 7.66 (d, J=7.6 Hz, 1H).

Example 43

4-(1-(4-Chloro-2-fluorobenzyl)-6-oxo-1,6-dihydropyridin-3-yl)phenyl methyl carbonate (Final Compound 6-39)

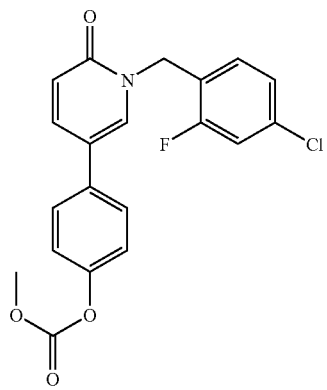 [SMILES: COC(=O)Oc1ccc(-c2ccc(=O)n(Cc3ccc(Cl)cc3F)c2)cc1]

According to Scheme 14 Method B: A suspension of 1-(4-chloro-2-fluorobenzyl)-5-(4-hydroxyphenyl)pyridin-2(1H)-one (1 eq, 0.61 mmol, 0.20 g, Example 20 Step 2), $K_2CO_3$ (10 eq, 6.10 mmol, 0.84 g) and methylchloroformate (4 eq, 2.43 mmol, 0.19 mL) in THF (10 mL) was stirred overnight at room temperature. Water was added to the reaction mixture, then the aqueous phase was extracted with AcOEt. The organic phase was dried over $MgSO_4$, filtered and evaporated. The resulting crude oil was purified by flash chromatography over silica gel (AIT Flashsmart prepacked column 109 $SiO_2$) using $CH_2Cl_2$/AcOEt 90/10 then washed with $Et_2O$ and was dried to afford 4-(1-(4-chloro-2-fluorobenzyl)-6-oxo-1,6-dihydropyridin-3-yl)phenyl methyl carbonate (0.36 mmol, 139 mg, 59%) as a white solid.

M.p.: 124° C.; LC (XTerra $RP_{18}$, 3.5 µm, 3.0×50 mm Column): RT=4.28 min; MS m/z (CI) $[MH]^+$=388, 390; $^1H$ NMR (300 MHz, $CDCl_3$) δ 3.84 (s, 3H), 5.19 (s, 2H), 6.53 (d, J=9.6 Hz, 1H), 7.17-7.27 (m, 2H), 7.27-7.33 (3H), 7.45 (dd, J=2.1 Hz and 9.9 Hz, 1H), 7.58-7.66 (m, 2H), 7.88 (dd, J=2.7 Hz and 9.9 Hz, 1H), 8.23 (d, J=2.7 Hz, 1H).

Example 44

1-(4-Chlorobenzyl)-5-((4-methoxyphenoxy)methyl)pyridin-2(1H)-one (Final Compound 16-02)

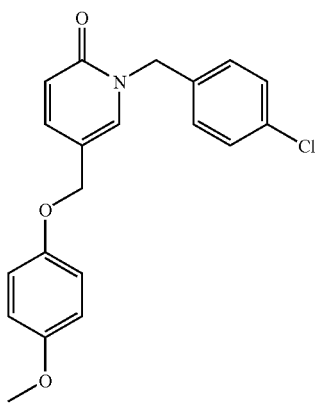 [SMILES: COc1ccc(OCc2ccc(=O)n(Cc3ccc(Cl)cc3)c2)cc1]

Step 1: 1-(4-Chlorobenzyl)-5-(hydroxymethyl)pyridin-2(1H)-one

According to Scheme 16 Method B: A solution of 1-(4-chlorobenzyl)-6-oxo-1,6-dihydropyridine-3-carbaldehyde (1 eq, 1.41 mmol, 0.35 g, Example 10 Step 1) and DIBAL (3 eq, 4.20 mmol, 4.20 mL) in THF (5 mL) was stirred for 30 min. at −78° C. and 1 hour at room temperature. After addition of AcOEt, the reaction mixture was diluted with water. The organic layer washed with saturated $NH_4Cl$ solution, dried over $Na_2SO_4$, filtered through celite and evaporated. The resulting crude residue was purified by silica gel chromatography (AIT Flashsmart prepacked column 25 g $SiO_2$) using $CH_2Cl_2$/MeOH 95/5 to afford 1-(4-chlorobenzyl)-5-(hydroxymethyl)pyridin-2(1H)-one (0.45 mmol, 0.11 g, 32%) as an orange oil.

LC (XTerra $RP_{18}$, 3.5 µm, 3.0×50 mm Column): RT=2.86 min; MS m/z (CI) $[MH]^+$=250, 252.

Step 2: 1-(4-Chlorobenzyl)-5-((4-methoxyphenoxy)methyl)pyridin-2(1H)-one

According to Scheme 16 Method B: 4-Methoxyphenol (1.5 eq, 0.68 mmol, 84.3 mg), $PPh_3$ (2.0 eq, 0.91 mmol, 0.30 g) and DEAD (2 eq, 0.91 mmol, 0.16 g) were added to a solution of 1-(4-chlorobenzyl)-5-(hydroxymethyl)pyridin-2 (1H)-one (1 eq, 0.45 mmol, 0.11 g) in THF (5 mL). The reaction mixture was stirred overnight at room temperature. After evaporation of the solvent, the reaction mixture was diluted with water. The organic layer washed with saturated NaHCO$_3$ solution, dried over Na$_2$SO$_4$, filtered and evaporated. The crude product was purified by silica gel chromatography (AIT Flashsmart prepacked column 25 g SiO$_2$) using cyclohexane/AcOEt 80/20 to afford 1-(4-chlorobenzyl)-5-((4-methoxyphenoxy)methyl)pyridin-2(1H)-one (0.19 mmol, 0.07 g, 42%) as a white solid.

M.p.: 114° C. LC (XTerra RP$_{18}$, 3.5 µm, 3.0×50 mm Column): RT=4.36 min; MS m/z (CI) [MH]$^+$=356, 358. $^1$H NMR (500 MHz, DMSO-d$^6$) δ 3.69 (s, 3H), 4.74 (s, 2H), 5.07 (s, 2H), 6.45 (d, J=9.3 Hz, 1H), 6.82-6.87 (m, 2H), 6.88-6.93 (m, 2H), 7.29 (d, J=8.5 Hz, 2H), 7.40 (d, J=8.5 Hz, 2H), 7.52 (dd, J=2.5 Hz and 9.0 Hz, 1H), 7.93 (d, J=2.3 Hz, 1H).

Example 45

1-(4-Chlorobenzyl)-5-(4-(2-(dimethylamino)ethylamino)phenyl)pyridin-2(1H)-one (Final Compound 2-50)

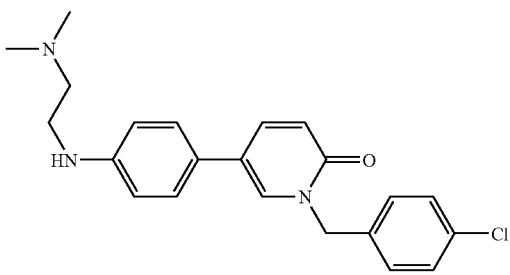 [SMILES: CN(C)CCNc1ccc(-c2ccc(=O)n(Cc3ccc(Cl)cc3)c2)cc1]

Step 1: tert-Butyl 4-(1-(4-chlorobenzyl)-6-oxo-1,6-dihydropyridin-3-yl)phenyl carbamate According to Scheme 19 Step 1: A suspension of 1-(4-chlorobenzyl)-5-bromopyridin-2(1H)-one (3.35 mmol, 1.00 g, Example 2 Step 1), N-tert-butoxycarbonyl-4-aminophenylboronic acid (6.03 mmol, 1.42 g), Pd(PPh$_3$)$_4$ (0.17 mmol, 195 mg), Na$_2$CO$_3$ (13.4 mmol, 1.42 g) in DME (20 mL) and H$_2$O (5 mL) was degassed to remove the oxygen. The mixture was heated at 85° C. for 20 hours. The resulting suspension was filtered off and the filtrate washed with CH$_2$Cl$_2$. The organic solvent was separated, dried (Na$_2$SO$_4$) and the solvent was evaporated under reduced pressure. The residue was purified in a manifold (vac.) using a Sep-Pak silica cartridge CH$_2$Cl$_2$/MeOH(NH$_3$)sat. 98/2. The product fractions were collected and the solvent was evaporated to yield the title compound (627 mg, 46%).

Step 2: tert-Butyl 4-(1-(4-chlorobenzyl)-6-oxo-1,6-dihydropyridin-3-yl)phenyl(2-(dimethylamino)ethyl)carbamate According to Scheme 19 Step 4: tert-Butyl 4-(1-(4-chlorobenzyl)-6-oxo-1,6-dihydropyridin-3-yl)phenylcarbamate (0.34 mmol 0.14 g) was dissolved in dry THF (4 mL) and the resulting solution was cooled at 0° C. Then, NaH (60% mineral oil; 1.02 mmol, 40.8 mg) was added, the mixture was stirred at 0° C. for 10 minutes, warmed at room temperature and stirred for 30 minutes. After, N,N-dimethylaminoethyl chloride (0.69 mmol) and KI (0.34 mmol, 57.0 mg) were added and the reaction mixture was heated at 90° C. for 16 hours. The resulting suspension was taken up in CH$_2$Cl$_2$, washed with water, washed with brine, filtered off and the filtrate washed with CH$_2$Cl$_2$. The organic solvent was separated, dried (Na$_2$SO$_4$) and the solvent was evaporated under reduced pressure. The residue was purified in a manifold (vac.) using a Sep-Pak silica cartridge (CH$_2$Cl$_2$/MeOH(NH$_3$) sat. 95/5). The product fractions were collected and the solvent was evaporated to yield tert-butyl 4-(1-(4-chlorobenzyl)-6-oxo-1,6-dihydropyridin-3-yl)phenyl(2-(dimethylamino)ethyl)carbamate (87.9 mg)

Step 3: 1-(4-Chlorobenzyl)-5-(4-(2-(dimethylamino)ethylamino)phenyl)pyridin-2(1H)-one According to Scheme 19 Step 5: tert-Butyl 4-(1-(4-chlorobenzyl)-6-oxo-1,6-dihydropyridin-3-yl)phenyl(2-(dimethylamino)ethyl)carbamate (0.16 mmol, 79.0 mg) was dissolved in dry CH$_2$Cl$_2$ (30 mL). Then TFA (7 mL) was added dropwise and the resulting solution was stirred at room temperature for 3 hours. Then the solvent was evaporated under reduced pressure and the resulting residue thus obtained was resulting suspension was taken up in CH$_2$Cl$_2$, washed with a saturated aqueous NaHCO$_3$ solution. The organic solvent was separated, dried (Na$_2$SO$_4$) and the solvent was evaporated under reduced pressure. The residue was purified in a manifold (vac.) using a Sep-Pak silica cartridge CH$_2$Cl$_2$/MeOH (NH$_3$)sat. 95/5. The product fractions were collected and the solvent was evaporated to yield 1-(4-chlorobenzyl)-5-(4-(2-(dimethylamino)ethylamino)phenyl)pyridin-2(1H)-one (16.4 mg, 26%)

LC (ACE Column): RT=3.23 min; MS m/z (CI) [MH]$^+$=382; $^1$H NMR (400 MHz, CDCl$_3$) δ 7.58 (dd, 1H, J=9.5, 2.6 Hz); 7.34 (d, 1H, J=2.6 Hz); 7.26-7.33 (m, 4H); 7.17 (d, 2H, J=8.7 Hz); 6.67 (d, 1H, J=9.5 Hz); 6.64 (d, 2H, J=8.4 Hz); 5.15 (s, 2H); 4.43 (s, 1H); 3.16 (t, 2H, J=5.8 Hz); 2.58 (t, 2H, J=5.8 Hz); 2.27 (s, 6H).

Example 46

1-(4-Chlorobenzyl)-5-((4-fluorophenyl)(methyl)amino)pyridin-2(1H)-one (Final Compound 3-21)

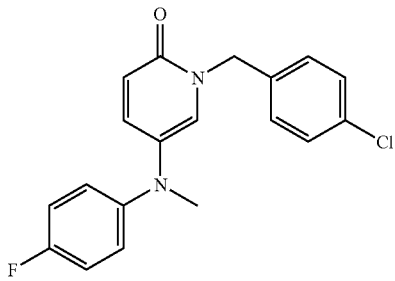 [SMILES: CN(c1ccc(F)cc1)c1ccc(=O)n(Cc2ccc(Cl)cc2)c1]

Step 1: N-(4-Fluorophenyl)-6-methoxy-N-methylpyridin-3-amine

According to Scheme 22 Method B: To a mixture of 5-bromo-2-methoxypyridine (1 eq, 1.06 mmol, 0.14 mL), KOtBu (1.5 eq, 1.60 mmol, 0.18 g), Pd(OAc)$_2$ (0.02 eq, 21 µmol, 48 mg), BINAP (0.04 eq, 42 µmol, 26 mg) in degassed DMF (1.5 mL) was added 4-fluoro-N-methylbenzenamine (1.2 eq, 1.28 mmol, 0.14 mL). The reaction mixture was microwaved at 130° C. for 5 min. The reaction mixture was quenched with water and the aqueous phase was extracted with AcOEt. The organic fraction washed brine, dried over $Na_2SO_4$, filtered and concentrated under reduced pressure. The crude product was purified by silica gel chromatography (AIT Flashsmart prepacked column 15 g $SiO_2$, $CH_2Cl_2$/AcOEt 90/10) to afford N-(4-fluorophenyl)-6-methoxy-N-methylpyridin-3-amine (0.08 mmol, 20 mg, 8%) as a yellow oil.

Rf=0.45 ($CH_2Cl_2$/AcOEt 80/20); LC (XTerra $RP_{18}$, 3.5 μm, 3.0×50 mm Column): RT=2.49 min; MS m/z (CI) $[MH]^+$=233.

Step 2: 1-(4-Chlorobenzyl)-5-((4-fluorophenyl)(methyl)amino)pyridin-2(1H)-one According to Scheme 22 Step 2: The title compound was prepared from N-(4-fluorophenyl)-6-methoxy-N-methylpyridin-3-amine (1 eq, 86 μmol, 20 mg) and 4-chloro-benzylbromide (1.7 eq, 0.15 mmol, 30 mg) according to the procedure described for Example 6 Step 2. Reaction conditions: 12 hours at 80° C. in acetonitrile. The crude product was purified by silica gel chromatography (AIT Flashsmart prepacked column 10 g $SiO_2$) using $CH_2Cl_2$/AcOEt 50/50 as eluent to afford 1-(4-chlorobenzyl)-5-((4-fluorophenyl)(methyl)amino)pyridin-2(1H)-one (29 μmol, 10 mg, 34%) as a yellow oil.

Rf=0.20 ($CH_2Cl_2$/AcOEt 90/10); LC (XTerra $RP_{18}$, 3.5 μm, 3.0×50 mm Column): RT=4.36 min; MS m/z (CI) $[MH]^+$=343, 345; $^1$H NMR (300 MHz, $CDCl_3$) δ 3.24 (s, 3H), 5.02 (s, 2H), 5.56 (dd, J=2.7 Hz and 7.7 Hz, 1H), 5.74 (d, J=2.7 Hz, 1H), 6.92 (d, J=7.7 Hz, 1H), 7.07-7.12 (m, 2H), 7.13-7.18 (m, 2H), 7.23 (d, J=8.4 Hz, 2H), 7.30 (d, J=8.4 Hz, 2H).

Example 47

N-(2-(4-(1-(4-Chlorobenzyl)-6-oxo-1,6-dihydropyridin-3-yl)benzyloxy)ethyl)acetamide (Final Compound 2-42)

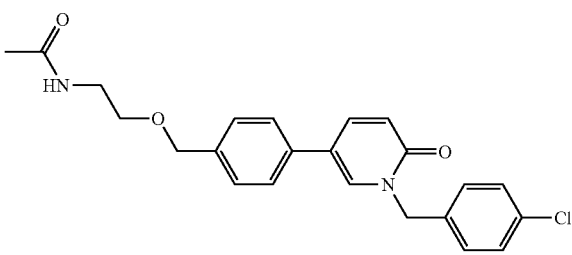 [SMILES: CC(=O)NCCOCc1ccc(-c2ccc(=O)n(Cc3ccc(Cl)cc3)c2)cc1]

Step 1: 1-(4-Chlorobenzyl)-5-(4-(bromomethyl)phenyl)pyridin-2(1H)-one

According to Scheme 25 Step 3: To a solution of 1-(4-chlorobenzyl)-5-(4-(hydroxymethyl)phenyl)pyridin-2(1H)-one (1 eq, 3.07 mmol, 1.00 g, Example 35 Step 1) in THF (8 mL) were added NBS (1.22 eq, 3.74 mmol, 0.67 g) and $PPh_3$ (1.20 eq, 3.68 mmol, 0.97 g) at −20° C. for 4 hours. After evaporation of the solvent, the crude product was purified by silica gel chromatography (AIT Flashsmart prepacked column 50 g $SiO_2$) using $CH_2Cl_2$/MeOH 98/2 to afford 1-(4-chlorobenzyl)-5-(4-(bromomethyl)phenyl)pyridin-2(1H)-one (2.06 mmol, 0.80 g, 67%).

LC (XTerra $RP_{18}$, 3.5 μm, 3.0×50 mm Column): RT=4.71 min; MS m/z (CI) $[MH]^+$=388, 390.

Step 2: N-(2-(4-(1-(4-Chlorobenzyl)-6-oxo-1,6-dihydropyridin-3-yl)benzyloxy)ethyl)acetamide According to Scheme 25 Step 4: The title compound was prepared from 1-(4-chlorobenzyl)-5-(4-(bromomethyl)phenyl)pyridin-2(1H)-one (1 eq, 0.26 mmol, 0.10 g) and (1.5 eq, 0.39 mmol, 0.04 g) according to the procedure described for Example 34 Step 3. The crude product was purified by flash chromatography over silica gel (AIT Flashsmart prepacked column 5 g $SiO_2$) using $CH_2Cl_2$/MeOH 98/2 as the eluent to afford N-(2-(4-(1-(4-chlorobenzyl)-6-oxo-1,6-dihydropyridin-3-yl)benzyloxy)ethyl)acetamide (0.13 mmol, 54 mg, 51%) as a white solid.

M.p.: 152° C.; LC (XTerra $RP_{18}$, 3.5 μm, 3.0×50 mm Column): RT=3.55 min; MS m/z (CI) $[MH]^+$=411, 413; $^1$H NMR (300 MHz, DMSO-$d^6$) δ 1.80 (s, 3H), 3.18-3.27 (m, 2H), 3.42 (t, J=6.0 Hz, 2H), 4.48 (s, 2H), 5.16 (s, 2H), 6.52 (d, J=9.6 Hz, 1H), 7.35-7.42 (6H), 7.56 (d, J=7.8 Hz, 2H), 7.86 (dd, J=2.7 Hz and 9.6 Hz, 2H), 8.28 (d, J=2.7 Hz, 1H).

Example 48

1-(4-Chlorobenzyl)-4-(2-methoxyethyl)-5-(4-methoxyphenyl)pyridin-2(1H)-one (Final Compound 9-17)

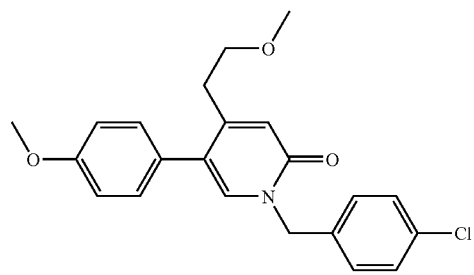 [SMILES: COCCc1cc(=O)n(Cc2ccc(Cl)cc2)cc1-c1ccc(OC)cc1]

Step 1: 2-Methoxy-5-(4-methoxyphenyl)-4-methylpyridine

According to Scheme 30 Step 1: The title compound was prepared from 5-bromo-2-methoxy-4-methylpyridine (1 eq, 15.8 mmol, 3.20 g) and 4-methoxyphenylboronic acid (1.5 eq, 23.8 mmol, 3.61 g) according to the procedure described for Example 1 Step 3. Reaction conditions: 21 hours at 80° C. The crude product was purified by flash chromatography over silica gel (AIT Flashsmart prepacked column 130 g $SiO_2$) using AcOEt/MeOH (95/5) as the eluent to afford 2-methoxy-5-(4-methoxyphenyl)-4-methylpyridine (12.8 mmol, 2.94 g, 81%) as a light yellow solid.

LC (Zorbax $C_{18}$, 3.5 μm, 4.60×50 mm Column): RT=4.52 min; MS m/z (CI) $[MH]^+$=230.

Step 2: 2-(2-Methoxy-5-(4-methoxyphenyl)pyridin-4-yl)ethanol

According to Scheme 30 Step 2: To a stirred solution of 2-methoxy-5-(4-methoxyphenyl)-4-methylpyridine (1 eq, 10.0 mmol, 2.30 g) in anhydrous THF (66 mL) at −78° C.

under argon was added dropwise butyl lithium (2.5M, 1.5 eq, 15.1 mmol, 6.0 mL). The reaction mixture was stirred for one hour and then allowed to warm slowly to 0° C. and stirred at 0° C. for a further 30 minutes. The reaction mixture was then cooled to −78° C. and paraformaldehyde (6.07 g) was added. The reaction mixture was then allowed to warm to room temperature and was stirred for 2 hours. The reaction was quenched with saturated aqueous NH$_4$Cl (30 mL), diluted with AcOEt and the aqueous phase was extracted (×3). The combined organic fractions were dried (Na$_2$SO$_4$), filtered and concentrated under reduced pressure. HCl 3M (15 mL) was added to the solution of the crude residue diluted in acetonitrile (10 mL). The reaction mixture was stirred for 2 hours at 60° C. The aqueous phase was extracted with Et$_2$O, then neutralized with NaHCO$_3$ (40 mL). The aqueous phase was extracted with CH$_2$Cl$_2$. The combined organic fractions were dried (Na$_2$SO$_4$), filtered and concentrated under reduced pressure. The crude product was purified by flash chromatography over silica gel (AIT Flashsmart prepacked column 20 g SiO$_2$) using CH$_2$Cl$_2$/AcOEt (99/1) as the eluent to afford 2-(2-methoxy-5-(4-methoxyphenyl)pyridin-4-yl)ethanol (0.62 mmol, 0.16 g, 6%) as a colorless oil.

LC (Zorbax C$_{18}$, 3.5 µm, 4.6×50 mm Column): RT=3.42 min; MS m/z (CI) [MH]$^+$=260.

Step 3: 1-(4-Chlorobenzyl)-4-(2-hydroxyethyl)-5-(4-methoxyphenyl)pyridin-2(1H)-one According to Scheme 30 Step 3: The title compound was prepared from 2-(2-methoxy-5-(4-methoxyphenyl)pyridin-4-yl)ethanol (1 eq, 0.62 mmol, 0.16 g) and 1-(bromomethyl)-4-chlorobenzene (1.5 eq, 0.93 mmol, 0.19 g) according to the procedure described for Example 6 Step 2. Reaction conditions: 19 hours under 90° C. The crude product was purified by silica gel chromatography (AIT Flashsmart prepacked column 10 g SiO$_2$) using CH$_2$Cl$_2$/MeOH 98/2 as eluent afford 1-(4-chlorobenzyl)-4-(2-hydroxyethyl)-5-(4-methoxyphenyl)pyridin-2(1H)-one (0.22 mmol, 82 mg, 36%) as a pale yellow solid.

LC (Zorbax C$_{18}$, 3.5 µm, 4.6×50 mm Column): RT=3.83 min; MS m/z (CI) [MH]$^+$=370, 372.

Step 4: 1-(4-Chlorobenzyl)-4-(2-methoxyethyl)-5-(4-methoxyphenyl)pyridin-2(4H)-one According to Scheme 30 Step 4: The title compound was prepared from 1-(4-chlorobenzyl)-4-(2-hydroxyethyl)-5-(4-methoxyphenyl)pyridin-2(1H)-one (1 eq, 0.14 mmol, 50 mg) and iodomethane (3 eq, 0.41 mmol, 58 mg) according to the procedure described for Example 34 Step 3. The product was further purified by flash chromatography over silica gel (AIT Flashsmart prepacked column 5 g SiO$_2$) using Et$_2$O/pentane 90/10 to afford 1-(4-chlorobenzyl)-4-(2-methoxyethyl)-5-(4-methoxyphenyl)pyridin-2(1H)-one (0.12 mmol, 47 mg, 91%) as a colorless oil.

LC (Zorbax C$_{18}$, 3.5 µm, 4.6×50 mm Column): RT=4.49 min; MS m/z (CI) [MH]$^+$=384, 386; $^1$H NMR (300 MHz, CDCl$_3$) δ 2.65 (t, J=6.7 Hz, 2H), 3.25 (s, 3H), 3.44 (t, J=6.7 Hz, 2H), 3.82 (s, 3H), 5.09 (s, 2H), 6.58 (s, 1H), 6.90 (d, J=8.7 Hz, 2H), 7.06 (s, 1H), 7.11 (d, J=8.7 Hz, 2H), 7.23-7.32 (4H).

Example 49

1-(4-Chloro-2-fluorobenzyl)-4-(methoxymethyl)-5-(4-methoxy phenyl)pyridin-2(1H)-one (Final Compound 9-16)

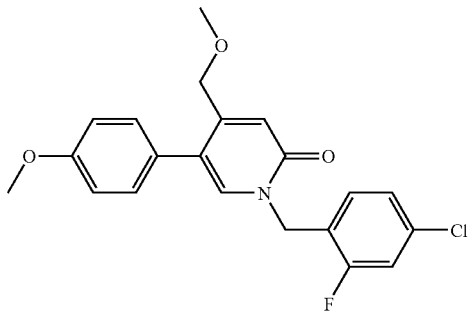 [SMILES: COCc1cc(=O)n(Cc2ccc(Cl)cc2F)cc1-c1ccc(OC)cc1]

Step 1: 4-(Bromomethyl)-2-methoxy-5-(4-methoxyphenyl)pyridine

According to Scheme 31 Step 2: To a solution of 2-methoxy-5-(4-methoxyphenyl)-4-methylpyridine (2.20 mmol, 0.50 g, Example 48 Step 1) in CCl$_4$ (10 mL) was added NBS (2 eq, 4.40 mmol, 0.78 g). The reaction was then heated to reflux and subjected to UV light for 48 hours. The reaction was allowed to cool, filtered and concentrated under reduced pressure to afford crude 4-(bromomethyl)-2-methoxy-5-(4-methoxyphenyl)pyridine (0.70 g) as a yellow oil which was used without any purification in the next step.

LC (XTerra RP$_{18}$, 3.5 µm, 3.0×50 mm Column): RT=4.87 min; MS m/z (CI) [MH]$^+$=307, 309.

Step 2: 2-Methoxy-4-(methoxymethyl)-5-(4-methoxyphenyl)pyridine

According to Scheme 31 Step 3: The title compound was prepared from 4-(bromomethyl)-2-methoxy-5-(4-methoxyphenyl)pyridine (1 eq, 2.30 mmol, 0.70 g) according to the procedure described for Example 33 Step 1. After work up, 2-methoxy-4-(methoxymethyl)-5-(4-methoxyphenyl)pyridine (0.66 mmol, 0.17 g) as a light yellow oil.

LC (XTerra RP$_{18}$, 3.5 µm, 3.0×50 mm Column): RT=4.56 min; MS m/z (CI) [MH]$^+$=260.

Step 3: 1-(4-Chloro-2-fluorobenzyl)-4-(methoxymethyl)-5-(4-methoxyphenyl)pyridin-2(1H)-one According to Scheme 31 Step 4: The title compound was prepared from 2-methoxy-4-(methoxymethyl)-5-(4-methoxyphenyl)pyridine (1 eq, 0.66 mmol, 0.17 g) and 1-(bromomethyl)-4-chloro-2-fluorobenzene (1.5 eq, 0.98 mmol, 0.22 g) according to the procedure described for Example 6 Step 2. Reaction conditions: 12 hours at 80° C. The crude product was purified by silica gel chromatography (AIT Flashsmart prepacked column 25 g SiO$_2$) using CH$_2$Cl$_2$/MeOH 98/2 as the eluent to afford 1-(4-chloro-2-fluorobenzyl)-4-(methoxymethyl)-5-(4-methoxyphenyl)pyridin-2(1H)-one (5 µmol, 2 mg, 1%) as yellow oil.

LC (XTerra RP$_{18}$, 3.5 μm, 3.0×50 mm Column): RT=3.83 min; MS m/z (CI) [MH]$^+$=388, 390; $^1$H NMR (300 MHz, CDCl$_3$) δ 1.64 (s, 2H), 2.07 (s, 3H), 3.83 (s, 3H), 5.12 (s, 2H), 6.48 (s, 1H), 6.93 (d, J=9.0 Hz, 2H), 7.13-7.28 (m, 5H), 7.40-7.46 (m, 1H).

Example 50

1-(4-Chlorobenzyl)-5-(4-fluorophenoxy)pyridin-2(1H)-one (Final Compound 3-13)

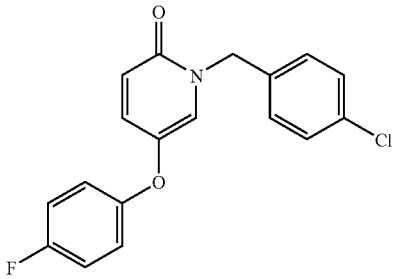 [SMILES: O=c1ccc(Oc2ccc(F)cc2)cn1Cc1ccc(Cl)cc1]

Step 1: 5-(4-Fluorophenoxy)-2-methoxypyridine

According to Scheme 32 Method A: 5-Bromo-2-methoxypyridine (5.32 mmol, 1.00 g), 4-fluorobenzylalcohol (7.98 mmol, 0.90 g), N,N-dimethylaminoacetic acid (15.9 mmol, 1.69 g), CuI (5.32 mmol, 1.01 g), CsCO$_3$ (12.4 mmol, 4.05 g) in dioxane (25 mL) and DMF (2.5 mL) were heated at 150° C. for 25 min. under microwave irradiation conditions. Then the cooled crude reaction was filtered off over celite. The filtrate was washed with saturated aqueous NH$_4$Cl solution and extracted with AcOEt. The organic layer was separated, dried (Na$_2$SO$_4$) and the solvent was evaporated under reduced pressure. The residue was purified in a manifold (vac.) using a Sep-Pak silica cartridge (heptane/AcOEt, 80/20). The product fractions were collected and the solvent was evaporated to give a mixture of the desired product contaminated with 4-fluorobenzylalcohol. This residue was taken up in AcOEt and washed with aqueous solution of NaOH 1N. The organic layer was separated, dried (Na$_2$SO$_4$) and the solvent was evaporated under reduced pressure giving 5-(4-fluorophenoxy)-2-methoxypyridine (520 mg, 45%).

Step 2: 1-(4-Chlorobenzyl)-5-(4-fluorophenoxy)pyridin-2(1H)-one

According to Scheme 32 Step 1: 5-(4-Fluorophenoxy)-2-methoxypyridine (2.37 mmol, 520 mg), 4-chlorobenzylchloride (3.55 mmol, 603 mg), NaI (2.37 mmol, 356 mg) in acetonitrile (15 mL) was heated at 150° C. for 20 minutes under microwave conditions. The cooled crude reaction washed with water, extracted with AcOEt. The organic layer was collected, dried (Na$_2$SO$_4$) and the solvent was evaporated under reduced pressure. The residue was purified in a manifold (vac.) using a Sep-Pak silica cartridge (heptane/AcOEt, 90:10 to CH$_2$Cl$_2$) and then CH$_2$Cl$_2$/acetone 90:10), following HPLC purification yielding 1-(4-chlorobenzyl)-5-(4-fluorophenoxy)pyridin-2(1H)-one (211 mg, 27%).

LC (ACE Column): RT=4.56 min; MS m/z (CI) [MH]$^+$=330.

Example 51

1-(4-Chlorobenzyl)-5-(4-methoxybenzyloxy)pyridin-2(1H)-one (Final Compound 3-17)

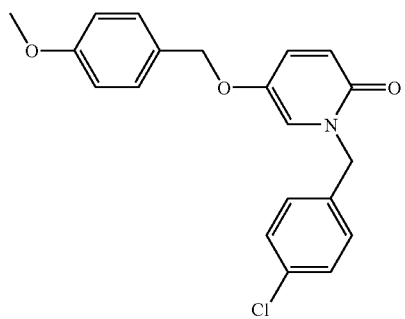 [SMILES: COc1ccc(COc2ccc(=O)n(Cc3ccc(Cl)cc3)c2)cc1]

Step 1: 2-Methoxy-5-(4-methoxybenzyloxy)pyridine

According to Scheme 32 Method B: To a mixture of 2-methoxy-5-hydroxypyridine (2.87 mmol, 0.36 g), 4-methoxybenzyl alcohol (5.75 mmol, 0.72 mL) and PPh$_3$ (5.29 mmol, 1.4 g) in THF (3.75 mL) cooled with an ice-water bath, was added dropwise DEAD (5.47 mmol, 0.86 ml). The resulting mixture was irradiated under microwave conditions at 90° C. for 30 minutes. The resulting reaction mixture was cooled, washed with a 1 N NaOH solution and extracted with AcOEt. The organic layer was separated, dried (Na$_2$SO$_4$) and the solvent was evaporated under reduced pressure. The residue triturated with diisopropyl ether. The precipitated obtained (PPh$_3$O) was filtered off. The residue was purified in a manifold (vac.) using a Sep-Pak silica cartridge heptane/CH$_2$Cl$_2$ 80/20 yielding 2-methoxy-5-(4-methoxybenzyloxy)pyridine (339 mg, 48%).

Step 2: 1-(4-Chlorobenzyl)-5-(4-methoxybenzyloxy)pyridine-2(1H)-one

According to Scheme 32 Step 1: 2-Methoxy-5-(4-methoxybenzyloxy)pyridine (1.38 mmol, 339 mg), 4-chlorobenzylchloride (2.76 mmol, 468 mg), NaI (1.38 mmol, 207 mg) in acetonitrile (15 mL) was heated at 150° C. for 50 minutes under microwave conditions. The cooled crude reaction washed with water, extracted with AcOEt. The organic layer was collected, dried (Na$_2$SO$_4$) and the solvent was evaporated under reduced pressure. The residue was purified in a manifold (vac.) using a Sep-Pak silica cartridge CH$_2$Cl$_2$ and CH$_2$Cl$_2$/acetone 90/10) yielding 1-(4-chlorobenzyl)-5-(4-methoxybenzyloxy)pyridine-2(1H)-one (141 mg, 29%).

LC (ACE Column): RT=4.39 min; MS m/z (CI) [MH]$^+$=355; $^1$H NMR (400 MHz, CDCl$_3$) δ 7.27-7.32 (m, 2H); 7.19-7.25 (m, 3H); 7.14-7.19 (m, 2H, J=8.3 Hz); 6.85-6.90 (m, 2H); 6.72 (d, 1H, J=3.1 Hz); 6.58 (d, 1H, J=9.7 Hz); 5.03 (s, 2H); 4.75 (s, 2H); 3.82 (s, 3H)

Example 52

1-((6-Ethylpyridin-3-yl)methyl)-5-(4-methoxyphenyl)pyridin-2(1H)-one (Final Compound 4-45)

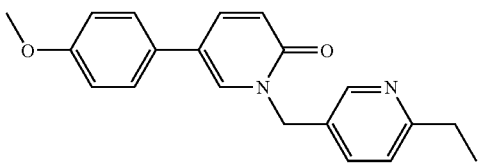 [SMILES: CCc1ccc(Cn2cc(-c3ccc(OC)cc3)ccc2=O)cn1]

Step 1: 1-((6-Chloropyridin-3-yl)methyl)-5-(4-methoxyphenyl)pyridin-2(1H)-one 5-(4-Methoxyphenyl)pyridine-2(1H)-one (4.20 mmol, 0.85 g), 2-chloro-5-(chloromethyl)pyridine (1.5 eq, 6.30 mmol, 1.02 g), $K_2CO_3$ (2 eq, 8.40 mmol, 1.17 g) in THF (10 mL) were heated at 70° C. for 2 hours. Then, the reaction was cooled to room temperature. The suspension was filtered off and the filtrate was evaporated under reduced pressure. The residue was puridied by short open column chromatography $CH_2Cl_2$/MeOH($NH_3$)sat. 1% yielding 1-((6-chloropyridin-3-yl)methyl)-5-(4-methoxyphenyl)pyridin-2(1H)-one as white solid (1.04 g, 75%)

Step 2: 1-((6-Iodopyridin-3-yl)methyl)-5-(4-methoxyphenyl)pyridin-2(1H)-one According to Scheme 33 Step 1: 1-((6-Chloropyridin-3-yl)methyl)-5-(4-methoxyphenyl)pyridin-2(1H)-one (2.54 mmol, 0.83 g), trimethylsilyl chloride (3.3 mmol, 0.42 mL) and NaI (7.60 mmol, 1.14 g) in propionitrile (20 mL) were heated at 140° C. for 20 minutes under microwave irradiation conditions. Then the suspension was filtered off and the solid obtained was partitioned between $CH_2Cl_2$/water. The aqueous layer was extracted several times with $CH_2Cl_2$; the organic layers were combined, dried ($Na_2SO_4$) and the solvent was evaporated under reduced pressure. The residue was treated with $Et_2O$ giving an 1-((6-iodopyridin-3-yl)methyl)-5-(4-methoxyphenyl)pyridin-2(1H)-one (600 mg, 61%) as a pale grey solid.

Step 3: 5-(4-Methoxyphenyl)-1-((6-(2-(trimethylsilyl)ethynyl)pyridin-3-yl)methyl)pyridin-2(1H)-one According to Scheme 33 Step 2: A mixture of 1-((6-iodopyridin-3-yl)methyl)-5-(4-methoxyphenyl)pyridin-2(1H)-one (0.48 mmol, 200 mg), $PdCl_2(PPh_3)_2$ (33 µmol, 23 mg), CuI (24 µmol, 4.5 mg), $^iPr_2EtN$ (0.99 mmol, 1.72 µl), trimethylsilylacetylene (1.43 mmol, 203 µL) and DMF (3 mL, previously deoxygenated) was stirred at room temperature for 2 hours. The solvent was evaporated under reduced pressure. The residue was purified in a manifold (vac.) using a Sep-Pak silica cartridge $CH_2Cl_2$/MeOH($NH_3$)sat. 3% yielding 5-(4-methoxyphenyl)-1-((6-(2-(trimethylsilyl)ethynyl)pyridin-3-yl)methyl)pyridin-2(1H)-one (174 mg, 93%).

Step 4: 1-((6-Ethynylpyridin-3-yl)methyl)-5-(4-methoxyphenyl)pyridin-2(1H)-one A mixture of 5-(4-methoxyphenyl)-1-((6-(2-(trimethylsilyl)ethynyl)pyridin-3-yl)methyl)pyridin-2(1H)-one (0.60 mmol, 240 mg), tetrabutylammonium fluoride (1.20 mmol, 1.2 mL) in THF (5 mL) and $H_2O$ (1 mL) was stirred at room temperature for 2 hours. The solvent was evaporated under reduced pressure. The residue was taken up in $CH_2Cl_2$, washed with water, dried ($Na_2SO_4$) and evaporated under reduced pressure. The residue was purified in a manifold (vac.) using a Sep-Pak silica cartridge $CH_2Cl_2$/MeOH($NH_3$) sat. 3%. The fractions were collected and evaporated. The residue thus obtained was triturated with diisopropyl ether. The precipitated solid was filtered off and dried. Further purification by circular chromatography-TLC $CH_2Cl_2$/MeOH($NH_3$)sat. 3% yielding 1-((6-ethynylpyridin-3-yl)methyl)-5-(4-methoxyphenyl)pyridin-2(1H)-one (68 mg, 35%).

M.p.: 273° C.; $^1$H NMR (400 MHz, $CDCl_3$) δ 8.61 (d, 1H, J=2.1 Hz); 7.72 (dd, 1H, J=8.1, 2.1 Hz); 7.60 (dd, 1H, J=9.4, 2.6 Hz); 7.46 (d, 1H, J=8.1 Hz); 7.40 (d, 1H, J=2.7 Hz); 7.28 (d, 2H, J=8.5 Hz); 6.94 (d, 2H, J=8.7 Hz); 6.64 (d, 2H, J=8.7 Hz); 7.28 (d, 2H, J=8.5 Hz); 6.94 (d, 2H, J=8.7 Hz); 6.70 (d, 1H, J=9.5 Hz); 5.21 (s, 2H); 3.83 (s, 3H); 3.16 (s, 1H).

Step 5: 1-((6-Ethylpyridin-3-yl)methyl)-5-(4-methoxyphenyl)pyridin-2(1H)-one According to Scheme 33 Step 3: To a suspension of Pd/C 10% (0.05 eq) in MeOH (10 mL) under $N_2$ atmosphere, a solution of 1-((6-ethynylpyridin-3-yl)methyl)-5-(4-methoxyphenyl)pyridin-2(1H)-one (0.15 mmol, 48 mg) was added at room temperature. The flask was evacuated and filled with hydrogen until the pressure reached 20 psi. The resulting suspension was shaken at room temperature for 1 hour. The catalyst was filtered off and the filtrate was evaporated under vacuum to give a residue. The residue was purified in a circular chromatography-TLC $CH_2Cl_2$/MeOH($NH_3$)sat. 2% yielding 1-((6-ethylpyridin-3-yl)methyl)-5-(4-methoxyphenyl)pyridin-2(1H)-one (30 mg, 61%).

M.p.: 130° C.; LC (ACE Column): RT=3.55 min; MS m/z (CI) [MH]$^+$=321; $^1$H NMR (400 MHz, $CDCl_3$) δ 8.53 (d, 1H, J=2.1 Hz); 7.66 (dd, 1H, J=8.0, 2.4 Hz); 7.58 (dd, 1H, J=9.5, 2.7 Hz); 7.42 (d, 1H, J=2.3 Hz); 7.25-7.30 (m, 2H); 7.15 (d, 1H, J=7.9 Hz); 6.90-6.95 (m, 2H); 6.69 (d, 1H, J=9.5 Hz); 5.18 (s, 2H); 3.83 (s, 3H); 2.81 (q, 2H, J=7.7 Hz); 1.29 (t, 3H, J=7.6 Hz).

Example 53

5-(4-Methoxyphenethoxy)-2-propylisoquinolin-1(2H)-one (Final Compound 13-06)

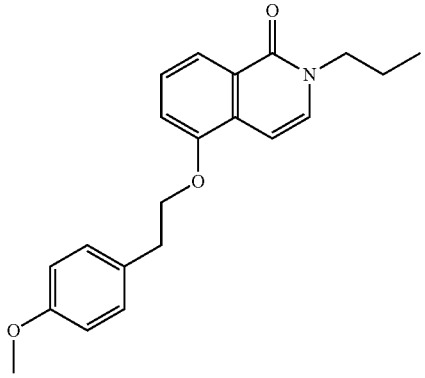 [SMILES: CCCn1ccc2c(OCCc3ccc(OC)cc3)cccc2c1=O]

Step 1: 5-Chloroisoquinoline-N-oxide

According to Scheme 34 Step 1: The title compound was prepared from isoquinolin-5-ol (1 eq, 6.89 mmol, 1.00 g)

according to the procedure described for Example 38 Step 1. The crude residue was recrystallized in CH$_2$Cl$_2$ to yield 5-chloroisoquinoline-N-oxide (6.58 mmol, 1.06 g, 96%) as a beige solid.

Step 2: 5-(4-Methoxyphenethoxy)isoquinoline-N-oxide

According to Scheme 34 Step 2: The title compound was prepared from 5-chloroisoquinoline-N-oxide (1 eq, 6.21 mmol, 1.00 g) and 1-(2-chloroethyl)-4-methoxybenzene (2 eq, 12.4 mmol, 2.12 g) according to the procedure described for Example 1 Step 2. Reaction conditions: microwaved at 180° C. for 15 min in acetonitrile. The crude product was purified by silica gel chromatography (AIT Flashsmart prepacked column 70 g SiO$_2$) using cyclohexane/AcOEt 85/15 to 50/50 and MeOH to afford 5-(4-methoxyphenethoxy)isoquinoline-N-oxide (2.73 mmol, 0.81 g, 44%).

LC (XTerra RP$_{18}$, 3.5 μm, 3.0×50 mm Column): RT=4.98 min; MS m/z (CI) [MH]$^+$=296.

Step 3: 5-(4-Methoxyphenethoxy)isoquinolin-1(2H)-one

According to Scheme 34 Step 3: The title compound was prepared from 5-(4-methoxyphenethoxy)isoquinoline-N-oxide (1 eq, 2.73 mmol, 0.81 g) according to the procedure described for Example 38 Step 2. The crude product was used without being purified and yielded 5-(4-methoxyphenethoxy)isoquinolin-1(2H)-one (1.08 mmol, 0.32 g, 40%) as a brown solid.

Step 4: 5-(4-Methoxyphenethoxy)-2-propylisoquinolin-1(2H)-one

According to Scheme 34 Step 4: The title compound was prepared from 5-(4-methoxyphenethoxy)isoquinolin-1(2H)-one (1 eq, 0.34 mmol, 0.10 g) and 1-bromopropyl (1.5 eq, 0.51 mmol, 46 μL) according to the procedure described for Example 1 Step 2. Reaction conditions: microwaved at 180° C. for 15 min. in acetonitrile. The crude product was purified by flash chromatography over silica gel (AIT Flashsmart prepacked column 25 g SiO$_2$) using pure CH$_2$Cl$_2$/MeOH 100/0 to 99/1 to afford 5-(4-methoxyphenethoxy)-2-propyl-isoquinolin-1(2H)-one (59 μmol, 20 mg, 17%) as an orange oil.

LC (XTerra RP$_{18}$, 3.5 μm, 3.0×50 mm Column): RT=4.84 min; MS m/z (CI) [MH]$^+$=338; $^1$H NMR (300 MHz, CDCl$_3$) δ 0.90 (t, J=7.7 Hz, 3H), 1.74 (q, J=8.5 Hz, 2H), 3.06 (t, J=6.6 Hz, 2H), 3.73 (s, 3H), 3.89 (t, J=7.4 Hz, 2H), 4.17 (t, J=6.6 Hz, 2H), 6.75-6.83 (m, 3H), 6.98 (t, J=7.2 Hz, 2H), 7.18 (d, J=8.2 Hz, 2H), 7.29 (t, J=8.2 Hz, 1H), 7.92 (d, J=8.2 Hz, 1H).

The compounds in the following Tables have been synthesized according to the previous examples, as denoted in the column denoted as "Exp. Nr". The compound denoted with the asterisk has been exemplified in the Examples. When it concerns the bivalent linkers V$_1$ and V$_2$, it is noted that the left part of the linkers V$_1$ and V$_2$ is attached to the pyridinyl-moiety.

TABLE 1

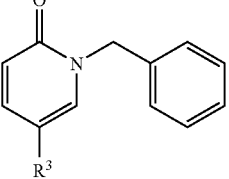

| Co.nr. | Exp. nr. | R$^3$ |
|---|---|---|
| 1-01 | 1 | 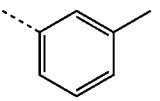 |
| 1-02 | 2 | 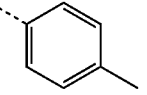 |
| 1-03 | 2 | 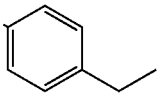 |
| 1-04 | 7 | 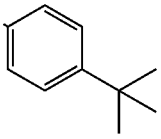 |
| 1-05 | 2 | 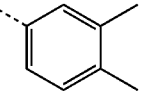 |
| 1-06 | 2 | 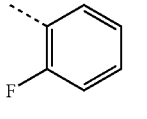 |
| 1-07 | 2 | 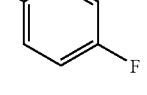 |
| 1-08 | 1 | 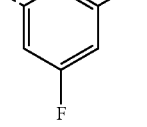 |
| 1-09 | 2 | 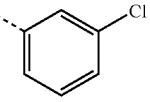 |
| 1-10 | 2 | 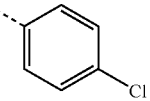 |
| 1-11 | 1 | |

TABLE 1-continued
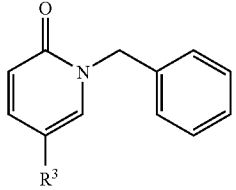
| Co.nr. | Exp. nr. | R³ |
|---|---|---|
| 1-12 | 2 | 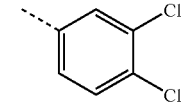 3,4-dichlorophenyl |
| 1-13 | 20 | 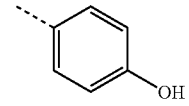 4-hydroxyphenyl |
| 1-14 | 2 | 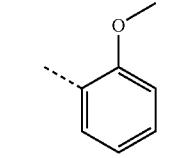 2-methoxyphenyl |
| 1-15 | 2 | 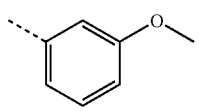 3-methoxyphenyl |
| 1-16 | 1 | 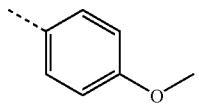 4-methoxyphenyl |
| 1-17 | 2 | 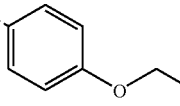 4-propoxyphenyl |
| 1-18 | 20 | 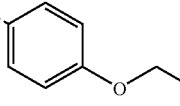 4-isobutoxyphenyl |
| 1-19 | 2 | 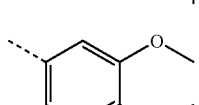 3,4-dimethoxyphenyl |
| 1-20 | 2 | 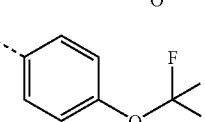 4-(trifluoromethoxy)phenyl |
| 1-21 | 2 | 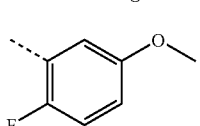 |
| 1-22 | 2 | 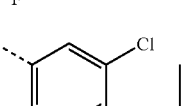 |
TABLE 1-continued
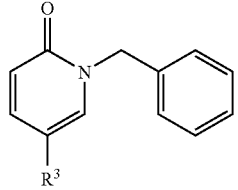
| Co.nr. | Exp. nr. | R³ |
|---|---|---|
| 1-23 | 2 | 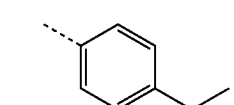 |
| 1-24 | 2 | 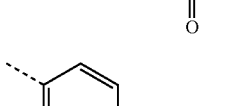 |
| 1-25 | 2 | 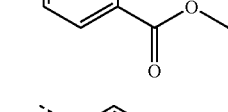 |
| 1-26 | 2 | 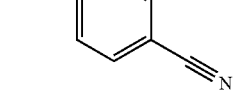 |
| 1-27 | 2 | 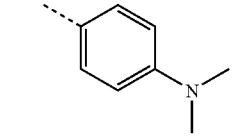 |
| 1-28 | 2 | 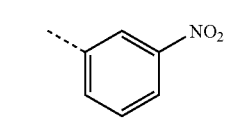 |
| 1-29 | 1 | 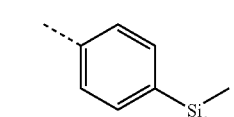 |
| 1-30 | 2 | 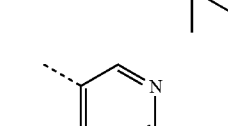 |
| 1-31 | 2 | 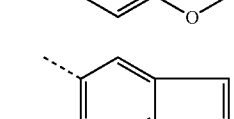 |
| 1-32 | 2 | 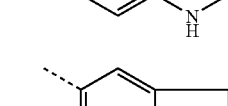 |

TABLE 2
| Co.nr. | Exp. nr. | R³ |
|---|---|---|
| 2-01 | 36* |  |
| 2-02 | 2 |  |
| 2-03 | 2 | 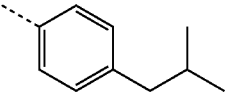 |
| 2-04 | 1 | 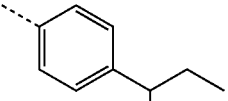 |
| 2-05 | 1 | 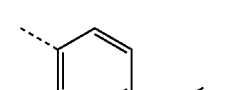 |
| 2-06 | 1 | 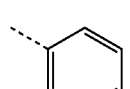 |
| 2-07 | 2 | 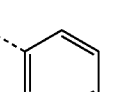 |
| 2-08 | 2 | 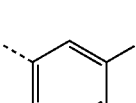 |
| 2-09 | 2 | 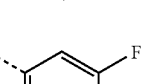 |
| 2-10 | 2 | 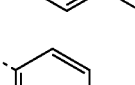 |
| 2-11 | 2 | 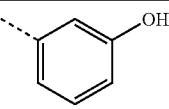 |
TABLE 2-continued
| Co.nr. | Exp. nr. | R³ |
|---|---|---|
| 2-12 | 20 | 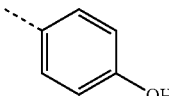 |
| 2-13 | 20 | 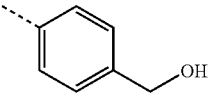 |
| 2-14 | 35 | 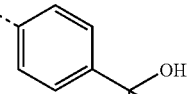 |
| 2-15 | 30* | 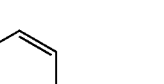 |
| 2-16 | 2* | 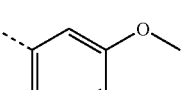 |
| 2-17 | 1 | 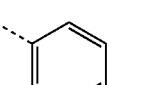 |
| 2-18 | 2 | 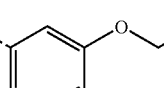 |
| 2-19 | 1 | 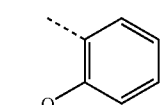 |
| 2-20 | 2 | 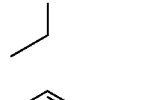 |
| 2-21 | 20 | 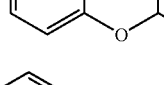 |
| 2-22 | 20 | |

TABLE 2-continued
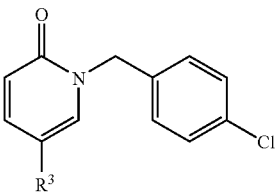
| Co. nr. | Exp. nr. | R³ |
|---|---|---|
| 2-23 | 2 | 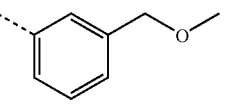 |
| 2-24 | 2 | 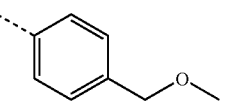 |
| 2-25 | 35* | 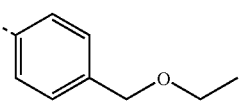 |
| 2-26 | 47 | 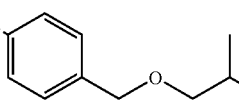 |
| 2-27 | 35 | 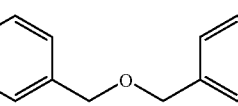 |
| 2-28 | 47 | 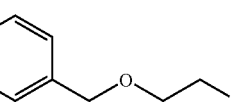 |
| 2-29 | 21 | 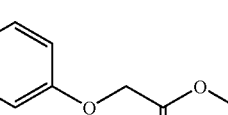 |
| 2-30 | 1 | 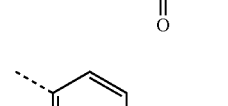 |
| 2-31 | 22 | 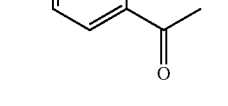 |
| 2-32 | 22 | 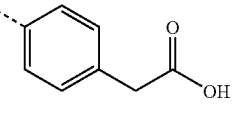 |
TABLE 2-continued
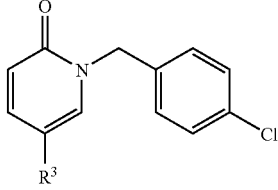
| Co. nr. | Exp. nr. | R³ |
|---|---|---|
| 2-33 | 2 | 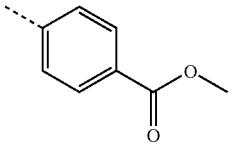 |
| 2-34 | 2 | 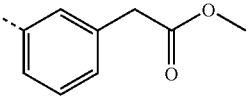 |
| 2-35 | 1 | 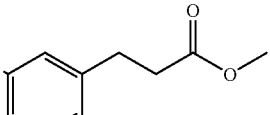 |
| 2-36 | 1 | 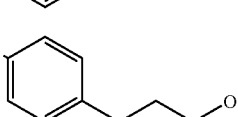 |
| 2-37 | 1 | 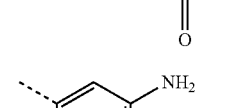 |
| 2-38 | 47 | 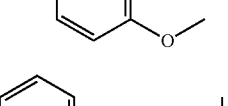 |
| 2-39 | 47 | 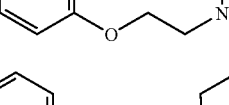 |
| 2-40 | 45 | 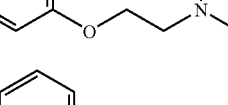 |
| 2-41 | 1 | 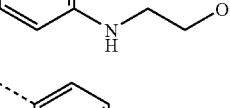 |
| 2-42 | 47* | 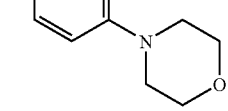 |

TABLE 2-continued
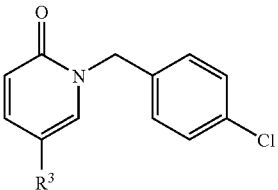
| Co.nr. | Exp. nr. | R³ |
|---|---|---|
| 2-43 | 22 | 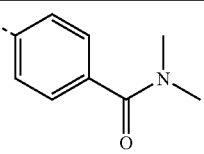 |
| 2-44 | 22* | 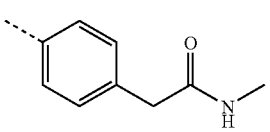 |
| 2-45 | 22 | 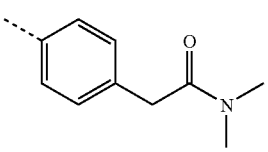 |
| 2-46 | 22 | 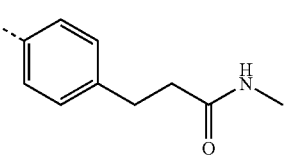 |
| 2-47 | 22 | 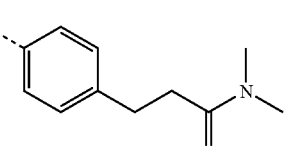 |
| 2-48 | 2 | 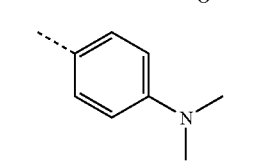 |
| 2-49 | 45 | 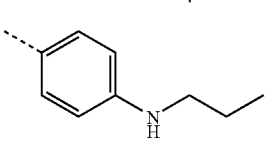 |
| 2-50 | 45* | 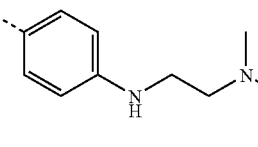 |
| 2-51 | 23* | 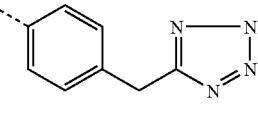 |
| 2-52 | 2 | 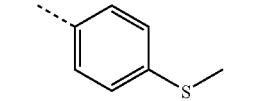 |
TABLE 2-continued
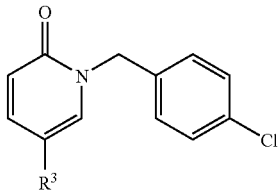
| Co.nr. | Exp. nr. | R³ |
|---|---|---|
| 2-53 | 1 | 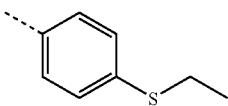 |
| 2-54 | 2 | 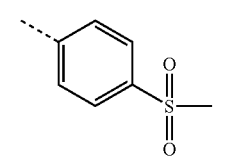 |
| 2-55 | 4 | 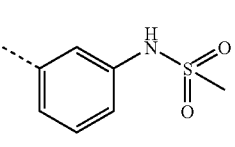 |
| 2-56 | 4* | 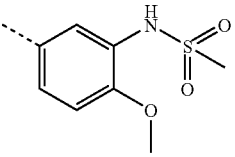 |
| 2-57 | 2 | 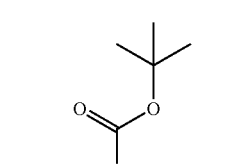 |
| 2-58 | 2 | 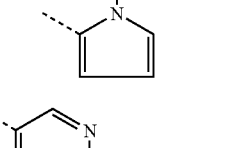 |
| 2-59 | 2 | 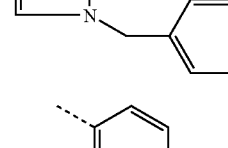 |
| 2-60 | 1 | 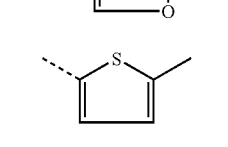 |
| 2-61 | 1 | 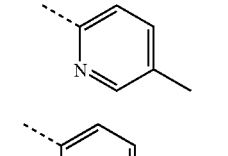 |
| 2-62 | 1 | 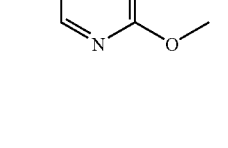 |

TABLE 2-continued
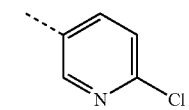
| Co.nr. | Exp. nr. | R³ |
|---|---|---|
| 2-63 | 1 | 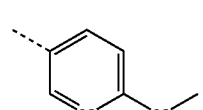 |
| 2-64 | 1 |  |
| 2-65 | 1 | 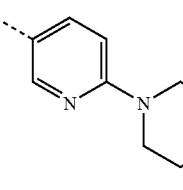 |
| 2-66 | 1 | 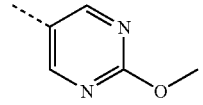 |
| 2-67 | 2 | 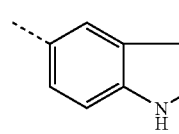 |
| 2-68 | 2 | 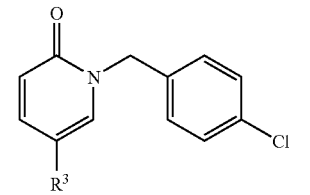 |
| 2-69 | 1 | 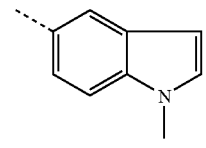 |
| 2-70 | 1 | 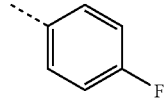 |
| 2-71 | 1 | 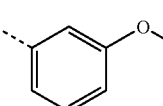 |
| 2-72 | 1 | 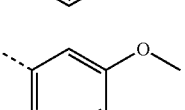 |
TABLE 3
| Co.nr. | Exp. nr. | V₂ | M₂ |
|---|---|---|---|
| 3-01 | 12 | --CH₂-- | 4-F-phenyl |
| 3-02 | 12* | --CH₂-- | 3-OMe-phenyl |
| 3-03 | 5 | --CH=CH-- | 3-OMe-phenyl (Z) |

TABLE 3-continued
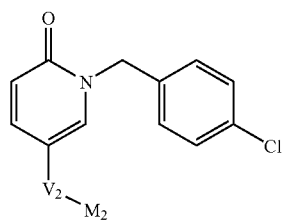
| Co.nr. | Exp. nr. | V₂ | M₂ |
|---|---|---|---|
| 3-04 | 5 | --CH=CH-- | 3-methoxyphenyl (E) |
| 3-05 | 32 | --CH₂--CH₂--CH₂--CH₂-- | --H |
| 3-07 | 10* | --CH₂--N(CH₃)-- | phenyl |
| 3-08 | 10 | --CH₂--N(CH₃)--CH₂-- | phenyl |
| 3-09 | 41 | --CH(OH)-- | 4-fluorophenyl |
| 3-10 | 41* | --CH(OH)-- | 3-methoxyphenyl |
| 3-12 | 11* | --C(=O)-- | 3-methoxyphenyl |
| 3-13 | 50* | --O-- | 4-fluorophenyl |
| 3-14 | 50 | --O-- | 4-methoxyphenyl |
| 3-15 | 51 | --O--CH₂-- | cyclohexyl |
| 3-16 | 51 | --O--CH₂-- | 4-fluorophenyl |
| 3-17 | 51* | --O--CH₂-- | 4-methoxyphenyl |

TABLE 3-continued

[Structure: 1-(4-chlorobenzyl)-5-(V₂-M₂)-pyridin-2(1H)-one]

| Co.nr. | Exp. nr. | V₂ | M₂ |
|---|---|---|---|
| 3-18 | 51 | --O--CH₂--CH₂-- | phenyl |
| 3-19 | 51 | --O--CH₂--CH₂--CH₂-- | --H |
| 3-21 | 46* | --N(CH₃)-- | 4-fluorophenyl |

TABLE 4

[Structure: 1-(CH₂-M₁)-5-(4-methoxyphenyl)-pyridin-2(1H)-one]

| Co.nr. | Exp. nr. | M₁ |
|---|---|---|
| 4-01 | 9 | cyclopropyl |
| 4-02 | 9 | cyclopentyl |
| 4-03 | 9* | cyclohexyl |
| 4-04 | 9 | 4-methylcyclohexyl |
| 4-05 | 7 | 2-methylphenyl |
| 4-06 | 7 | 4-methylphenyl |

TABLE 4-continued

[Structure: 1-(CH₂-M₁)-5-(4-methoxyphenyl)-pyridin-2(1H)-one]

| Co.nr. | Exp. nr. | M₁ |
|---|---|---|
| 4-07 | 7 | 4-(trifluoromethyl)phenyl |
| 4-08 | 7 | 2-fluorophenyl |
| 4-09 | 7 | 3-fluorophenyl |
| 4-10 | 7 | 4-fluorophenyl |
| 4-11 | 7 | 3,4-difluorophenyl |

TABLE 4-continued
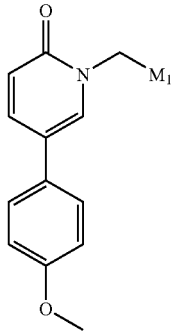
| Co.nr. | Exp. nr. | M₁ |
|---|---|---|
| 4-12 | 7 | 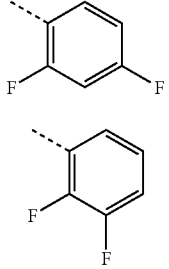 2,4-diF phenyl |
| 4-13 | 7 | 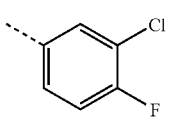 2,3-diF phenyl |
| 4-14 | 7 | 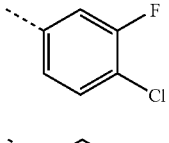 3-Cl-4-F phenyl |
| 4-15 | 7 | 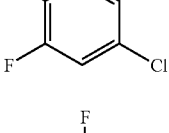 3-F-4-Cl phenyl |
| 4-16 | 7 | 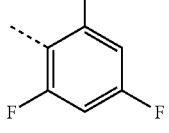 3-F-4-Cl phenyl |
| 4-17 | 7 | 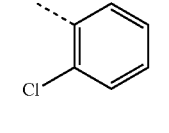 2,3,5-triF phenyl |
| 4-18 | 7 | 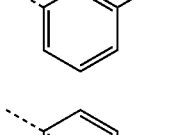 2-Cl phenyl |
| 4-19 | 1 | 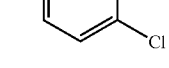 3-Cl phenyl |
| 4-20 | 7 | 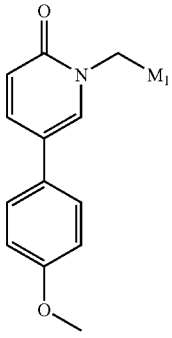 4-Cl phenyl |
| 4-21 | 7 | 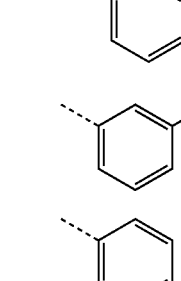 3,4-diCl phenyl |
| 4-22 | 7 | 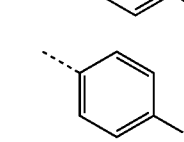 3-OMe phenyl |
| 4-23 | 7 | 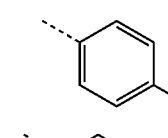 4-OMe phenyl |
| 4-24 | 34 | 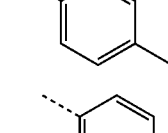 4-OEt phenyl |
| 4-25 | 34* | 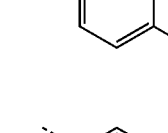 4-CH₂OMe phenyl |
| 4-26 | 34 | 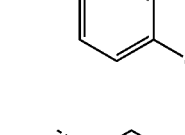 4-CH₂OEt phenyl |
| 4-27 | 7 | 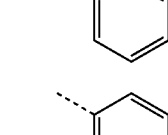 4-C(O)OMe phenyl |
| 4-28 | 7 | 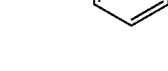 4-OC(O)Me phenyl |
| 4-29 | 7 | 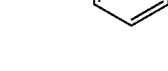 3-CN phenyl |
| 4-30 | 7 | 4-CN phenyl |

TABLE 4-continued

| Co.nr. | Exp. nr. | M₁ |
|---|---|---|
| 4-31 | 7 | 4-(trifluoromethoxy)phenyl |
| 4-32 | 7 | 3-nitrophenyl |
| 4-33 | 7 | 4-nitrophenyl |
| 4-34 | 7 | 3-fluoro-4-(trifluoromethyl)phenyl |
| 4-35 | 7 | 2-fluoro-4-(trifluoromethyl)phenyl — substituent attached at position shown |
| 4-36 | 7 | 3-fluoro-4-methylphenyl |
| 4-37 | 7 | 4-chloro-3-(trifluoromethyl)phenyl |
| 4-38 | 7 | naphthalen-2-yl |
| 4-39 | 7 | 5-(trifluoromethyl)furan-2-yl |
| 4-40 | 7 | 5-methylisoxazol-3-yl |
| 4-41 | 7 | 5-phenyl-1,2,4-oxadiazol-3-yl |
| 4-42 | 16* | 3-(4-fluorophenyl)-1,2,4-oxadiazol-5-yl |
| 4-43 | 8 | pyridin-3-yl |
| 4-44 | 8 | 6-chloropyridin-3-yl |
| 4-45 | 52* | 6-ethylpyridin-3-yl |
| 4-46 | 8 | 6-methoxypyridin-3-yl · HCl |
| 4-47 | 8* | 6-(trifluoromethyl)pyridin-3-yl |
| 4-48 | 52 | 6-cyanopyridin-3-yl |

TABLE 4-continued
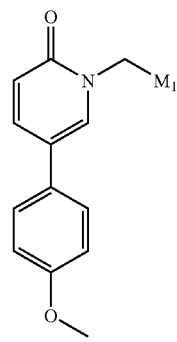
| Co.nr. | Exp. nr. | M$_1$ |
|---|---|---|
| 4-49 | 52 | (5-(4-methoxyphenyl)pyridin-2-yl) |
| 4-50 | 8 | (5-methylpyrazin-2-yl) |
| 4-51 | 15* | (5-fluorobenzo[d]oxazol-2-yl) |
TABLE 4-continued
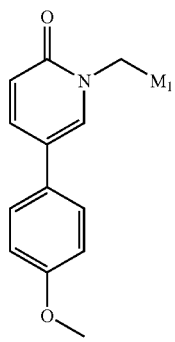
| Co.nr. | Exp. nr. | M$_1$ |
|---|---|---|
| 4-52 | 8 | (2-methylthiazol-5-yl) |
| 4-53 | 7 | (benzo[d]thiazol-2-yl) |
| 4-54 | 15 | (4-fluorobenzo[d]thiazol-2-yl) |
TABLE 5
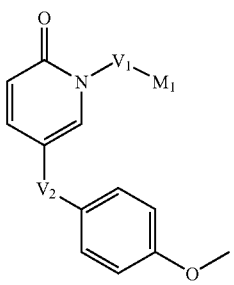
| Co.nr. | Exp. nr. | V$_1$ | M$_1$ | V$_2$ |
|---|---|---|---|---|
| 5-01 | 13 | --CH$_2$-- | (3-fluoro-4-chlorophenyl) | --CH$_2$--CH$_2$-- |
| 5-02 | 12 | --CH$_2$-- | (2-fluoro-4-chlorophenyl) | --CH$_2$-- |
| 5-03 | 13 | --CH$_2$-- | (2-fluoro-4-chlorophenyl) | --CH$_2$--CH$_2$--CH$_2$--CH$_2$-- |

TABLE 5-continued

| Co.nr. | Exp. nr. | V₁ | M₁ | V₂ |
|---|---|---|---|---|
| 5-04 | 7 | --CH₂--CH₂-- | 4-F-phenyl | cb |
| 5-05 | 7 | --CH(CH₃)-- | phenyl | cb |
| 5-06 | 9 | --CH₂--CH₂--CH(CF₃)-- | --H | cb |
| 5-07 | 7 | --CH₂--CH₂--CH₂-- | phenyl | cb |
| 5-08 | 9 | --CH₂--CH₂--CH₂--CH₂-- | --H | cb |
| 5-09 | 7 | --CH₂--CH₂--CH₂--CH₂-- | phenyl | cb |
| 5-10 | 9 | --CH₂--CH(CH₃)--CH₂-- | --H | cb |
| 5-11 | 9 | --CH₂--CH₂--CH₂--CH₂--CH₂-- | --H | cb |
| 5-12 | 9 | --CH(CH₃)--CH₂--CH₂--CH₂-- | --H | cb |
| 5-13 | 9 | --CH₂CH₂--CH(CH₃)--CH₂-- | --H | cb |
| 5-15 | 9 | --CH₂CH₂--C(CH₃)₂--CH₂-- | --H | cb |
| 5-16 | 9 | --CH₂CH₂--CH₂--C≡C-- | --H | cb |
| 5-17 | 7 | --CH₂--O-- | 4-Cl-phenyl | cb |
| 5-18 | 7* | --CH₂--CH₂--O-- | phenyl | cb |
| 5-19 | 7 | --C(=O)-- | phenyl | cb |
| 5-20 | 14 | --CH₂--C(=O)--N(CH₃)--CH₂-- | phenyl | cb |
| 5-21 | 14 | --CH₂--C(=O)--N(CH₃)--CH₂-- | 4-methyl-phenyl | cb |

TABLE 5-continued

| Co.nr. | Exp. nr. | V₁ | M₁ | V₂ |
|---|---|---|---|---|
| 5-22 | 14 | -CH₂-C(O)-N(CH₃)- | 4-F-phenyl | cb |
| 5-23 | 14 | -CH₂-C(O)-N(CH₃)- | 4-CF₃-phenyl | cb |
| 5-24 | 14* | -CH₂-C(O)-N(CH₃)- | 3-Cl-phenyl | cb |
| 5-25 | 14 | -CH₂-C(O)-N(CH₃)- | 3-OMe-phenyl | cb |
| 5-26 | 14 | -CH₂-C(O)-N(CH₃)- | 4-NO₂-phenyl | cb | cb = covalent bond

TABLE 6

| Co.nr. | Exp. nr. | M₁ | R³ |
|---|---|---|---|
| 6-01 | 1 | 4-methylphenyl | phenyl |
| 6-02 | 1 | 3-chlorophenyl | phenyl |

TABLE 6-continued
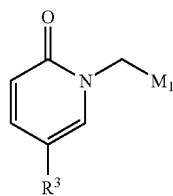
| Co.nr. | Exp. nr. | M₁ | R³ |
|---|---|---|---|
| 6-03 | 1 | 3-Cl-phenyl | 4-F-phenyl |
| 6-04 | 2 | 3-F-phenyl | 4-methyl-phenyl |
| 6-05 | 1 | 3,4-diF-phenyl | 2-thienyl |
| 6-06 | 1 | 3,4-diF-phenyl | phenyl |
| 6-07 | 1 | 3,4-diF-phenyl | 4-F-phenyl |
| 6-08 | 1 | 3,4-diF-phenyl | 2-benzofuryl |
| 6-09 | 1 | 3,4-diF-phenyl | 4-Cl-phenyl |
| 6-10 | 2 | 3,4-diF-phenyl | 3-OMe-phenyl |
| 6-11 | 2 | 3,4-diF-phenyl | 4-(CH₂OMe)-phenyl |
| 6-12 | 2 | 3,4-diF-phenyl | 4-acetyl-phenyl |
| 6-13 | 2 | 3,4-diF-phenyl | 4-CN-phenyl |

TABLE 6-continued
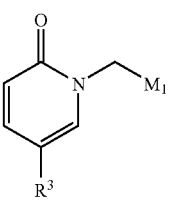
| Co.nr. | Exp. nr. | M₁ | R³ | |
|---|---|---|---|---|
| 6-14 | 4 | 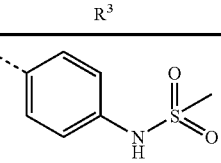 | 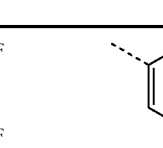 | |
| 6-15 | 2 | 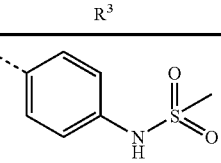 |  | |
| 6-16 | 1 | 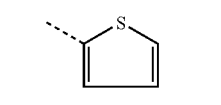 |  | |
| 6-17 | 2 | 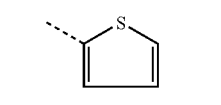 |  | |
| 6-18 | 1 | 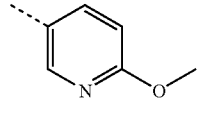 |  | |
| 6-19 | 6* | 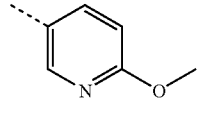 |  | |
| 6-20 | 1 | 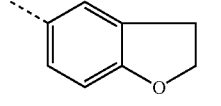 | --Br | |
| 6-21 | 20 |  | 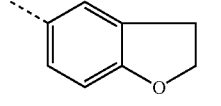 | |
| 6-22 | 28 |  | 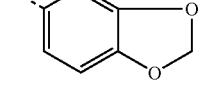 | |
| 6-23 | 28* |  | 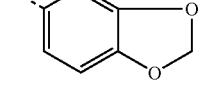 | •HCl |
| 6-24 | 28 |  | 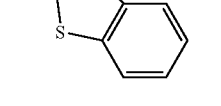 | |

TABLE 6-continued
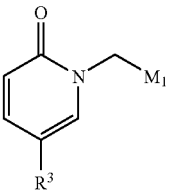
| Co.nr. | Exp. nr. | M₁ | R³ |
|---|---|---|---|
| 6-25 | 2 | 3-F, 4-Cl phenyl | 3-cyanophenyl |
| 6-26 | 2 | 3-F, 4-Cl phenyl | 4-(hydroxymethyl)phenyl |
| 6-27 | 1 | 3-F, 4-Cl phenyl | 4-(trifluoromethyl)phenyl |
| 6-28 | 1 | 3-F, 4-Cl phenyl | 3-methyl-4-methoxyphenyl |
| 6-29 | 2 | 3-F, 4-Cl phenyl | 3,5-dimethyl-4-methoxyphenyl |
| 6-30 | 1 | 3-F, 4-Cl phenyl | 3-fluoro-4-methoxyphenyl |
| 6-31 | 1 | 3-F, 4-Cl phenyl | 3,4-dimethoxyphenyl |
| 6-32 | 20 | 3-F, 4-Cl phenyl | 4-propoxyphenyl |
| 6-33 | 20 | 3-F, 4-Cl phenyl | 4-isobutoxyphenyl |
| 6-34 | 20 | 3-F, 4-Cl phenyl | 4-(3-hydroxypropoxy)phenyl |

TABLE 6-continued
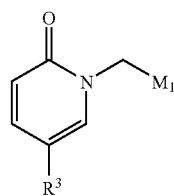
| Co.nr. | Exp. nr. | M₁ | R³ |
|---|---|---|---|
| 6-35 | 20 | 3-F, 4-Cl phenyl | 4-(OCH₂CH(OH)CH₃)phenyl |
| 6-36 | 20 | 3-F, 4-Cl phenyl | 4-(OCH₂CH₂OCH₃)phenyl |
| 6-37 | 20 | 3-F, 4-Cl phenyl | 4-(OCH₂-2-furyl)phenyl |
| 6-38 | 1 | 3-F, 4-Cl phenyl | 3,4-dihydro-2H-1,5-benzodioxepin-7-yl |
| 6-39 | 43* | 3-F, 4-Cl phenyl | 4-(OC(O)OCH₃)phenyl |
| 6-40 | 21* | 3-F, 4-Cl phenyl | 4-(OCH₂C(O)CH₃)phenyl |
| 6-41 | 21 | 3-F, 4-Cl phenyl | 4-(OCH₂C(O)OCH₃)phenyl |
| 6-42 | 28 | 3-F, 4-Cl phenyl | 4-(OCH₂CH₂NH₂)phenyl |
| 6-43 | 28 | 3-F, 4-Cl phenyl | 4-(OCH₂CH₂CH₂NH₂)phenyl |
| 6-44 | 20 | 3-F, 4-Cl phenyl | 4-(OCH₂CH₂N(CH₃)₂)phenyl |

TABLE 6-continued
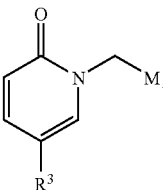
| Co.nr. | Exp. nr. | M₁ | R³ |
|---|---|---|---|
| 6-45 | 20 | 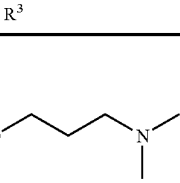 | 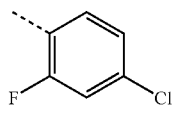 |
| 6-46 | 20* | 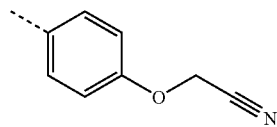 | 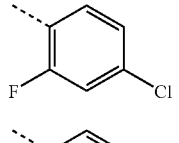 |
| 6-47 | 20 | 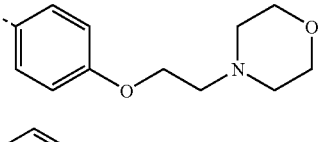 | 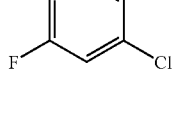 |
| 6-48 | 20 | 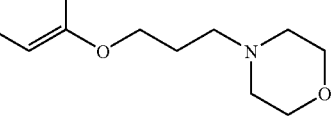 | 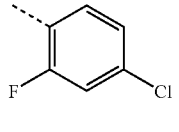 |
| 6-49 | 20 | 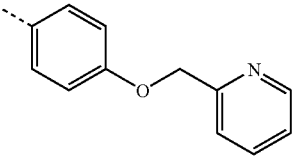 | 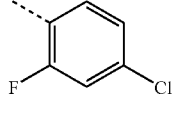 |
| 6-50 | 20 | 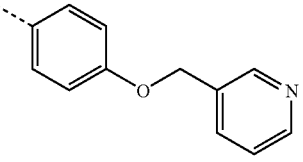 | 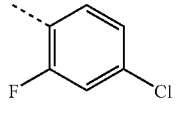 |
| 6-51 | 1* | 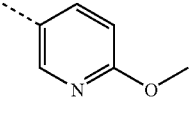 | 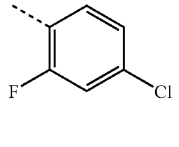 |
| 6-52 | 21 | 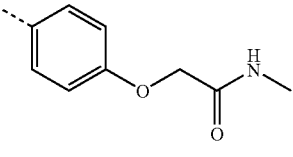 | 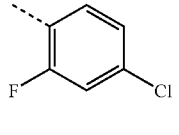 |
| 6-53 | 29* | 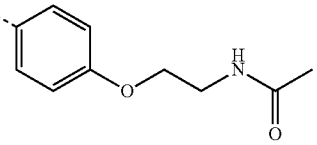 |  |

TABLE 6-continued

| Co.nr. | Exp. nr. | M₁ | R³ |
|---|---|---|---|
| 6-54 | 29 | 3-F, 4-Cl phenyl | 4-(O-CH₂CH₂CH₂-NH-C(O)CH₃)phenyl |
| 6-55 | 29 | 3-F, 4-Cl phenyl | 4-(O-CH₂CH₂-N(C(O)CH₃)₂)phenyl |
| 6-56 | 29 | 3-F, 4-Cl phenyl | 4-(O-CH₂CH₂CH₂-N(C(O)CH₃)₂)phenyl |
| 6-57 | 29 | 3-F, 4-Cl phenyl | 3-(NH-C(O)CH₃)phenyl |
| 6-58 | 29 | 3-F, 4-Cl phenyl | 4-(NH-C(O)CH₃)phenyl |
| 6-59 | 29 | 3-F, 4-Cl phenyl | 4-(NH-C(O)O-tBu)phenyl |
| 6-60 | 29 | 3-F, 4-Cl phenyl | 3-(CH₂-NH-C(O)CH₃)phenyl |
| 6-61 | 29 | 3-F, 4-Cl phenyl | 4-(CH₂-NH-C(O)CH₃)phenyl |
| 6-62 | 20 | 3-F, 4-Cl phenyl | 4-(O-CH₂CH₂-(2-oxopyrrolidin-1-yl))phenyl |

TABLE 6-continued
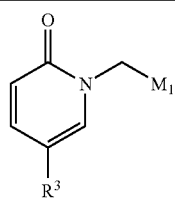
| Co.nr. | Exp. nr. | M₁ | R³ |
|---|---|---|---|
| 6-63 | 20 | 3-F,4-Cl-phenyl | 4-[(5-methylisoxazol-3-yl)methoxy]phenyl |
| 6-64 | 20 | 3-F,4-Cl-phenyl | 4-[(1-methylimidazol-2-yl)methoxy]phenyl |
| 6-65 | 24* | 3-F,4-Cl-phenyl | 4-[(2H-tetrazol-5-yl)methoxy]phenyl |
| 6-82 | 24 | 3-F,4-Cl-phenyl | 4-[(2-methyl-2H-tetrazol-5-yl)methoxy]phenyl |
| 6-66 | 20 | 3-F,4-Cl-phenyl | 4-[(2-methylthiazol-4-yl)methoxy]phenyl |
| 6-67 | 23 | 3-F,4-Cl-phenyl | 3-(2H-tetrazol-5-yl)phenyl |
| 6-68 | 23 | 3-F,4-Cl-phenyl | 4-(1H-tetrazol-5-yl)phenyl |
| 6-69 | 26* | 3-F,4-Cl-phenyl | benzo[b]thiophen-5-yl |

TABLE 6-continued

| Co.nr. | Exp. nr. | M₁ | R³ |
|---|---|---|---|
| 6-70 | 29 | 3-F, 4-Cl-phenyl | 4-(O-CH₂CH₂-NH-SO₂-CH₃)-phenyl |
| 6-71 | 29 | 3-F, 4-Cl-phenyl | 4-(O-CH₂CH₂CH₂-NH-SO₂-CH₃)-phenyl |
| 6-72 | 29 | 3-F, 4-Cl-phenyl | 3-(CH₂-NH-SO₂-CH₃)-phenyl |
| 6-73 | 29 | 3-F, 4-Cl-phenyl | 4-(CH₂-NH-SO₂-CH₃)-phenyl |
| 6-74 | 1 | 3-F, 4-Cl-phenyl | 4-(morpholinosulfonyl)-phenyl |
| 6-75 | 1 | 3-F, 4-Cl-phenyl | 4-(pyrrolidinosulfonyl)-phenyl |
| 6-76 | 2 | 4-OCH₃-phenyl | 4-acetyl-phenyl |
| 6-77 | 2 | 4-OCH₃-phenyl | 4-CN-phenyl |
| 6-78 | 1 | 3-CF₃-phenyl | phenyl |

TABLE 6-continued
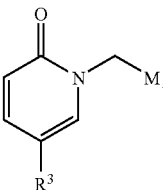
| Co.nr. | Exp. nr. | M₁ | R³ |
|---|---|---|---|
| 6-79 | 1 |  | 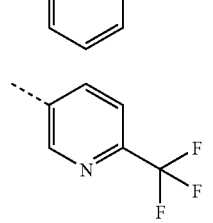 |
| 6-80 | 1 | 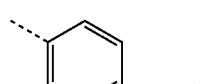 | 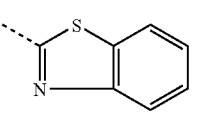 |
| 6-81 | 2 | 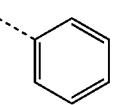 | 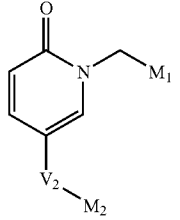 |
TABLE 7
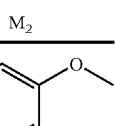
| Co.nr. | Exp. nr. | M₁ | V₂ | M₂ |
|---|---|---|---|---|
| 7-01 | 5 |  | --C≡C-- | 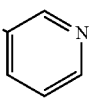 |
| 7-02 | 5* |  | --C≡C-- | 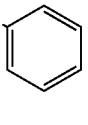 |
| 7-03 | 42* |  | --O--CH₂--CH₂-- | 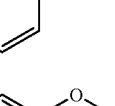 |
| 7-04 | 13 | 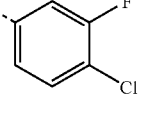 | --CH₂--CH₂-- | 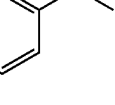 |
| 7-06 | 13* | (F, Cl-substituted phenyl) | --CH₂--CH₂-- | (methoxyphenyl) |

TABLE 7-continued
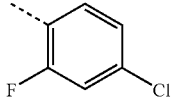
| Co.nr. | Exp. nr. | M₁ | V₂ | M₂ |
|---|---|---|---|---|
| 7-07 | 12 | 4-Cl-2-F-phenyl | --CH₂-- | 2-methoxyphenyl |
| 7-08 | 32* | 4-Cl-2-F-phenyl | --CH₂--CH₂--CH₂-- | phenyl |
| 7-09 | 32 | 4-Cl-2-F-phenyl | --CH(CH₃)--CH₂-- | --H |
| 7-10 | 32 | 4-Cl-2-F-phenyl | --CH₂--CH₂--CH₂--CH₂-- | phenyl |
| 7-11 | 13 | 4-Cl-2-F-phenyl | --CH₂--CH₂--CH₂--CH₂-- | 3-methoxyphenyl |
| 7-15 | 13 | phenyl | --CH₂--CH₂-- | phenyl |
| 7-16 | 5 | phenyl | --C≡C-- | phenyl |
TABLE 8
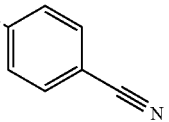
| Co.nr. | Exp. nr. | V₁ | M₁ | R³ |
|---|---|---|---|---|
| 8-01 | 3 | --CH₂--CH₂--CH(CH₃)--CH₂-- | --H | 4-cyanophenyl |

TABLE 8-continued
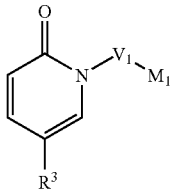
| Co.nr. | Exp. nr. | V$_1$ | M$_1$ | R$^3$ |
|---|---|---|---|---|
| 8-02 | 3* | --CH$_2$—CH$_2$—CH(CH$_3$)—CH$_2$-- | --H | 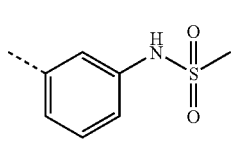 |
TABLE 9
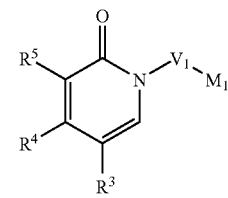
| Co.nr. | Exp. nr. | R$^4$ | R$^5$ | V$_1$ | M$_1$ | R$^3$ |
|---|---|---|---|---|---|---|
| 9-01 | 2 | --H | --Cl | --CH$_2$-- |  | 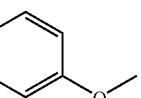 |
| 9-02 | 2 | --H | --Cl | --CH$_2$-- |  | 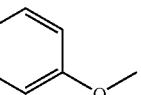 |
| 9-03 | 2 | --H | --Cl | --CH$_2$-- |  |  |
| 9-04 | 3 | --H | --Cl | --CH$_2$—CH$_2$—CH(CH$_3$)—CH$_2$-- | --H | 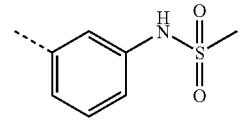 |
| 9-05 | 2 | --H | --Cl | --CH$_2$-- |  | 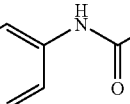 |
| 9-06 | 6 | --H | --F | --CH$_2$-- |  | 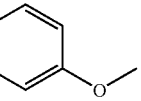 |
| 9-07 | 2 | --H | --CH$_3$ | --CH$_2$-- |  | 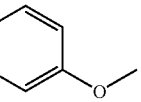 |

TABLE 9-continued
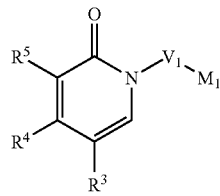
| Co.nr. | Exp. nr. | R⁴ | R⁵ | V₁ | M₁ | R³ |
|---|---|---|---|---|---|---|
| 9-08 | 27* | --H | --CH₂OH | --CH₂-- | 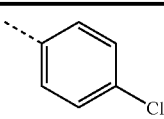 | 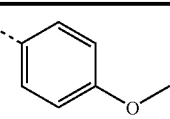 |
| 9-09 | 1 | --H | --COOCH₃ | --CH₂-- | 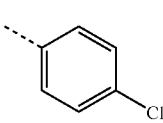 | 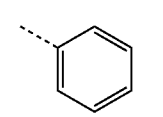 |
| 9-10 | 40* | --H | --O--CH₃ | --CH₂-- | 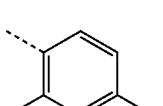 | 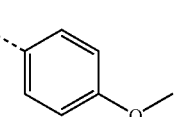 |
| 9-11 | 2 | --H | --NO₂ | --CH₂-- | 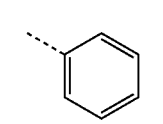 | 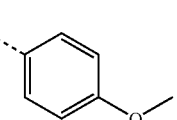 |
| 9-12 | 2 | --CH₃ | --H | --CH₂-- | 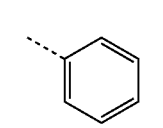 | 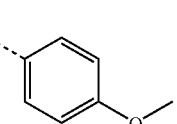 |
| 9-13 | 2 | --CH₃ | --H | --CH₂-- | 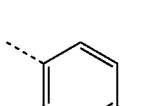 | 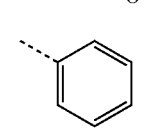 |
| 9-14 | 2 | --CH₃ | --H | --CH₂-- | 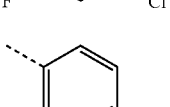 | 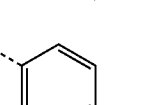 |
| 9-15 | 48 | --CH₂--CH₂--OH | --H | --CH₂-- | 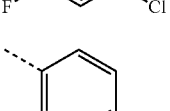 | 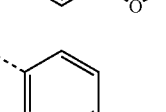 |
| 9-16 | 49* | --CH₂--O--CH₃ | --H | --CH₂-- | 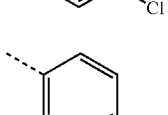 | 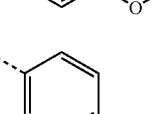 |
| 9-17 | 48* | --CH₂--CH₂--O--CH₃ | --H | --CH₂-- | 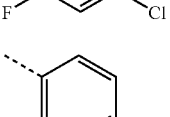 | 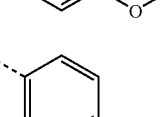 |
| 9-18 | 33* | --OCH₃ | --H | --CH₂-- | 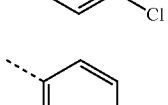 | 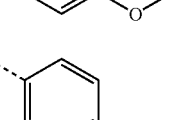 |

TABLE 10
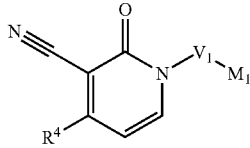
| Co.nr. | Exp. nr. | V₁ | M₁ | R⁴ |
|---|---|---|---|---|
| 10-10 | 2 | --CH₂-- | 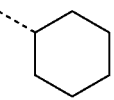 | 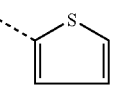 |
| 10-11 | 31 | --CH₂-- | 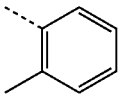 | 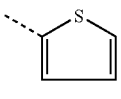 |
| 10-12 | 31 | --CH₂-- | 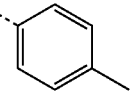 | 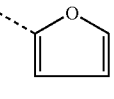 |
| 10-13 | 31 | --CH₂-- | 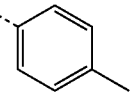 | 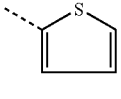 |
| 10-14 | 31 | --CH₂-- | 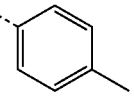 | 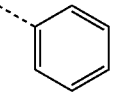 |
| 10-15 | 31 | --CH₂-- | 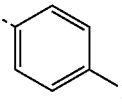 | 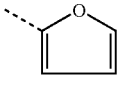 |
| 10-16 | 31 | --CH₂-- | 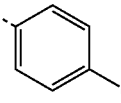 | 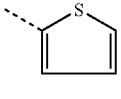 |
| 10-17 | 31 | --CH₂— | 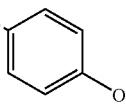 | 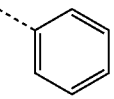 |
| 10-18 | 31 | --CH₂— | 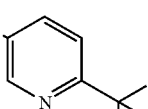 | 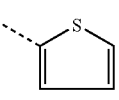 |
| 10-19 | 31 | --CH₂—CH₂—CH₂-- | --H | 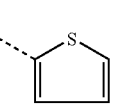 |
| 10-20 | 31 | --CH₂—CH₂—CH₂-- | 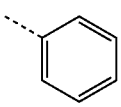 | 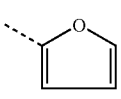 |
| 10-21 | 31 | --CH₂—CH₂—CH₂-- | 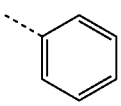 | 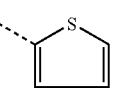 |

TABLE 10-continued

Structure: 3-cyano-1-(V₁-M₁)-4-R⁴-pyridin-2(1H)-one

| Co.nr. | Exp. nr. | V₁ | M₁ | R⁴ |
|---|---|---|---|---|
| 10-22 | 31 | --CH₂—CH=CH-- | phenyl | thienyl |
| 10-23 | 31 | --CH₂—CH₂—CH₂—CH₂-- | --H | thienyl |
| 10-24 | 31 | —CH₂—CH(CH₃)—CH₂-- | --H | thienyl |
| 10-25 | 31 | —CH(CH₃)—CH₂—CH₂—CH₂-- | --H | thienyl |
| 10-26 | 31 | —CH₂—CH(CH₃)CH₂—CH₂-- | --H | phenyl |
| 10-27 | 31 | --CH₂—CH₂—CH(CH₃)—CH₂-- | --H | furyl |
| 10-28 | 31* | --CH₂—CH₂—CH(CH₃)—CH₂-- | --H | thienyl |
| 10-29 | 31 | --CH₂—CH₂—CH(CH₃)—CH₂-- | --H | phenyl |
| 10-30 | 31 | --CH₂—CH₂—CH(CH₃)—CH₂-- | --H | benzo[1,3]dioxolyl |

TABLE 11

Structure: 1-(V₁-M₁)-3-R⁵-4-R⁴-5-R³-pyridin-2(1H)-one

| Co.nr. | Exp. nr. | V₁ | M₁ | R³ | R⁴ | R⁵ |
|---|---|---|---|---|---|---|
| 11-01 | 1 | --CH₂-- | 3-F-4-Cl-phenyl | --Br | --CH₃ | --H |

TABLE 11-continued

Structure: pyridinone with N-V₁-M₁, R³ at 5-position, R⁴ at 4-position, R⁵ at 3-position

| Co.nr. | Exp. nr. | V₁ | M₁ | R³ | R⁴ | R⁵ |
|---|---|---|---|---|---|---|
| 11-02 | 19 | --CH₂-- | 3-F-phenyl | --H | phenyl | --H |
| 11-03 | 19* | --CH₂-- | 3-F-phenyl | --H | 4-methoxyphenyl | --H |

TABLE 12

Structure: pyrimidinone/triazinone with Z₄, Z₅, N-V₁-M₁, R³

| Co.nr. | Exp. nr. | Z₄ | Z₅ | V₁ | M₁ | R³ |
|---|---|---|---|---|---|---|
| 12-01 | 37 | C | N | --CH₂-- | phenyl | 4-methoxyphenyl |
| 12-02 | 37 | C | N | --CH₂-- | 4-Cl-phenyl | 4-methoxyphenyl |
| 12-03 | 37 | C | N | --CH₂-- | 2,4-diCl-phenyl | 4-methoxyphenyl |
| 12-04 | 37 | C | N | isobutyl | --H | 4-methoxyphenyl |
| 12-05 | 37 | N | C | --CH₂-- | 4-Cl-phenyl | phenyl |
| 12-06 | 37* | N | C | --CH₂-- | 4-Cl-phenyl | 4-methoxyphenyl |

TABLE 12-continued

[Structure: pyrimidinone with N-V₁-M₁, Z₄, Z₅, and R³ substituents]

| Co.nr. | Exp. nr. | Z₄ | Z₅ | V₁ | M₁ | R³ |
|---|---|---|---|---|---|---|
| 12-07 | 37 | N | C | —CH₂CH₂CH(CH₃)— | —H | 4-methoxyphenyl |

TABLE 13

[Structure: isoquinolinone with N-V₁-M₁, V₂-M₂, and R³ substituents]

| Co.nr. | Exp. nr. | V₁ | M₁ | V₂ | M₂ | R³ |
|---|---|---|---|---|---|---|
| 13-01 | 17* | —CH₂— | 4-fluorophenyl | cb | —H | —H |
| 13-04 | 38 | —CH₂—CH₂—CH₂— | —H | —NH—CH₂—CH— | 4-methoxyphenyl | —H |
| 13-05 | 38* | —CH₂—CH₂—CH₂— | —H | —NH—CH₂—CH₂— | 4-hydroxyphenyl | —H |
| 13-06 | 53* | —CH₂—CH₂—CH₂— | —H | —O—CH₂—CH₂— | 4-methoxyphenyl | —H |

TABLE 14
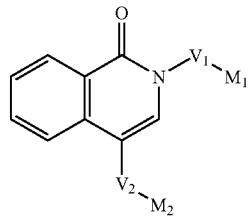
| Co.nr. | Exp. nr. | V₁ | M₁ | V₂ | M₂ |
|---|---|---|---|---|---|
| 14-01 | 39* | --CH₂—CH₂—CH₂-- | --H | --CH₂—CH₂-- | 4-methoxyphenyl |
TABLE 15
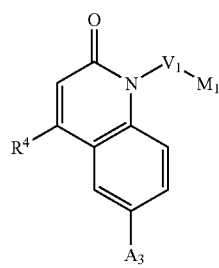
| Co.nr. | Exp. nr. | V₁ | M₁ | A₃ | R⁴ |
|---|---|---|---|---|---|
| 15-01 | 18 | --CH₂-- | 4-chlorophenyl | OCH₃ | --CH₃ |
| 15-02 | 18 | --CH₂—CH(CH₃)—CH₂-- | --H | --H | --CH₃ |
| 15-03 | 18 | --CH₂—CH(CH₃)—CH₂-- | --H | --Cl | --H |
| 15-04 | 18* | --CH₂-- | 4-chlorophenyl | --H | --H |
| 15-05 | 18 | --CH₂-- | 4-chlorophenyl | --H | --CH₃ |

TABLE 16

Compounds with T₂ equal to an (C₁₋₆)alkyl-radical

| Co.nr. | Exp. nr. | Structure |
|---|---|---|
| 16-01 | 10 | 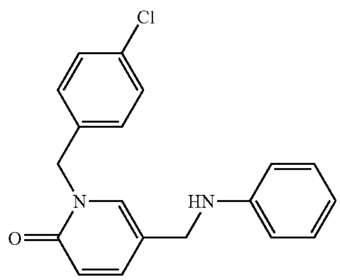 [SMILES: O=c1ccc(CNc2ccccc2)cn1Cc1ccc(Cl)cc1] |
| 16-02 | 44* | 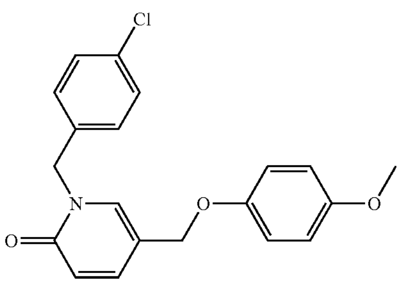 [SMILES: COc1ccc(OCc2ccc(=O)n(Cc3ccc(Cl)cc3)c2)cc1] |
| 16-03 | 25* | 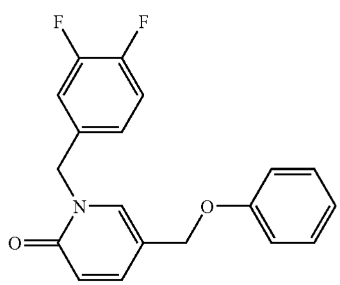 [SMILES: O=c1ccc(COc2ccccc2)cn1Cc1ccc(F)c(F)c1] |
| 16-04 | 25 | 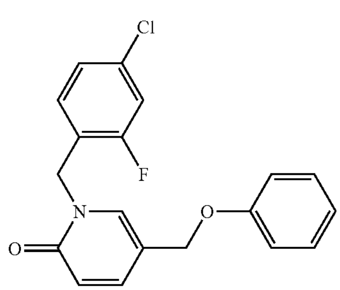 [SMILES: O=c1ccc(COc2ccccc2)cn1Cc1ccc(Cl)cc1F] |
| 16-05 | 25 | 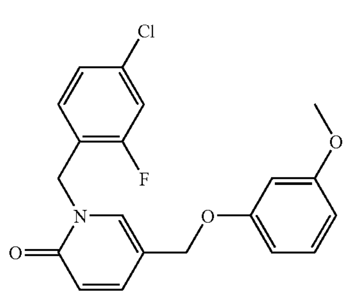 [SMILES: COc1cccc(OCc2ccc(=O)n(Cc3ccc(Cl)cc3F)c2)c1] |
| 16-06 | 32 | |
| 16-07 | 25 | |
| 16-08 | 25 | |
| 16-09 | 51 | |

Physico-Chemical Data

¹H NMR spectra were recorded on Bruker 500 MHz or 300 MHz. Chemical shifts are expressed in parts of million (ppm, δ units). Coupling constants are in units of hertz (Hz). Splitting patterns describe apparent multiplicities and are designated as s (singulet), d (doublet), t (triplet), q (quadruplet), m (multiplet).

LCMS were recorded on a Waters Micromass ZQ 2996 system by the following conditions. Column 3.0*50 mm stainless steel packed with 5 μm XTerra RP C-18; flow rate 1 ml/min; mobile phase: A phase=0.1% formic acid in water, B phase=0.07% formic acid in acetonitrile. 0-0.5 min (A: 95%, B: 5%), 0.5-6.0 min (A: 0%, B: 100%), 6.0-6.5 min (A: 95%, B: 5%), 6.5-7 min (A: 95%, B: 5%); UV detection Diode Array: 200-400 nm; Injection volume: 3 μl. For the ACE-C₁₈ column (3.0 μm, 4.6×30 mm) from Advanced Chromatography Technologies, with a flow rate of 1.5 mL/min. The standard gradient conditions used are: 80% A (0.5 g/l ammonium acetate solution), 10% B (acetonitrile), 10% C (methanol) to 50% B and 50% C in 6.5 min., to 100% B at 7 min. and equilibrated to initial conditions at 7.5 min. until 9.0 min. A 5 µL volume of the sample was injected. In some cases sodium bicarbonate (1 g/l) was used as buffer. All mass spectra were taken under electrospray ionisation (ESI) methods.

Most of the reaction were monitored by thin-layer chromatography on 0.25 mm Macherey-Nagel silica gel plates (60F-2254), visualized with UV light. Flash column chromatography was performed on silica gel (220-440 mesh, Fluka).

Melting point determination was performed on a Buchi B-540 apparatus.

TABLE 17

Physico-chemical data

| Co.Nr | Melting point (° C.) | [MH+] | RT (min) | Physical form |
|---|---|---|---|---|
|  | 273° c. | 381 | 4.32 | n |
|  | 145-157° c. | 426, 428 | 4.08, 4.30 | beige soild |
| 1-01 | — | — | — | white semi-solid |
| 1-02 | — | 276 | 4.28 | brown oil |
| 1-03 | 110° c. | 276 | 4.29 | white solid |
| 1-04 | 80° c. | 290 | 3.99 | orange solid |
| 1-05 | 145° c. | 318 | 5.31 | white solid |
| 1-06 | 118° c. | 290 | 4.04 | white solid |
| 1-07 | — | 280 | 4.08 | brown oil |
| 1-09 | 98° c. | 298 | 4.46 | brown solid |
| 1-10 | 120° c. | 296 | 4.41 | white solid |
| 1-12 | 134° c. | 330, 332 | 4.24 | white solid |
| 1-13 | 202° c. | — | — | beige solid |
| 1-14 | — | 292 | 4.04 | yellow oil |
| 1-15 | — | 292 | 4.04 | colorless oil |
| 1-17 | 88° c. | 320 | 4.88 | brown solid |
| 1-18 | 110° c. | 334 | 4.31 | beige solid |
| 1-19 | 120° c. | 322 | 3.69 | white solid |
| 1-20 | 115° c. | 346 | 4.59 | white solid |
| 1-21 | — | 310 | 4.11 | brown oil |
| 1-22 | — | 354 | 4.76 | brown oil |
| 1-23 | 118° c. | 304 | 3.71 | white solid |
| 1-24 | 115° c. | 334 | 4.31 | white solid |
| 1-25 | 131° c. | 287 | 3.89 | white solid |
| 1-26 | 153° c. | 305 | 2.76 | dark yellow solid |
| 1-27 | 149° c. | 307 | 4.04 | colorless solid |
| 1-28 | 132° c. | 334 | 5.51 | white solid |
| 1-29 | 180-181° c. | 293 | 3.81 | white solid |
| 1-30 | 93° c. | 301 | 3.96 | brown solid |
| 1-31 | — | 304 | 3.61 | orange semi-solid |
| 1-32 | 114° c. | 312 | 4.63 | brown solid |
| 2-01 | 72° c. | 302, 304 | 5.07 | beige solid |
| 2-02 | — | 296, 298 | 4.53 | brown oil |
| 2-03 | 126-128° c. | 310, 312 | 4.86 | white solid |
| 2-04 | 115° c. | 352 | 5.69 | beige solid |
| 2-05 | 73° c. | 352 | 5.64 | beige solid |
| 2-06 | 125° c. | 322 | 4.93 | beige solid |
| 2-07 | — | 314, 316 | 4.61 | brown oil |
| 2-08 | — | 314 | 4.49 | light yellow oil |
| 2-09 | — | 332 | 4.64 | colorless oil |
| 2-10 | 109-112° c. | 328, 330 | 4.93 | white solid |
| 2-11 | 89° c. | 344, 346 | 4.56 | white solid |
| 2-12 | — | 312, 314 | 3.78 | beige solid |
| 2-13 | 202° c. | 312, 314 | 3.68 | beige solid |
| 2-14 | 155° c. | 326 | 3.47 | yellow solid |
| 2-15 | 157° c. | 354, 356 | 3.85 | white solid |
| 2-16 | 165° c. | 354, 356 | 3.78 | white solid |
| 2-17 | — | 326 | 4.58 | brown oil |
| 2-18 | — | 340, 342 | 4.69 | brown oil |
| 2-19 | — | 340 | 4.86 | oil |
| 2-20 | 120-121° c. | 340, 342 | 4.88 | white solid |
| 2-21 | 118° c. | 354 | 4.99 | white solid |
| 2-22 | — | 368 | 5.33 | yellow oil |
| 2-23 | — | 340, 342 | 4.49 | colorless oil |
| 2-24 | 109° c. | 340, 342 | 4.46 | white solid |
| 2-25 | 109° c. | 354, 356 | 4.62 | white solid |

TABLE 17-continued

Physico-chemical data

| Co.Nr | Melting point (° C.) | [MH+] | RT (min) | Physical form |
|---|---|---|---|---|
| 2-26 | 91° c. | 382, 384 | 5.38 | white solid |
| 2-27 | 101° c. | 416, 418 | 5.18 | white solid |
| 2-28 | 79° c. | 384, 386 | 4.26 | white solid |
| 2-29 | — | 398 | 4.48 | colorless oil |
| 2-30 | 162° c. | 338 | 4.21 | yellow solid |
| 2-31 | 180° c. | 354, 356 | 3.57 | white solid |
| 2-32 | 185° c. | 368, 370 | 3.89 | white solid |
| 2-33 | 175° c. | 354, 356 | 4.36 | white solid |
| 2-34 | — | 368, 370 | 4.24 | brown oil |
| 2-35 | — | 382 | 4.61 | oil |
| 2-36 | 105° c. | 382 | 4.59 | yellow solid |
| 2-37 | 175° c. | 341, 343 | 3.62 | white solid |
| 2-38 | 70° c. | 397, 399 | 2.95 | white solid |
| 2-39 | 68° c. | 439, 441 | 2.89 | white solid |
| 2-40 | 106° c. | 369 | 4.25 | — |
| 2-41 | 126° c. | 381 | 4.18 | white solid |
| 2-42 | 152° c. | 411, 413 | 3.55 | white solid |
| 2-43 | 176° c. | 367, 369 | 3.52 | white solid |
| 2-44 | 183° c. | 367, 369 | 3.32 | white solid |
| 2-45 | 161° c. | 381, 383 | 3.66 | white solid |
| 2-46 | 197° c. | 381, 383 | 3.52 | white solid |
| 2-47 | 104° c. | 395, 397 | 3.86 | white solid |
| 2-48 | 155° c. | 339, 341 | 4.28 | grey solid |
| 2-49 | — | 353 | 5.02 | — |
| 2-50 | — | 382 | 3.23 | — |
| 2-51 | 231° c. | 376, 378 | 3.56 | white solid |
| 2-52 | 132° c. | 342, 344 | 4.84 | yellow solid |
| 2-53 | 109° c. | 356 | 5.13 | white solid |
| 2-54 | 199-200° c. | 374 | 3.76 | white solid |
| 2-55 | 169° c. | 389 | 3.83 | white solid |
| 2-56 | 151° c. | 419, 421 | 3.73 | white solid |
| 2-57 | — | 385, 387 | 4.96 | brown semi-solid |
| 2-58 | 140-144° c. | 376, 378 | 4.26 | beige solid |
| 2-59 | 112-114° c. | 286, 288 | 4.16 | white solid |
| 2-60 | 101° c. | 316 | 4.7 | white solid |
| 2-61 | 135° c. | 311, 313 | 4.01 | beige solid |
| 2-62 | 191° c. | 327 | 4.19 | white solid |
| 2-63 | 169° c. | 331, 333 | 4.07 | yellow solid |
| 2-64 | 164° c. | 340, 342 | 2.53 | beige solid |
| 2-65 | 154° c. | 382, 384 | 3.21 | white solid |
| 2-66 | 191° c. | 328, 330 | 3.56 | beige solid |
| 2-67 | — | 335, 337 | 4.04 | brown oil |
| 2-68 | 144-147° c. | 349, 351 | 4.69 | beige solid |
| 2-69 | 119° c. | 338 | 4.51 | orange solid |
| 2-70 | 165° c. | 347, 349 | 4.06 | white solid |
| 2-71 | 261° c. | 347, 349 | 3.43 | yellow solid |
| 2-72 | 120° c. | 348, 350 | 3.78 | yellow solid |
| 3-01 | 93° c. | 328 | 4.54 | white solid |
| 3-02 | — | 340, 342 | 4.49 | yellow oil |
| 3-03 | 164° c. | 352, 354 | 4.83 | yellow pale crystals |
| 3-04 | 167° c. | 352, 354 | 4.83 | yellow pales crystals |
| 3-05 | — | 276 | 4.7 | light yellow oil |
| 3-07 | 106° c. | 339, 341 | 4.43 | white solid |
| 3-08 | — | 353, 355 | 2.59 | pale oil |
| 3-09 | 175-177° c. | 344 | 3.83 | pale beige solid |
| 3-10 | 120° c. | 356, 358 | 3.76 | yellow solid |
| 3-12 | 104° c. | 354, 356 | 4.41 | white solid |
| 3-13 | — | 330 | 4.56 | — |
| 3-14 | 199° c. | 342 | 4.46 | — |
| 3-15 | 217° c. | 332 | 5.51 | — |
| 3-16 | 83° c. | 344 | 4.49 | — |
| 3-17 | — | 355 | 4.39 | — |
| 3-18 | — | 340 | 4.81 | — |
| 3-19 | 104° c. | 278 | 4.17 | black solid |
| 3-21 | — | 343, 345 | 4.36 | yellow oil |
| 4-01 | — | 256 | 3.84 | yellow oil |
| 4-02 | — | 284 | 4.45 | colorless oil |
| 4-03 | — | 298 | 4.72 | colorless oil |
| 4-04 | — | 312 | 5.06 | colorless oil |
| 4-05 | 122° c. | 306 | 4.38 | white solid |
| 4-06 | 123-124° c. | 306 | 4.48 | clear yellow solid |
| 4-07 | 131-132° c. | 360 | 4.59 | white solid |
| 4-08 | — | 310 | 3.69 | yellow oil |
| 4-09 | 89° c. | 310 | 3.69 | white solid |
| 4-10 | 103° c. | 310 | 3.71 | white solid |

TABLE 17-continued

Physico-chemical data

| Co.Nr | Melting point (° C.) | [MH+] | RT (min) | Physical form |
|---|---|---|---|---|
| 4-11 | — | 328 | 4.33 | colorless oil |
| 4-12 | 109° c. | 328 | 4.28 | white solid |
| 4-13 | 71° c. | 328 | 4.26 | white solid |
| 4-14 | — | 344 | 4.53 | brown oil |
| 4-15 | — | 344, 346 | 4.51 | white solid |
| 4-16 | 88° c. | 344, 346 | 4.58 | white solid |
| 4-17 | 112° c. | 346 | 4.24 | white solid |
| 4-18 | 125° c. | 326 | 4.44 | white solid |
| 4-20 | 142° c. | 326 | 3.91 | white solid |
| 4-21 | — | 360, 362 | 4.16 | pale yellow solid |
| 4-22 | — | 322 | 4.14 | yellow oil |
| 4-23 | 103° c. | 322 | 3.64 | clear yellow solid |
| 4-24 | — | — | — | yellow oil |
| 4-25 | 72° c. | 336 | 3.92 | white solid |
| 4-26 | — | 350 | 4.22 | yellow oil |
| 4-27 | 147-150° c. | 350 | 4.11 | white solid |
| 4-28 | — | 350 | 3.85 | clear yellow oil |
| 4-29 | 165° c. | 317 | 3.51 | white solid |
| 4-30 | 119-120° c. | 317 | 3.98 | white solid |
| 4-31 | 130° c. | 376 | 4.64 | white solid |
| 4-32 | — | 337 | 3.69 | yellow oil |
| 4-33 | 95° c. | 337 | 3.69 | white solid |
| 4-34 | 131-134° c. | 378 | 4.68 | brown solid |
| 4-35 | 82-84° c. | 378 | 4.64 | white solid |
| 4-36 | 98-100° c. | 324 | 4.51 | white solid |
| 4-37 | — | 394, 396 | 4.83 | yellow oil |
| 4-38 | 145-148° c. | 342 | 4.68 | white solid |
| 4-39 | 120° c. | 350 | 4.25 | white solid |
| 4-40 | 100-102° c. | 297 | 3.66 | white solid |
| 4-41 | 104° c. | 360 | 4.12 | yellow solid |
| 4-42 | 123° c. | 378 | 4.39 | yellow solid |
| 4-43 | — | 293 | 2.24 | yellow oil |
| 4-44 | 135° c. | 327, 329 | 3.83 | white solid |
| 4-45 | 130° c. | 321 | 3.55 | — |
| 4-46 | 126° c. | 323 | 3.73 | yellow solid |
| 4-47 | 168° c. | 361 | 4.06 | white solid |
| 4-48 | 273° c. | 317 | 3.18 | — |
| 4-49 | — | 399 | 4.31 | — |
| 4-50 | — | 308 | 3.43 | brown oil |
| 4-51 | 115° c. | 351 | 4.06 | white solid |
| 4-52 | 127-130° c. | 313 | 3.54 | beige solid |
| 4-53 | 121° c. | 349 | 3.68 | beige solid |
| 4-54 | 126° c. | 367 | 4.1 | brown solid |
| 5-01 | 69° c. | 372 | 4.68 | pale beige solid |
| 5-02 | — | 358, 360 | 4.61 | yellow oil |
| 5-03 | — | 400 | 5.35 | colorless oil |
| 5-04 | 125° c. | 324 | 4.28 | white solid |
| 5-05 | 92° c. | 306 | 3.73 | clear yellow solid |
| 5-06 | 75° c. | 312 | 3.97 | white solid |
| 5-07 | — | 320 | 4.51 | colorless oil |
| 5-08 | — | 258 | 4.03 | colorless oil |
| 5-09 | 79° c. | 334 | 4.79 | yellow solid |
| 5-10 | 70° c. | 258 | 3.98 | white solid |
| 5-11 | — | 272 | 4.38 | yellow oil |
| 5-12 | 85° c. | 272 | 4.33 | white solid |
| 5-13 | 75° c. | 272 | 4.32 | white solid |
| 5-15 | 85° c. | 286 | 4.63 | white solid |
| 5-16 | — | 268 | 3.73 | colourless oil |
| 5-17 | — | 342 | 4.56 | colorless oil |
| 5-18 | — | 322 | 4.31 | yellow oil |
| 5-19 | 126° c. | 320 | 3.89 | white solid |
| 5-20 | — | 363 | 3.79 | yellow oil |
| 5-21 | 65° c. | 377 | 3.99 | white solid |
| 5-22 | — | 381 | 3.93 | clear yellow oil |
| 5-23 | — | 431 | 4.18 | brown oil |
| 5-24 | — | 397, 399 | 4.06 | yellow oil |
| 5-25 | — | 393 | 3.81 | yellow oil |
| 5-26 | 160° c. | 408 | 3.78 | yellow solid |
| 6-04 | 112-113° c. | 294 | 4.59 | clear brown solid |
| 6-10 | — | 328 | 4.34 | grey solid |
| 6-11 | 85° c. | 342 | 4.21 | pale gray crystals |
| 6-12 | 142° c. | 340 | 3.99 | pale pink crystals |
| 6-13 | 139° c. | 323 | 4.09 | white solid |
| 6-14 | — | 391 | 3.58 | pale brown glass oil |
| 6-15 | 96° c. | 304 | 4.24 | pale grey solid |
| 6-16 | 120° c. | 329 | 3.94 | white solid |
| 6-17 | 99° c. | 340 | 4.24 | pale grey crystals |
| 6-18 | 181° c. | 342 | 4.23 | white solid |
| 6-19 | 164° c. | 371, 373 | 4.89 | pale beige solid |
| 6-20 | 102° c. | 316, 318 | 4.12 | white solid |
| 6-21 | 224° c. | 330 | 3.67 | white solid |
| 6-22 | 70° c. | 329, 331 | 3.45 | beige solid |
| 6-23 | 266° c. | 329, 331 | 3.18 | beige solid |
| 6-24 | 139° c. | 343, 345 | 2.52 | beige solid |
| 6-25 | 140° c. | 339, 341 | 4.26 | white solid |
| 6-26 | 176° c. | 344, 346 | 3.53 | white solid |
| 6-27 | 127° c. | 382 | 5.03 | white solid |
| 6-28 | 104° c. | 358, 360 | 4.85 | white solid |
| 6-29 | — | 372, 374 | 5.08 | yellow oil |
| 6-30 | — | 362, 364 | 4.69 | brown oil |
| 6-31 | 141° c. | 374, 376 | 4.13 | white solid |
| 6-32 | 107° c. | 372, 374 | 5.38 | white solid |
| 6-33 | 88° c. | 386 | 5.45 | white solid |
| 6-34 | 129° c. | 354.1, 356.1 | 4.62 | white solid |
| 6-35 | — | 388, 390 | 3.92 | pale oil |
| 6-36 | 90° c. | 388 | 4.3 | yellow solid |
| 6-37 | 114° c. | 410, 412 | 4.78 | white solid |
| 6-38 | — | 386, 388 | 4.53 | beige oil |
| 6-39 | 124° c. | 388, 390 | 4.28 | white solid |
| 6-40 | 127° c. | 386, 388 | 4.02 | white solid |
| 6-41 | 119° c. | 402 | 4.3 | white solid |
| 6-42 | 226° c. | 373, 375 | 2.63 | white solid |
| 6-43 | 253° c. | 387, 389 | 2.8 | white solid |
| 6-44 | 85° c. | 401 | 2.67 | white solid |
| 6-45 | 104° c. | 415 | 2.83 | white solid |
| 6-46 | 160° c. | 369, 371 | 4.2 | pale beige solid |
| 6-47 | 80° c. | 444 | 2.67 | yellow solid |
| 6-48 | 153° c. | 457 | 2.9 | beige solid |
| 6-49 | — | 421 | 4.34 | yellow solid |
| 6-50 | — | 421 | 3.73 | yellow oil |
| 6-51 | 136° c. | 345, 347 | 4.13 | beige solid |
| 6-52 | 162° c. | 401, 403 | 3.58 | white solid |
| 6-53 | 153° c. | 415 | 3.51 | white solid |
| 6-54 | — | 429, 431 | 3.63 | pale oil |
| 6-55 | 121° c. | 457, 459 | 4.24 | white solid |
| 6-56 | 131° c. | 471, 473 | 4.34 | white solid |
| 6-57 | 194° c. | 371, 373 | 3.72 | beige solid |
| 6-58 | 230° c. | 371, 373 | 3.53 | beige solid |
| 6-59 | 126° c. | 443, 445 | 4.62 | brown solid |
| 6-60 | 143° c. | 385 | 3.47 | beige solid |
| 6-61 | 150° c. | 385, 387 | 3.42 | beige solid |
| 6-62 | 180° c. | 441, 443 | 3.9 | beige solid |
| 6-63 | 135° c. | 425, 427 | 4.57 | white solid |
| 6-64 | — | 424, 426 | 2.87 | brown oil |
| 6-65 | 197° c. | 412, 414 | 3.57 | white solid |
| 6-66 | 90° c. | 441, 443 | 4.55 | white solid |
| 6-67 | 240° c. | 382, 384 | 3.6 | white solid |
| 6-68 | 241° c. | 382 | 3.6 | white solid |
| 6-69 | 110° c. | 370, 372 | 5.03 | beige solid |
| 6-70 | 139° c. | 451 | 3.75 | beige solid |
| 6-71 | 157° c. | 465, 467 | 3.88 | white solid |
| 6-72 | 110° c. | 421, 423 | 3.77 | beige solid |
| 6-73 | 165° c. | 421 | 3.7 | beige solid |
| 6-74 | 141° c. | 463, 465 | 4.07 | white solid |
| 6-75 | 177° c. | 447, 449 | 4.33 | pink solid |
| 6-76 | 97° c. | 334 | 3.72 | white solid |
| 6-77 | 134° c. | 317 | 3.83 | white solid |
| 6-80 | 160° c. | 362 | 3.6 | beige solid |
| 6-81 | 149° c. | 319 | 4.08 | grey solid |
| 7-01 | 105° c. | 334 | 4.74 | brown solid |
| 7-02 | 179° c. | 305 | 3.68 | solid |
| 7-03 | 93° c. | 324 | 4.41 | white solid |
| 7-04 | — | 356 | 4.44 | colorless oil |
| 7-06 | — | 372, 374 | 4.68 | yellow oil |
| 7-07 | — | 358 | 4.72 | green oil |
| 7-08 | — | 356, 358 | 5.09 | yellow oil |
| 7-09 | 53° c. | 280 | 2.53 | colourless solid |
| 7-10 | — | 370, 372 | 5.36 | orange oil |
| 7-11 | — | 400, 402 | 5.24 | yellow oil |
| 7-15 | — | 290 | 4.46 | oily solid |

TABLE 17-continued

Physico-chemical data

| Co.Nr | Melting point (° C.) | [MH+] | RT (min) | Physical form |
|---|---|---|---|---|
| 7-16 | 123° c. | 286 | 4.11 | white solid |
| 8-01 | 78° c. | 267 | 4.06 | white solid |
| 8-02 | 159° c. | 335 | 3.49 | white solid |
| 9-01 | 121° c. | 344, 346 | 4.61 | beige solid |
| 9-02 | — | 360 | 4.79 | green oil |
| 9-03 | — | 330 | 4.86 | colorless oil |
| 9-04 | 155-157° c. | 369 | 3.95 | beige solid |
| 9-05 | 212-213° c. | 387 | 4.02 | white solid |
| 9-06 | 261° c. | 362 | 4.7 | beige solid |
| 9-07 | 109-110° c. | 306 | 4.49 | white solid |
| 9-08 | 128° c. | 356, 358 | 3.98 | beige solid |
| 9-09 | 125° c. | 354, 356 | 4.43 | beige solid |
| 9-10 | — | 374, 376 | 4.53 | brown oil |
| 9-11 | 148-150° c. | 337 | 4.44 | orange solid |
| 9-12 | 79° c. | 306 | 4.49 | white solid |
| 9-13 | — | 328, 330 | 4.79 | white solid |
| 9-14 | 125° c. | 358, 360 | 4.71 | white solid |
| 9-15 | 151° c. | 370 | 3.83 | pale yellow solid |
| 9-16 | — | 388, 390 | 3.83 | green oil |
| 9-17 | — | 384, 386 | 4.49 | white oil |
| 9-18 | — | 374, 376 | 4.62 | yellow oil |
| 10-10 | 148° c. | 299 | 4.59 | white solid |
| 10-12 | 155° c. | 291 | 4.19 | yellow solid |
| 10-13 | 118° c. | — | — | white solid |
| 10-15 | 175° c. | 295 | 3.97 | beige solid |
| 10-16 | 180° c. | 327, 329 | 4.54 | pink solid |
| 10-18 | 185° c. | 362 | 3.96 | white solid |
| 10-19 | 135° c. | 245 | 3.85 | yellow solid |
| 10-20 | 86° c. | 305 | 4.29 | yellow solid |
| 10-21 | 118° c. | 321 | 4.4 | yellow solid |
| 10-23 | 103° c. | 259 | 4.18 | yellow solid |
| 10-24 | 108° c. | 259 | 3.92 | beige solid |
| 10-25 | 103° c. | 273 | 4.22 | white solid |
| 10-26 | 149° c. | 267 | 4.45 | white solid |
| 10-27 | 112° c. | 257 | 4.13 | yellow solid |
| 10-28 | 123° c. | 273 | 4.29 | yellow solid |
| 10-29 | 138-140° c. | 267 | 4.3 | white powder |
| 10-30 | 120-121° c. | 311 | 4.23 | beige powder |
| 11-01 | 107° c. | 331, 333 | 4.36 | beige solid |
| 11-02 | 119° c. | 280 | 4.14 | beige solid |
| 11-03 | 114° c. | 310 | 4.18 | white solid |
| 12-01 | 200° c. | 293, 294 | 3.7 | brown solid |
| 12-02 | 188° c. | 327, 329 | 4.02 | yellow solid |
| 12-04 | 130° c. | 273 | 3.93 | white powder |
| 12-05 | 116° c. | 297, 299 | 4.46 | orange solid |
| 12-06 | 133° c. | 327, 329 | 4.41 | brown oil |
| 12-07 | 104° c. | 273 | 4.4 | white solid |
| 13-01 | 107° c. | 254 | 3.76 | white solid |
| 13-04 | 109-110° c. | 387.1 | 4.02 | white powder |
| 13-05 | 170-171° c. | 323 | 3.78 | grey powder |
| 13-06 | — | 338 | 4.84 | — |
| 14-01 | — | 322 | 4.89 | orange oil |
| 15-01 | 172° c. | 314 | 4.48 | white solid |
| 15-02 | 67° c. | 230 | 4.68 | white solid |
| 15-03 | 67° c. | 245 | 3.83 | white solid |
| 15-04 | 139° c. | 270, 272 | 4.43 | white |
| 15-05 | — | 284 | 4.61 | white solid/glass oil |
| 16-01 | 142° c. | 325, 327 | 4.09 | white solid |
| 16-02 | 114° c. | 356, 358 | 4.36 | white solid |
| 16-03 | 89° c. | 328 | 4.29 | white solid |
| 16-04 | 86° c. | 344, 346 | 4.54 | brown solid |
| 16-05 | — | 374, 376 | 4.49 | white semi-solid |
| 16-06 | — | 372, 374 | 4.97 | colorless oil |
| 16-07 | 119-121° c. | 361 | 4.07 | orange solid |
| 16-08 | — | 302 | 4.24 | yellow oil |
| 16-19 | — | 294 | 3.08 | — |

TABLE 18

NMR-data

| Co.Nr | NMR-data |
|---|---|
| 1-02 | $^1$H NMR(500 MHz, CDCl$_3$) δ 2.39(s, 3H), 5.23(s, 2H), 6.75(d, J = 9.4 Hz, 1H), 7.15(m, 3H), 7.32(m, 6H), 7.48(d, J = 2.6 Hz, 1H), 7.64(dd, J = 2.6 Hz, J = 9.4 Hz, 1H). |
| 1-03 | $^1$H NMR(500 MHz, CDCl$_3$) δ 2.37(s, 3H), 5.22(s, 2H), 6.71(d, J = 9.4 Hz, 1H), 7.20(d, J = 8.2 Hz, 2H), 7.25(d, J = 8.2 Hz, 2H), 7.28-7.42(m, 5H), 7.45(d, J = 2.7 Hz, 1H), 7.61(dd, J = 9.4 Hz, J = 2.7 Hz, 1H). |
| 1-06 | $^1$H NMR(500 MHz, CDCl$_3$) δ 2.28(s, 3H), 2.29(s, 3H), 5.23(s, 2H), 6.73(dd, J = 2.4 Hz and 9.4 Hz, 1H), 7.09(dd, J = 2.0 Hz and 7.8 Hz, 1H), 7.12-7.17(2H), 7.29-7.38(5H), 7.45(d, J = 2.6 Hz, 1H), 7.62(dd, J = 2.6 Hz and 9.4 Hz, 1H). |
| 1-07 | $^1$H NMR(500 MHz, CDCl$_3$) δ 5.23(s, 2H), 6.74(d, J = 9.4 Hz, 1H), 7.15(m, 2H), 7.32(m, 7H), 7.58(m, 2H). |
| 1-09 | $^1$H NMR(500 MHz, CDCl$_3$) δ 5.23(s, 2H), 6.71-6.78(2H), 6.84-6.90(2H), 7.32-7.41(5H), 7.49(d, J = 2.7 Hz, 1H), 7.56(dd, J = 2.7 Hz and 9.5 Hz, 1H). |
| 1-10 | $^1$H NMR(500 MHz, CDCl$_3$) δ 5.24(s, 2H), 6.77(d, J = 9.4 Hz, 1H), 7.20-7.40(m, 9H), 7.50(d, J = 2.7 Hz, 1H), 7.60(dd, J = 9.4 Hz, J = 2.7 Hz, 1H). |
| 1-14 | $^1$H NMR(500 MHz, CDCl$_3$) δ 3.78(s, 3H), 5.20(s, 2H), 6.74(d, J = 9.4 Hz, 1H), 6.94(d, J = 8.3, 1H), 6.99(t, J = 7.5 Hz, 1H), 7.19(dd, J = 1.6 Hz, J = 7.5 Hz, 1H), 7.32(m, 2H), 7.37(d, J = 4.3 Hz, 4H), 7.54(d, J = 2.5 Hz, 1H), 7.61(dd, J = 2.5 Hz, J = 9.4 Hz, 1H) |
| 1-15 | $^1$H NMR(500 MHz, CDCl$_3$) δ 3.84(s, 3H), 5.24(s, 2H), 6.78(d, J = 9.4 Hz, 1H), 6.84-6.90(2H), 6.94(d, J = 7.7 Hz, 1H), 7.29-7.39(6H), 7.51(d, J = 2.6 Hz, 1H), 7.64(dd, J = 2.6 Hz and 9.4 Hz, 1H). |
| 1-19 | $^1$H NMR(500 MHz, CDCl$_3$) δ 3.90(s, 3H), 3.91(s, 3H), 5.24(s, 2H), 6.75(d, J = 9.4 Hz, 1H), 6.84(s, 1H), 6.89(d, J = 0.9 Hz, 2H), 7.29-7.39(5H), 7.42(d, J = 2.6 Hz, 1H), 7.61(dd, J = 2.6 Hz and 9.4 Hz, 1H). |
| 1-21 | $^1$H NMR(500 MHz, CDCl$_3$) δ 3.80(s, 3H), 5.22(s, 2H), 6.73(d, J = 9.5 Hz, 1H), 6.78(m, 2H), 7.03(m, 1H), 7.32-7.38(m, 5H), 7.56(s, 1H), 7.58(s, 1H). |
| 1-22 | $^1$H NMR(500 MHz, CDCl$_3$) δ 1.31(d, J = 5.0 Hz, 6H), 4.48(p, J = 6.1 Hz, 1H), 5.14(s, 2H), 6.64(d, J = 9.4 Hz, 1H), 6.88(d, J = 8.5 Hz, 1H), 7.08(dd, J = 2.3 Hz, J = 8.5 Hz, 1H), 7.19(s, 1H), 7.27(m, 5H), 7.34(d, J = 2.6 Hz, 1H), 7.48(dd, J = 2.6 Hz, J = 9.4 Hz, 1H). |
| 1-23 | $^1$H NMR(500 MHz, CDCl$_3$) δ 2.62(s, 3H), 5.24(s, 2H), 6.75(d, J = 9.5 Hz, 1H), 7.29-7.41(m, 5H), 7.45(d, J = 8.6 Hz, 2H), 7.58(d, J = 2.7 Hz, 1H), 7.66(dd, J = 9.5 Hz, J = 2.7 Hz, 1H), 7.98(d, J = 8.6 Hz, 2H). |
| 1-24 | $^1$H NMR(500 MHz, CDCl$_3$) δ 1.41(t, J = 7.1 Hz, 3H), 4.39(q, J = 7.1 Hz, 2H), 5.24(s, 2H), 6.75(d, J = 9.4 Hz, 1H), 7.30-7.40(5H), 7.42(d, J = 8.3 Hz, 2H), 7.56(d, J = 2.6 Hz, 1H), 7.66(dd, J = 2.6 Hz and 9.4 Hz, 1H), 8.06(d, J = 8.3 Hz, 2H). |
| 1-25 | $^1$H NMR(500 MHz, CDCl$_3$) δ 5.25(s, 2H), 6.78(d, J = 9.5 Hz, 1H), 7.31-7.41(m, 5H), 7.46(d, J = 8.5 Hz, 2H), 7.56(d, J = 2.6 Hz, 1H), 7.63(dd, J = 9.5 Hz, J = 2.6 Hz, 1H), 7.68(d, J = 8.4 Hz, 2H). |
| 1-27 | $^1$H NMR(500 MHz, CDCl$_3$) δ 5.26(s, 2H), 6.81(d, J = 9.4 Hz, 1H), 7.31-7.40(5H), 7.56-7.60(2H), 7.64-7.70(2H), 8.15-8.18(m, 1H), 8.22-8.25(m, 1H). |

TABLE 18-continued

NMR-data

| Co.Nr | NMR-data |
|---|---|
| 1-28 | ¹H NMR(500 MHz, CDCl₃) δ 0.28(s, 9H), 5.23(s, 2H), 6.73(d, J = 9.4 Hz, 1H), 7.29-7.39(7H), 7.48(d, J = 2.6 Hz, 1H), 7.53-7.57(2H), 7.63(dd, J = 2.6 Hz and 9.4 Hz, 1H). |
| 1-29 | ¹H NMR(500 MHz, CDCl₃) δ 3.93(s, 3H), 5.22(s, 2H), 6.73(d, J = 9.4 Hz, 1H), 6.77(dd, J = 8.6 Hz, J = 0.7 Hz, 1H), 7.30-7.40(m, 5H), 7.54(m, 2H), 8.15(dd, J = 2.6 Hz, J = 0.7 Hz, 1H). |
| 1-30 | ¹H NMR(500 MHz, CDCl₃) δ 5.25(s, 2H), 6.57(m, 1H), 6.75(d, J = 9.4 Hz, 1H), 7.19(dd, J = 8.4 Hz, J = 1.8 Hz, 1H), 7.24-7.39(m, 6H), 7.42(d, J = 8.4 Hz, 1H), 7.50(d, J = 2.6 Hz, 1H), 7.62(s, 1H), 7.70(dd, J = 9.4 Hz, J = 2.6 Hz, 1H), 8.24(s, 1H). |
| 1-31 | ¹H NMR(500 MHz, CDCl₃) δ 3.24(t, J = 8.7 Hz, 2H), 4.61(t, J = 8.7 Hz, 2H), 5.31(s, 2H), 6.80(d, J = 8.3 Hz, 1H), 6.90(m, 1H), 7.10(dd, J = 8.2 Hz, J = 1.2 Hz, 1H), 7.19(s, 1H), 7.29-7.41(m, 5H), 7.43(d, J = 2.8 Hz, 1H), 7.62(m, 1H). |
| 1-32 | ¹H NMR(500 MHz, CDCl₃) δ 5.28(s, 2H), 6.79(d, J = 9.4 Hz, 1H), 7.30-7.54(m, 8H), 7.62(d, J = 2.6 Hz, 1H), 7.78(dd, J = 9.4 Hz, J = 2.6 Hz, 1H), 7.80-7.89(m, 4H). |
| 2-01 | ¹H NMR(300 MHz, CDCl₃) δ 1.07-1.43(5H), 1.63-1.86(5H), 2.13-2.28(m, 1H), 5.08(s, 2H), 6.58(d, J = 9.5 Hz, 1H), 6.99(d, J = 2.6 Hz, 1H), 7.20-7.25(m, 2H), 7.26-7.30(m, 2H), 7.31-7.33(m, 1H). |
| 2-02 | ¹H NMR(500 MHz, CDCl₃) δ 5.15(s, 2H), 6.52(d, J = 9.4 Hz, 1H), 7.30(m, 1H), 7.40(m, 6H), 7.56(d, J = 8.2 Hz, 2H), 7.85(dd, J = 9.4 Hz, J = 2.70 Hz, 1H), 8.27(d, J = 2.7 Hz, 1H). |
| 2-03 | ¹H NMR(500 MHz, CDCl₃) δ 2.37(s, 3H), 5.18(s, 2H), 6.70(d, J = 9.4 Hz, 1H), 7.16-7.35(m, 8H), 7.43(d, J = 2.4 Hz, 1H), 7.62(dd, J = 9.4 Hz, J = 2.4 Hz, 1H). |
| 2-07 | ¹H NMR(500 MHz, CDCl₃) δ 5.17(s, 2H), 6.71(d, J = 9.4 Hz, 1H), 7.11-7.20(m, 2H), 7.28-7.35(m, 7H), 7.54(d, J = 2.5 Hz, 1H). |
| 2-08 | ¹H NMR(300 MHz, CDCl₃) δ 5.10(s, 2H), 6.65(d, J = 9.5 Hz, 1H), 7.05(m, 2H), 7.25(m, 6H), 7.35(d, J = 2.0 Hz, 1H), 7.50(dd, J = 2.8 Hz, J = 9.5 Hz, 1H). |
| 2-09 | ¹H NMR(500 MHz, CDCl₃) δ 5.18(s, 2H), 6.71(d, J = 10.0 Hz, 1H), 6.99(m, 2H), 7.09(m, 1H), 7.32(dd, J = 10.0 Hz, J = 6.4 Hz, 4H), 7.56(s, 2H). |
| 2-10 | ¹H NMR(500 MHz, CDCl₃) δ 2.29(s, 3H), 5.18(s, 2H), 6.71(d, J = 9.4 Hz, 1H), 7.02(t, J = 11.7 Hz, 2H), 7.20(t, 8.3 Hz, 1H), 7.32(m, 4H), 7.44(d, J = 2.6 Hz, 1H), 7.59(d, J = 9.4 Hz, J = 2.7 Hz, 1H). |
| 2-12 | ¹H NMR(300 MHz, DMSO-d⁶) δ 5.07(s, 2H), 6.42(d, J = 9.9 Hz, 1H), 6.62(d, J = 7.8 Hz, 1H), 6.83(s, 1H), 6.88(d, J = 8.4 Hz, 1H), 7.21(t, J = 8.1 Hz, 1H), 7.31(s, 3H), 7.68(d, J = 11.7 Hz, 1H), 8.11(s, 1H), 9.44(s, 1H). |
| 2-14 | NMR(300 MHz, CDCl₃) δ 4.50(d, J = 6.4 Hz, 2H), 5.16(s, 2H), 5.22(t, J = 4.3 Hz, 1H), 6.51(d, J = 9.0 Hz, 1H), 7.31-7.44(m, 6H), 7.54(d, J = 9.0 Hz, 2H), 7.86(dd, J = 10.7 Hz, J = 3.9 Hz, 1H), 8.27(d, J = 2.3 Hz, 1H). |
| 2-15 | ¹H NMR(300 MHz, DMSO-d⁶) δ 1.42(s, 6H), 5.05(s, 1H), 5.15(s, 2H), 6.52(d, J = 9.7 Hz, 1H), 7.32-7.43(m, 4H), 7.43-7.52(m, 3H), 7.84(dd, J = 1.8, 9.5 Hz, 1H), 8.22(d, J = 1.8 Hz, 1H). |
| 2-16 | 1H NMR(300 MHz, DMSO-d⁶) δ 1.64-1.77(m, 2H), 2.61(t, J = 7.3 Hz, 2H), 3.32-3.46(m, 2H), 4.48(t, J = 5.1 Hz, 1H), 5.15(s, 2H), 6.52(d, J = 9.5 Hz, 1H), 7.24(d, J = 8.1 Hz, 2H), 7.35-7.44(4H), 7.47(d, J = 8.1 Hz, 2H), 7.83(dd, J = 2.6 Hz, 9.5 Hz, 1H), 8.23(d, J = 2.6 Hz, 1H). |
| 2-17 | ¹H NMR(DMSO-d⁶) δ 8.28(dd, 1H, J = 2.5 Hz, J = 9.4 Hz); 7.84-7.81(dd, 1H, J = 2.5 Hz); 7.33(m, 4H); 7.30(m, 1H); 7.13(m, 2H); 6.87(d, 1H, J = 9.4 Hz); 6.49(m, 1H); 5.15(s, 2H); 3.79(s, 3H). |
| 2-18 | ¹H NMR(500 MHz, CDCl₃) δ 2.21(s, 3H), 3.85(s, 3H), 5.41(s, 2H), 6.62(d, J = 9.3 Hz, 1H), 6.93(d, J = 8.8 Hz, 2H), 7.14(m, 4H), 7.31(m, 3H). |
| 2-19 | ¹H NMR(DMSO-d⁶) δ 8.28(dd, 1H, J = 2.5 Hz, J = 9.4 Hz); 7.84-7.81(dd, 1H, J = 2.5 Hz); 7.33(m, 4H); 7.30(m, 1H); 7.13(m, 2H); 6.87(d, 1H, J = 9.45 Hz); 6.49(m, 1H); 5.15(s, 2H); 4.13-4.09(q, 2H), 1.55(t, 3H). |
| 2-22 | ¹H NMR(500 MHz, CDCl₃) δ 0.99(t, J = 7.4 Hz, 3H), 1.31(d, J = 6.1 Hz, 3H), 1.75(p, J = 6.3 Hz, 2H), 4.31(s, J = 6.1 Hz, 1H), 5.18(s, 2H), 6.72(d, J = 9.4 Hz, 1H), 6.92(d, J = 8.7 Hz, 2H), 7.24-7.34(m, 6H), 7.38(d, J = 2.6 Hz, 1H), 7.60(dd, J = 2.6 Hz, 9.4 Hz, 1H). |
| 2-23 | ¹H NMR(500 MHz, CDCl₃) δ 3.43(s, 3H), 4.49(s, 2H), 5.18(s, 2H), 6.71(d, J = 9.4 Hz, 1H), 7.26-7.41(m, 8H), 7.48(d, J = 2.6 Hz, 1H), 7.65(dd, J = 9.4 Hz, J = 2.6 Hz, 1H). |
| 2-24 | ¹H NMR(500 MHz, CDCl₃) δ 3.42(s, 3H), 4.48(s, 2H), 5.19(s, 2H), 6.72(d, J = 9.5 Hz, 1H), 7.34(m, 8H), 7.46(d, J = 2.2 Hz, 1H), 7.63(dd, J = 9.4 Hz, J = 2.7 Hz, 1H). |
| 2-25 | ¹H NMR(300 MHz, DMSO-d⁶) δ 1.15(t, J = 6.9 Hz, 3H), 3.47(q, J = 6.9 Hz, 2H), 4.45(s, 2H), 5.16(s, 2H), 6.53(d, J = 9.6 Hz, 1H), 7.32-7.40(4H), 7.55(d, J = 8.4 Hz, 2H), 7.85(dd, J = 2.7 Hz and 9.3 Hz, 1H), 8.28(d, J = 2.7 Hz, 1H). |
| 2-29 | ¹H NMR(500 MHz, CDCl₃) δ 1.32(t, J = 7.1 Hz, 3H), 4.29(q, J = 7.1 Hz, 2H), 4.64(s, 2H), 5.17(s, 2H), 6.70(d, J = 9.4 Hz, 1H), 6.94(d, J = 8.9 Hz, 2H), 7.28-7.34(m, 6H), 7.39(d, J = 2.6 Hz, 1H), 7.58(dd, J = 2.7 Hz, J = 9.4 Hz, 1H). |
| 2-30 | ¹H NMR(500 MHz, DMSO-d⁶) δ 2.58(s, 3H), 5.17(s, 2H), 6.55(d, J = 9.4 Hz, 1H), 7.37-7.42(4H), 7.74(d, J = 2.6 Hz, 2H), 7.95(dd, J = 2.6 Hz and 9.4 Hz, 1H), 7.99(d, J = 8.6 Hz, 2H), 8.45(d, J = 2.6 Hz, 1H). |
| 2-32 | ¹H NMR(DMSO-d⁶) δ 12.10(s, 1H); 8.23(dd, 1H, J = 2.5 Hz, J = 9.4 Hz); 7.84-7.81(dd, 1H, J = 2.5 Hz); 7.48-7.47(m, 2H); 7.39(m, 4H); 7.27-7.26(m, 2H); 6.52(d, 1H, J = 9.4 Hz); 5.15(s, 2H); 3.58(s, 3H); 2.82(m, 2H); 2.52(m, 2H). |
| 2-34 | ¹H NMR(300 MHz, CDCl₃) δ 3.64(s, 2H), 3.70(s, 3H), 5.17(s, 2H), 6.71(d, J = 9.5 Hz, 1H), 7.28-7.35(8H), 7.43(d, J = 2.6 Hz, 1H), 7.61(dd, J = 2.8 Hz and 9.5 Hz, 1H). |
| 2-35 | ¹H NMR(500 MHz, DMSO-d⁶) δ 2.67(t, J = 8.0 Hz, 2H), 2.87(t, J = 7.6 Hz, 2H), 3.57(s, 3H), 5.15(s, 2H), 6.52(d, J = 9.4 Hz, 1H), 7.15(d, J = 7.4 Hz, 1H), 7.32(t, J = 7.6 Hz, 1H), 7.36-7.41(m, 5H), 7.44(s, 1H), 7.85(dd, J = 2.7 Hz, J = 9.5 Hz, 1H), 8.25(d, J = 2.6 Hz, 1H). |
| 2-36 | ¹H NMR(DMSO-d⁶) δ 8.23(dd, 1H, J = 2.5 Hz, J = 9.4 Hz); 7.84-7.81(dd, 1H, J = 2.5 Hz); 7.48-7.47(m, 2H); 7.39(m, 4H); 7.27-7.26(m, 2H); 6.52(d, 1H, J = 9.4 Hz); 5.15(s, 2H); 3.58(s, 3H) 2.82(m, 2H); 2.52(m, 2H). |
| 2-42 | ¹H NMR(300 MHz, DMSO-d⁶) δ 1.80(s, 3H), 3.18-3.27(m, 2H), 3.42(t, J = 6.0 Hz, 2H), 4.48(s, 2H), 5.16(s, 2H), 6.52(d, J = 9.6 Hz, 1H), 7.35-7.42(6H), 7.56(d, J = 7.8 Hz, 2H), 7.86(dd, J = 2.7 Hz and 9.6 Hz, 2H), 8.28(d, J = 2.7 Hz, 1H). |
| 2-44 | ¹H NMR(300 MHz, DMSO-d⁶) δ 2.56(d, J = 4.6 Hz, 3H), 3.36(s, 2H), 5.15(s, 2H), 6.52(d, J = 9.5 Hz, 1H), 7.29(d, J = 8.2 Hz, 2H), 7.33-7.45(4H), 7.49(d, J = 8.2 Hz, 2H), 7.83(dd, J = 2.6 Hz, 9.45 Hz, 1H), 7.92-8.01(m, 1H), 8.24(d, J = 2.6 Hz, 1H). |
| 2-50 | ¹H NMR(400 MHz, CDCl₃) δ 7.58(dd, 1H, J = 9.5, 2.6 Hz); 7.34(d, 1H, J = 2.6 Hz); 7.26-7.33(m, 4H); 7.17(d, 2H, J = 8.7 Hz); 6.67(d, 1H, J = 9.5 Hz); 6.64(d, 2H, J = 8.4 Hz); 5.15(s, 2H); 4.43(s, 1H); 3.16(t, 2H, J = 5.8 Hz); 2.58(t, 2H, J = 5.8 Hz); 2.27(s, 6H). |
| 2-51 | ¹H NMR(500 MHz, DMSO-d⁶) δ 3.99(s, 2H), 5.13(s, 2H), 6.48(d, J = 9.5 Hz, 1H), 7.25(d, J = 8.4 Hz, 2H), 7.35-7.40(4H), 7.42(d, J = 8.4 Hz, 2H), 7.80(dd, J = 2.7 Hz and 9.5 Hz, 1H), 8.21(d, J = 2.5 Hz, 1H). |
| 2-52 | ¹H NMR(500 MHz, CDCl₃) δ 2.51(s, 3H), 5.18(s, 2H), 6.71(d, J = 9.4 Hz, 1H), 7.30(m, 8H), 7.43(d, J = 2.6 Hz, 1H), 7.61(dd, J = 9.4 Hz, J = 2.7 Hz, 1H). |

TABLE 18-continued

NMR-data

| Co.Nr | NMR-data |
|---|---|
| 2-55 | $^1$H NMR(500 MHz, DMSO-d$^6$) δ 3.00(s, 3H), 5.16(s, 2H), 6.54(d, J = 9.4 Hz, 1H), 7.12-7.17(m, 1H), 7.26-7.31(m, 2H), 7.34-7.43(5H), 7.74(dd, J = 2.6 Hz and 9.4 Hz, 1H), 8.19(d, J = 2.6 Hz, 1H), 9.70-9.80(br. s, 1H). |
| 2-56 | $^1$H NMR(300 MHz, DMSO-d$^6$) δ 2.88(s, 3H), 3.76(s, 3H), 5.08(s, 2H), 6.44(d, J = 10.9 Hz, 1H), 7.05(d, J = 10.9 Hz, 1H), 7.27-7.35(m, 3H), 7.42-7.60(m, 3H), 7.68(dd, J = 3.5 Hz, J = 10.9 Hz, 1H), 8.08(d, J = 3.5 Hz, 1H), 8.94(s, 1H). |
| 2-57 | $^1$H NMR(500 MHz, CDCl$_3$) δ 1.45(s, 9H), 5.12(s, 2H), 6.09(q, J = 1.8 Hz, 1H), 6.18(t, J = 3.3 Hz, 1H), 6.60(d, J = 9.4 Hz, 1H), 7.29-7.34(m, 5H), 7.35(dd, J = 2.5 Hz, J = 9.4 Hz, 1H). |
| 2-58 | $^1$H NMR(500 MHz, CDCl$_3$) δ 5.13(s, 2H), 5.32(s, 2H), 6.66(d, J = 9.4 Hz, 1H), 7.25(m, 3H), 7.35(m, 8H), 7.45(dd, J = 9.4 Hz, J = 2.6 Hz, 1H), 7.59(s, 1H). |
| 2-59 | $^1$H NMR(500 MHz, CDCl$_3$) δ 5.15(s, 2H), 6.46(m, 1H), 6.68(d, J = 9.8 Hz, 1H), 7.32(m, 5H), 7.45(t, 1.7 Hz, 1H), 7.48(dd, J = 9.4 Hz, J = 2.6 Hz, 1H), 7.55(s, 1H). |
| 2-62 | $^1$H NMR(500 MHz, DMSO-d$^6$) δ 3.86(s, 3H), 5.12(s, 2H), 6.52(d, J = 9.4 Hz, 1H), 6.87(dd, J = 0.6 Hz and 8.6 Hz, 1H), 7.37-7.41(4H), 7.83(dd, J = 2.7 Hz and 9.4 Hz, 1H), 7.90(dd, J = 2.6 Hz and 8.6 Hz, 1H), 8.37(d, J = 2.5 Hz, 1H), 8.37(dd, J = 0.6 Hz and 2.6 Hz, 1H). |
| 2-67 | $^1$NMR(500 MHz, CDCl$_3$) δ 5.20(s, 2H), 6.58(s, 1H), 6.76(d, J = 9.4 Hz, 1H), 7.19(d, J = 1.8 Hz, 1H), 7.34(s, 5H), 7.44(d, J = 8.4 Hz, 1H), 7.47(s, 1H), 7.62(s, 1H), 7.71(dd, J = 9.4 Hz, J = 2.6 Hz, 1H), 8.30(s, 1H). |
| 2-68 | $^1$H NMR(500 MHz, CDCl$_3$) δ 3.82(s, 3H), 5.20(s, 2H), 6.50(dd, J = 3.1 Hz, J = 0.8 Hz, 1H), 6.73(d, J = 9.4 Hz, 1H), 7.10(d, J = 3.1 Hz, 1H), 7.21(dd, J = 8.5 Hz, J = 1.2 Hz, 1H), 7.30-7.37(m, 5H), 7.47(d, J = 2.2 Hz, 1H), 7.60(d, J = 1.2 Hz, 1H), 7.72(dd, J = 9.40 Hz, J = 2.20 Hz, 1H). |
| 2-69 | $^1$H NMR(DMSO-d$^6$) δ 8.13(d, 1H, J = 2.8 Hz); 7.78-7.75(dd, 1H, J = 2.8 Hz, J = 9.4 Hz); 7.43-7.39(m, 5H); 7.27-7.25(m, 1H); 6.78(d, 1H, J = 9.4 Hz); 6.49-6.47(m, 1H); 5.15(m, 2H); 4.56-4.52(m, 2H); 3.21-3.18(m, 2H). |
| 2-70 | $^1$H NMR(500 MHz, CDCl$_3$) δ 5.23(s, 2H), 6.81(d, J = 9.4 Hz, 1H), 7.35(m, 4H), 7.60(dd, J = 8.2 Hz, J = 0.9 Hz, 1H), 7.62(d, J = 2.7 Hz, 1H), 7.72(d, J = 1.6 Hz, 1H), 7.75(dd, J = 9.4 Hz, J = 2.7 Hz, 1H), 7.84(dd, J = 8.2 Hz, J = 1.6 Hz, 1H), 8.11(d, J = 2.3 Hz, 1H), 8.20(d, J = 8.7 Hz, 1H), 8.96(d, J = 2.3 Hz, 1H). |
| 2-72 | $^1$H NMR(300 MHz, CDCl$_3$) δ 5.15(s, 2H), 6.72(d, J = 9.5 Hz, 1H), 7.26(m, 4H), 7.61(d, J = 2.6 Hz, 1H), 7.71(m, 2H), 8.01(m, 1H), 8.07(d, J = 8.6 Hz, 1H), 8.77(d, J = 6.2 Hz, 2H) |
| 3-01 | $^1$H NMR(500 MHz, CDCl$_3$) δ 7.33(dd, 2H); 7.24(dd, 2H); 7.14(dd, 1H, J = 2.6 Hz, J = 9.5 Hz); 7.08(dd, 2H); 7.01-6.98(m, 3H); 6.57(d, 1H, J = 9.3 Hz); 5.07(s, 2H); 3.65(s, 2H). |
| 3-02 | $^1$H NMR(500 MHz, CDCl$_3$) δ 3.65(s, 2H), 3.78(s, 3H), 5.08(s, 2H), 6.57(d, J = 9.3 Hz, 1H), 6.63-6.66(m, 1H), 6.70-6.73(m, 1H), 6.76-6.80(m, 1H), 7.02(d, J = 1.9 Hz, 1H), 7.18(dd, J = 2.5 Hz and 9.3 Hz, 1H), 7.21-7.25(3H), 7.32(d, J = 8.5 Hz, 2H). |
| 3-05 | $^1$H NMR(300 MHz, CDCl$_3$) δ 0.75(t, J = 7.0 Hz, 3H), 1.15(s, J = 7.0 Hz, 2H), 1.40(q, J = 7.1 Hz, 2H), 2.21(t, J = 8.0 Hz, 2H), 3.25(s, 3H), 6.25(d, J = 9.2 Hz, 1H), 7.20(d, J = 8.4 Hz, 2H), 7.25(dd, J = 2.5 Hz, J = 9.2 Hz, 1H), 7.30(d, J = 8.4 Hz, 2H), 7.49(d, J = 2.5 Hz, 1H). |
| 3-07 | $^1$H NMR(500 MHz, DMSO-d$^6$) δ 2.88(s, 3H), 4.25(s, 2H), 5.03(s, 2H), 6.37(d, J = 9.3 Hz, 1H), 6.61-6.66(m, 1H), 6.75(dd, J = 0.9 Hz and 8.8 Hz, 2H), 7.11-7.17(m, 2H), 7.21-7.25(m, 2H), 7.30(dd, J = 2.6 Hz and 9.3 Hz, 1H), 7.33-7.38(m, 2H), 7.67(d, J = 2.0 Hz, 1H). |
| 3-08 | $^1$NMR(300 MHz, DMSO-d$^6$) δ 2.03(s, 3H), 3.23(s, 2H), 3.44(s, 2H), 5.06(s, 2H), 6.42(d, J = 9.3 Hz, 1H), 7.22-7.31(m, 7H), 7.37-7.68(m, 3H), 7.68(s, 1H). |
| 3-09 | $^1$H NMR(500 MHz, CDCl$_3$) δ 7.79(d, 1H, J = 2.5 Hz); 7.41(d, 2H); 7.37(dd, 2H); 7.34(d, 2H); 7.25(dd, 1H, J = 9.4 Hz, J = 2.6 Hz); 7.15(dd, 2H); 6.36(d, 1H, J = 9.4 Hz); 5.92(d, 1H, J = 4.0 Hz); 5.48(d, 1H, J = 3.7 Hz); 5.05(dd, 2H, J = 6.2 Hz, J = 4.5 Hz). |
| 3-10 | $^1$H NMR(500 MHz, CDCl$_3$) δ 2.13(d, J = 3.4 Hz, 1H), 3.80(s, 3H), 5.09(s, 2H), 5.56(d, J = 3.5 Hz, 1H), 6.57(d, J = 9.4 Hz, 1H), 6.84-6.90(3H), 7.22-7.35(5H). |
| 3-12 | $^1$H NMR(500 MHz, CDCl$_3$) δ 3.83(s, 3H), 5.13(s, 2H), 6.65(d, J = 9.6 Hz, 1H), 7.11-7.17(3H), 7.26-7.29(m, 2H), 7.33-7.39(3H), 7.89(dd, J = 2.6 Hz and 9.6 Hz, 1H), 7.97(s, 1H). |
| 3-17 | $^1$H NMR(400 MHz, CDCl$_3$) δ ppm 7.27-7.32(m, 2H); 7.19-7.25(m, 3H); 7.14-7.19(m, 2H, J = 8.3 Hz); 6.85-6.90(m, 2H); 6.72(d, 1H, J = 3.1 Hz); 6.58(d, 1H, J = 9.7 Hz); 5.03(s, 2H); 4.75(s, 2H); 3.82(s, 3H) |
| 3-21 | $^1$H NMR(300 MHz, CDCl$_3$) δ 3.24(s, 3H), 5.02(s, 2H), 5.56(dd, J = 2.7 Hz and 7.7 Hz, 1H), 5.74(d, J = 2.7 Hz, 1H), 6.92(d, J = 7.7 Hz, 1H), 7.07-7.12(m, 2H), 7.13-7.18(m, 2H), 7.23(d, J = 8.4 Hz, 2H), 7.30(d, J = 8.4 Hz, 2H). |
| 4-01 | $^1$H NMR(300 MHz, CDCl$_3$) δ 0.39-0.46(m, 2H), 0.60-0.67(m, 2H), 1.23-1.38(m, 1H), 3.84(s, 3H), 3.87(d, J = 7.2 Hz, 2H), 6.66(d, J = 9.5 Hz, 1H), 6.96(d, J = 8.7 Hz, 2H), 7.33(d, J = 8.7 Hz, 2H), 7.51(d, J = 2.6 Hz, 1H), 7.58(dd, J = 2.8 Hz and 9.5 Hz, 1H). |
| 4-02 | $^1$H NMR(300 MHz, CDCl$_3$) δ 1.21-1.36(m, 2H), 1.48-1.83(6H), 2.37-2.50(m, 1H), 3.84(s, 3H), 3.94(d, J = 7.7 Hz, 2H), 6.65(d, J = 9.5 Hz, 1H), 6.95(d, J = 8.4 Hz, 2H), 7.32(d, J = 8.4 Hz, 2H), 7.39(d, J = 2.6 Hz, 1H), 7.56(dd, J = 2.8 Hz and 9.5 Hz, 1H). |
| 4-03 | $^1$H NMR(300 MHz, CDCl$_3$) δ 0.85-1.09(m, 2H), 1.09-1.32(m, 3H), 1.53-1.78(m, 5H), 1.78-2.00(m, 1H), 3.74(d, J = 7.3 Hz, 2H), 3.77(s, 3H), 6.57(d, J = 9.4 Hz, 1H), 6.88(d, J = 8.7 Hz, 2H), 7.29-7.35(3H), 7.49(dd, J = 2.7 Hz, 9.4 Hz, 1H). |
| 4-06 | $^1$H NMR(500 MHz, CDCl$_3$) δ 2.34(s, 3H), 3.83(s, 3H), 5.17(s, 2H), 6.70(d, J = 9.3 Hz, 1H), 6.92(d, J = 8.8 Hz, 2H), 7.16(d, J = 7.8 Hz, 2H), 7.23-7.29(m, 4H), 7.40(d, J = 2.6, 1H), 7.57(dd, J = 9.3 Hz, J = 2.6 Hz, 1H). |
| 4-07 | $^1$H NMR(500 MHz, CDCl$_3$) δ 3.84(s, 3H), 5.16(s, 2H), 6.70(d, J = 10.0 Hz, 1H), 6.94(d, J = 13.0 Hz, 2H), 7.10(t, J = 9.0 Hz, 2H), 7.16(t, J = 9.0 Hz, 1H), 7.27(m, 3H), 7.38(d, J = 4.0 Hz, 1H), 7.59(dd, J = 1.5 Hz, J = 9.0 Hz, 1H). |
| 4-08 | $^1$H NMR(500 MHz, CDCl$_3$) δ 3.84(s, 3H), 5.25(s, 2H), 6.67(d, J = 9.4 Hz, 1H), 6.93-6.96(m, 2H), 7.06-7.16(2H), 7.28-7.33(3H), 7.47-7.52(m, 1H), 7.53-7.55(m, 1H), 7.58(dd, J = 2.6 Hz and 9.4 Hz, 1H). |
| 4-09 | $^1$H NMR(500 MHz, CDCl$_3$) δ 3.83(s, 3H), 5.21(s, 2H), 6.72(d, J = 9.4 Hz, 1H), 6.94(d, J = 8.8 Hz, 2H), 7.01(m, 1H), 7.04(d, J = 9.5 Hz, 1H), 7.12(d, J = 8.2 Hz, 1H), 7.29(d, J = 8.8 Hz, 2H), 7.32(m, 1H), 7.39(d, J = 2.6 Hz, 1H), 7.61(dd, J = 9.4 Hz, J = 2.6 Hz, 1H). |
| 4-10 | $^1$H NMR(500 MHz, CDCl$_3$) δ 3.83(s, 3H), 5.18(s, 2H), 6.70(d, J = 9.4 Hz, 1H), 6.94(d, J = 8.8 Hz, 2H), 7.04(m, 2H), 7.28(d, J = 8.8 Hz, 2H), 7.35(m, 2H), 7.40(d, J = 2.7 Hz, 1H), 7.59(dd, J = 9.4 Hz, J = 2.7, 1H). |
| 4-11 | $^1$H NMR(500 MHz, CDCl$_3$) δ 3.84(s, 3H), 5.15(s, 2H), 6.71(d, J = 9.4, 1H), 6.95(d, J = 8.8 Hz, 2H), 7.07-7.22(m, 3H), 7.29(d, J = 8.8 Hz, 2H), 7.39(d, J = 2.6 Hz, 1H), 7.61(dd, J = 9.4 Hz, J = 2.6 Hz, 1H). |
| 4-12 | $^1$H NMR(500 MHz, CDCl$_3$) δ 3.76(s, 3H), 5.16(s, 2H), 6.48(d, J = 9.4 Hz, 1H), 6.96-7.01(m, 2H), 7.02-7.08(m, 1H), 7.22-7.30(2H), 7.45-7.50(m, 2H), 7.81(dd, J = 2.7 Hz and 9.4 Hz, 1H), 8.08(d, J = 2.7 Hz, 1H). |
| 4-13 | $^1$H NMR(500 MHz, CDCl$_3$) δ 3.76(s, 3H), 5.24(s, 2H), 6.50(d, J = 9.4 Hz, 1H), 6.93-7.01(3H), 7.13-7.19(m, 1H), 7.32-7.39(m, 1H), 7.47-7.51(m, 2H), 7.83(dd, J = 2.7 Hz and 9.4 Hz, 1H), 8.12(d, J = 2.7 Hz, 1H). |
| 4-14 | $^1$H NMR(500 MHz, CDCl$_3$) δ 3.84(s, 3H), 5.14(s, 2H), 6.71(d, J = 9.4 Hz, 1H), 6.95(d, J = 8.8 Hz, 2H), 7.10-7.14(m, 1H), 7.23-7.27(m, 1H), 7.30(d, J = 8.8 Hz, 2H), 7.39(d, J = 2.5 Hz, 1H), 7.42(dd, J = 2.1 Hz, 6.9 Hz, 1H), 7.61(dd, J = 2.6 Hz, 9.4 Hz, 1H). |

TABLE 18-continued

NMR-data

| Co.Nr | NMR-data |
|---|---|
| 4-15 | $^1$H NMR(500 MHz, CDCl$_3$) δ 3.84(s, 3H), 5.16(s, 2H), 6.71(d, J = 9.4 Hz, 1H), 6.95(d, J = 8.7 Hz, 2H), 7.09(d, J = 8.2 Hz, 1H), 7.15(dd, J = 8.2 Hz, J = 1.89, 1H), 7.28(t, J = 8.7 Hz, 2H), 7.38(m, 2H), 7.61(dd, J = 9.4 Hz, J = 2.6 Hz, 1H). |
| 4-16 | $^1$H NMR(500 MHz, CDCl$_3$) δ 3.84(s, 3H), 5.19(s, 2H), 6.66(d, J = 9.4 Hz, 1H), 6.95(d, J = 8.8 Hz, 2H), 7.13(m, 2H), 7.31(d, J = 8.8 Hz, 2H), 7.49(dd, J = 8.6 Hz, J = 8.0 Hz, 1H), 7.52(m, 1H), 7.59(dd, J = 9.4 Hz, J = 2.6 Hz, 1H). |
| 4-17 | $^1$H NMR(500 MHz, CDCl$_3$) δ 3.77(s, 3H), 5.15(s, 2H), 6.40(d, J = 9.4 Hz, 1H), 6.97-7.02(m, 2H), 7.14-7.22(m, 2H), 7.42-7.49(m, 2H), 7.77(dd, J = 2.7 Hz and 9.4 Hz, 1H), 8.09(s, 1H). |
| 4-20 | $^1$H NMR(500 MHz, CDCl$_3$) δ 3.83(s, 3H), 5.17(s, 2H), 6.70(d, J = 9.4 Hz, 1H), 6.94(d, J = 8.8 Hz, 2H), 7.28(d, J = 8.8 Hz, 2H), 7.29-7.35(m, 4H), 7.38(d, J = 2.6 Hz, 1H), 7.59(dd, J = 9.4 Hz, J = 2.6 Hz, 1H). |
| 4-21 | $^1$H NMR(500 MHz, CDCl$_3$) δ 3.84(s, 3H), 5.17(s, 2H), 6.71(d, J = 9.4 Hz, 1H), 6.95(dd, J = 2.1 Hz, J = 8.3 Hz, 1H), 7.30(m, 2H), 7.38(d, J = 2.6 Hz, 1H), 7.42(d, J = 8.3 Hz, 1H), 7.45(d, J = 2.1 Hz, 1H), 7.61(dd, J = 2.6 Hz, J = 9.4 Hz, 1H). |
| 4-22 | $^1$H NMR(500 MHz, CDCl$_3$) δ 3.80(s, 3H), 3.83(s, 3H), 5.19(s, 2H), 6.70(d, J = 9.4 Hz, 1H), 6.85(dd, J = 2.4 Hz, J = 7.67 Hz, 1H), 6.83-6.95(m, 4H), 7.26-7.29(m, 3H), 7.40(d, J = 2.5, 1H), 7.58(dd, J = 2.7 Hz, J = 9.4 Hz, 1H). |
| 4-23 | $^1$H NMR(500 MHz, CDCl$_3$) δ 3.80(s, 3H), 3.83(s, 3H), 5.15(s, 2H), 6.69(d, J = 9.4 Hz, 1H), 6.89(d, J = 8.6 Hz, 2H), 6.92(d, J = 8.8 Hz, 2H), 7.27(d, J = 8.8 Hz, 2H), 7.31(d, J = 8.6 Hz, 2H), 7.40(d, J = 2.6 Hz, 1H), 7.56(dd, J = 9.4 Hz, J = 2.6 Hz). |
| 4-25 | $^1$H NMR(300 MHz, CDCl$_3$) δ 3.25(s, 3H), 3.77(s, 3H), 4.36(s, 2H), 5.15(s, 2H), 6.50(d, J = 9.3 Hz, 1H), 6.98(d, J = 9.0 Hz, 2H), 7.25-7.39(m, 4H), 7.49(d, J = 9.0 Hz, 2H), 7.80(dd, J = 2.7 Hz and 9.6 Hz, 1H), 8.15(d, J = 2.7 Hz, 1H). |
| 4-26 | $^1$H NMR(300 MHz, DMSO-d$^6$) δ 1.11(t, J = 7.1 Hz, 3H), 3.45(q, J = 7.1 Hz, 2H), 3.68(s, 3H), 4.40(s, 2H), 5.15(s, 2H), 6.50(d, J = 9.5 Hz, 1H), 6.97(d, J = 9.0 Hz, 2H), 7.32(q, J = 8.2 Hz, 4H), 7.50(d, J = 8.7 Hz, 2H), 7.80(dd, J = 2.8 Hz, J = 9.5 Hz, 1H), 8.15(d, J = 2.6 Hz, 1H). |
| 4-27 | $^1$H NMR(500 MHz, CDCl$_3$) δ 3.83(s, 3H), 3.92(s, 3H), 5.29(s, 2H), 6.72(d, J = 9.7 Hz, 1H), 6.93(d, J = 8.8 Hz, 2H), 7.29(s, 2H), 7.40(m, 3H), 7.62(dd, J = 2.8 Hz, J = 9.7 Hz, 1H), 8.03(d, J = 8.3 Hz, 2H). |
| 4-28 | $^1$H NMR(300 MHz, CDCl$_3$) δ 2.28(s, 3H), 3.82(s, 3H), 5.19(s, 2H), 6.69(d, J = 9.5 Hz, 1H), 6.92(d, J = 8.2 Hz, 2H), 7.07(d, J = 8.2 Hz, 2H), 7.23-7.30(m, 2H), 7.34-7.36(m, 1H), 7.36-7.43(m, 2H), 7.58(dd, J = 2.8 Hz and 9.5 Hz, 1H). |
| 4-30 | $^1$H NMR(500 MHz, CDCl$_3$) δ 3.84(s, 3H), 5.26(s, 2H), 6.72(d, J = 9.4 Hz, 1H), 6.95(d, J = 8.8 Hz, 2H), 7.30(d, J = 8.8 Hz, 2H), 7.39(d, J = 2.6 Hz, 1H), 7.44(d, J = 8.5 Hz, 2H), 7.62(d, J = 2.6, 1H), 7.65(m, 2H). |
| 4-31 | $^1$H NMR(500 MHz, CDCl$_3$) δ 3.76(s, 3H), 5.17(s, 2H), 6.50(d, J = 9.4 Hz, 1H), 6.97(d, J = 8.8 Hz, 2H), 7.33(d, J = 8.0 Hz, 2H), 7.45-7.51(4H), 7.80(dd, J = 2.7 Hz and 9.4 Hz, 1H), 8.19(d, J = 2.7 Hz, 1H). |
| 4-32 | $^1$H NMR(500 MHz, CDCl$_3$) δ 3.84(s, 3H), 5.30(s, 2H), 6.72(d, J = 9.4 Hz, 1H), 6.95(m, 2H), 7.31(m, 2H), 7.44(d, J = 2.4 Hz, 1H), 7.55(t, J = 7.9 Hz, 1H), 7.64(dd, J = 2.6 Hz, J = 9.5 Hz, 1H), 7.73(d, J = 7.7 Hz, 1H), 8.18(m, 2H). |
| 4-34 | $^1$H NMR(500 MHz, CDCl$_3$) δ 3.85(s, 3H), 5.27(s, 2H), 6.68(d, J = 9.4 Hz, 1H), 6.96(d, J = 8.8 Hz, 2H), 7.32(d, J = 6.7 Hz, 2H), 7.37(d, J = 9.9 Hz, 1H), 7.42(d, J = 8.0 Hz, 1H), 7.53(s, 1H), 7.62(m, 2H). |
| 4-35 | $^1$H NMR(500 MHz, CDCl$_3$) δ 3.84(s, 3H), 5.24(s, 2H), 6.73(d, J = 9.5 Hz, 1H), 6.95(d, J = 8.8 Hz, 2H), 7.19(m, 2H) 7.31(d, J = 8.8 Hz, 2H), 7.40(d, J = 2.5 Hz, 1H), 7.59(t, J = 7.6 Hz, 1H), 7.64(dd, J = 2.6 Hz, J = 9.5 Hz, 1H). |
| 4-36 | $^1$H NMR(500 MHz, CDCl$_3$) δ 1.57(s, 3H), 3.84(s, 3H), 5.28(s, 2H), 6.71(d, J = 9.4 Hz, 1H), 6.92(d, J = 8.8 Hz, 2H), 7.29(d, J = 8.8 Hz, 1H), 7.40(d, J = 2.5 Hz, 1H), 7.46(d, J = 8.1 Hz, 2H), 7.62(m, 3H). |
| 4-37 | $^1$H NMR(500 MHz, CDCl$_3$) δ 3.84(s, 3H), 5.20(s, 2H), 6.72(d, J = 9.5 Hz, 1H), 6.96(m, 2H), 7.30(m, 2H), 7.40(d, J = 2.6 Hz, 1H), 7.49(s, 2H), 7.63(dd, J = 2.6 Hz, 9.4 Hz, 1H), 7.68(s, 1H). |
| 4-38 | $^1$H NMR(500 MHz, CDCl$_3$) δ 3.81(s, 3H), 5.39(s, 2H), 6.75(d, J = 9.4 Hz, 1H), 6.91(d, J = 8.8 Hz, 2H), 7.25(s, 2H), 7.45(d, J = 2.6 Hz, 1H), 7.47(d, J = 1.7 Hz, 1H), 7.49(m, 2H), 7.60(dd, J = 2.6 Hz, J = 9.4 Hz, 1H), 7.79(s, 1H), 7.83(m, 3H). |
| 4-39 | $^1$H NMR(300 MHz, DMSO) δ 3.70(s, 3H), 5.16(s, 2H), 6.43(d, J = 9.5 Hz, 1H), 6.52(d, J = 3.1 Hz, 1H), 6.91(d, J = 8.8 Hz, 2H), 7.10(m, 1H), .40(d, J = 8.8 Hz, 2H), 7.74(dd, J = 9.5 Hz, J = 2.5 Hz, 1H), 8.05(d, J = 2.5 Hz, 1H). |
| 4-41 | $^1$H NMR(500 MHz, CDCl$_3$) δ 3.84(s, 3H), 5.41(s, 2H), 6.73(d, J = 9.5 Hz, 1H), 6.95(d, J = 8.7 Hz, 2H), 7.35(d, J = 8.7 Hz, 2H), 7.52(m, 2H), 7.60(m, 2H), 7.64(dd, J = 9.5 Hz, J = 2.6 Hz, 1H), 8.12(m, 2H). |
| 4-42 | $^1$H NMR(500 MHz, CDCl$_3$) δ 3.85(s, 3H), 5.46(s, 2H), 6.73(d, J = 9.5 Hz, 1H), 6.98(d, J = 8.8 Hz, 2H), 7.13-7.18(m, 2H), 7.36(d, J = 8.8 Hz, 2H), 7.53(d, J = 2.3 Hz, 1H), 7.68(dd, J = 9.5 Hz and 2.3 Hz, 1H), 8.05-8.08(m, 2H). |
| 4-43 | $^1$H NMR(500 MHz, CDCl$_3$) δ 3.83(s, 3H), 5.22(s, 2H), 6.70(d, J = 9.4 Hz), 6.94(d, J = 8.8 Hz, 2H), 7.29(d, J = 8.8 Hz, 2H), 7.31(m, 1H), 7.42(d, J = 2.6 Hz, 1H), 7.60(dd, J = 9.4 Hz, J = 2.6 Hz, 1H), 7.75(dd, J = 7.9 Hz, J = 1.2 Hz, 1H), 8.57(dd, J = 4.7 Hz, J = 1.2, 1H), 8.65(s, 1H). |
| 4-44 | $^1$H NMR(500 MHz, CDCl$_3$) δ 3.84(s, 3H), 5.18(s, 2H), 6.70(d, J = 9.4 Hz, 1H), 6.95(d, J = 8.8 Hz, 2H), 7.29(d, J = 8.8 Hz, 2H), 7.32(d, J = 8.3 Hz, 1H), 7.41(d, J = 2.6 Hz, 1H), 7.61(dd, J = 9.4 Hz, J = 2.6 Hz, 1H), 7.75(dd, J = 8.3 Hz, J = 2.3 Hz, 1H), 8.43(d, J = 2.3 Hz, 1H). |
| 4-45 | $^1$H NMR(400 MHz, CDCl$_3$) δ 8.53(d, 1H, J = 2.1 Hz); 7.66(dd, 1H, J = 8.0, 2.4 Hz); 7.58(dd, 1H, J = 9.5, 2.7 Hz); 7.42(d, 1H, J = 2.3 Hz); 7.25-7.30(m, 2H); 7.15(dd, 1H, J = 7.9 Hz); 6.90-6.95(m, 2H); 6.69(d, 1H, J = 9.5 Hz); 5.18(s, 2H); 3.83(s, 3H); 2.81(q, 2H, J = 7.7 Hz); 1.29(t, 3H, J = 7.6 Hz). |
| 4-46 | $^1$H NMR(500 MHz, DMSO-d$^6$) δ 3.76(s, 3H), 3.80(s, 3H), 5.08(s, 2H), 6.47(d, J = 9.4 Hz, 1H), 6.78(dd, J = 0.4 Hz and 8.5 Hz, 1H), 6.95-7.00(m, 2H), 7.46-7.51(m, 2H), 7.74-7.76(m, 1H), 7.76-7.79(m, 1H), 8.20(d, J = 2.5 Hz, 1H), 8.26(d, J = 2.1 Hz, 1H). |
| 4-47 | $^1$H NMR(500 MHz, CDCl$_3$) δ 3.76(s, 3H), 5.27(s, 2H), 6.51(d, J = 9.4 Hz, 1H), 6.98(d, J = 6.7 Hz, 2H), 7.51(d, J = 6.7 Hz, 2H), 7.83(dd, J = 2.7 Hz and 9.4 Hz, 1H), 7.88(d, J = 8.2 Hz, 1H), 8.00(dd, J = 1.7 Hz and 8.2 Hz, 1H), 8.28(d, J = 2.5 Hz, 1H), 8.81(d, J = 1.7 Hz, 1H). |
| 4-50 | $^1$H NMR(300 MHz, CDCl$_3$) δ 2.47(s, 3H), 3.75(s, 3H), 5.18(s, 2H), 6.57(d, J = 9.5 Hz, 1H), 6.85-6.88(m, 2H), 7.23-7.28(m, 2H), 7.50-7.59(m, 2H), 8.30(s, 1H), 8.58(s, 1H). |
| 4-51 | $^1$H NMR(500 MHz, CDCl$_3$) δ 3.84(s, 3H), 5.46(s, 2H), 6.74(d, J = 9.5 Hz, 1H), 6.96(d, J = 8.8 Hz, 2H), 7.05-7.12(m, 1H), 7.35(d, J = 8.8 Hz, 2H), 7.40(dd, J = 8.3 Hz and 2.6 Hz, 1H), 7.46(dd, J = 9.1 Hz and 4.2 Hz, 1H), 7.58(d, J = 2.6 Hz, 1H), 7.66(dd, J = 9.5 Hz and 2.6 Hz, 1H). |
| 4-53 | $^1$H NMR(500 MHz, CDCl$_3$) δ 3.83(s, 3H), 5.59(s, 2H), 6.73(d, J = 9.4 Hz, 1H), 6.94(d, J = 8.8 Hz, 2H), 7.32(d, J = 8.8 Hz, 2H), 7.41(ddd, J = 8.3 Hz, J = 8.3 Hz, J = 1.1 Hz, 1H), 7.49(ddd, J = 8.3 Hz, J = 8.3 Hz, J = 1.2 Hz, 1H), 7.63(dd, J = 9.4 Hz, J = 2.6 Hz, 1H), 7.76(d, J = 2.6 Hz, 1H), 7.87(dd, J = 8.3 Hz, J = 1.2 Hz, 1H), 8.03(dd, J = 8.3 Hz, J = 1.1 Hz, 1H). |

TABLE 18-continued

NMR-data

| Co.Nr | NMR-data |
|---|---|
| 4-54 | $^1$H NMR(300 MHz, CDCl$_3$) δ 3.76(s, 3H), 5.52(s, 2H), 6.66(d, J = 9.4 Hz, 1H), 6.86(d, J = 8.8 Hz, 2H), 7.11(m, 1H), 7.25(d, J = 8.8 Hz, 2H), 7.29(m, 1H), 7.56(m, 1H), 7.58(m, 1H), 7.61(m, 1H). |
| 5-01 | $^1$H NMR(500 MHz, CDCl$_3$) δ 7.32(dd, 1H, J = 7.9 Hz); 7.21(dd, 1H, J = 9.3 Hz, J = 2.5 Hz); 7.00(dd, 1H, J = 9.1 Hz, J = 2.0 Hz); 6.96(dd, 2H); 6.90(dd, 1H); 6.80-6.77(m, 3H); 6.58(d, 1H, J = 9.3 Hz); 4.98(s, 2H); 3.74(s, 3H); 2.76(t, 2H, J = 7.3 Hz); 2.63(t, 2H, J = 7.3 Hz). |
| 5-02 | $^1$H NMR(300 MHz, CDCl$_3$) δ 3.60(s, 2H), 3.73(s, 3H), 5.05(s, 2H), 6.65(d, J = 9.2 Hz, 1H), 6.78(d, J = 8.1 Hz, 2H), 6.96-7.23(m, 6H), 7.37(t, J = 7.8 Hz, 1H). |
| 5-03 | $^1$H NMR(300 MHz, CDCl$_3$) δ 1.49(m, 4H), 2.28(t, J = 8.3 Hz, 2H), 2.50(t, J = 8.4 Hz, 2H), 3.69(s, 3H), 5.00(s, 2H), 6.45(d, J = 9.4 Hz, 1H), 6.73(d, J = 8.0 Hz, 2H), 6.97-7.23(m, 6H), 7.32(t, J = 8.4 Hz, 1H). |
| 5-05 | $^1$H NMR(500 MHz, CDCl$_3$) δ 1.78(d, J = 7.09 Hz, 3H), 3.81(s, 3H), 6.52(q, J = 7.09 Hz, 1H), 6.70(d, J = 9.4 Hz, 1H), 6.90(d, J = 8.8 Hz, 2H), 7.19(d, J = 8.8 Hz, 2H), 7.23(d, J = 2.6 Hz, 1H), 7.30-7.41(m, 5H), 7.54(dd, J = 9.4 Hz, J = 2.6 Hz, 1H). |
| 5-07 | $^1$H NMR(500 MHz, CDCl$_3$) δ 2.51(d, J = 7.7 Hz, 2H), 2.74(t, J = 7.8 Hz, 2H), 3.85(s, 3H), 4.03(t, J = 7.5 Hz, 2H), 6.66(d, J = 9.4 Hz, 1H), 6.96(d, J = 8.7 Hz, 2H), 7.22(m, 3H), 7.31(m, 5H), 7.58(dd, J = 9.4 Hz, J = 2.7 Hz, 1H). |
| 5-08 | $^1$H NMR(300 MHz, DMSO) δ 0.82(t, J = 7.4 Hz, 3H), 1.21(m, 2H), 1.56(m, 2H), 3.68(s, 3H), 3.84(t, J = 7.3 Hz, 2H), 6.35(d, J = 9.4 Hz, 1H), 6.89(d, J = 8.8 Hz, 2H), 7.40(d, J = 8.8 Hz, 2H), 7.66(dd, J = 9.4 Hz, J = 2.7 Hz, 1H), 7.88(d, J = 2.7 Hz, 1H). |
| 5-09 | $^1$H NMR(500 MHz, CDCl$_3$) δ 1.58(m, 2H), 1.85(m, 4H), 2.73(t, J = 7.1 Hz, 2H), 3.87(s, 3H), 4.38(t, J = 6.3 Hz, 2H), 6.78(d, J = 8.8 Hz, 1H), 6.98(d, J = 8.8 Hz, 2H), 7.26(m, 3H), 7.46(d, J = 8.8 Hz, 2H), 7.75(dd, J = 8.6 Hz, J = 2.6 Hz, 1H), 8.33(d, J = 2.5 Hz, 1H). |
| 5-10 | $^1$H NMR(300 MHz, CDCl$_3$) δ 0.90(d, J = 6.69 Hz, 6H), 2.16(m, 1H), 3.73(d, J = 7.4 Hz, 2H), 3.77(s, 3H), 6.57(d, J = 9.4 Hz, 1H), 6.88(d, J = 8.7 Hz, 2H), 7.25(d, J = 8.7 Hz, 2H), 7.27(d, J = 2.6 Hz, 1H), 7.49(dd, J = 9.4 Hz, J = 2.6 Hz, 1H). |
| 5-11 | $^1$H NMR(300 MHz, CDCl$_3$) δ 0.91(t, J = 6.7 Hz, 3H), 1.30-1.43(m, 4H), 1.73-1.85(m, 2H), 3.84(s, 3H), 3.93-4.02(m, 2H), 6.64(d, J = 9.2 Hz, 1H), 6.95(d, J = 8.5 Hz, 2H), 7.32(d, J = 8.5 Hz, 2H), 7.39(d, J = 2.6 Hz, 1H), 7.56(dd, J = 2.8 Hz and 9.5 Hz, 1H). |
| 5-13 | $^1$H NMR(300 MHz, CDCl$_3$) δ 0.91(d, J = 6.2 Hz, 6H), 1.61(m, 3H), 3.77(s, 3H), 3.93(t, J = 7.4 Hz, 2H), 6.56(d, J = 9.4 Hz, 1H), 6.88(d, J = 8.7 Hz, 2H), 7.25(d, J = 8.7 Hz, 2H), 7.31(d, J = 2.6 Hz, 1H), 7.48(dd, J = 9.4 Hz, J = 2.6 Hz, 1H). |
| 5-16 | $^1$H NMR(300 MHz, CDCl$_3$) δ 1.99(3H), 2.20(td, J = 6.8 Hz, J = 2.6 Hz, 2H), 3.77(s, 3H), 4.06(t, J = 6.8 Hz, 2H), 6.57(d, J = 9.4 Hz, 1H), 6.88(d, J = 8.6 Hz, 2H), 7.26(d, J = 8.6 Hz, 2H), 7.41(d, J = 2.6 Hz, 1H), 7.51(d, J = 9.4, J = 2.6 Hz, 1H). |
| 5-17 | $^1$H NMR(500 MHz, CDCl$_3$) δ 3.84(s, 3H), 5.95(s, 2H), 6.66(d, J = 9.4 Hz, 1H), 6.95(d, J = 8.8 Hz, 2H), 7.04(d, J = 9.1 Hz, 2H), 7.26(m, 2H), 7.31(d, J = 8.8 Hz, 2H), 7.56(d, J = 3.2 Hz, 1H), 7.60(dd, J = 2.7 Hz, 9.5 Hz, 1H). |
| 5-18 | $^1$H NMR(500 MHz, CDCl$_3$) δ 3.86(s, 3H), 4.33-4.37(m, 2H), 4.38-4.43(m, 2H), 6.67(d, J = 10.1 Hz, 1H), 6.87-6.90(m, 2H), 6.95-6.99(m, 3H), 7.25-7.30(m, 2H), 7.32-7.35(m, 2H), 7.59-7.62(m, 2H). |
| 5-20 | $^1$H NMR(500 MHz, CDCl$_3$) δ 2.77(s, 3H), 3.77(s, 3H), 4.52(s, 2H), 4.92(s, 2H), 6.48(d, J = 9.6 Hz, 1H), 7.00(d, J = 8.7 Hz, 2H), 7.26(d, J = 7.6 Hz, 2H), 7.33(d, J = 7.6 Hz, 2H), 7.40(m, 1H), 7.48(d, J = 8.7 Hz, 2H), 7.80(dd, J = 9.6 Hz, J = 2.9 Hz, 1H), 7.96(d, J = 2.9 Hz, 1H). |
| 5-22 | $^1$H NMR(500 MHz, CDCl$_3$) δ 3.0 & 3.08(s, 3H), 3.84(s, 3H), 4.59 & 4.85(s, 2H), 4.69-4.82(s, 2H), 6.65-6.70(d, J = 9.4 Hz, 1H), 6.95(d, J = 8.6 Hz, 2H), 7.02(dd, J = 8.6 Hz, J = 1.9 Hz, 2H), 7.09(m, 1H), 7.22-7.31(m, 2H), 7.34(m, 2H), 7.47(d, J = 2.2 Hz, 1H), 7.63-7.66(dd, J = 9.4 Hz, J = 2.2 Hz, 1H). |
| 5-23 | $^1$H NMR(500 MHz, DMSO) mixture 2:1 of isomers δ 2.81(s, 3Hb), 3.06(s, 3Ha), 3.77(s, 3Ha, 3Hb), 4.62(s, 2Ha), 4.79(s, 2Hb), 4.90(s, 2Hb), 4.94(s, 2Ha), 6.44-6.49(m, 1Ha, 1Hb), 6.99(d, J = 8.8 Hz, 2Ha, 2Hb), 7.45-7.49(m, 4Ha, 4Hb), 7.60-7.63(m, 1Hb), 7.70(d, J = 8.1 Hz, 2Ha), 7.75-7.80(m, 1Hb), 7.81(dd, J = 2.7 Hz and 9.4 Hz, 1Ha, 1Hb), 7.94-7.97(m, 1Ha, 1Hb). |
| 5-24 | $^1$H NMR(500 MHz, CDCl$_3$) mixture 2:1 of isomers δ 2.79(s, 3Hb), 3.05(s, 3Ha), 3.77(s, 3Ha, 3Hb), 4.54(s, 2Ha), 4.70(s, 2Hb), 4.93(s, 2Hb), 4.93(s, 2Ha), 6.47(d, J = 9.5 Hz, 1Hb), 6.49(d, J = 9.5 Hz, 1Ha), 7.00(d, J = 8.5 Hz, 2Ha, 2Hb), 7.23(d, J = 7.6 Hz, 1Ha), 7.30-7.35(m, 2Ha, 2Hb), 7.35-7.41(m, 1Ha, 3Hb), 7.41-7.51(m, 2Ha, 2Hb), 7.82(dd, J = 2.8 Hz and 9.5 Hz, 1Ha, 1Hb), 7.96(d, J = 2.5 Hz, 1Ha), 7.98(d, J = 2.5 Hz, 1Hb). |
| 5-25 | $^1$H NMR(500 MHz, DMSO) mixture 2:1 of isomers δ 2.78(s, 3Hb), 3.02(s, 3Ha), 3.73(s, 3Ha), 3.77(s, 3Ha, 3Hb), 3.79(s, 3Hb), 4.50(s, 2Ha), 4.63(s, 2Hb), 4.93(s, 2Ha, 2Hb), 6.43-6.49(m, 1Ha, 1Hb), 6.77-6.90(m, 3Ha, 3Hb), 6.95-7.03(m, 2Ha, 2Hb), 7.22-7.26(m, 1Ha), 7.29-7.33(m, 1Hb), 7.44-7.50(m, 2Ha, 2Hb), 7.81(dd, J = 2.1 Hz and 9.4 Hz, 1Ha, 1Hb), 7.93-7.97(m, 1Ha, 1Hb). |
| 6-04 | $^1$H NMR(500 MHz, CDCl$_3$) δ 2.38(s, 3H), 5.21(s, 2H), 6.72(d, J = 9.4 Hz, 1H), 7.00(dd, J = 8.3 Hz, J = 2.5 Hz, 1H), 7.04(ddd, J = 9.6 Hz, J = 2.3 Hz, J = 1.7 Hz, 1H), 7.12(dd, J = 7.7 Hz, J = 0.6 Hz, 1H), 7.21(d, J = 8.0 Hz, 2H), 7.26(d, J = 8.0 Hz, 2H), 7.32(m, 1H), 7.44(d, J = 2.6 Hz, 1H), 7.63(dd, J = 9.4 Hz, J = 2.6 Hz, 1H). |
| 6-10 | $^1$H NMR(500 MHz, CDCl$_3$) δ 3.85(s, 3H), 5.15(s, 2H), 6.71(d, J = 9.4 Hz, 1H), 6.86-6.91(2H), 6.94-6.97(m, 1H), 7.07-7.11(m, 1H), 7.11-7.16(m, 1H), 7.16-7.23(m, 1H), 7.31-7.36(m, 1H), 7.46(d, J = 2.6 Hz, 1H), 7.63(dd, J = 2.6 Hz and 9.4 Hz, 1H). |
| 6-11 | $^1$H NMR(500 MHz, CDCl$_3$) δ 3.41(s, 3H), 4.48(s, 2H), 5.16(s, 2H), 6.72(d, J = 9.4 Hz, 1H), 7.07-7.23(3H), 7.34-7.42(4H), 7.46(d, J = 2.6 Hz, 1H), 7.65(dd, J = 2.6 Hz and 9.4 Hz, 1H). |
| 6-14 | $^1$H NMR(500 MHz, DMSO-d$^6$) δ 2.98(s, 3H), 5.12(s, 2H), 6.51(d, J = 9.5 Hz, 1H), 7.24(d, J = 8.7 Hz, 3H), 7.39-7.62(m, 4H), 7.81(dd, J = 2.7 Hz, J = 9.5 Hz, 1H), 8.23(d, J = 2.6 Hz, 1H). |
| 6-15 | $^1$H NMR(500 MHz, CDCl$_3$) δ 5.12(s, 2H), 6.51(d, J = 9.4 Hz, 1H), 7.08(dd, J = 3.6 and 5.1 Hz, 1H), 7.18-7.23(m, 1H), 7.32(dd, J = 1.2 Hz and 3.6 Hz, 1H), 7.38-7.43(m, 1H), 7.44-7.49(2H), 7.77(dd, J = 2.7 Hz and 9.5 Hz, 1H), 8.24(d, J = 2.5 Hz, 1H). |
| 6-16 | $^1$H NMR(500 MHz, CDCl$_3$) δ 3.84(s, 3H), 5.11(s, 2H), 6.52(d, J = 9.4 Hz, 1H), 6.88(d, J = 8.6 Hz, 1H), 7.22-7.26(m, 1H), 7.36-7.43(m, 1H), 7.46-7.52(m, 1H), 7.83(dd, J = 2.7 Hz and 9.4 Hz, 1H), 7.91(dd, J = 2.6 Hz and 8.6 Hz, 1H), 8.26(d, J = 2.6 Hz, 1H), 8.38(d, J = 2.7 Hz, 1H). |
| 6-17 | $^1$H NMR(500 MHz, CDCl$_3$) δ 3.25(t, J = 8.7 Hz, 2H), 4.62(t, J = 8.7 Hz, 2H), 5.15(s, 2H), 6.70(d, J = 9.4 Hz, 1H), 6.82(d, J = 8.3 Hz, 1H), 7.07-7.16(3H), 7.16-7.22(2H), 7.36(d, J = 2.6 Hz, 1H), 7.59(dd, J = 2.6 Hz and 9.4 Hz, 1H). |
| 6-19 | $^1$H NMR(500 MHz, CDCl$_3$) δ 5.26(s, 2H), 6.61(d, J = 9.5 Hz, 1H), 7.22-7.25(m, 1H), 7.41-7.45(m, 1H), 7.45-7.48(m, 1H), 7.50-7.54(m, 1H), 7.56-7.60(m, 1H), 7.96(d, J = 7.7 Hz, 1H), 8.11(dd, J = 2.7 and 9.5 Hz, 1H), 8.11-8.13(m, 1H), 8.81(d, J = 2.6 Hz, 1H). |
| 6-22 | $^1$H NMR(300 MHz, DMSO-d$^6$) δ 5.19(s, 2H), 6.47-6.54(m, 2H), 6.64-6.70(m, 2H), 7.01-7.10(m, 1H), 7.14-7.23(m, 1H), 7.28(dd, J = 2.0 Hz and 8.5 Hz, 1H), 7.46(dd, J = 2.0 Hz and 10.2 Hz, 1H), 7.73(dd, J = 2.6 Hz and 9.5 Hz, 1H), 8.03(d, J = 2.6 Hz, 1H). |
| 6-23 | $^1$H NMR(300 MHz, DMSO-d$^6$) δ 3.10-3.70(br s, 3H), 5.19(s, 2H), 6.53(d, J = 9.5 Hz, 1H), 7.16-7.24(m, 1H), 7.24-7.37(3H), 7.46(dd, J = 1.8 and 10.2 Hz, 1H), 7.63(dd, J = 8.2 Hz, 1H), 7.87(dd, J = 2.6 Hz and 9.5 Hz, 1H), 8.23(s, 1H). |
| 6-26 | $^1$H NMR(300 MHz, DMSO-d$^6$) δ 4.51(d, J = 5.4 Hz, 2H), 5.19(s, 2H), 5.19-5.26(m, 1H), 6.52(d, J = 9.5 Hz, 1H), 7.16-7.24(m, 1H), 7.27(dd, J = 2.0 and 8.2 Hz, 1H), 7.36(d, J = 8.2 Hz, 2H), 7.46(dd, J = 2.0 and 10.2 Hz, 1H), 7.53(d, J = 8.2 Hz, 2H), 7.88(dd, J = 2.8 and 9.5 Hz, 1H), 8.21(d, J = 2.3 Hz, 1H). |
| 6-29 | $^1$H NMR(300 MHz, CDCl$_3$) δ 2.50(s, 6H), 3.65(s, 3H), 5.17(s, 2H), 6.49(d, J = 9.3 Hz, 1H), 7.12-7.30(m, 4H), 7.06(dd, J = 2.1 Hz, J = 9.9 Hz, 1H), 7.83(dd, J = 2.7 Hz, J = 9.3 Hz, 1H), 8.12(d, J = 2.4 Hz, 1H). |

TABLE 18-continued

NMR-data

| Co.Nr | NMR-data |
|---|---|
| 6-30 | $^1$H NMR(500 MHz, DMSO-d$^6$) δ 3.78(s, 3H), 5.17(s, 2H), 6.49(d, J = 9.5 Hz, 1H), 6.86(dd, J = 2.6 Hz and 8.6 Hz, 1H), 6.93(dd, J = 2.6 Hz and 13.0 Hz, 1H), 7.20-7.25(m, 1H), 7.28(dd, J = 2.0 Hz and 8.6 Hz, 1H), 7.37-7.42(m, 1H), 7.45(dd, J = 2.0 Hz and 10.1 Hz, 1H), 7.63-7.67(m, 1H), 7.97(d, J = 2.3 Hz, 1H). |
| 6-31 | $^1$H NMR(500 MHz, DMSO-d$^6$) δ 3.76(s, 3H), 3.80(s, 3H), 5.18(s, 2H), 6.49(d, J = 9.5 Hz, 1H), 6.98(d, J = 8.3 Hz, 1H), 7.07(d, J = 2.1 Hz and 8.3 Hz, 1H), 7.12(d, J = 2.1 Hz 1H), 7.13-7.18(m, 1H), 7.27(dd, J = 1.9 Hz and 8.3 Hz, 1H), 7.46(dd, J = 2.1 Hz and 10.1 Hz, 1H), 7.87(dd, J = 2.6 Hz and 9.5 Hz, 1H), 8.14(d, J = 2.6 Hz, 1H). |
| 6-35 | $^1$H NMR(300 MHz, DMSO-d$^6$) δ 1.01-1.14(m, 3H), 3.64-3.79(m, 2H), 3.82-3.91(m, 1H), 4.72-4.83(m, 1H), 5.02-5.13(m, 2H), 6.33-6.45(m, 1H), 6.79-6.95(m, 2H), 7.06-7.20(m, 2H), 7.29-7.43(m, 3H), 7.70-7.78(m, 1H), 7.97-8.05(m, 1H). |
| 6-38 | $^1$H NMR(300 MHz, DMSO-d$^6$) δ 2.02(p, J = 5.1 Hz, 2H), 4.05(q, J = 5.5 Hz, 4H), 5.08(s, 2H), 6.39(d, J = 9.0 Hz, 1H), 6.91(d, J = 9.0 Hz, 1H), 7.03-7.20(m, 4H), 7.37(dd, J = 3 Hz, J = 9.0 Hz, 1H), 7.74(dd, J = 3.0, J = 9 Hz, 1H), 8.08(d, J = 3.0 Hz, 1H). |
| 6-39 | $^1$H NMR(300 MHz, CDCl$_3$) δ 3.84(s, 3H), 5.19(s, 2H), 6.53(d, J = 9.6 Hz, 1H), 7.17-7.27(m, 2H), 7.27-7.33(3H), 7.45(dd, J = 2.1 Hz and 9.9 Hz, 1H), 7.58-7.66(m, 2H), 7.88(dd, J = 2.7 Hz and 9.6 Hz, 1H), 8.23(d, J = 2.7 Hz, 1H). |
| 6-40 | $^1$H NMR(300 MHz, CDCl$_3$) δ 2.16(s, 3H), 4.83(s, 2H), 5.18(s, 2H), 6.50(d, J = 9.3 Hz, 1H), 6.93-7.02(m, 2H), 7.15-7.24(m, 1H), 7.27(dd, J = 2.1 Hz and 8.7 Hz, 1H), 7.42-7.51(3H), 7.83(dd, J = 2.4 Hz and 9.3 Hz, 1H), 8.11(d, J = 2.4 Hz, 1H). |
| 6-41 | $^1$H NMR(300 MHz, CDCl$_3$) δ 3.70(s, 3H), 4.83(s, 2H), 5.18(s, 2H), 6.50(d, J = 9.3 Hz, 1H), 6.95-7.02(m, 2H), 7.14-7.24(m, 1H), 7.27(dd, J = 2.1 Hz and 8.4 Hz, 1H), 7.43-7.51(3H), 7.83(dd, J = 2.4 Hz and 9.3 Hz, 1H), 8.12(d, J = 2.4 Hz, 1H). |
| 6-45 | $^1$H NMR(300 MHz, CDCl$_3$) δ 2.14-2.27(m, 2H), 2.56(s, 6H), 2.82-2.92(m, 2H), 4.08(t, J = 6.0 Hz, 2H), 5.18(s, 2H), 6.65(d, J = 9.6 Hz, 1H), 6.88-6.95(m, 2H), 7.08-7.12(m, 1H), 7.12-7.15(m, 1H), 7.26-7.31(m, 2H), 7.43-7.51(2H), 7.56(dd, J = 2.7 Hz and 9.6 Hz, 1H). |
| 6-46 | $^1$H NMR(300 MHz, CDCl$_3$) δ 5.19(s, 2H), 5.20(s, 2H), 6.52(d, J = 9.5 Hz, 1H), 7.11-7.16(m, 2H), 7.18-7.23(m, 1H), 7.27(dd, J = 2.0 Hz and 8.4 Hz, 1H), 7.46(dd, J = 2.0 Hz and 10.1 Hz, 1H), 7.55-7.60(m, 1H), 7.86(dd, J = 2.7 Hz and 9.5 Hz, 1H), 8.16(d, J = 2.7 Hz, 1H). |
| 6-48 | $^1$H NMR(300 MHz, CDCl$_3$) δ 2.43-2.56(m, 2H), 2.57-2.80(m, 1H), 2.83-3.01(m, 2H), 3.16-3.29(m, 2H), 3.50-3.55(m, 1H), 3.99(d, J = 3.3 Hz, 1H), 4.03(d, J = 3.3 Hz, 1H), 4.10-4.17(m, 2H), 4.27-4.40(m, 2H), 5.26(s, 2H), 6.93(d, J = 8.7 Hz, 1H), 7.10-7.16(m, 1H), 7.17(d, J = 8.7 Hz, 2H), 7.33(d, J = 8.7 Hz, 2H), 7.48-7.56(m, 1H), 7.65-7.69(m, 1H), 7.73(dd, J = 2.7 Hz and 9.6 Hz, 1H). |
| 6-50 | $^1$H NMR(300 MHz, CDCl$_3$) δ 5.11(s, 2H), 5.18(s, 2H), 6.66(d, J = 9.2 Hz, 1H), 7.01(d, J = 8.7 Hz, 2H), 7.08-7.16(m, 2H), 7.27-7.40(4H), 7.43-7.53(m, 2H), 7.54-7.63(m, 1H), 7.80(d, J = 9.2 Hz, 1H), 8.55-8.79(m, 1H). |
| 6-51 | 1H NMR(300 MHz, DMSO-d$^6$) δ 3.87(s, 3H), 5.17(s, 2H), 6.53(d, J = 9.5 Hz, 1H), 6.89(d, J = 8.7 Hz, 1H), 7.17-7.24(m, 1H), 7.27(dd, J = 2.0 Hz and 8.4 Hz, 1H), 7.46(dd, J = 2.0 Hz and 10.2 Hz, 1H), 7.84-7.94(m, 2H), 8.20(d, J = 2.6 Hz, 1H), 8.38(d, J = 2.3 Hz, 1H). |
| 6-53 | $^1$H NMR(300 MHz, DMSO-d$^6$) δ 3.16(s, 3H), 3.99(t, J = 5.6 Hz, 2H), 5.18(s, 2H), 5.75(s, 1H), 6.51(d, J = 9.5 Hz, 1H), 7.00(d, J = 8.7 Hz, 2H), 7.15-7.23(m, 1H), 7.23-7.29(m, 1H), 7.43-7.53(m, 3H), 7.84(dd, J = 2.8 Hz and 9.5 Hz, 1H), 8.09-8.20(m, 1H). |
| 6-54 | $^1$H NMR(300 MHz, CDCl$_3$) δ 1.92(s, 3H), 3.40(q, J = 6.4 Hz, 2H), 3.98(t, J = 5.9 Hz, 2H), 5.11(s, 2H), 6.59(d, J = 9.5 Hz, 1H), 6.85(d, J = 8.7 Hz, 2H), 7.02-7.07(m, 2H), 7.18-7.23(m, 4H), 7.37-7.52(m, 3H). |
| 6-64 | $^1$H NMR(300 MHz, DMSO-d$^6$) δ 3.59(s, 2H), 5.05-5.12(m, 2H), 6.39-6.46(m, 1H), 6.73(d, J = 8.7 Hz, 1H), 6.78(s, 1H), 7.02-7.23(m, 4H), 7.27(d, J = 8.7 Hz, 1H), 7.34-7.46(m, 3H), 7.63-7.80(m, 1H), 7.95(m, 1H), 8.06(s, 1H), 9.46(bs, 1H). |
| 6-65 | $^1$H NMR(300 MHz, CDCl$_3$) δ 3.00-3.60(br. s, 1H), 5.18(s, 2H), 5.35(s, 2H), 6.50(d, J = 9.5 Hz, 1H), 7.11-7.17(m, 1H), 7.18-7.23(m, 1H), 7.27(dd, J = 2.0 Hz and 8.4 Hz, 1H), 7.45(dd, J = 2.0 Hz and 10.2 Hz, 1H), 7.47-7.60(m, 2H), 7.84(dd, J = 2.7 Hz and 9.5 Hz, 1H), 8.13(d, J = 2.7 Hz, 1H). |
| 6-69 | $^1$H NMR(500 MHz, DMSO-d$^6$) δ 5.21(s, 2H), 6.55(d, J = 9.5 Hz, 1H), 7.19-7.24(m, 1H), 7.26-7.30(m, 1H), 7.43-7.49(m, 2H), 7.57(dd, J = 1.8 Hz and 8.6 Hz, 1H), 7.80(d, J = 5.4 Hz, 1H), 7.95(dd, J = 2.7 Hz and 9.4 Hz, 1H), 8.05(d, J = 8.4 Hz, 1H), 8.07(d, J = 1.6 Hz, 1H), 8.28(d, J = 2.3 Hz, 1H). |
| 6-76 | $^1$H NMR(500 MHz, CDCl$_3$) δ 2.57(s, 3H), 3.70(s, 3H), 5.10(s, 2H), 6.52(d, J = 9.5 Hz, 1H), 6.89(d, J = 8.7 Hz, 2H), 7.35(d, J = 8.7 Hz, 2H), 7.72(d, J = 8.7 Hz, 2H), 7.85(dd, J = 2.7 Hz and 9.5 Hz, 1H), 7.97(d, J = 8.7 Hz, 2H), 8.42(d, J = 2.7 Hz, 1H). |
| 7-01 | $^1$H NMR(DMSO-d$^6$) δ 8.31(s, 1H); 7.56(dd, 1H); 7.41-7.40(m, 1H); 7.32(dd, 1H); 7.20-7.13(m, 3H); 7.03(m, 2H); 6.98-6.96(m, 1H); 5.12(s, 2H); 3.76(s, 3H). |
| 7-02 | $^1$H NMR(500 MHz, DMSO-d$^6$) δ 5.12(s, 2H), 6.50(d, J = 9.4 Hz, 1H), 7.11-7.20(3H), 7.37-7.43(m, 1H), 7.51(dd, J = 5.0 Hz and 8.0 Hz, 1H), 7.58(dd, J = 2.5 Hz and 9.4 Hz, 1H), 7.96-8.00(m, 1H), 8.37(d, J = 2.4 Hz, 1H), 8.59(dd, J = 1.6 Hz and 5.0 Hz, 1H), 8.73(d, J = 2.1 Hz, 1H). |
| 7-03 | $^1$H NMR(500 MHz, DMSO-d$^6$) δ 3.00(t, J = 6.7 Hz, 2H), 4.18(t, J = 6.7 Hz, 2H), 5.01(s, 2H), 5.84(s, 2.7 Hz, 1H), 5.95(dd, J = 2.7 Hz and 7.6 Hz, 1H), 7.03-7.11(3H), 7.18-7.25(m, 1H), 7.29(d, J = 4.7 Hz, 4H), 7.32-7.38(m, 1H), 7.66(d, J = 7.6 Hz, 1H). |
| 7-06 | $^1$H NMR(500 MHz, CDCl$_3$) δ 2.65(t, J = 7.4 Hz, 2H), 2.79(t, J = 7.4 Hz, 2H), 3.76(s, 3H), 4.98(s, 2H), 6.59(d, J = 9.2 Hz, 1H), 6.60-6.65(2H), 6.72-6.75(m, 1H), 6.79-6.82(m, 1H), 6.90-6.94(m, 1H), 6.99(d, J = 2.0 Hz and 9.6 Hz, 1H), 7.13-7.18(m, 1H), 7.23(dd, J = 2.5 Hz and 9.2 Hz, 1H), 7.31-7.36(m, 1H). |
| 7-07 | $^1$H NMR(300 MHz, CDCl$_3$) δ 3.64(s, 2H), 3.70(s, 3H), 5.06(s, 2H), 6.58-6.62(m, 1H), 6.77-6.86(m, 3H), 6.99-7.07(m, 4H), 7.14-7.20(m, 1H), 7.27-7.40(m, 1H). |
| 7-08 | $^1$H NMR(300 MHz, CDCl$_3$) δ 1.76-1.93(m, 2H), 2.30-2.46(m, 2H), 2.52-2.70(m, 2H), 5.09(s, 2H), 6.54(d, J = 9.2 Hz, 1H), 7.04-7.35(9H), 7.35-7.50(m, 1H). |
| 7-11 | $^1$H NMR(300 MHz, CDCl$_3$) δ 1.42-1.59(m, 4H), 2.25-2.35(m, 2H), 2.47-2.56(m, 2H), 3.72(s, 3H), 5.01(s, 2H), 6.48(m, 1H), 6.62-6.72(m, 3H), 7.00-7.25(m, 5H), 7.29-7.37(m, 1H). |
| 7-15 | $^1$H NMR(DMSO-d$^6$) δ 7.77(m, 1H); 7.59-7.57(m, 1H); 7.44-7.43(m, 1H); 7.28(m, 7H); 7.22-7.18(m, 4H); 6.81(m, 1H); 5.53(s, 2H) |
| 7-16 | $^1$H NMR(DMSO-d$^6$) δ 8.27(m, 1H); 7.55-7.47(m, 1H); 7.40-7.3(m, 8H); 6.47(m, 1H), 5.12(s, 2H). |
| 8-02 | 1H NMR(300 MHz, DMSO-d$^6$) δ 0.93(d, 6H), 1.49-1.62(m, 3H), 3.02(s, 3H), 3.91-4.00(m, 2H), 6.48(d, J = 9.4 Hz, 1H), 7.10-7.18(m, 1H), 7.28-7.42(m, 3H), 7.70(dd, J = 2.6 Hz, 9.4 Hz, 1H), 8.03(d, J = 2.6 Hz, 1H), 9.78(s, 1H). |
| 9-01 | $^1$H NMR(DMSO-d$^6$) δ 7.80(d, 1H, J = 2.5 Hz); 7.36(d, 1H, J = 2.5 Hz); 7.33-7.31(m, 1H); 7.27-7.26(m, 3H); 7.15(m, 1H); 7.06(m, 2H); 6.94(m, 2H); 5.23(s, 2H); 3.83(s, 3H). |
| 9-03 | $^1$H NMR(300 MHz, CDCl$_3$) δ 5.17(s, 2H), 5.23(s, 2H), 6.65(d, J = 9.4 Hz, 1H), 7.02(d, J = 8.7 Hz, 2H), 7.08-7.15(m, 2H), 7.25-7.31(m, 4H), 7.42-7.61(m, 3H), 7.71-7.76(m, 1H), 8.54(s, 1H). |
| 9-07 | $^1$H NMR(500 MHz, CDCl$_3$) δ 2.26(s, 3H), 3.83(s, 3H), 5.23(s, 2H), 6.92(d, J = 8.8 Hz, 2H), 7.29(d, J = 8.8 Hz, 2H), 7.30-7.37(m, 6H), 7.47(m, 1H). |
| 9-08 | $^1$H NMR(300 MHz, DMSO-d$^6$) δ 3.77(s, 3H), 4.37(d, J = 5.8 Hz, 2H), 5.12-5.19(3H), 7.00(d, J = 8.9 Hz, 2H), 7.35-7.43(m, 4H), 7.44-7.52(m, 2H), 7.72-7.76(m, 1H), 8.07-8.10(m, 1H). |
| 9-10 | $^1$H NMR(300 MHz, CDCl$_3$) δ 3.83(s, 3H), 3.87(s, 3H), 5.22(s, 2H), 6.82(d, J = 2.3 Hz, 1H), 6.95(d, J = 8.7 Hz, 2H), 7.07-7.12(m, 2H), 7.13-7.15(m, 1H), 7.32(d, J = 9.0 Hz, 2H), 7.47-7.55(m, 1H). |
| 9-12 | $^1$H NMR(500 MHz, CDCl$_3$) δ 2.08(s, 3H), 3.83(s, 3H), 5.16(s, 2H), 6.53(s, 1H), 6.91(d, J = 8.7 Hz, 2H), 7.09(s, 1H), 7.11(d, J = 8.7 Hz, 2H), 7.28-7.37(m, 5H). |
| 9-13 | $^1$H NMR(500 MHz, CDCl$_3$) δ 2.09(s, 3H), 5.14(s, 2H), 6.51(s, 1H), 7.10(dd, J = 9.8 Hz, J = 2.0 Hz, 1H), 7.13(dd, J = 8.4 Hz, J = 2.5 Hz, 1H), 7.23(m, 3H), 7.39(m, 3H), 7.48(t, J = 8.2 Hz, 1H). |

TABLE 18-continued

NMR-data

| Co.Nr | NMR-data |
|---|---|
| 9-14 | $^1$H NMR(500 MHz, CDCl$_3$) δ 2.08(s, 3H), 3.84(s, 3H), 5.12(s, 2H), 6.49(s, 1H), 6.93(d, J = 8.8 Hz, 2H), 7.13(m, 4H), 7.19(s, 1H), 7.48(t, J = 8.2 Hz, 1H). |
| 9-16 | $^1$H NMR(300 MHz, CDCl$_3$) δ 1.64(s, 2H), 2.07(s, 3H), 3.83(s, 3H), 5.12(s, 2H), 6.48(s, 1H), 6.93(d, J = 9.0 Hz, 2H), 7.13-7.28(m, 5H), 7.40-7.46(m, 1H). |
| 9-17 | $^1$H NMR(300 MHz, CDCl$_3$) δ 2.65(t, J = 6.7 Hz, 2H), 3.25(s, 3H), 3.44(t, J = 6.7 Hz, 2H), 3.82(s, 3H), 5.09(s, 2H), 6.58(s, 1H), 6.90(d, J = 8.7 Hz, 2H), 7.06(s, 1H), 7.11(d, J = 8.7 Hz, 2H), 7.23-7.32(4H). |
| 9-18 | $^1$H NMR(300 MHz, CDCl$_3$) δ 3.78(s, 3H), 3.82(s, 3H), 5.11(s, 2H), 5.99(s, 1H), 6.88-6.95(m, 2H), 7.08-7.15(m, 2H), 7.20-7.30(m, 3H), 7.40-7.50(m, 1H). |
| 10-28 | $^1$H NMR(300 MHz, DMSO-d$^6$) δ 0.92(d, J = 5.6 Hz, 6H), 1.48-1.63(m, 3H), 3.90-4.02(m, 2H), 6.72(d, J = 7.2 Hz, 1H), 7.32(d, J = 8.4 Hz, 1H), 7.96-8.04(m, 2H), 8.08(d, J = 7.2 Hz, 1H). |
| 11-03 | $^1$H NMR(500 MHz, DMSO-d$^6$) δ 3.80(s, 3H), 5.11(s, 2H), 6.62(dd, J = 2.1 Hz and 7.2 Hz, 1H), 6.66(d, J = 2.0 Hz, 1H), 7.02(d, J = 8.9 Hz, 2H), 7.09-7.17(m, 3H), 7.36-7.42(m, 1H), 7.70(dd, J = 2.1 Hz and 6.8 Hz, 2H), 7.85(d, J = 7.1 Hz, 1H). |
| 12-06 | $^1$H NMR(300 MHz, DMSO-d$^6$) δ 3.78(s, 3H), 5.12(s, 2H), 7.00(d, J = 9.0 Hz, 2H), 7.40-7.50(m, 4H), 7.77(d, J = 9.0 Hz, 2H), 8.14(s, 1H), 8.39(s, 1H). |
| 13-01 | $^1$H NMR(DMSO-d$^6$) δ 5.16(s, 2H), 6.67(d, J = 7.2 Hz, 1H), 7.14-7.18(m, 2H), 7.37-7.39(m, 2H), 7.51(m, 1H), 7.60(d, J = 7.2 Hz, 1H), 7.66(m, 1H), 7.71(m, 1H), 8.23(m, 1H). |
| 13-05 | $^1$H NMR(300 MHz, DMSO-d$^6$) δ 0.96(t, J = 7.4 Hz, 3H), 1.40-1.72(br. s, 1H), 1.72-1.87(m, 2H), 2.99(t, J = 7.2 Hz, 2H), 3.47(t, J = 6.9 Hz, 2H), 3.95(t, J = 7.4 Hz, 2H), 6.35-6.47(m, 1H), 6.79(d, J = 8.4 Hz, 2H), 6.99-7.12(m, 4H), 7.34-7.42(m, 1H), 7.91-8.02(m, 1H). |
| 13-06 | $^1$H NMR(300 MHz, CDCl$_3$) δ 0.90(t, J = 7.7 Hz, 3H), 1.74(q, J = 8.5 Hz, 2H), 3.06(t, J = 6.6 Hz, 2H), 3.73(s, 3H), 3.89(t, J = 7.4 Hz, 2H), 4.17(t, J = 6.6 Hz, 2H), 6.75-6.83(m, 3H), 6.98(t, J = 7.2 Hz, 2H), 7.18(d, J = 8.2 Hz, 2H), 7.29(t, J = 8.2 Hz, 1H), 7.92(d, J = 8.2 Hz, 1H). |
| 14-01 | $^1$H NMR(300 MHz, CDCl$_3$) δ 0.83(t, J = 7.4 Hz, 3H), 1.55-1.70(m, 2H), 2.75-2.90(4H), 3.72(s, 3H), 3.81(t, J = 7.3 Hz, 2H), 6.60(s, 1H), 6.75(d, J = 8.7 Hz, 2H), 6.97(d, J = 8.6 Hz, 2H), 7.40-7.50(m, 1H), 7.62-7.68(m, 2H), 8.40-8.45(m, 1H). |
| 15-04 | $^1$H NMR(300 MHz, CDCl$_3$) δ 5.52(s, 2H), 6.80(d, J = 9.5 Hz, 1H), 7.13-7.24(4H), 7.25-7.30(m, 2H), 7.40-7.48(m, 1H), 7.58(dd, J = 1.5 Hz and 7.9 Hz, 1H), 7.75(d, J = 9.5 Hz, 1H). |
| 16-01 | $^1$H NMR(500 MHz, DMSO-d$^6$) δ 3.95(d, J = 5.9 Hz, 2H), 5.03(s, 2H), 5.97-6.02(m, 1H), 6.40(d, J = 9.3 Hz, 1H), 6.50-6.55(m, 1H), 6.57(d, J = 7.7 Hz, 2H), 7.01-7.06(m, 2H), 7.28(d, J = 8.5 Hz, 2H), 7.35-7.39(m, 2H), 7.44(dd, J = 2.5 Hz and 9.3 Hz, 1H), 7.77(d, J = 2.1 Hz, 1H). |
| 16-02 | $^1$H NMR(500 MHz, DMSO-d$^6$) δ 3.69(s, 3H), 4.74(s, 2H), 5.07(s, 2H), 6.45(d, J = 9.3 Hz, 1H), 6.82-6.87(m, 2H), 6.88-6.93(m, 2H), 7.29(d, J = 8.5 Hz, 2H), 7.40(d, J = 8.5 Hz, 2H), 7.52(dd, J = 2.5 Hz and 9.0 Hz, 1H), 7.93(d, J = 2.3 Hz, 1H). |
| 16-03 | $^1$H NMR(500 MHz, DMSO-d$^6$) δ 4.80(s, 2H), 5.06(s, 2H), 6.45(d, J = 9.3 Hz, 1H), 6.91-6.96(m, 1H), 6.96-6.99(m, 2H), 7.12-7.17(m, 1H), 7.25-7.30(m, 2H), 7.36-7.43(m, 2H), 7.53(dd, J = 2.5 Hz and 9.3 Hz, 1H), 7.99(d, J = 2.3 Hz, 1H). |
| 16-04 | $^1$H NMR(500 MHz, DMSO-d$^6$) δ 4.82(s, 2H), 5.10(s, 2H), 6.45(d, J = 9.4 Hz, 1H), 6.91-6.96(m, 1H), 6.97(d, J = 7.8 Hz, 2H), 7.13-7.19(m, 1H), 7.24-7.30(3H), 7.45(dd, J = 2.3 Hz and 10.1 Hz, 1H), 7.55(dd, J = 2.3 Hz and 9.3 Hz, 1H), 7.90(d, J = 2.3 Hz, 1H). |
| 16-05 | $^1$H NMR(300 MHz, CDCl$_3$) δ 3.71(s, 3H), 4.67(s, 2H), 5.05(s, 2H), 6.39-6.58(m, 4H), 7.01-7.06(m, 2H), 7.12(t, J = 8.2 Hz, 1H), 7.19(s, 1H), 7.32-7.38(m, 2H). |
| 16-06 | $^1$H NMR(300 MHz, CDCl$_3$) δ 1.91(p, J = 7.7 Hz, 2H), 2.49(t, J = 7.4 Hz, 2H), 3.85(t, J = 5.9 Hz, 2H), 4.98(s, 2H), 6.49(d, J = 9.2 Hz, 1H), 6.78(d, J = 8.7 Hz, 2H), 6.86-7.24(m, 7H), 7.30(t, J = 8.4 Hz, 1H). |
| 16-08 | $^1$H NMR(300 MHz, CDCl$_3$) δ 0.89(d, J = 6.1 Hz, 6H), 1.18-1.23(m, 1H), 1.52-1.61(m, 2H), 3.71(s, 3H), 3.86(t, J = 7.9 Hz, 2H), 4.65(s, 2H), 6.52(d, J = 9.2 Hz, 1H), 6.75-6.82(m, 4H), 7.19-7.26(m, 1H), 7.30(dd, J = 2.4 Hz, J = 9.2 Hz, 1H). |

Pharmacology

The compounds provided in the present invention are positive allosteric modulators of mGluR2. As such, these compounds do not appear to bind to the orthosteric glutamate recognition site, and do not activate the mGluR2 by themselves. Instead, the response of mGluR2 to a concentration of glutamate or mGluR2 agonist is increased when compounds of Formula (I) are present. Compounds of Formula (I) are expected to have their effect at mGluR2 by virtue of their ability to enhance the function of the receptor. The behavior of positive allosteric modulators, more particular the ones described by Formula (I), at mGluR2 is shown in Example A, which is suitable for the identification of such compounds.

Example A

[$^{35}$S]GTPγS Binding Assay

The [$^{35}$S]GTPγS binding is a functional membrane-based assay used to study G-protein coupled receptor (GPCR) function. This method is using a binding assay to assess the initial step in receptor-mediated G protein activation in membranes prepared from cells expressing recombinant GPCR or using membranes from discrete area of the rat brain. In brief, the assay is measuring the activation of G proteins by catalyzing the exchange of guanosine 5'-diphosphate (GDP) by guanosine 5'-triphosphate (GTP) at the α subunit. The GTP-bounded G proteins dissociate into two subunits, Gα-GTP and Gβγ, which in turn regulate intracellular enzymes and ion channels. GTP is rapidly hydrolysed by the Gα-subunit (GTPases) and the G protein is deactivated and ready for new GTP exchange cycle (Harper (1998) Curr Protoc Pharmacol 2.6.1-10, John Wiley & Sons, Inc.). [$^{35}$S]GTPγS, a non-hydrolyzed analogue of GTP, is used for this purpose.

This method is widely used to study receptor activation of G protein in membranes prepared from rat brain tissue, including mGluR2 receptors (Schaffhauser et al 2003, Pinkerton et al, 2004). mGluR2 receptors are expressed in the rat brain cortex (Mutel et al (1998) J. Neurochem. 71:2558-64; Schaffhauser et al (1998) Mol. Pharmacol. 53:228-33) and are coupled to Gαi-protein, a preferential coupling for this method. The study of the pharmacological characterisation of metabotropic glutamate receptor-mediated high-affinity GTPase activity (Nishi et al (2000) Br. J. Pharmacol. 130: 1664-1670) showed that the activation of G-proteins in rat cerebral cortical membranes is mediated by group II mGluRs, and in particular by mGluR2.

[$^{35}$S]GTPγS binding assay using cortical rat brain membranes preparation was used and adapted from Schaffhauser et al ((2003) Mol. Pharmacol. 4:798-810) for the detection of the positive allosteric modulator properties of the compounds of this invention on native rat mGluR2. In order to eliminate the possible interference with group III Gαi-protein coupled mGluRs (mGluR4, mGluR7, mGluR8; mGluR6 is not expressed in the cortex (Laurie et al (1997) Neuropharmacol. 36:145-52)), the potentiation of the response to a selective mGluR2 agonist, such as DCG-IV (Cartmell et al. (1998) Br. J. Pharmacol. 123(3):497-504) or LY379268 (Monn et al.

(1999) J. Med. Chem 42:1027-40), by compounds described in the present invention was performed.

Membrane Preparation.

Cortices were dissected out from brains of 200-300 g Sprague-Dawley rats (Charles River Laboratories, L'Arbresle, France). Tissues were homogenized in 6 volumes (vol/wt) of 10% sucrose at 4° C. using a glass-teflon homogenizer. The homogenate was centrifuged at 1250 g for 10 min, and the supernatant was centrifuged at 40,000 g for 20 min (4° C.). The pellet was resuspended in 25 ml water using a Polytron disrupter (Kinematica AG, Luzern, Switzerland) and centrifuged for 10 min at 3000 g. (4° C.). The supernatant was centrifuged at 40,000 g for 20 min (4° C.). The supernatant was discarded and the pellet washed twice by resuspension in 10 volumes 5 mM HEPES-KOH, pH 7.4. The homogenate was frozen and thawed twice and centrifuged at 40,000 g for 20 min. The final pellet was resuspended in 5 mM HEPES-KOH, pH 7.4 and stored at −80° C. before its use. Protein concentration was determined by the Bradford method (Bio-Rad protein assay, Reinach, Switzerland) with bovine serum albumin as standard.

[$^{35}$S]GTPγS Binding Assay.

Measurement of mGluR2 positive allosteric modulators properties in rat cortical membranes was performed as follows: rat cortical membrane (1.5 µg) were incubated in 96-well microplates for 15 min at 30° C. in assay buffer (50 mM HEPES pH 7.4, 100 mM NaCl, 5 mM MgCl$_2$, 10 µM GDP, 10 µg/ml saponin, EGTA 0.2 mM) with increasing concentrations of positive allosteric modulator (from 1 nM to 10 µM) and a minimal concentration of DCG-IV or LY379268, a selective mGluR2 agonist, that has been determined in previous experiments and that corresponds to the $EC_{20}$, a concentration that gives 20% of the maximal response of the agonist, and is in accordance to published data (Pin et al. (1999) Eur. J. Pharmacol. 375:277-294). Likewise, 10-point concentration-response curves of an mGluR2 selective agonist such as DCG-IV or LY379268, were tested in the absence or in the presence of 3 or 10 µM of positive allosteric modulator in order to detect a leftward-shift of the concentration-response curve of the agonist (appreciated by a decrease in the $EC_{50}$) and/or an increase of its maximal efficacy. After addition of 0.1 nM [$^{35}$S]GTPγS to achieve a total reaction volume of 200 µl, microplates were shaken for 1 min and further incubated at 30° C. for 30 min. The incubation was stopped by rapid vacuum filtration over glass-fiber filter plates (Unifilter 96-well GF/C filter plates, Perkin-Ehmer, Schwerzenbach, Switzerland) microplate using a 96-well plate cell harvester (Filtermate, Perkin-Ehmer, Downers Grove, USA). The Unifilter plate was washed three times with 300 µl of ice-cold wash buffer (20 mM HEPES pH 7.4, 100 mM NaCl). When filters are dried, 40 µl of liquid scintillation cocktail (Microscint 20) was added to each well. The amount of membrane-bound [$^{35}$S]GTPγS is measured using a 96-well plate reader (Top-Count, Perkin-Ehmer, Downers Grove, USA). Non specific [$^{35}$S]GTPγS binding is determined in the presence of 10 µM of GTP.

Data Analysis.

The concentration-response curves of representative compounds of the present invention in the presence of $EC_{20}$ of mGluR2 agonist were generated using the Prism Graph-Pad program (Graph Pad Software Inc, San Diego, USA). The curves were fitted to a four-parameter logistic equation (Y=Bottom+(Top−Bottom)/(1+10^((LogEC$_{50}$−X)*Hill Slope) allowing determination of $EC_{50}$ values. Each curve was performed using triplicate sample per data point and 10 concentrations. The concentration-response curves of a selective mGluR2 agonist in the absence or in the presence of representative compounds of the present invention were also generated using Prism Graph-Pad program (Graph Pad Software Inc, San Diego, USA). The curves were fitted to a four-parameter logistic equation (Y=Bottom+(Top−Bottom)/(1+10^((LogEC$_{50}$−X)*Hill Slope) allowing determination of $EC_{50}$ values of the selective mGluR2 agonist. Each curve was performed using triplicate sample per data point and 10 concentrations.

Data presented in FIG. 1 represent the ability of 10 µM of Compound 4-16 to increase the [GTPγ$^{35}$S] binding induced by 50 nM of DCG-IV, an mGluR2 agonist. Said compound has no statistically significant agonistic activity when tested in the absence of 50 nM DCG-IV, as compared to buffer value (0% of maximal response). Instead, when compounds are added together with an mGluR2 agonist like glutamate or DCG-IV, the effect measured is significantly potentiated compared to the effect of the agonist alone at the same concentration. Each bar graph in FIG. 1 is the mean and S.E.M. of triplicate data points and is representative of three independent experiments.

Table 19 shows representative compounds of the present invention that were clustered into three classes according to their ability to leftward-shift the concentration-response curve of a selective mGluR2 agonist such as LY379268 and/or to increase its maximal efficacy.

TABLE 19

Activity data for selected compounds

| Compound no. | Activity |
|---|---|
| 15-04 | + |
| 7-02 | + |
| 11-03 | + |
| 9-18 | + |
| 12-06 | + |
| 7-14 | + |
| 15-02 | + |
| 9-17 | + |
| 13-01 | ++ |
| 2-32 | ++ |
| 2-55 | ++ |
| 3-02 | ++ |
| 6-16 | ++ |
| 6-73 | ++ |
| 3-17 | ++ |
| 2-61 | ++ |
| 16-07 | ++ |
| 9-04 | ++ |
| 4-20 | +++ |
| 4-47 | +++ |
| 6-65 | +++ |
| 9-06 | +++ |
| 5-13 | +++ |
| 10-28 | +++ |
| 13-04 | +++ |
| 13-05 | +++ |
| 10-30 | +++ |

+: left-ward shift of agonist mGluR2 concentration-response curve [<2]
++: left-ward shift of agonist mGluR2 concentration-response curve [2- to 3.5-fold]
+++: left-ward shift of agonist mGluR2 concentration-response curve [>3.5]

Thus, the positive allosteric modulators provided in the present invention are expected to increase the effectiveness of glutamate or mGluR2 agonists at mGluR2, and therefore, these positive allosteric modulators are expected to be useful for treatment of various neurological and psychiatric disorders associated with glutamate dysfunction described to be treated herein and others that can be treated by such positive allosteric modulators.

Example B

Animal Models of Schizophrenia

Phencyclidine (PCP) Model of Schizophrenia

PCP-induced increases in locomotor ambulation are a widely accepted animal model of schizophrenia. This model is based on the evidence that phencyclidine induces a schizophrenia-like syndrome in humans including increased motor behaviors, disruption of cognition and impairment of working memory (Steinpreis R E (1996) Behav Br Res. 74:45-55; Abi-Saab et al. (1998) Pharmacopsychiatry, 31:104-109). Further, it has also been shown that antipsychotic drugs that are effective in the treatment of schizophrenia reduce the locomotor activating effect of PCP (Gleason & Shannon (1997) Psychopharmacology, 129:79-84). These results demonstrate that locomotor activation induced by PCP is a useful model for screening of compounds which may be useful in the treatment of schizophrenia.

Amphetamine Model of Schizophrenia

Amphetamine-induced increases in locomotor ambulation are well known and are widely used as a model of the positive symptoms of schizophrenia. This model is based on evidence that amphetamine increases motor behaviors and can induce a psychotic state in humans (Yui et al. (2000) Ann NY Acad Sci 914:1-12). Further, it is well known that amphetamine-induced increases in locomotor activity are blocked by antipsychotics drugs that are effective in the treatment of schizophrenia (Arnt (1995) Eur J Pharmacol 283:55-62). These results demonstrate that locomotor activation induced by amphetamine is a useful model for screening of compounds which may be useful in the treatment of schizophrenia.

Subjects:

The present studies were performed in accordance with the animal care and use policies of Addex Pharmaceuticals and the EEC directives on the protection of animals used for experimental and other scientific purposes (86/609/EEC and subsequent revisions). Male C57BL6/j mice (20-30 g) 7 weeks of age at the time of delivery were group housed in a temperature and humidity controlled facility on a 12 hour light/dark cycle for at least 5 days before use. Mice had access to food and water ad libitum except during locomotor activity experiments.

Assessment of Locomotor (Ambulatory) Activity:

The effects of compounds on PCP- or amphetamine-induced locomotor activation in mice were tested. Locomotor activity of mice was tested in white plastic boxes 35 cm×35 cm square with walls 40 cm in height. Locomotor activity (ambulations) was monitored by a videotracking system (VideoTrack, Viewpoint, Champagne au Mont d'Or, France) that recorded the ambulatory movements of mice. Mice were naïve to the apparatus prior to testing. On test days, test compounds (200 mg/kg i.p. (intraperitoneal)) or vehicle were administered immediately before the PCP (5 mg/kg s.c. (subcutaneous), amphetamine (3.0 mg/kg s.c.) or saline injection. Mice were placed into the locomotor boxes immediately after the PCP, amphetamine or saline vehicle injection and their locomotor activity, defined as the distance traveled in centimeters (cm), was measured for 60 minutes.

Compound Administration:

Compounds were dissolved in dimethyl sulfoxide (DMSO) (4% of final volume) and then mixed with Labrafil M1944 CS (apricot kernel oil—Gattefossé, Saint Priest, France) (40% of final volume), sterile water (56% of final volume) and Tween 80 (10 µL per 10 ml solution) and administered in a volume of 10 ml/kg. Compound-vehicle-treated mice received the equivalent volume of vehicle solution i.p. in the absence of added compound. PCP hydrochloride (Sigma, Switzerland) was dissolved in saline and was administered at a dose of 5 mg/kg s.c. in a volume of 10 ml/kg. PCP-vehicle-treated mice received an equal volume of saline vehicle injected s.c. D-amphetamine sulfate (Amino AG, Neuenhof, Switzerland) was dissolved in saline and administered at a dose of 3.0 mg/kg s.c. in a volume of 10 ml/kg. D-amphetamine-vehicle-treated mice received an equivalent volume of saline vehicle injected s.c.

Statistical Analyses:

Statistical analyses were performed using GraphPad PRISM statistical software (GraphPad, San Diego, Calif., USA). Data were analyzed using unpaired t-tests. The significance level was set at $p<0.05$.

Effect of Compounds on PCP-Induced Locomotor Activity in Mice

Data from such an experiment using a representative compound is shown below.

Figure 2:
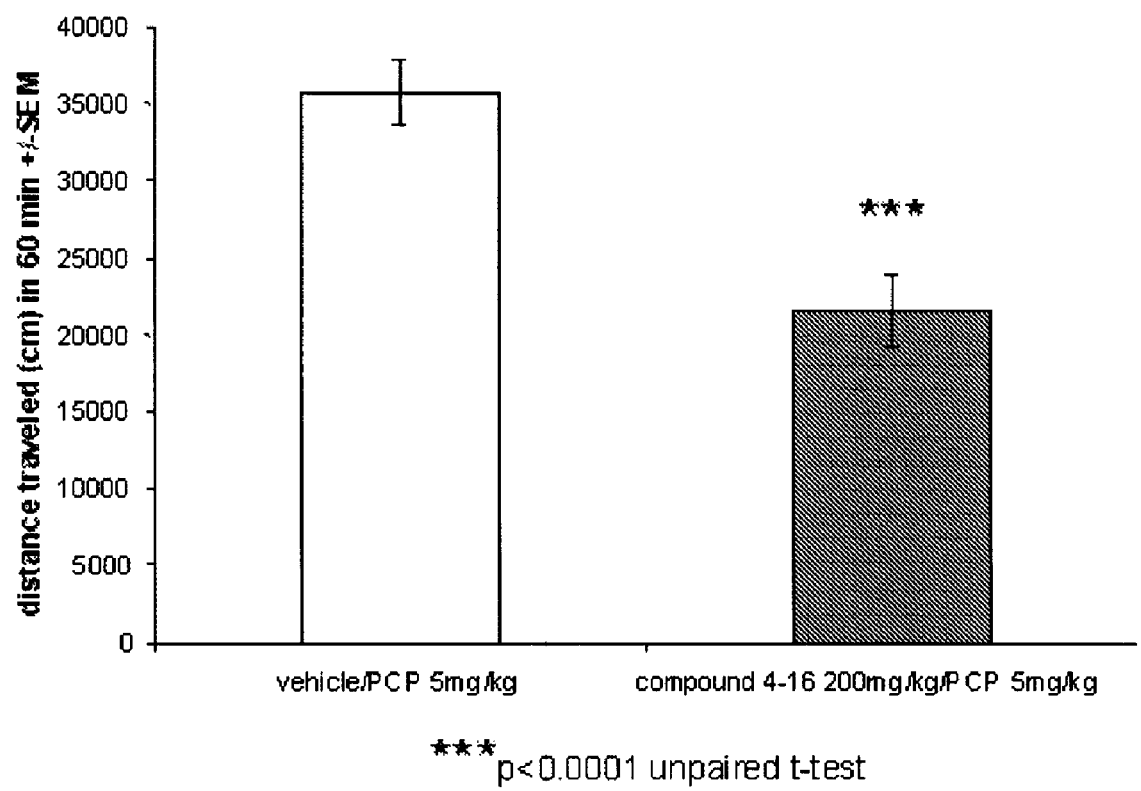
FIG. 2 shows compound 4-16 significantly attenuated the increase in locomotor activity induced by PCP (t=4.491, df=29, n=15 veh/PCP group; n=16 Compound 4-16/PCP group).

As can be seen in FIG. 2, the representative compound significantly attenuated the increase in locomotor activity induced by PCP (t=4.491, df=29, n=15 veh/PCP group; n=16 Compound 4-16/PCP group). These results suggest that compounds of Formula (I) may be useful in the treatment of schizophrenia.

Effect of Compounds on Amphetamine-Induced Locomotor Activity in Mice

Data from such an experiment using a representative compound is shown below.

Figure 3:
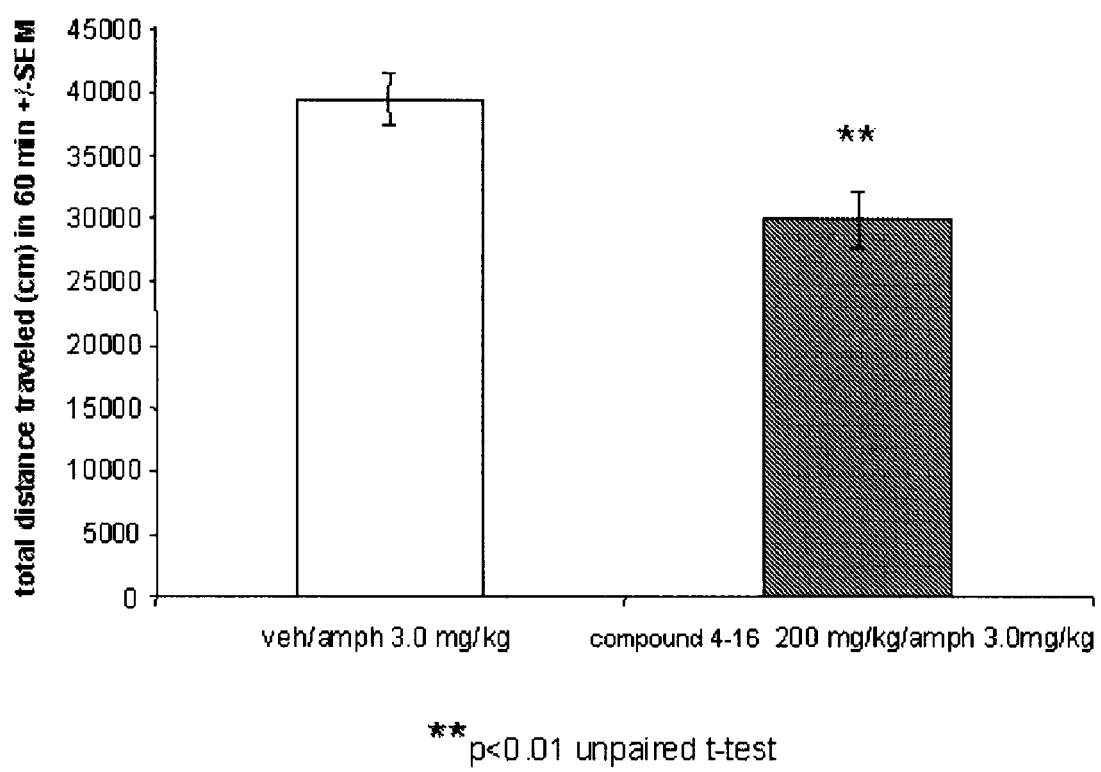
FIG. 3 shows compound 4-16 significantly attenuated the increase in locomotor activity induced by amphetamine (t=3.213, df=30, n=16 mice per group).

As can be seen in FIG. 3, the representative compound significantly attenuated the increase in locomotor activity induced by amphetamine (t=3.213, df=30, n=16 mice per group). These results suggest that compounds of Formula I may be useful in the treatment of schizophrenia.

Effect of Compounds on Baseline Exploratory Locomotor Activity

The effect of Compound 4-16, a representative compound of the present invention, on exploratory (saline-treated) locomotor activity in mice is shown in below.

Figure 4:
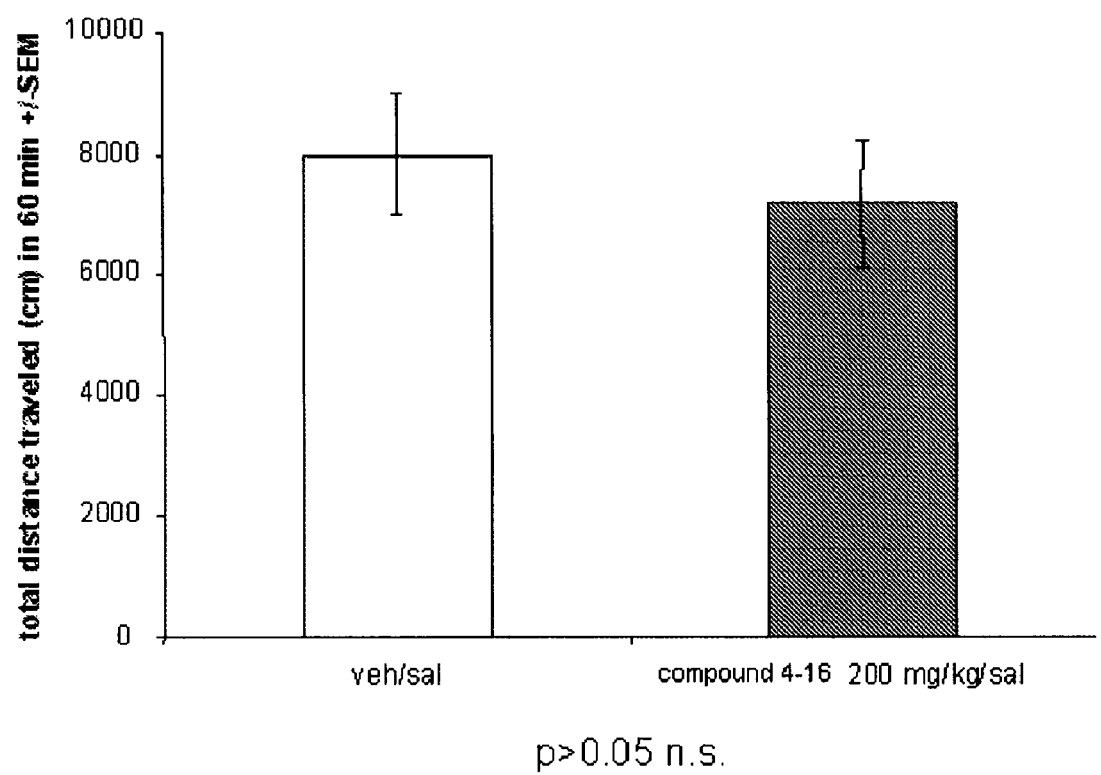
FIG. 4 shows compound 4-16 had no statistically significant effect on locomotor activity in mice (t=0.5793, df=30, n=16 mice per group).

As can be seen in FIG. 4, Compound 4-16, had no statistically significant effect on locomotor activity in mice (t=0, 5793, df=30, n=16 mice per group). These results demonstrate that Compound 4-16 has no effect on exploratory locomotor activity in non-habituated, saline-treated mice. Thus, attenuation by Compound 4-16, a representative compound of the present invention, of the hyperlocomotion induced by either PCP or amphetamine is specific to PCP- or amphetamine-induced hyperlocomotion and not a non-specific decrease in locomotor activity. These results further support the potential of compounds of Formula (I) in the treatment of schizophrenia.

FORMULATION EXAMPLES

Typical examples of recipes for the formulation of the invention are as follows:

1. Tablets

| | |
|---|---|
| Compound 4-16 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, Compound 4-16 can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol and water.

4. Ointment

|  |  |
|---|---|
| Compound 4-16 | 5 to 1000 mg |
| Stearyl alcohol | 3 g |
| Lanoline | 5 g |
| White petroleum | 15 g |
| Water | ad 100 g |

In this Example, Compound 4-16 can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A method for treating or controlling schizophrenia in a mammal comprising administering to a patient in need thereof a compound according to the Formula (I),

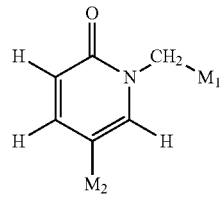

(I)

a pharmaceutically acceptable acid or base addition salt thereof, a stereochemically isomeric form thereof or an N-oxide form thereof, wherein:

$M_1$ is a phenyl group having at least one halo group; and
$M_2$ is a phenyl group substituted with at least one substituent selected from the group consisting of $(C_1-C_6)$alkyloxy, pyridinyl-$(C_1-C_6)$alkyloxy, morpholinyl-$(C_1-C_6)$alkyloxy, pyrrolidinyl-$(C_1-C_6)$alkyloxy optionally substituted with oxo, isoxazolyl-$(C_1-C_6)$alkyloxy, imidazolyl-$(C_1-C_6)$alkyloxy, tetrazolyl-$(C_1-C_6)$alkyloxy or thiazolyl-$(C_1-C_6)$alkyloxy, wherein the isoxazolyl, imidazolyl, tetrazolyl or thiazolyl rings may be optionally substituted with methyl.

2. The method of claim 1, wherein $M_1$ is a phenyl group having at least one fluoro or chloro group.

3. The method of claim 1, wherein $M_1$ is a phenyl group having one fluoro group and one chloro group.

4. The method of claim 1, wherein $M_1$ is

5. The method of claim 1, wherein $M_2$ is a phenyl group substituted with at least one $(C_1-C_6)$alkyloxy.

6. The method of claim 1, wherein $M_2$ is a phenyl group substituted with a methoxy group.

7. The method of claim 1, wherein $M_2$ is a phenyl group substituted with at least one tetrazolyl-$(C_1-C_6)$alkyloxy.

8. The method of claim 1, wherein $M_2$ is a phenyl group substituted with

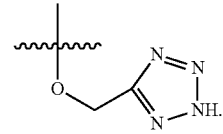 [SMILES: *OCc1nn[nH]n1]

9. The method of claim 1, wherein the compound is administered as a pharmaceutical composition comprising a therapeutically effective amount of the compound and a pharmaceutically acceptable carrier and/or excipient.

* * * * *

UNITED STATES PATENT AND TRADEMARK OFFICE
CERTIFICATE OF CORRECTION

PATENT NO. : 8,399,493 B2  
APPLICATION NO. : 11/575433  
DATED : March 19, 2013  
INVENTOR(S) : Hassan Julien Imogai, Jose Maria Cid-Nunez and Guillaume Albert Jacques Duvey Page 1 of 1

It is certified that error appears in the above-identified patent and that said Letters Patent is hereby corrected as shown below:

On the Title page on the patent, Item (75) please replace the list of inventors with the following inventors:

-- Hassan Julien IMOGAI, Geneva (CH)  
  Jose Maria CID-NUNEZ , Toledo (ES)  
  Guillaume Albert Jacques DUVEY, Geneva (CH) --

Signed and Sealed this  
Sixteenth Day of July, 2013

Teresa Stanek Rea  
*Acting Director of the United States Patent and Trademark Office*

UNITED STATES PATENT AND TRADEMARK OFFICE
CERTIFICATE OF CORRECTION

PATENT NO.         : 8,399,493 B2                                    Page 1 of 1
APPLICATION NO.    : 11/575433
DATED              : March 19, 2013
INVENTOR(S)        : Bolea et al.

It is certified that error appears in the above-identified patent and that said Letters Patent is hereby corrected as shown below:

On the title page, item (73), delete "Addex Pharmaceuticals S.A." and replace with
--ADDEX PHARMA, SA--

Signed and Sealed this
Twenty-eighth Day of January, 2014

Michelle K. Lee
*Deputy Director of the United States Patent and Trademark Office*